(12) United States Patent
Seismann et al.

(10) Patent No.: US 8,802,836 B2
(45) Date of Patent: Aug. 12, 2014

(54) **CLONING AND RECOMBINANT PRODUCTIONS OF *VESPULA* VENOM PROTEASE AND METHODS OF USE THEREOF**

(75) Inventors: Henning Seismann, Nienwohld (DE); Ingke Braren, Hamburg (DE); Thomas Grunwald, Hamburg (DE)

(73) Assignee: PLS-Design GmbH, Hamburg (DE)

( * ) Notice: Subject to any disclaimer, the term of this patent is extended or adjusted under 35 U.S.C. 154(b) by 421 days.

(21) Appl. No.: 13/254,644

(22) PCT Filed: Mar. 3, 2010

(86) PCT No.: PCT/EP2010/001329
§ 371 (c)(1),
(2), (4) Date: Sep. 2, 2011

(87) PCT Pub. No.: WO2010/099956
PCT Pub. Date: Sep. 10, 2010

(65) Prior Publication Data
US 2012/0009187 A1 Jan. 12, 2012

(30) Foreign Application Priority Data
Mar. 3, 2009 (EP) .................... 09003033

(51) Int. Cl.
*C12N 15/62* (2006.01)
*C12N 15/63* (2006.01)
*C12N 9/64* (2006.01)
*A61K 39/36* (2006.01)

(52) U.S. Cl.
USPC ..... 536/23.2; 435/226; 435/252.3; 435/320.1

(58) Field of Classification Search
CPC .............................. C12N 9/6408; C12N 15/52
See application file for complete search history.

(56) References Cited

U.S. PATENT DOCUMENTS 5,593,877 A 1/1997 King

FOREIGN PATENT DOCUMENTS

WO 99/38978 8/1999

OTHER PUBLICATIONS

Petersen, et al., "Investigations on the carbohydrate moieties of glycoprotein allergens," J. Chromat. B 2001; 756:141-150.
Powers D.B. et al. "Expression of single-chain Fv-Fc fusions in *Pichia pastoris*,"J. Immunol Meth. 2001; 251:123-135.
Quevillon E. et al. "InterProScan: protein domains identifier." [online, last accessed Jan. 23, 2009] http://www.ebi.ac.uk/Tools/InterProScan/Nucleic Acids Res. 2005; 33(Web Server issue):W116-W120.
Reid, M.J. et al. "Seasonal asthma in northern California: allergic causes and efficacy of immunotherapy." J. Allergy Clin. Immunol. 1986; 78:590-600.
Rudensky, et al. "Sequence analysis of peptides bound to MHC class II molecules." Nature 1991; 353:622-627.
Schmidt et al. "Expression systems for production of recombinant allergens." Int. Arch. Allergy Immunol. 2002; 128: 264-270.

(Continued)

*Primary Examiner* — Manjunath Rao
*Assistant Examiner* — William W Moore
(74) *Attorney, Agent, or Firm* — Casimir Jones S.C.

(57) ABSTRACT

The invention relates to nucleic acids encoding a novel *Vespula* venom protease or fragments thereof, in particular the protease Ves v 4, recombinant vectors comprising such nucleic acids, and host cells containing the recombinant vectors. The invention is further directed to the expression of such nucleic acids to produce a recombinant *Vespula* venom protease, or recombinant fragments thereof, or synthetic peptides thereof. Such a protease or fragments thereof or synthetic peptides thereof are useful for diagnosis of insect venom allergy and for therapeutic treatment of insect venom allergy.

8 Claims, 12 Drawing Sheets

(56) References Cited

OTHER PUBLICATIONS

Shreffler, et al., "Microarray immunoassay (MIA) for the parallel IgE and IgG4 epitope mapping of milk allergens," J Allergy Clin Immunol. 2004; 113(No. 2 supplement): S238.
Steinberger P. et al. "Construction of a Combinatorial IgE Library from a Allergic Patient." J. Biol. Chem. 1996; 271: 10967-10972.
Tomiya, N. et al. "Comparing N-glycan processing in mammalian cell lines to native and engineered lepidopteran insect cell lines." Glycoconjugate J. 2004; 21: 343-360.
Valenta R. et al. "The Immunoglobulin E-Allergen Interaction : A Target for Therapy of Type I Allergic Diseases." Int. Arch. Immunol. 1998; 116: 167-176.
Varney V.A. et al. "Influence of grass pollen immunotherapy on cellular infiltration and cytokine mRNA expression during allergen-induced late-phase cutaneous responses." J. Clin. Invest. 1993; 92:644-651.
Varney V.A. et al. "Usefulness of immunotherapy in patients with severe summer hay fever uncontrolled by antiallergic drugs." British Medical J. 1991; 302: 265-269.
Wang P. et al. "A Systematic Assessment of MHC Class II Peptide Binding Predictions and Evaluation of a Consensus Approach," PloS Comp Biol 2008; 4:1-10.
Wetterwald A. et al. "Isotypic and idiotypic characterization of anti-bee venom phospholipase A2 antibodies." Int. Arch. Allergy Appl. Immunol. 1985; 77:195-197.
Winningham K.M. et al., "Hymenoptera venom protease allergens." J Allergy Clin Immunol. Oct. 2004;114(4):928-33.
Winter G. et al., "Man-made antibodies" Nature 1991; 349:93-299.
Yamamoto T. et al. "Identification of proteins from venom of the paralytic spider wasp *Cyphonyx dorsalis*," Insect Biochem. Mol. Biol. 2007; 37:278-286.
Zhang, Q. et al. "Immune epitope database analysis resource (IEDB-AR)," Nucleic Acid Res. 2008; 36:W513-W518.
Akdis et al., "Differential regulation of human T cell cytokine patterns and IgE and IgG4 responses by conformational antigen variants," Eur J Immunol. 1998; 28(3): 914-925.
Altschul, et al., "Basic local alignment search tool." J. Mol. Biol. 1990;215:403-410.
Arnold K. et al., "The Swiss-Model Workspace: A web-based environment for protein structure homology modelling." Bioinformatics 2006, 22,195-201.
Asgari S., et al. "A serine proteinasde homolog venom protein from endoparasitoid wasp inhibits melanization of the host hemolymph." Insect Biochem. Mol. Biol. 2003; 33:1017-1024.
Barnard, J.H. "Studies of 400 Hymenoptera sting deaths in United States." J. Allergy Clin Immunol 1973;52:259-264.
Benjamin D.C. et al.. "The Antigenic Structure of Proteins : A Reappraisal." Ann. Rev. Immunol. 1984; 2: 67-101.
Bilo, B.M., et al. "Diagnosis of Hymenoptera venom allergy." Allergy 2005; 60:1339-1349.
Blank S. et al . "Identification and recombinant expression of a novel IgE-reactive 70 kDa carboxylesterase from *Apis mellifera* venom." Uniprot entry B2D0J5. Retrieved on Aug. 22, 2011.
Boel E. et al. "Functional human monoclonal antibodies of all isotypes constructed from phage display library-derived single-chain Fv antibody fragments," J. Immunol. Meth. 2000; 26: 153-166.
Bork P. et al., "The CUB domain : a widespread module in developmentally regulated proteins." J. Mol. Biol. 1993; 231:539-545.
Briner et al. "Peripheral T-cell tolerance induced in naive and primed mice by subcutaneous injection of peptides from the major cat allergen Fel d I." Proc. Natl. Acad. Sci. USA 1993; 90:7608-7612.
Carballido J.M. et al. "T Cell Epitope Specificity in Human Allergic and Nonallergic Subjects to Bee Venom Phospholipase A2." J. Immunol. 1993; 150:3582-3591.
Chou P.Y., et al. "Prediction of protein conformation," Biochemistry 1974; 13:222-245.
Dhillon M. et al. Mapping human T cell epitopes on phospholipase A2 : The major bee-venom allergen. J. Allergy Clin. Immunol. 1992; 90:42-51.

Edwards M.R. et al. "Analysis of IgE Antibodies from a Patient with Atopic Dermatitis : Biased V Gene Usage and Evidence for Polyreactive IgE Heavy Chain Complementary-Determining Region 3." J Immunol 2002; 168: 6305-6313.
Elbein A.D. "The Role of N-linked Oligosaccharides in Glycoprotein function." Trends in Biotech 1991; 9:346-352.
Emanuelsson O. et al.. "Locating proteins in the cell using TargetP, SignalP, and related tools." Nature Protocols 2007; 2(4):953-971.
Finkelman F.D. et al. "Lymphokine Control of in vivo Immunoglobulin Isotype Selection," Ann. Rev. Immunol. 1990; 8:303-333.
Fraternali F. et al., "Parameter optimized surfaces(POPS) : analysis of interactions and conformational changes in the ribosome." Nucleic Acids Res. 2002; 30:2950-2960.
Ganglberger E. et al. "Allergen mimotopes for 3-dimensional epitope search and induction of antibodies inhibiting human IgE." FASEB J. 2000; 14:2177-2184.
Greene A., et al. "Avoidance of bee and wasp stings: an entomological perspective."Curr. Opin. Allergy Clin. Immunol.2005; 5:337-341.
Haim B. et al. "Characterization and anticoagulant activity of a proteolytic enzyme from *Vespa orientalis* venom." Toxicon 1999; 37:825-829.
Han J. et al.. "An anticoagulant serine protease from the wasp venom of *Vespa magnifica*. NCBI nucleic acid database entry EU267370." Toxicon 2008; 51:914-922.
Hancock K. et al. "False positive reactivity of recombinant, diagnostic, glycoproteins produced in High Five insect cells: Effect of glycosylation." J. Immunol. Meth. 2008; 330:130-136.
Hemmer W. et al "Identification by immunoblot of venom glycoproteins displaying immunoglobulin E-binding N-glycans as cross-reactive allergens in honeybee and yellow jacket venom." Clin. Exp. Allergy 2004; 34:460-469.
Hoffman D.R. et al., "Allergens in Hymenoptera venom XXVII: Bumblebee enom allergy and allergens. UniProtKB database entry Q7M4I3 and Q7M4I6." J Allergy Clin Immunol 1996; 97:812-21.
Hoffman, D.R. "Allergens in Hymenoptera venom XIII: isolation and purification of protein components from three species of vespid venoms." J. Allergy Clin. Immunol. 1985; 75:599-605.
Hopp T.P. et al. "Prediction of protein antigenic determinants from amino acid sequences." Proc. Natl. Acad. Sci. USA 1981; 78:3824-3828.
Hoyne G.F. et al. "Inhibition of T Cell and Antibody Response to House Dust Mite Allergen by Inhalation of the Dominant T Cell Epitope in Naive and Sensitized Mice." J. Exp. Med. 1993; 178:1783-1788.
Jutel M. et al. "Mechanism of allergen specific immunotherapy—T-cell tolerance and more." Allergy 2006; 61:796-807.
Karamloo F. et al. "Prevention of allergy by a recombinant multi-allergen vaccine with reduced IgE binding and preserved T cell epitopes." Eur. J. Immunol. 2005; 35:3268-3276.
King T.P. "Insect venom allergens." Monogr. Allergy 1990; 28: 84-100.
King T.P., et al. "Structure and biology of stinging insect venom allergens." Int. Arch. Allergy Immunol. 2000; 123:99-106.
Korber B. et al. "Immunoinformatics comes of age," PLoS Computational Biology 2006; 2:0484-0492.
Larkin M.A. et al. "ClustalW and ClustalX version 2" Bioinformatics 2007; 23:2947-2948.
Larsen J.E.P. et al. "Improved method for predicting linear B cell epitopes," Immunome Research 2006; 2:2.
Lebecque S. et al. "Immunologic characterization of monoclonal antibodies that modulate human IgE binding to the major birch pollen allergen Bet v 1." J. Allergy Clin. Immunol. 1997; 99:374-384.
Littler et al., "Allergenic components of bald-faced hornet (V. maculate) venom" Toxicon. 1986; 24(7): 738.
Goujon et al., "A new bioinformatics analysis tools framework at EMBL-EBI," Nucleic Acids Research, 2010; 38(Web Server issue): W695-W699.
Mackenzie T. et al., "Clonal and Molecular Characterization of the Human IgE-Committed B Cell Subset," J. Exp. Med. 1989; 169: 407-430.

(56) References Cited

OTHER PUBLICATIONS

Mirza O. et al. "Dominant Epitopes and Allergic Cross-Reactivity : Complex Formation Between a Fab Fragment of a Monoclonal Murine IgG Antibody and the Major Allergen from Birch Pollen Bet v 1," J. Immunol. 2000; 165:331-338.

Morgulis A et al. "Database indexing for production MegaBLAST searches." Bioinformatics 2008;15:1757-1764.

Müller U. et al. "Successful immunotherapy with T-cell epitope peptides of bee venom phospholipase A2 induces specific T-cell anergy in patients allergic to bee venom." J. Allergy Clin. Immunol. 1998; 101:747-754.

Niederberger V. et al. "Vaccination with genetically engineered allergens prevents progression of allergic disease." Proc. Natl. Acad. Sci. USA 2004; 101:14677-14682.

Nielsen M. et al. "Quantitative predictions of peptide binding to any HLA-DR molecule of known sequence: NetMHCIIpan. NetMHCIIpan" PLoS Comput Biol. 2008;4(7):e1000107.

Nielsen M.. et al. "Prediction of MHC class II binding affinity using SMM-align, a novel stabilization matrix alignment method." BMC Bioinformatics. Jul. 4, 2007;8:238.

O'Hehir R.E. et al. "The Specificity and Regulation of T-Cell Responsiveness to Allergens." Ann. Rev. Immunol. 1991; 6:67-95.

Panjkovich A., et al., "Comparison of different melting temperature calculation methods for short DNA sequences." Bioinformatics 2005; 21:711-722.

Cloning and expression of Ves v 4

FIG. 2

Multiple alignment of protease protein sequences with Ves v 4

```
Ves v 4     ---MKLDNFFLILYVLLSIIKSNGTIDLNCGYTQKLKSDVNYCVYNPDFPNYYMGEHNCR 57
Magnvesin   ------------------------------------------------------------
Pol d 4     ------------------------------------------------------------
Api m 7     VVLVKKVKIVLLIFYGSIMFSMTQVNKEECDYYQNLNLGEIYYIYNPRYPLPYSGSK-CT 59
Bom p 4     ------------------------------------------------------------

Ves v 4     WSARSNTRIKLNCTVFDVPPSSNCSLDFMKVKVDDDIEYVFCGLNSFAVESIASKMTIKF 117
Magnvesin   -----------------------------MKVKVDD-IEYYFCGLNSFTVESIASKMTIKF 31
Pol d 4     -------------------------------------MN-------CGKIILLF 10
Api m 7     WTITSYHRINLKCSLVEFSENKNCNAG--SLTVKKNFANKYCGNITLNIESTSNKMTVIL 117
Bom p 4     ------------------------------------------------------------

Ves v 4     HSRYNTYGGKFRCNLRSVKEKCRCGWKNPSRIVGGVETGVNEYPMMAGI------IHLAT 171
Magnvesin   HSRYNTYGGKFRCILRVVKEECRCGWKNPSRIVGGVETGVNEYPMMAGI------VHLDT 85
Pol d 4     IT---IIG-----VAKSREENCKCGWDNPSRIVNGVETEINEFPMVARL------IYPSP 56
Api m 7     TPPGRFFCEVRPIKRVKDSTNCNCGWKNPSRIVGGTNTGINEFPMMAGI------KRTYE 171
Bom p 4     -------------------------------VVGGKPAKLGAWPWMVALGFHNYRQPKKS 29
                                           :*.*   : :. :* :. :

Ves v 4     RFLYCGATIITPQHVLTAAHCVARYKRILYI-LGVVVGEHNTWAINDTKATQLYLIDDII 230
Magnvesin   RFLYCGATIITPQHVLTAAHCVALYKKSLYI-LGVIVGEHNIRTINNTKTTRLYLIDDII 144
Pol d 4     -GMYCGGTIITPQHIVTAAHCLQKYKRTNYTGIHVVVGEHDYTTDTETNVTKRYTIAEVT 115
Api m 7     PGMICGATIISKRYVLTAAHCIIDEN---TTKLAIVVGEHDWSSKTETNATVLHSINKVI 228
Bom p 4     PEWKCGGSLRISRHVLTAAHCAIHRS-----LYVVRIADLNLKRDDDGAHPIQMGIESKL 84
                **.::   ::::***** .       : :.: :     :    . * .

Ves v 4     VHPNYRP------KLNDLAVIKLQKRLKYSMRIGPACLPFYYMQRN--FVDTVVTAVGWG 282
Magnvesin   VHPNYRP------KLNDLAVIKLQKRLEYSMRIGPACLPFYYTWRN--FTGTVVTAVGWG 196
Pol d 4     IHPNYNS------HNNDIAIVKTNERFEYSMKVGPVCLPFNYMTRN--LTNETVTALGWG 167
Api m 7     IHPKYDIIEKDDWQINDIALLKTEKDIKFGDKVGPACLPFQHFLDS--FAGSDVTVLGWG 286
Bom p 4     IHPDYVYS----EHHDDIAILKLEKDVSFSEYIRPICLPIEESLRNNNFIGYNPFVAGWG 140
             :**.*      : :*:*::* :: ..:. : * ***:    . :.   .***

Ves v 4     LTNFYGVKSEVLRKVDLHVVSMKKCVKYH--FLATPKQLCTFDMGKDACQFDSGGPILWQ 340
Magnvesin   HTNFYGIKSDVLRKVDLHVISMKECIKYH--FLATCKQLCTFDIGKDACQFDSGGPILWQ 254
Pol d 4     KLRYNGQNSKVLRKVDLHVITREQCETHYGAAIANANLLCTFDVGRDACQNDSGGPILWR 227
Api m 7     HTSFNGMLSHILQKTTLNMLTQVECYKYYG--NIMVNAMCAYAKGKDACQMDSGGPVLWQ 344
Bom p 4     RLRYKGPLSDALMEVQVPVVRNKVCKRAYSDVSDTVICAGYPKGRKDSCQGDSGGPLMIP 200
              : *  *. * :. : ::     *  :        :*;** *****::

Ves v 4     NPKSKRIFLLGVINYGRTCAD-EAPGVNLRVTSYLDFITRSTPGEIYCQAY 390
Magnvesin   NPRSNRVFLLGVINYGKTCAD-EAPGVNLRVTSYLDFIRRSTPEETYCQAY 304
Pol d 4     SPTTDNLILVGVVNFGRTCAD-DAPGGNARVTSFMEFIHNATIGETYCKAD 277
Api m 7     NPRTKRLVNIGIISWGAECG--KYPNGNTKVGSYIDWIVSQTPDAEYCVIE 393
Bom p 4     QEST--YYEIGVVSYGHECALPKYPGVYTRVTSYLDSFILPALKK------ 243
              . :      :*::..:*  *.  .*.   :* *::: :    :
```

\* = identical residues
: = strongly homologous residues
. = weakly homologous residues

FIG. 3

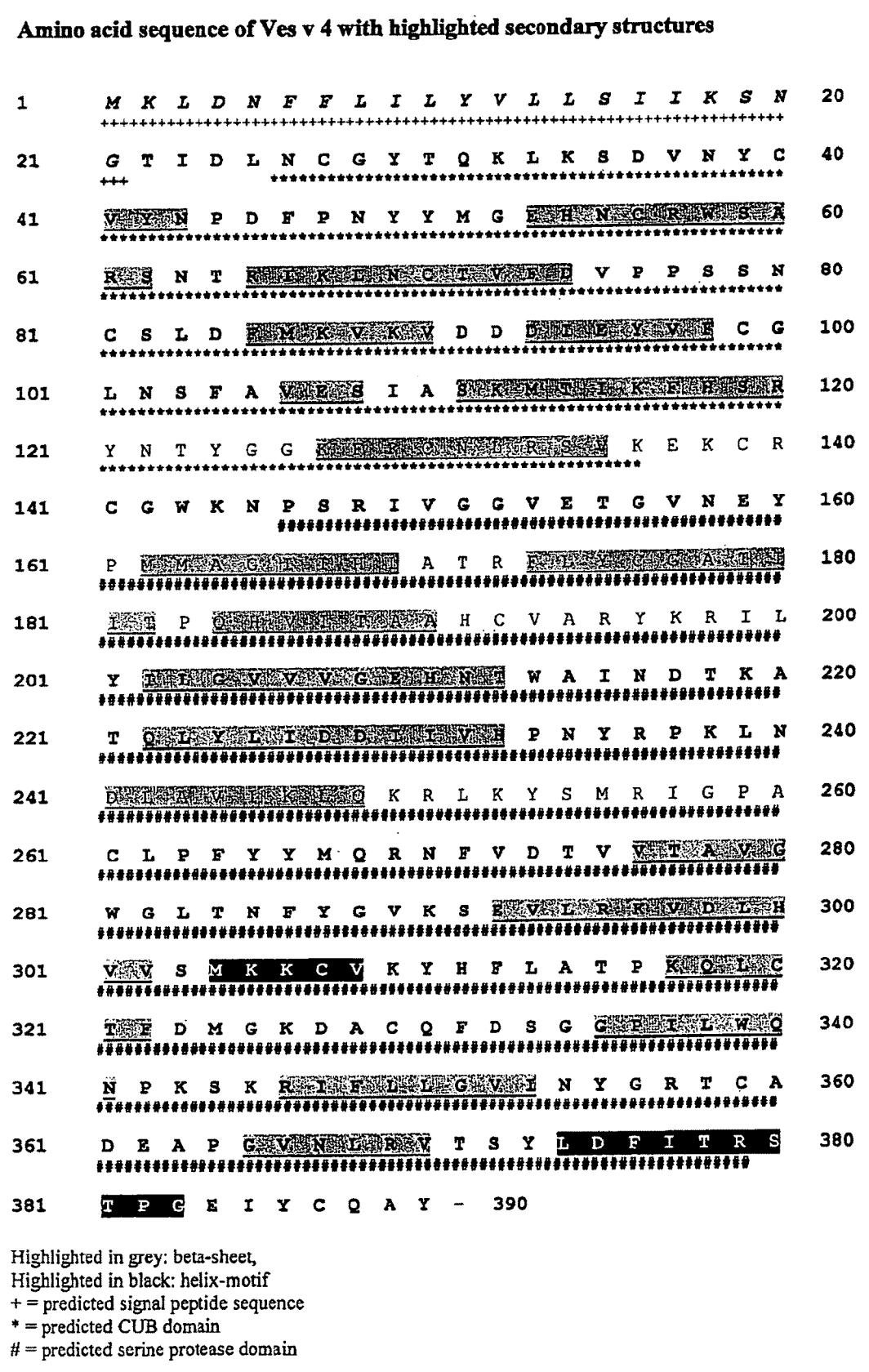

Amino acid sequence of Ves v 4 with highlighted secondary structures

```
1    M K L D N F F L I L Y V L L S I I K S N

Screening of patient sera with recombinant Ves v 4

Graphical overview of peptide fragments F1-F5 positions

Graphical overview of peptide fragments F6-F12 positions

Graphical overview of peptide fragments F13-25 positions

Southern Blot analysis of other insect species utilizing Ves v 4 probes

Fig. 11
Sequence data:

SEQ ID NO:1
(Nucleic acid sequence of Ves v 4)

<210> 1
<211> 1173
<212> DNA
<213> Vespula vulgaris

<400> 1

| | | | | | |
|---|---|---|---|---|---|
| atgaaattag | ataattttt | tttaatactt | tatgtgctac | taagcattat | aaaatccaat | 60 |
| ggtactatcg | atctcaattg | tggctacacc | caaaaattaa | aatcagatgt | taattattgc | 120 |
| gtgtataatc | ctgattttcc | gaattattac | atgggagaac | ataattgtcg | gtggagtgct | 180 |
| aggagcaata | ctcgaattaa | attgaattgc | acagttttcg | atgttcctcc | gagttcgaat | 240 |
| tgttcattgg | attttatgaa | agtcaaagtc | gacgatgaca | tcgagtacgt | tttctgtgga | 300 |
| ttaaattctt | ttgcagtgga | atcaatagca | tcgaaaatga | ctataaaatt | ccattcaaga | 360 |
| tacaatactt | atggaggcaa | atttcgatgt | aatctcagat | cagtcaaaga | gaaatgtaga | 420 |
| tgtggttgga | agaatccgtc | gagaatcgta | ggcggtgttg | aaacaggagt | gaatgaatat | 480 |
| cctatgatgg | ctggtataat | acatcttgca | acgcgttttc | tctattgcgg | tgcaactata | 540 |
| ataactccgc | aacatgtatt | aacggctgct | cattgcgttg | cgaggtataa | aaggatttta | 600 |
| tatattctag | gagttgttgt | tggagaacat | aatacatggg | caattaacga | tacaaaggca | 660 |
| actcaacttt | atcttattga | tgatataatc | gtacatccga | attataggcc | aaaattaaac | 720 |
| gatttagctg | ttataaaatt | gcagaagagg | ttaaaatatt | ctatgagaat | tggtccagct | 780 |
| tgtcttccgt | tctattacat | gcagcgaaac | tttgtagaca | ctgttgttac | agctgtagga | 840 |
| tggggtctta | cgaatttta | tggtgtcaag | tctgaagttt | tgagaaaagt | cgatttgcat | 900 |
| gtagtttcaa | tgaagaaatg | cgtcaagtat | cactttctgg | ctacacctaa | gcaactttgt | 960 |
| acattcgata | tgggaaagga | tgcttgccag | ttcgacagtg | gtggtccaat | tttatggcaa | 1020 |
| aatccaaaaa | gcaaacgtat | tttccttctt | ggagtcatca | attatggaag | aacatgtgcc | 1080 |
| gatgaagctc | ctggtgttaa | cttgagagtc | actagttatt | tagatttttat | tacaagatca | 1140 |
| acacctggag | aaatatattg | tcaggcgtat | taa | | | 1173 |

Fig. 12 A
SEQ ID NO:2
(Translated protein sequence of Ves v 4)

```
<210>  2
<211>  390
<212>  PRT
<213>  Vespula vulgaris
<400>  2
```

| Met | Lys | Leu | Asp | Asn | Phe | Phe | Leu | Ile | Leu | Tyr | Val | Leu | Leu | Ser | Ile |
|1|||| 5 |||||10|||||15||

Ile Lys Ser Asn Gly Thr Ile Asp Leu Asn Cys Gly Tyr Thr Gln Lys
              20              25              30

Leu Lys Ser Asp Val Asn Tyr Cys Val Tyr Asn Pro Asp Phe Pro Asn
          35             40               45

Tyr Tyr Met Gly Glu His Asn Cys Arg Trp Ser Ala Arg Ser Asn Thr
    50               55               60

Arg Ile Lys Leu Asn Cys Thr Val Phe Asp Val Pro Pro Ser Ser Asn
65               70              75             80

Cys Ser Leu Asp Phe Met Lys Val Lys Val Asp Asp Asp Ile Glu Tyr
             85              90            95

Val Phe Cys Gly Leu Asn Ser Phe Ala Val Glu Ser Ile Ala Ser Lys
          100           105          110

Met Thr Ile Lys Phe His Ser Arg Tyr Asn Thr Tyr Gly Gly Lys Phe
          115           120          125

Arg Cys Asn Leu Arg Ser Val Lys Glu Lys Cys Arg Cys Gly Trp Lys
    130             135            140

Asn Pro Ser Arg Ile Val Gly Gly Val Glu Thr Gly Val Asn Glu Tyr
145             150            155          160

Pro Met Met Ala Gly Ile Ile His Leu Ala Thr Arg Phe Leu Tyr Cys
          165           170          175

Gly Ala Thr Ile Ile Thr Pro Gln His Val Leu Thr Ala Ala His Cys
          180           185          190

Val Ala Arg Tyr Lys Arg Ile Leu Tyr Ile Leu Gly Val Val Val Gly
          195           200          205

Glu His Asn Thr Trp Ala Ile Asn Asp Thr Lys Ala Thr Gln Leu Tyr
          210           215          220

Leu Ile Asp Asp Ile Ile Val His Pro Asn Tyr Arg Pro Lys Leu Asn
225             230            235          240

Asp Leu Ala Val Ile Lys Leu Gln Lys Arg Leu Lys Tyr Ser Met Arg
          245           250          255

Ile Gly Pro Ala Cys Leu Pro Phe Tyr Tyr Met Gln Arg Asn Phe Val
          260           265          270

Asp Thr Val Val Thr Ala Val Gly Trp Gly Leu Thr Asn Phe Tyr Gly

Fig. 12 B

```
              275                    280                    285
Val Lys Ser Glu Val Leu Arg Lys Val Asp Leu His Val Val Ser Met
    290                 295                 300
Lys Lys Cys Val Lys Tyr His Phe Leu Ala Thr Pro Lys Gln Leu Cys
305                 310                 315                 320
Thr Phe Asp Met Gly Lys Asp Ala Cys Gln Phe Asp Ser Gly Gly Pro
                325                 330                 335
Ile Leu Trp Gln Asn Pro Lys Ser Lys Arg Ile Phe Leu Leu Gly Val
                340                 345                 350
Ile Asn Tyr Gly Arg Thr Cys Ala Asp Glu Ala Pro Gly Val Asn Leu
                355                 360                 365
Arg Val Thr Ser Tyr Leu Asp Phe Ile Thr Arg Ser Thr Pro Gly Glu
    370                 375                 380
Ile Tyr Cys Gln Ala Tyr
385                 390
```

CLONING AND RECOMBINANT PRODUCTIONS OF *VESPULA* VENOM PROTEASE AND METHODS OF USE THEREOF

This application is a §371 US National Entry of International Application No. PCT/EP2010/001329, filed Mar. 3, 2010, which is incorporated herein by reference and which claims the benefit of European Application No. 09003033.9, filed Mar. 3, 2009.

The present invention relates to nucleic acids encoding a novel *Vespula* venom protease or fragments thereof, recombinant vectors comprising such nucleic acids, and host cells containing the recombinant vectors. The invention is further directed to expression of such nucleic acids to produce a recombinant *Vespula* venom protease, or recombinant fragments thereof, or synthetic peptides thereof. Such a protease or fragments thereof or synthetic peptides thereof are useful for diagnosis of insect venom allergy and for therapeutic treatment of insect venom allergy.

BACKGROUND OF THE INVENTION

Immunoglobulin E (IgE)-mediated insect sting allergy to Hymenoptera is of common occurrence. Hymenoptera stings are classified into normal local reactions, large local reactions, systemic anaphylactic reactions, systemic toxic reactions, and unusual reactions. The most frequent clinical patterns are large local and systemic anaphylactic reactions. Based on the results of four studies, the prevalence of large local sting reactions ranges from 2.4% and 26.4% (for a review, see Biló et al 2005). In children the prevalence yielded by one study is 19%. Nine epidemiologic studies report a prevalence of self-reported systemic anaphylactic sting reactions between 0.3% and 7.5% (for a review, see Biló et al 2005). For most venom-allergic patients an anaphylactic reaction after a sting is a very traumatic event resulting in an altered health-related quality of life. In some instances the anaphylactic reaction may cause death, and this fatal outcome can occur as the first manifestation after a sting (Barnard 1973). Risk factors influencing the outcome of an anaphylactic reaction include the time interval between stings, the number of stings, the severity of the preceding reaction, age, cardiovascular diseases and drug intake, insect type, elevated serum tryptase, and mastocytosis.

Hymenoptera include the family Apidae consisting of the genera *Apis* (including the species *Apis mellifera*, honeybee) and *Bombus* (bumblebees), and the family Vespidae (vespids) consisting of the Vespinae and Polistinae subfamilies. The Vespinae subfamily includes the three genera *Vespula* (called wasps in Europe, yellow jackets in the USA), *Dolichovespula* (called hornets in the USA) and *Vespa* (called hornets in Europe and the USA). In the USA there are many species of *Vespula*, *Dolichovespula* and *Polistes* (called paper wasps in Europe and the USA) (King 1994). Vespine wasps are generally considered to be the most common source of stings, due to their abundance, aggressiveness and relatively large colony size (up to several thousand workers) of some species. In areas with mild winters, including Florida, California and Hawaii multiple queens may inhabit the same nest and produce enormous perennial colonies with a high potential for mass stinging (Greene and Breitsch 2005). Polistine wasps have small colonies of usually no more than a few dozen workers, but their nests can be extremely abundant around human habitations. The most pestiferous species is the recently arrived *Polistis dominulus*, an invasive European wasp (Greene and Breitsch 2005). Although honeybees are often invoked as a sting hazard, accidental disturbance of feral colonies in the US was rare until recently, because nests were typically located within tree cavities or structural voids. The arrival of Africanized bees (*Apis mellifera scutellata*) in 1990 markedly increased the stinging risk in several southwestern states, as this subspecies has an extremely low defensive response threshold and is capable of some of the most severe attacks known for any social insect (Greene and Breitsch 2005).

In Europe *Vespula* species *V. vulgaris* and *V. germanica* are dominating. In the genus *Dolichovespula* the most common species in Europe are *D. media*, *D. saxonia* and *D. sylvestris* and in the genus *Vespa*, *Vespa crabro* (European hornet) is the most prevalent in Europe. Among Polistinae (called paper wasps in Europe and the USA), *Polistes gallicus*, *P. nimpha* and *P. dominulus* are widespread especially in the Mediterranean area. In central and northern Europe vespid (mainly *Vespula* spp.) and honeybee stings are the most prevalent, whereas in the Mediterranean area stings from *Polistes* and *Vespula* are more frequent than honeybee stings, bumblebee stings are rare throughout Europe and more of an occupational hazard (Biló et al 2005).

The symptoms of IgE-mediated (type I) sting allergic reactions are due to release of mediators (e.g. histamine) resulting from cross-linking of effector cell-bound IgE antibodies by venom allergens. The symptoms can be suppressed by various pharmacologic treatments, but allergen-specific immunotherapy (SIT) represents the only curative approach. A rise in allergen-blocking IgG antibodies, particularly of the IgG4 class (Wetterwald et al 1985), a reduction in the number of mast cells and eosinophils, and a decreased release of mediators (Varney et al 1993) were found to be associated with successful SIT. Based on these observations, determination of the serum levels of allergen-specific IgE and IgG4 antibodies is useful to describe the immune status of an allergic patient.

In vitro measurement of specific serum IgE antibodies can be performed by the radio-allergosorbent test (RAST), various enzyme-linked immunosorbent assays (ELISA) and other IgE-binding techniques such as immunoelectrophoresis, immunoblot, immunodotblotting, bead array technology and various fluid phase systems. The analytes can also be allergen-specific antibodies of the IgG4 or other IgG subclasses. As an alternative to the above listed assay systems, basophil cells derived from patients or from basophil cell lines such as the KU812 have been used for the in vitro measurement of allergen-specific IgE antibodies in serum by in vitro mediator release assays (MRA). Furthermore, in vivo tests for diagnosis of hymenoptera venom allergy are performed by skin prick or intradermal testing. Such tests are well known in the art (Biló et al 2005).

Composition of Vespid Venoms

Knowledge of the composition of venoms and structural as well as immunological features of individual venom allergens is a prerequisite for the accurate diagnosis and treatment of insect venom allergy. Hymenoptera venoms contain a number of toxins, enzymes, and biologically active peptides. Since it was easy to obtain sufficient quantities of material, honeybee venom has been well studied. Honeybee venom contains at least 18 active substances. Many of the proteins and polypeptides in honeybee venom have been identified as hypersensitizing agents including phospholipase A2 (Api m 1), hyaluronidase (Api m 2), acid phosphatase (Api m 3), melittin (Api m 4), dipeptidylpeptidase (Api m 5; allergen C), Api m 6 polypeptides (4 isoforms), a 39 kDa protease (Api m 7), and a 70 kDa protease (Biló et al 2005; Winningham et al 2004, Blank et al 2008. Vespid venoms (venoms of the Vespidae family) are also complex mixtures of toxins, enzymes including phospholipases, hyaluronidases and proteases, and biologically active peptides. These venom components can act on the cardiovascular system, nervous system and immunological system of mammalians. Antikoagulant effects of vespid venom obtained from a hornet species (*Vespa orientalis*) was attributed to the proteolytic degradation of coagulation factors. The purified Protease migrated under reducing conditions as a double band (42 kDa and 44 kDa) on sodium dodecyl sulfate polyacrylamide gel electrophoresis (SDS-PAGE) (Haim et al 1999). Potential allergenic properties of this enzyme (or enzymes) have not been determined.

Another anticoagulant protease has been purified from the venom of a different hornet species (*Vespa magnifica*) (Han et al 2008). This protein, named magnvesin, contains serine protease-like avitivity and inhibits blood coagulation. The cDNA of magnvesin cloned from the venom sac cDNA library of *Vespa magnifica* (GenBank accession EU267370) encodes a protein precursor of 305 amino acids and a mature protease of 242 amino acids with a molecular weight of 27.4 kDa (Han et al 2008). Potential allergenic properties of this enzyme have not been determined.

Proteases have been identified also in the venom of *Polistis* species. A cDNA cloned from the venom sac cDNA library of *Polistis dominulus* (GenBank accession AY285998) encodes a protease of 244 amino acids (Winningham et al 2004). This protease contains 6 potential N-linked glycosylation sites, 4 of which appear to be glycosylated in the natural molecule. Due to its IgE binding activity the protease has been assigned the name Pol d 4 by the IUIS Allergen Nomenclature Subcommittee (Winningham et al 2004). Another protease prepared by benzamidine affinity chromatography from *Polistis exclamans*, has been reported to migrate in SDS-PAGE with the phospholipase as a protease from *Polistis gallicus* (Winningham et al 2004), but for none of these proteases a molecular weight or sequence information is provided by the authors. All three proteases are claimed to be highly cross-reactive, although the identity of the proteases from *Polistis exclamans* and *Polistis gallicus* remains to be elucidated.

An elastase-like protein was purified from the venom of the solitary spider wasp *Cyphonyx dorsalis* of the family Pompilidae which is part of the Vespoidea superfamily (Yamamoto at al 2007). The cDNA cloned from total RNA of a whole body (GenBank accession AB264172) encodes a protein of 256 amino acids with a calculated molecular weight of 25.7 kDa (Yamamoto et al 2007). The result of a homology search showed a 30.1% homology with the elastase-tike serine proteinase from the red fire ant *Solenopsis invicta*. Potential allergenic properties of this enzyme have not been determined.

A protein (Vn50) isolated from the venom of the endoparasitoid wasp *Cotesia rubecula* has been shown to be homologous to serine proteinase homologs (Asgari et al 2003). The cDNA cloned from total RNA from the venom gland of *Cotesia rubecula* encodes a protein of 388 amino acids. Vn50 contains two structural domains, a carboxy-terminal serine proteinase domain and an amino-terminal "clip" domain. However, the serine proteinase domain is not functional since it lacks a serine residue at the conserved site (Asgari et al 2003). Potential allergenic properties of this enzyme analog have not been determined.

Although in Europe *Vespula* species (*V. vulgaris* and *V. germanica*) are dominating, only few *Vespula* proteins and polypeptides have been identified as allergens so far including those in the venom of *Vespula vulgaris*, Ves v 1 (phospholipase A1), Ves v 2 (Hyaluronidase) and Ves v 5 (antigen 5) (for a review, see Biló et al 2005). The presence of proteases in the venom of *Vespula* species has not been reported and according to several publications there is no evidence for the presence of significant amounts of proteases in these venoms (Winningham et al 2004; King and Spangfort 2000; Hoffman 1985). Considering the complex venom composition of honeybees, however, the venom of *Vespula* species is likely to contain more than three allergens. Therefore, there is a need in the art to for more information about allergens in the venom of *Vespula* species to optimize accurate diagnosis and treatment of venom allergy caused by these species.

B and T Cell Epitopes

In order to fully address the basis for allergic response to *Vespula* venom allergens and the molecular mechanism of allergen-based immunotherapies, there is a particular need in the art to delineate B and helper T cell epitopes of *Vespula* venom allergens. Antibody responses to a protein require the collaboration of T helper and B lymphocytes and antigen presenting cells (APC). T helper cells are activated when their T cell receptor binds to complexes of antigenic peptide-MHC class II molecule on the surface of APC. On the basis of their patterns of lymphokine production, T helper cells are divided into two groups: TH1 cells producing IL-2 and IFN-γ, and TH2 cells producing IL-4 and IL-5. These lymphokines in turn influence antigen-activated B cells to differentiate and proliferate into plasma cells secreting antibodies of different isotypes. IL-4 is one lymphokine known to influence IgE synthesis (Finkelman et al 1990).

B cell epitopes of proteinaceous allergens can include native protein structures (conformational or discontinuous or topographic epitopes), linear peptides (linear epitopes) and carbohydrates. The conformational type consists of amino acid residues which are spatially adjacent but may or may not be sequentially adjacent. The vast majority of IgE epitopes has been reported to be of the conformational type (King 1990). The linear type consists of only sequentially adjacent residues. However, even linear B cell epitopes are often conformation-dependent, and antibody-antigen interactions are improved when the epitope is displayed in the context of the folded protein. It is believed that the entire accessible surface of a protein molecule can be recognized as epitopes by the antigen receptor of B cells, although all epitopes are not necessarily recognized with equal likelihood (Benjamin et al 1984). Programs have been developed for the prediction of both linear and conformational B cell epitopes (Zhang et al 2008). For example, DiscoTope is a method for discontinuous epitope prediction that uses protein 3D structural data as input. It is based on amino acid statistics, spatial information and surface accessibility for a set of discontinuous epitopes determined by X-ray crystallography of antibody-proteinaceous antigen-complexes.

T cell epitopes consist of only the linear type since they are peptides that have been processed in the lysosomes of APC by proteases. Analysis of naturally processed antigenic peptides bound to MHC class II molecules indicates that their size ranges typically from about 13 to 25 amino acid residues, but analysis of synthetic peptide-MHC class II molecule complexes for their T cell proliferative response suggests a minimal size of about 9 amino acid residues (Rudensky et al 1991, Wang at al 2008). T cell epitopes are distributed throughout the entire protein molecule, and they may function as major or minor determinants depending on the MHC haplotype of the immunized host (O'Hehir 1991). MHC proteins are highly polymorphic and each binds to a limited set of peptides. Thus, the particular combination of MHC alleles present in a host limits the range of potential epitopes that are recognized.

Because of the central role of TH2 cells in determining the isotype switch event of B cells, the T cell epitopes of several allergens have been mapped (O'Hehir 1991). However, defining epitope sequence specificity for a particular host including cleavage of the polypeptide by the proteasome, transport of peptides into the endoplasmatic reticulum by the transporter associated with processing (TAP) and binding to MHC molecules poses serious problems. Therefore, an abundance of methods has been developed for the prediction of T cell epitopes (see, e.g., Zhang et al 2008; Korber at 2006). The MHC class II binding prediction provided by a publication in 2008 in Nucleic Acid Res. (Zhang et al) includes 4 methods, ARB, SMM_align, the method of Sturniolo which is also the basis of TEPITOPE, and a consensus approach, all of which have been identified as top performing ones.

In order to avoid undesirable systemic reactions on specific immunotherapy with natural allergens, there has been continued interest in the development of modified allergens with reduced allergenic activities for immunotherapy. In one approach T cell epitopes are used to modulate allergen-specific immune responses. It has been observed in vivo in mice for the allergen Fel d 1 (cat hair), Der p 1 (acarian: *Dematophagoides pterissimus*) and Bet v 1 (birch pollen) that the nasal, oral or subcutaneous administration of peptides carrying T cell epitopes of these allergens inhibits the activation of the specific T lymphocytes (Briner et al 1993; Hoyne et al 1993; Bauer et al 1997). Based on these results allergen peptide fragments capable of stimulating T lymphocytes in allergic patients were evaluated in clinical studies. In the case of the major honeybee venom allergen Api m 1 fragments 50-69 and 83-97 have been described as being active during a study comprising a single patient (Dhillon et al. 1992). In a study comprising forty patients (Carballido et al 1993) Api m 1 fragments 45-62, 81-92 and 113-124 proved to be active. However, these three fragments proved to be T cell epitopes for only 25 to 45% of the patients, pointing to the existence of other epitopes. Nevertheless, the three peptides have been used successfully for desentization of five allergic patients whose T lymphocytes proliferated in the presence of these peptides (Müller et al 1998). No serious systemic effect was observed and the patients became tolerant to honeybee stings. This demonstrates the benefit of using peptides for desensitization. Therefore, there is a need in the field to identify peptide fragments of allergens in vespid venoms capable of stimulating T lymphocytes in allergic patients, and in particular from allergens in the venom of *Vespula* species.

In another approach, B cell epitopes of allergens are modified to decrease the risk of potential systemic reactions. The aim of such allergen modification is to decrease the allergenicity while retaining its immunogenicity. Since allergenicity depends on the interaction of a multivalent allergen with basophil- or mast cell-bound IgE antibodies, allergenicity can be reduced by decreasing the density of B cell epitopes. One approach is by partial or complete denaturation of allergens on chemical modification because the vast majority of B cell epitopes are of the discontinuous type, being dependent on the native conformation of proteins. However, there are serious limitations to the use of such molecules. While linear T cell epitopes are preserved, the surface structure is not maintained and, thereby, the capacity of such molecules to stimulate an allergen-specific non IgE antibody response is severely limited. Similar considerations apply to an approach in which the accessibility of B cell epitopes is reduced by polymerization on formaldehyde or glutaraldehyde treatment or by attachment of nonimmunogenic polymers. Usually near-complete loss of the discontinuous B cell epitopes occurs when allergens are modified with >100-fold reduction in allergenicity.

Using recombinant DNA technology well defined allergens can be produced which allow the determination of their three-dimensional structure and site-directed modifications of their surface structure. Unfortunately, however, knowledge of IgE-specific B cell epitopes is scarce and useful tools for reliable identification of such epitopes are not available. While several IgE epitopes could be determined by mapping with synthetic overlapping peptides synthesized according to the allergen amino acid sequence, many relevant IgE epitopes could not be identified because peptides frequently fail to display conformations mimicking discontinuous epitopes. There is no doubt that naturally occurring IgE antibodies represent ideal tools for structural analyses of IgE epitopes. However, the number of monoclonal allergen-specific IgE antibodies isolated from blood lymphocytes of allergic patients so far is extremely limited. In an alternative approach, animal derived monoclonal allergen-specific antibodies can be useful to identify IgE epitopes. For example, from a panel of mouse monoclonal antibodies that effectively inhibited binding of birch pollen allergen Bet v 1 to specific IgE, several monoclonal antibodies identified a continuous epitope within an exposed surface area of Bet v 1 that could be part of a discontinuous IgE epitope (Lebecque et al 1997) Provided such antibodies bind to Bet v 1 with high affinity, they represent useful tools for further structural analyses by X-ray diffraction of crystals obtained from allergen-antibody complexes. Although the surface area recognized by animal-derived allergen-specific antibodies may not be identical with that recognized by human IgE antibodies, both areas are closely related as indicated by the inhibition experiments. Therefore, structural information obtained from the analysis of such allergen-antibody complexes provide a valuable basis for the modification of IgE epotopes by site-directed mutagenesis. One problem of this approach, however, is the need of a panel of high affinity antibodies with different epitope specificities for each allergen to allow for a detailed analysis of the total spectrum of potential IgE epitopes. Assuming that a B cell epitope takes up an area of approximately 900 $A^2$, the vast majority of allergens is likely to display more than one IgE epitope, in the case of allergens with a molecular weight of >40 kDa most likely several IgE epitopes. Therefore, there is a need in the field to develop high affinity allergen-specific antibody panels that are capable of inhibiting IgE binding.

Another serious problem associated with the design of hypoallergenic molecules for an improved immunotherapy is the lack of understanding of the immune response that guarantees a lasting protection after specific immunotherapy. The aim to decrease the allergenicity of a given allergen while retaining its immunogenicity is widely accepted, but the term immunogenicity remains to be defined. Evaluation of modified recombinant allergens with a strongly reduced IgE reactivity that display the full spectrum of linear T cell epitopes but a different surface structure as compared to the corresponding natural allergen, have demonstrated that such molecules are capable of reducing specific IgE development towards the native allergen (Niederberger et al 2004; Karamloo et al 2005). However, a long lasting protective effect after treatment with these molecules has not been demonstrated. Apparently, the capacity of recombinant allergens to stimulate a long lasting protective allergen-specific non IgE antibody response requires also a surface structure that is closely related to that of the corresponding natural allergen. Since disruption of IgE epitopes is associated with a significant alteration of the surface structure, there is a need in the field to identify those surface structures of allergens that mediate an appropriate non-IgE response for a long lasting protection. There is a particular need in the field to identify those surface structures of allergens in the venom of *Vespula* species that mediate an appropriate non-IgE response for a long lasting protection.

There is a further need to determine whether there is cross reaction of the B and T cell epitopes of vespid venom allergens with other environmental and/or homologous proteins. Thus, there is a need to determine whether vespid venom allergens share partial identity with environmental and/or homologous proteins, and more importantly, to obtain the sequences of the regions of the partial identity, in particular the specific amino acid sequence of partial identity. There is a further need to determine the level of cross reactivity of vespid allergens with other proteins at the B cell and T cell level, the relevance of this cross reactivity, and whether such cross reactivity is pathological, i.e., involved in or responsible for allergy, or beneficial, i.e., inhibitory of allergy.

SUMMARY OF THE INVENTION

The invention is based, in part, on the discovery of a novel *Vespula* venom protease, which has been named Ves v 4. This protease or fragments, derivatives or analogs thereof can be used, e.g., for diagnosis of insect venom allergy and for therapeutic treatment of insect venom allergy.

The present invention provides a nucleic acid molecule encoding a novel *Vespula* venom protease, fragments thereof, or derivatives or analogs thereof. In a specific embodiment, nucleic acid molecules of the invention encode polypeptide fragments containing one or more B cell epitopes of the *Vespula* venom protease. In another specific embodiment, nucleic acid molecules of the invention encode T cell epitope-containing polypeptide fragments of the *Vespula* venom protease capable of stimulating T cells of subjects allergic to Ves v 4. In another specific embodiment, nucleic acid molecules of the invention encode polypeptide fragments containing one or more T cell epitopes and one or more B cell epitopes of the *Vespula* venom protease. In a preferred embodiment, the polypeptide fragments are between 20-150 amino acids in length.

The present invention further provides methods for isolating nucleic acid molecules from any species of the family Vespidae which are hybridizable under moderate or high stringency conditions to a nucleic acid having the nucleotide sequence shown in SEQ ID NO:1.

In one embodiment the invention provides a nucleic acid molecule comprising the nucleotide sequence as shown in SEQ ID NO: 1 and nucleic acids hybridizable to the nucleotide sequence as shown in SEQ ID NO: 1 under moderate or high stringency conditions, and fragments, derivatives, mutants and analogs thereof.

In one embodiment the invention provides a nucleic acid molecule comprising the nucleotide sequence as shown in SEQ ID NO: 1 and nucleic acids that are at least 70% identical, preferably more than 80% identical and more preferably more than 90% identical to the nucleotide sequence as shown in SEQ ID NO: 1, and fragments, derivatives, mutants and analogs thereof.

In one embodiment the invention provides a nucleic acid molecule comprising the nucleotide sequence as shown in SEQ ID NO: 1 and nucleic acids hybridizable to the nucleotide sequence as shown in SEQ ID NO: 1 under moderate or high stringency conditions, and nucleic acids that are at least 70% identical, preferably more than 80% identical and more preferably more than 90% identical to the nucleotide sequence as shown in SEQ ID NO: 1, and fragments, derivatives, mutants and analogs thereof.

The present invention further provides polypeptides encoded by the nucleic acids of the invention wherein the polypeptides comprise an amino acid sequence that is at least 70% identical, and more preferably 90% identical, to the amino acid sequence of SEQ ID NO:2.

In a further embodiment, the polypeptide of the invention comprises the amino acid sequence as shown in SEQ ID NO:2 and polypeptides that are at least 70% identical, preferably more than 80% identical, more preferably more than 90% identical, more preferably more than 95% identical and most preferably more than 99% identical to the amino sequence as shown in SEQ ID NO: 2, and fragments, derivatives and analogs thereof.

In a specific embodiment, the invention provides polypeptide fragments of the Ves v 4 polypeptides of the invention, containing one or more B cell epitopes of the *Vespula* venom protease. In another specific embodiment, the invention provides T cell epitope-containing polypeptide fragments of the *Vespula* venom protease capable of stimulating T cells of subjects allergic to Ves v 4. In another specific embodiment, the invention provides polypeptide fragments containing one or more T cell epitopes and one or more B cell epitopes of the *Vespula* venom protease. In a preferred embodiment, the polypeptide fragments are between 20-150 amino acids in length. In still another specific embodiment, the invention provides T cell epitope-containing peptides of at least 9 amino acids corresponding to a consecutive amino acid sequence within the *Vespula* venom protease wherein the peptides are capable of stimulating T cells of subjects allergic to Ves v 4. Such peptides of the invention are preferably immunomodulatory peptides as well in that they induce T cell anergy when administered to a subject allergic to the *Vespula* venom protease, or otherwise affect the immune response of the subject.

In another embodiment, the present invention provides methods for identification and modification via site-directed mutagenesis of those amino acid residues involved in the interaction of the polypeptides of this invention with human IgE and IgG antibodies, including IgG4 antibodies. In specific embodiments, the present invention provides methods for decreasing the allergenicity (IgE reactivity) of the polypeptides of this invention in a structure-based approach via mutagenesis of IgE epitopes with limited impairment of the residual surface structure important for IgG and IgG, including IgG4, immunological responses. In a preferred embodiment, the allergenicity of the polypeptides of this invention is reduced by at least 50% while at least 50% of IgG epitopes, including IgG4 epitopes, are maintained. In a more preferred embodiment, the allergenicity of the polypeptides of this invention is reduced by at least 70% while at least 50% of IgG epitopes, including IgG4 epitopes, are maintained. In a most preferred embodiment allergenicity is reduced by at least 90% while at least 50% of IgG epitopes, including IgG4 epitopes, are maintained.

In another embodiment, the present invention provides methods for modification of N-glycosylation of the polypeptides of this invention. In a specific embodiment, the present invention provides polypeptides comprising N-linked glycosides without detectable core α(1,3)-fucosylation. In another specific embodiment, the present invention provides polypeptides comprising mutated N-glycosylation sites instead of N-glycosylation sites with Asn-Xaa-Ser/Thr sequences. In still another specific embodiment, the present invention provides polypeptides lacking N-glycosylation.

The present invention further provides expression vectors comprising the nucleic acids of the invention operationally associated with a promoter. The present invention also provides methods for producing the polypeptides encoded by the nucleic acids of the invention. In particular, the present invention provides for culturing cells transformed with an expression vector of the invention so that the *Vespula* venom protease, fragments thereof, or derivatives or analogs thereof are expressed by the cells, and recovering these polypeptides so expressed from the culture.

In a further embodiment, the present invention features a pharmaceutical composition that includes the Ves v 4 polypeptides of the invention and a pharmaceutically acceptable carrier. In some embodiments, the pharmaceutical composition includes an additional polypeptide, e.g., a second, third, fourth, or more *Vespula* venom polypeptide or polypeptides. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In a further embodiment, the present invention features a pharmaceutical composition comprising Ves v 4 polypeptide fragments of the invention, preferably between 20-150 amino acids in length, wherein each fragment contains one or more B cell epitopes and one or more T cell epitopes, and a pharmaceutically acceptable carrier. In a preferred embodiment, the composition comprises a set of polypeptide fragments that map the total length of the Ves v 4 polypeptide. In some embodiments, the pharmaceutical composition includes polypeptide fragments derived from an additional polypeptide, e.g., a second, third, fourth, or more *Vespula* venom polypeptide or polypeptides. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In a further embodiment, the present invention features a pharmaceutical composition comprising T cell epitope containing peptides of at least 9 amino acids corresponding to a consecutive amino acid sequence within the *Vespula* venom protease (Ves v 4) wherein the peptides are capable of stimulating T cells of subjects allergic to Ves v 4. In a preferred embodiment, the composition comprises a set of T cell epitope-containing peptides capable of stimulating T cells of the great majority of subjects allergic to Ves v 4. In some embodiments, the pharmaceutical composition includes T cell epitope-containing peptides of at least 9 amino acids corresponding to a consecutive amino acid sequence within an additional polypeptide, e.g., a second, third, fourth, or more *Vespula* venom polypeptide or polypeptides. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In another aspect, the present invention features a method of modulating an immune response. The method includes administering a Ves v 4 polypeptide of the invention, or a set of polypeptide fragments thereof wherein each of the polypeptide fragments contains one or more T cell epitopes and one or more B cell epitopes of the *Vespula* venom protease, to a subject in need thereof in an amount sufficient to inhibit an immune reaction by the subject against the Ves v 4 polypeptide. If desired, one or more additional *Vespula* venom polypeptides, or sets of fragments thereof, may also be administered to the subject. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In another aspect, the present invention features a method of modulating an immune response by administering T cell epitope-containing peptides of at least 9 amino acids corresponding to a consecutive amino acid sequence within the *Vespula* venom protease (Ves v 4), to a subject in need thereof in an amount sufficient to inhibit an immune reaction by the subject against the Ves v 4 polypeptide. If desired, T cell epitope-containing peptides of at least 9 amino acids corresponding to a consecutive amino acid sequence within one or more additional *Vespula* venom polypeptides may also be administered to the subject. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In a further aspect, the present invention provides methods for identifying an individual at risk for *Vespula* venom hypersensitivity. One method includes administering to the individual the Ves v 4 polypeptide, or a set of polypeptide fragments thereof, and measuring an immune response raised against the polypeptide or fragments thereof. A detectable immune response indicates that the individual is at risk for *Vespula* venom hypersensitivity. In preferred embodiments, the Ves v 4 polypeptide, or a set of polypeptide fragments thereof, is administered intradermally. Another method includes in vitro measurement of Ves v 4-specific serum IgE antibodies by a variety of techniques, e.g., radio-allergosorbent test (RAST), enzyme-linked immunosorbent assays (ELISA), immunoelectrophoresis, immunoblot, immunodotblotting, bead array technology, fluid phase systems, and by in vitro mediator release assays (MRA).

In a further aspect, the present invention provides methods for evaluating the success of immunotherapeutical treatment of a subject allergic to Ves v 4 by in vitro measurement of the ratio of Ves v 4-specific serum IgE and IgG4 antibodies by a variety of techniques, e.g., radio-allergosorbent test (RAST), enzyme-linked immunosorbent assays (ELISA), immunoelectrophoresis, immunoblot, immunodotblotting, bead array technology, fluid phase systems, and by in vitro mediator release assays (MRA).

Also provided by the invention is a kit that includes, in one or more containers, a Ves v 4 polypeptide of the invention, or polypeptide fragments thereof, one or more anti-Ves v 4 antibodies (e.g., monoclonal or polyclonal), or a combination of these polypeptides, polypeptide fragments, and antibodies.

Unless otherwise defined, all technical and scientific terms used herein have the same meaning as commonly understood by one of ordinary skill in the art to which this invention belongs. Although methods and materials similar or equivalent to those described herein can be used in practicing or testing the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE FIGURES AND TABLES

FIG. 2 shows a multiple alignment of the protease sequences of Magnvesin, Pol d 4, Api m 7 and Bom p 4 with Ves v 4, as explained in Example 5.

FIG. 3 shows the amino acid sequence of Ves v 4 with highlighted secondary structures as predicted in Example 6.

FIG. 11 shows the 1173-nucleotide sequence of the cDNA encoding the *Vespula vulgaris* Ves v 4 venom protease.

FIGS. 12A and 12B show the 390-amino acid sequence of the *Vespula vulgaris* Ves v 4 polypeptide translated from the cDNA sequence shown in FIG. 11.

Figure 5:
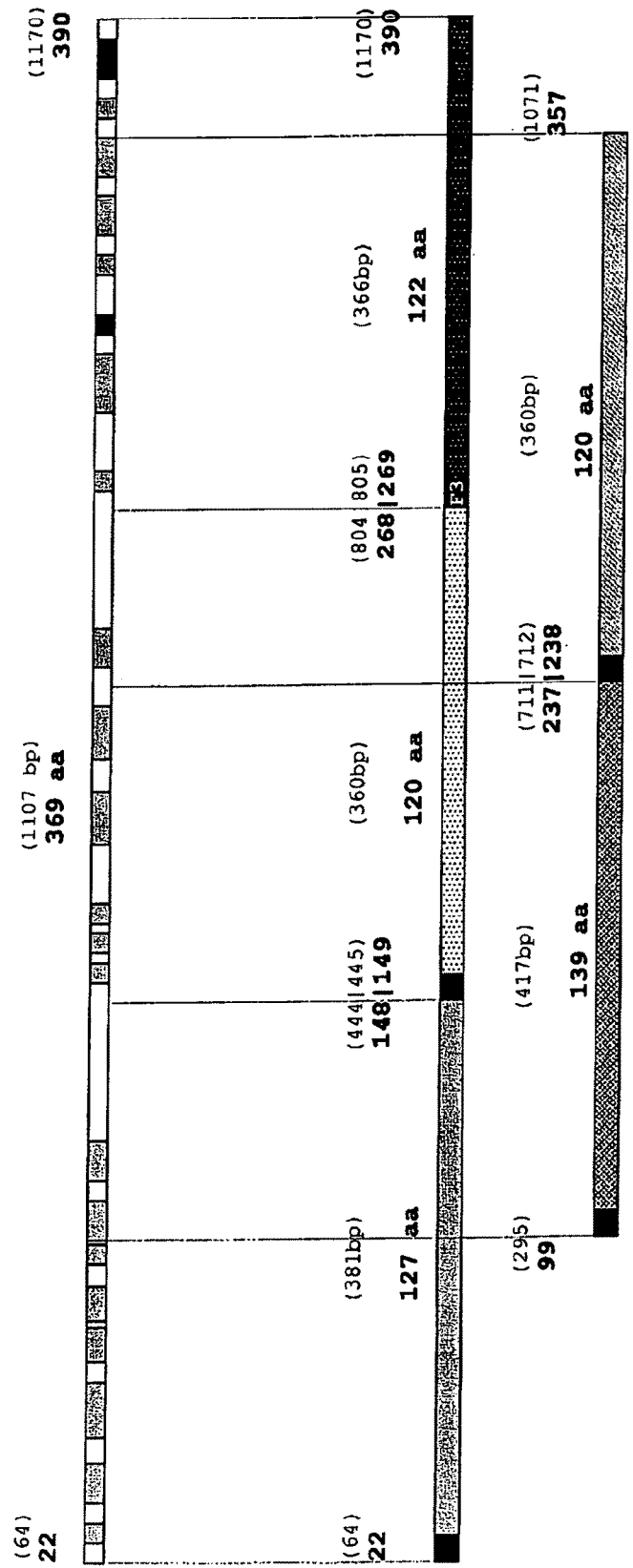
FIG. 5 is a graphical overview of peptide fragments F1-F5 of Ves v 4 as explained in Example 7. The selection of fragments and position in the Ves v 4 molecule with the respective fragment length is given in Table 1.
Figure 6:
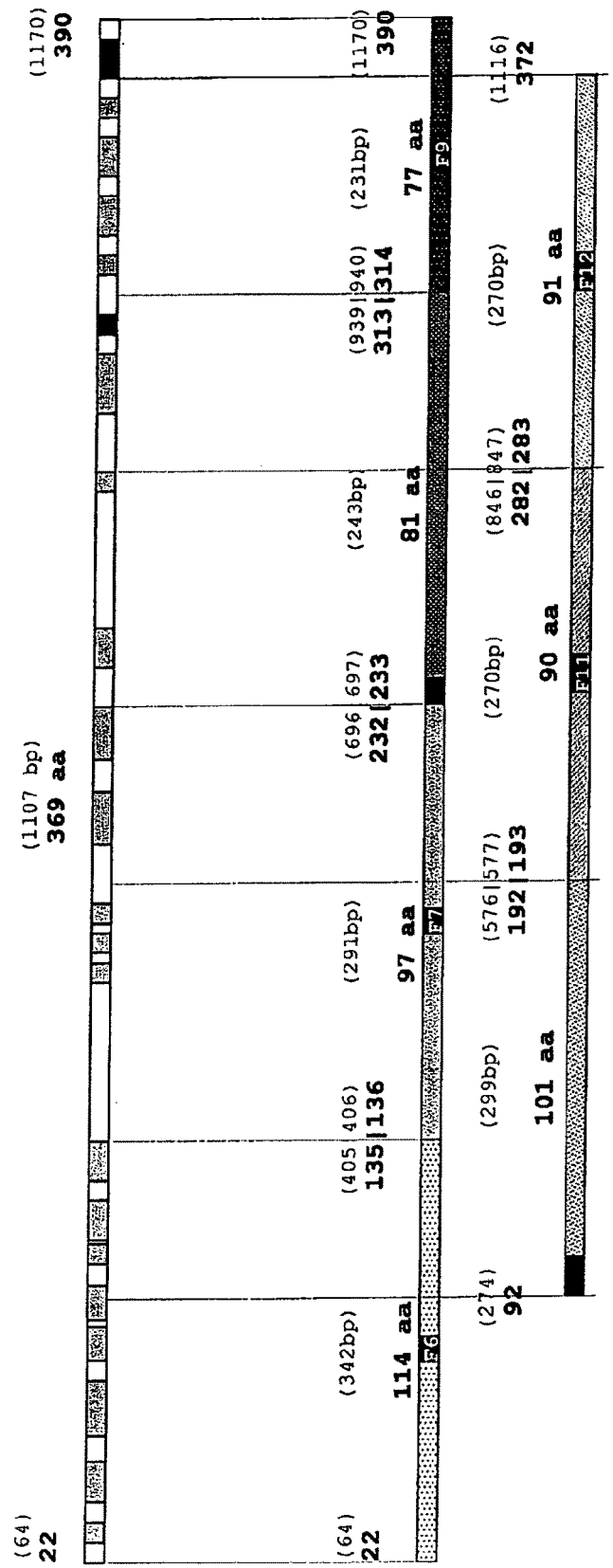
FIG. 6 is a graphical overview of peptide fragments F6-F12 of Ves v 4 as explained in Example 7. The selection of fragments and position in the Ves v 4 molecule with the respective fragment length is given in Table 1.
Figure 7:
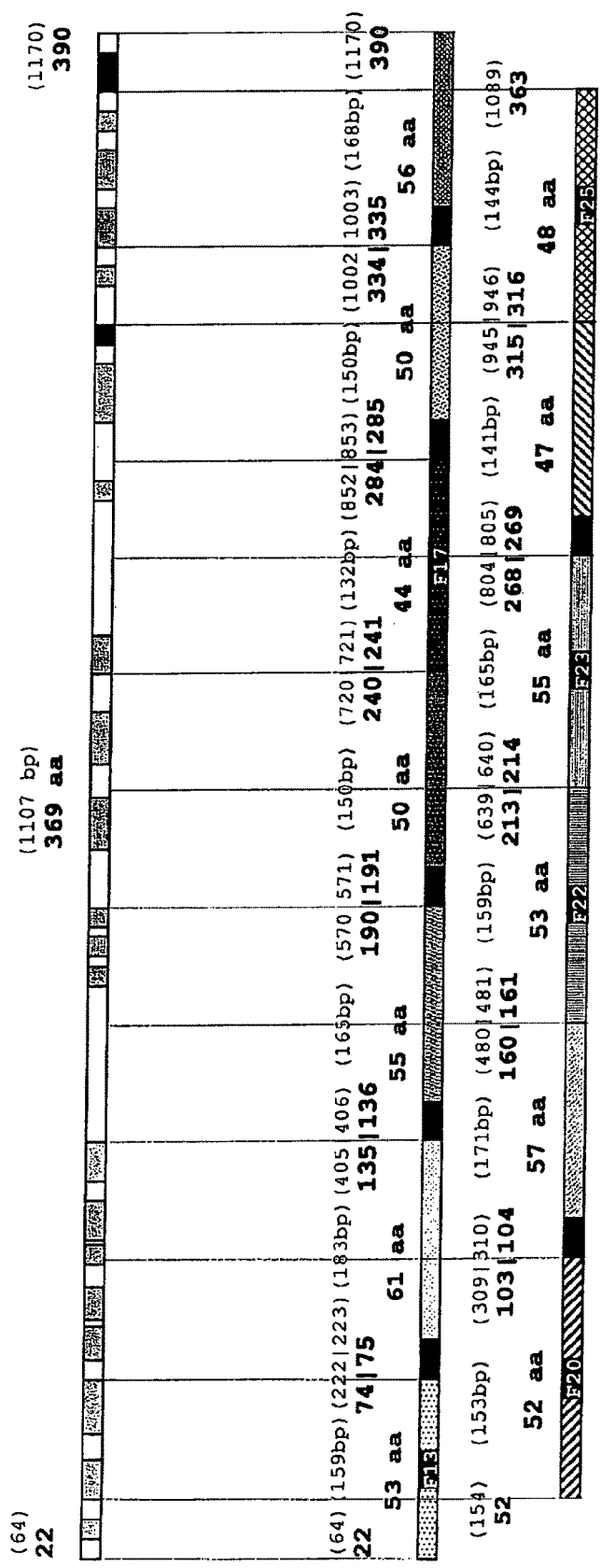
FIG. 7 is a graphical overview of peptide fragments F13-F25 of Ves v 4 as explained in Example 7. The selection of fragments and position in the Ves v 4 molecule with the respective fragment length is given in Table 1.

Table 1 shows the position of peptide fragments F1-F25 on the Ves v 4 polypeptide and on the encoding Ves v 4 nucleic acid, as explained in Example 7 and as shown in FIGS. 5, 6 and 7.

Tables 2 and 3 show predicted T cell epitopes on the Ves v 4 polypeptide and on the encoding Ves v 4 nucleic acid, as explained in Example 8.

Table 4 shows a calculation of putative surface IgE epitopes for a number of antigens per protein size ratio, as explained in section VII.

Table 5 shows a calculation of the average number of IgE epitopes on a number of allergens, as explained in section VII.

Table 6 shows a prediction of linear B cell epitopes on the Ves v 4 polypeptide, as explained in Example 9.

DEFINITIONS

A "nucleic acid molecule" refers to the phosphate ester polymeric form of ribonucleosides (RNA molecules) or deoxy ribonucleosides (DNA molecules) in either single stranded form, or double stranded form. Double strande DNA-DNA, DNA-RNA, and RNA-RNA helices are possible. The term nucleic acid molecule refers to the primary and secondary structure of the molecule, but does not limit it to any particular tertiary forms. Thus, this term includes double stranded DNA found in linear or circular DNA molecules (e.g., restriction fragments), viruses, plasmids, and chromosomes. DNA sequences may be described herein according to the normal convention of giving only the sequence in the 5' to 3' direction along the nontranscribed strand of DNA (i.e., the strand having a sequence homologous to the mRNA). A recombinant DNA molecule is a DNA molecule that has undergone a molecular biological manipulation.

A DNA "coding sequence" is a double-stranded DNA sequence which is transcribed and translated into a polypeptide in vivo when placed under the control of appropriate regulatory sequences. The boundaries of the encoding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence. Transcriptional and translational control sequences are DNA regulatory sequences, such as promoters, enhancers, terminators, and the like, that provide for the expression of a coding sequence in a host cell. A promoter sequence is a DNA regulatory region capable of binding RNA polymerase in a cell and initiating transcription of a downstream (3' direction) coding sequence. For purposes of the present invention, the promoter sequence is bounded at its 3' terminus by the transcription initiation site and extends upstream (5' direction) to include the minimum number of bases or elements to initiate transcription at levels detectable above background. Within the promoter sequence will be found a transcription initiation site, as well as protein binding domains (consensus sequences) responsible for the binding of RNA polymerase. Eukaryotic promoters will often, but not always, contain "TATA" boxes and "CAT" boxes. A coding sequence is under the control of transcriptional and translational control sequences in a cell when RNA polymerase transcribes the coding sequence into mRNA, which is then translated into the protein encoded by the coding sequence. A signal sequence can be included before the coding sequence. This sequence encodes a signal peptide, N-terminal to the polypeptide, that directs the host cell to transport the polypeptide to the cell surface or secrete the polypeptide into the media, and this signal peptide is usually selectively degraded by the cell upon exportation. Signal sequences can be found associated with a variety of proteins native to prokaryotes and eukaryotes. In accordance with the present invention there may be employed conventional molecular biology, microbiology, and recombinant DNA techniques within the skill of the art. Such techniques are explained fully in the literature.

As used herein, the term "coding region" refers to the nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA). The term "encoding" or "encodes" refers to said "coding sequence" and said "coding region".

As used herein, the term "amino acid sequence" is recited herein to refer to an amino acid sequence of a protein molecule. The term "amino acid sequence" and like terms such as "polypeptide" or "protein" are not meant to limit the amino add sequence to the complete, native amino acid sequence associated with the recited protein molecule. Rather the terms "amino acid sequence" and "protein" encompass partial sequences, fragments of the protein or polypeptide and modified sequences.

The term "wild type" refers to a nucleic acid molecule, a gene or gene product that has the characteristics of that nucleic acid molecule, gene or gene product when isolated from a naturally occurring source. A wild type gene is that which is most frequently observed in a population and is thus arbitrarily designated the "normal" or "wild-type" form of the gene.

In contrast, the terms "modified," "mutant", and "comprising a mutation" refer to a nucleic acid molecule, gene or gene product that displays modifications in sequence and or functional properties (i.e., altered characteristics) when compared to the wild-type nucleic acid molecule, gene or gene product. In some embodiments, the modification comprises at least one insertion, deletion, or substitution of one or more nucleotides or amino acids, respectively. A "mutation" in a nucleic acid sequence or gene can lead to an amino acid substitution in the corresponding amino acid sequence, wherein the amino acid substitution can be "conservative" or "non-conservative" or "random".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophane), beta-branched side chains (e.g., threonine, valine, isoleucine), and aromatic side chains (e.g., tyrosine, phenylalanine, tryptophane, histidine). Thus, a predicted non-essential amino acid residue in a polypeptide according to the invention, preferably the Ves v 4 polypeptide, fragments, and analogs thereof is preferably replaced with another amino acid residue from the same side chain family.

In the context of the present invention, the term "nucleic acid homology" is equivalent to "nucleic acid identity". In the context of the present invention, the term "amino acid homology" is equivalent to "amino acid identity". The percent homology between two sequences is a function of the number of identical positions shared by the sequences (i.e., percent homology equals the number of identical positions divided by the total number of positions times 100). For comparison purposes the sequences are aligned, wherein gaps can be introduced in the sequence of a first amino acid sequence for optimal alignment with a second amino acid sequence.

As used herein, the term "vespid" is used according to the practice of those in the field of allergy, and refers to insects belonging to the worldwide family of Vespidae consisting of the Vespinae and Polistinae subfamilies. The Vespinae subfamily includes the three genera *Vespula* (called wasps in Europe, yellow jackets in the USA), *Dolichovespula* (called hornets in the USA) and *Vespa* (called hornets in Europe and the USA). Species in the genus *Polistes* (called paper wasps in Europe and the USA) include but are not limited to *P. annularis* (Linnaeus), *P. exclamans* (Viereck), *P. metricus* (Say), *P. fuscatus* (Fabricius), and *P. apachus* (Saussure). Species in the genus *Vespa* include but are not limited to *V. crabro* (L.) and *V. orientalis* (Linnaeus). Species in the genus *Dolichovespula* include but are not limited to *D. maculata* (L.) and *D. arenaria* (Fab.). Species in the genus *Vespula* include but are not limited to *V. germanica* (Fab.), *V. squamosa* (Drury), *V. maculifrons* (Buysson), *V. flavopilosa* (Jacobson), *V. vulgaris* (L.), and *V. pensylvanica* (Saussure).

In the context of the present invention, the term "amino acid homology" is equivalent to "amino acid identity". The percent homology between two sequences is a function of the number of identical positions shared by the sequences (i.e., percent homology equals the number of identical positions divided by the total number of positions times 10). For comparison purposes the sequences are aligned, wherein gaps can be introduced in the sequence of a first amino acid sequence for optimal alignment with a second amino acid sequence.

The term "homology" refers to a degree of complementarity. There may be partial homology or complete homology. One example of analyzing such homology is shown in Example 5 and in FIG. 2.

A nucleic acid molecule is "hybridizable" to another acid molecule, such as cDNA, genomic DNA, or RNA, when a single stranded form of the nucleic acid molecule can anneal to the other nucleic acid molecule under the appropriate conditions of temperature and solution ionic strength. The conditions of temperature and solution ionic strength determine the "stringency" of the hybridization. Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementarily, variables well known in the art.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ ("melting temperature") of the formed hybrid, and the G:C ratio within the nucleic acids.

As used herein the term "stringency" is used in reference to the conditions of temperature, ionic strength, and the presence of other compounds such as organic solvents, under which nucleic acid hybridizations are conducted. The term "stringency" can refer to e.g. conditions in PCR (such as in e.g. Example 1) or to conditions in Southern Blotting (such as in e.g. Example 11 and in e.g. FIG. 8). Those skilled in the art will recognize that "stringency" conditions may be altered by varying the parameters just described either individually or in concert.

With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity).

With moderate stringency conditions, nucleic acid base pairing will occur between nucleic acids with an intermediate frequency of complementary base sequences (e.g., hybridization under "moderate stringency" conditions may occur between homologs with 50-70% identity).

Thus, conditions of "weak" or "low" stringency are often required with nucleic acids that are derived from organisms that are genetically diverse, as the frequency of complementary sequences is usually less.

Standard stringency conditions in general PCR can not be defined because of the variety of different polymerase molecules that can be employed for the reaction, having different optimal temperature conditions and buffer compositions.

Standard reaction mix conditions for Taq (*Thermus aquaticus*) polymerase consist of 10 mM Tris-HCl (pH 8.8 at 25 degree Celcius), 50 mM KCl, 0.08% Nonidet P40, 100 pM each primer, 200 μM each dNTP, 1.5 mM $MgCl_2$, 1.25 U polymerase and 100 pg template DNA.

Standard cycle conditions are: Denaturating step at 95 degree Celsius for 0.5-2 minutes. The temperature of the following annealing step is specified by the primers. The annealing time will be between 0.5-2 minutes. Each specific amplification primer exhibits an individual optimal hybridisation temperature based on oligonucleotide length and base sequence. Annealing temperature should be 5 degree Celsius lower than the calculated melting temperature (TM) of the primer with the lowest Tm. The extending step is performed at 72 degree Celsius temperature for 1 min each 1000 base pairs. The number of cycles will be between 25-35. Usually, a final extension step at 72 degree Celsius for 5-15 minutes is performed.

In general, stringency in PCR is related to the annealing temperature in relation to the theoretical Tm of the used primers and magnesium concentration in the buffer. The optimal stringency must be empirically determined, e.g. by temperature gradient experiments. Using shorter cycle times will result in the preferred amplification of smaller sequence fragments. Low stringency conditions can be defined by using standard buffer conditions and annealing temperatures below Tm-minus-5 degree Celsius. Standard stringency conditions will use standard buffer conditions and annealing temperatures between the theoretical Tm and Tm-minus-5 degree Celsius (Fermentas GmbH, St. Leon-Rot, Product Manual). High stringency conditions will use standard buffer conditions and annealing temperatures above the theoretical Tm, preferably 3 degree Celsius above Tm. If several calculation models for Tm exist, the accepted model with the highest resulting Tin should be used (Panjkovich and Melo 2005).

"High stringency conditions" when used in reference to nucleic acid hybridization in Southern Blotting comprise conditions equivalent to binding or hybridization at 42° C. in a solution comprising 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 100 to about 1000 nucleotides in length is employed.

"Moderate stringency conditions" when used in reference to nucleic acid hybridization in Southern Blotting comprise conditions equivalent to binding or hybridization at 42° C. in a solution comprising 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 100 to about 1000 nucleotides in length is employed.

"Low stringency conditions" comprise Southern Blotting conditions equivalent to binding or hybridization at 42° C. in a solution comprising 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 100 to about 1000 nucleotides in length is employed.

Figure 8:
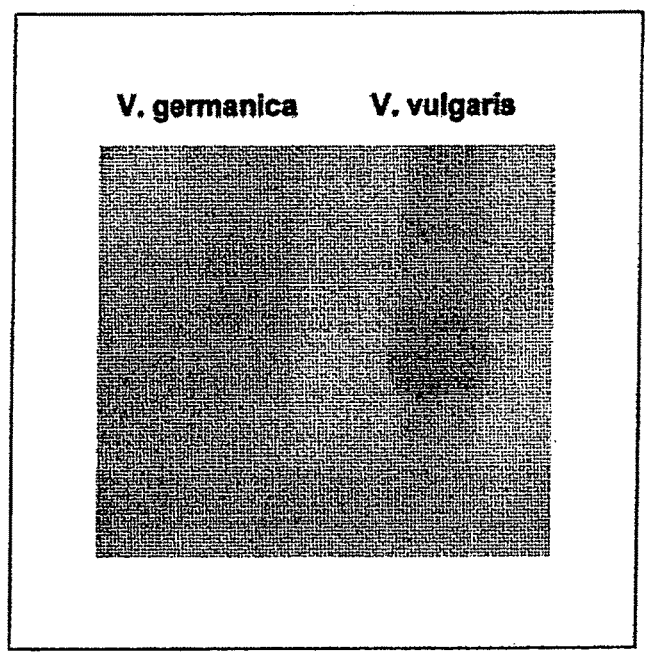
FIG. 8 shows a Southern Blot of the Ves v 4 fragment as a probe with the genomic DNA from *Vespula germanica*, as explained in Example 11.

Standard hybridization as done in e.g. Example 11 and in e.g. FIG. 8 was carried out in SSC buffer (SSC=Saline Sodium Chloride). The standard hybridization solution was 5×SSC, 0.1% N-Lauroylsarcosine w/v (liquid), 0.02% SDS, wherein the addition of 50% formamide allows hybridization at 42-45 degree Celsius. A 2×SSC solution was 300 mM NaCl, 30 mM Sodium Citrate, adjusted with HCl to pH 7.0. A standard wash was done with 2×SSC, 0.1% SDS.

For "low stringency conditions" the wash was done in 2×SSC, 0.1% SDS ("Low stringency wash").

For "moderate stringency conditions" the wash was done in 0.5×SSC, 0.1% SDS ("Moderate stringency wash").

For "increased stringency conditions" the wash was done in 0.1×SSC, 0.1% SDS ("Increased stringency wash").

For "high stringency conditions" the wash was done in 0.01×SSC, 0.1% SDS ("High stringency wash").

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al 1989).

The term "recombinant DNA molecule" as used herein refers to a DNA molecule that is comprised of segments of DNA joined together by means of molecular biological techniques. Similarly, the term "recombinant protein" or "recombinant polypeptide" or "recombinant antibody" as used herein refers to a protein molecule that is expressed from a recombinant DNA molecule.

The term "native protein" as used herein refers to a protein that does not contain amino acid residues encoded by vector sequences. That is the native protein contains only those amino acids found in the protein as it occurs in nature. A native protein may be produced by recombinant means or may be isolated from a naturally occurring source.

The term "fragment" when used in reference to a nucleotide sequence (as in "fragment of a given nucleotide sequence") refers to partial segments of that sequence. The fragments may range in size from 4 nucleotides to the entire nucleotide sequence minus one nucleotide (10 nucleotides, 20, 30, 40, 50, 100, 200, etc.).

Similarly, the term "fragment" when used in reference to a polypeptide sequence refers to partial segments of that sequence. In some embodiments, the fragment has an amino-terminal and/or carboxy-terminal deletion as compared to the native protein, but the remaining amino acid sequence is identical to the corresponding positions in the amino acid sequence deduced from a full-length cDNA sequence. Fragments are preferably at least 4 amino acids long, more preferably at least 15 amino acids long, more preferably at least 20 amino acids long and most preferably at least 50 amino acids long or longer (the entire amino acid sequence minus on amino acid).

In one embodiment, the invention provides polypeptide fragments of the Ves v 4 polypeptides of the invention containing one or more B cell epitopes of the *Vespula* venom protease. In another embodiment, the invention provides T cell epitope-containing polypeptide fragments of the *Vespula* venom protease capable of stimulating T cells of subjects allergic to Ves v 4. In a preferred embodiment, the invention provides polypeptide fragments containing one or more T cell epitopes and one or more B cell epitopes of the *Vespula* venom protease.

Fragments provide important advantages for the development of therapeutic approaches for the treatment of individuals allergic to Ves v 4. For example, recombinant fragments are easier to modify by site-directed mutagenesis than the full-length polypeptide, a fact that allows fast analysis of amino acid residues involved in the formation of B cell epitopes.

In a preferred embodiment, Ves v 4 polyptide fragments are selected on the basis of their immunological features and structural characteristics. The evaluation of immunological features includes, but is not limited to, analysis of the reactivity of IgE and IgG antibodies obtained from subjects allergic to venom of an insect from the family of Vespidae, with the polypeptide fragment, a predictive analysis of B cell epitopes, and a predictive analysis of T cell epitopes.

As used herein, the term "derivative or analog thereof" refers to any nucleic acid related to the nucleic acid shown in SEQ ID NO: 1 and to any polyeptide related to the polypeptide shown in SEQ ID NO: 2. In a derivative or analog according to the invention, the structure of the polypeptide can be modified to increase resistance of, for example, the Ves v 4 polypeptide and fragments thereof to proteolytic degradation in vivo. For this purpose, amino acid residues of a polypeptide of the invention, preferably the Ves v 4 polypeptide and fragments thereof, can be substituted by D-amino acids, non-natural amino acids or non-amino acid analogs, or such non-natural amino acids and analogs can be added to produce a modified peptide within the scope of the invention.

A "derivative" according to the invention can be selected from the group consisting of chimeric or fusion protein, a mutant comprising one or more amino acid substitutions, a mutant comprising one or more amino acid substitutions that increase resistance of the polypeptide to proteolytic degradation and a mutant comprising one or more amino acid substitutions that introduce one or more canonical protease sensitive sites, and wherein the chimeric or fusion protein preferably comprises a non-Ves v 4 polypeptide selected from the group consisting of poly-Histidine tag (His tag), glutathione-S-transferase (GST), maltose binding protein (MBP), a chitin binding domain (CBD), β-galactosidase, an IgG-Fc, a therapeutic polypeptide, preferably a cytokine, and other vespid venom proteins or fragments thereof.

The term "epitope" and "antigenic determinant" as used herein refer to that portion of an antigen that makes contact with a particular antibody and/or T cell receptor. The terms "epitope" and "antigenic determinant" can be used interchangeably. When a protein or fragment of a protein is used to immunize a host animal, numerous regions of the protein may induce the production of antibodies that bind specifically to a given region or three-dimensional structure on the protein; these regions or structures are referred to as "epitopes" or "antigenic determinants". Antigens, which are generally very large and complex, are not recognized in their entirety by lymphocytes. Instead, both B and T lymphocytes recognize discrete sites on the antigen called "epitopes" or antigenic determinants" via their B-cell receptors ("antibodies") and T-cell receptors, respectively. An epitope or antigenic determinant may compete with the intact antigen (i.e., the "immunogen" used to elicit the immune response) for binding to an antibody.

The term "B cell epitope" as used herein refers to an antigenic determinant (protein or carbohydrate) to which a single antibody molecule binds. B cell epitopes may comprise linear epitopes (amino acids adjacent to each other in the primary sequence) or conformational epitopes (moieties distant from each other in the primary sequence, but brought into close proximity of one another during folding of the antigen) of at least four amino acid residues.

The term "T cell epitope" as used herein refers to an antigenic determinant presented by a MHC class I or a MHC class II molecule, for binding by a single T cell receptor. T cell epitopes are linear epitopes comprising at least seven amino acid residues. In some embodiments of the present invention, the term T cell epitope comprises a T helper cell epitope, an antigen fragment presented by an MI-IC class II molecule for binding to T cell receptor on the surface of a helper T cell (e.g., generally CD4⁺).

In the context of the invention, the term "epitope recognized by human IgE (IgE epitope) or human IgG (IgG epitope), including human IgG4 (IgG4 epitope)", relates to the surface area of an allergen that is in contact to these antibodies upon binding to the allergen. It also relates to the surface area of the allergen that is in contact with an antibody construct comprised in the composition of the invention, that overlaps with the first-mentioned IgE epitope or IgG epitope, including IgG4 epitope", so binding of the antibody construct can inhibit binding of the human IgE or IgG, including IgG4; from the sera of patients allergic to the allergen (IgE related epitopes, IgG-related epitopes, IgG4 related epitopes). Preferably, the epitopes overlap by 20% or more, 50% or more, 60% or more, 70% or more, or 80% or more. Most preferably, the epitopes overlap by 90 or 95% or more or are identical. With reference to the number of epitopes of an allergen, the first-mentioned epitopes and the related epitopes are considered to represent the same epitopes.

The terms "antigen" and "antigenic" refer to any substance that is capable of inducing a specific humoral and/or cell-mediated immune response. An antigen generally contains at least one epitope. Antigens are exemplified by, but not restricted to molecules that contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. An "antigen" can be or can be present on an "allergen". "Antigens" can be the polypeptides of the invention, such as the Ves v 4 polypeptide, or fragments derivatives and analogs thereof.

As used herein, the term "allergy" refers to an inappropriate immune reaction in response to an antigen, wherein the terms "allergy" and "hypersensitivity" can be used interchangeably. There are four types of hypersensitive responses (Type I, II, III and IV), wherein IgE-mediated allergy or hypersensitivity is termed "Type I hypersensitivity". Immunoglobulin E (IgE)-mediated insect sting allergy to Hymenoptera is of common occurrence. The symptoms of IgE-mediated (type I) sting allergic reactions are due to release of mediators (e.g. histamine) resulting from cross-linking of effector cell-bound IgE antibodies by venom allergens. The symptoms can be suppressed by various pharmacologic treatments, but allergen specific immunotherapy (SIT) represents the only curative approach. A rise in allergen-blocking IgG antibodies, particularly of the IgG4 class, a reduction in the number of mast cells and eosinophils, and a decreased release of mediators are known to be associated with successful SIT. Based on these observations, determination of the serum levels of allergen-specific IgE and IgG4 antibodies is useful to describe the immune status of an allergic patient.

As used herein, the term "allergen" describes an antigen that is capable of eliciting an allergic or hypersensitive reaction in a patient. Such an allergen can induce a humoral antibody response resulting in the generation of antibody-secreting plasma cells and memory cell, wherein the plasma cells secrete IgE. For example, an allergen can be present in the venom of the family Vespidae (vespids), such as in the venom of *Vespula vulgaris*. One example of such an allergen is the Ves v 4 polypetide. Other examples of allergens are shown in Tables 4 and 5.

As used herein, the term "allergenicity" can be used interchangeably with "IgE reactivity", which can be described as the capability of a given antigen or allergen to bind to serum IgE in a patient. In specific embodiments, the present invention provides methods for decreasing the allergenicity (IgE reactivity) of the polypeptides of the invention in a structure-based approach via mutagenesis of IgE epitopes present on the polypeptide with limited impairment of the residual surface structure important for IgG immunological responses. In a preferred embodiment, the allergenicity of the polypeptides of the invention is reduced by at least 50% while at least 50% of IgG epitopes are maintained. In a more preferred embodiment, the allergenicity of the polypeptides of the invention is reduced by at least 70% while at least 50% of IgG epitopes are maintained. In a most preferred embodiment allergenicity is reduced by at least 90% while at least 50% of IgG epitopes are maintained. One Example of detecting or measuring "allergenicity" or "IgE reactivity", respectively is shown in Example 10 and in FIG. 4. The "allergenicity" or "IgE reactivity" of a given allergen, such as an allergen from the venom of *Vespula vulgaris*, and such as the polypeptides of the invention, can be measured by standard ELISA techniques, e.g. as shown in Example 10 and in FIG. 4.

The term "chimeric protein" or "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal, β-galactosidase) or may provide a tool for isolation purposes (e.g., GST). The chimeric or fusion protein preferably comprises a non-Ves v 4 polypeptide selected from the group consisting of poly-Histidine tag (His tag), glutathione-S-transferase (GST), maltose binding protein (MBP), a chitin binding domain (CBD), β-galactosidase, an IgG-Fc, a therapeutic polypeptide, preferably a cytokine, and other vespid venom proteins or fragments thereof.

Suitable systems for production of recombinant proteins include but are not limited to prokaryotic (e.g., *Escherichia coli*), yeast (e.g., *Saccharomyces cerevisiae*), insect (e.g., baculovirus), mammalian (e.g., Chinese hamster ovary), plant (e.g., safflower), and cell-free systems (e.g., rabbit reticulocyte lysate).

As used herein, the term "T cell anergy" refers to a state of nonresponsiveness of a given T cell clone. $T_H$-cell recognition of an antigenic peptide-MHC complex can result in such state of nonresponsiveness, which is marked by the inability of the T cell to proliferate in response to the peptide-MHC complex. Such antigenic peptide capable of inducing T cell anergy can be an "immunomodulatory" peptide of the invention. The polypeptides or peptides of the invention are preferably "immunomodulatory" peptides in that they induce T-cell anergy when administered to a subject allergic to the *Vespula* venom protease Ves v 4, or otherwise affect the immune response of the subject.

As used herein, the term "vector" is used in reference to nucleic acid molecules that 15 transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably or operationally linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a cell culture or in a transgenic animal. The invention can make use of eukaryotic expression systems including yeast, mammalian, plant, and insect cells for the production of the polypeptides of the present invention. Mammalian cells are also suitable for the production of the polypeptides of the present invention, but do not produce high yields. In addition, both intact plants and cell lines are suitable for the production of the polypeptides of the present invention. The recombinant polypeptides can be expressed by either transgenic technology or by infection with chimeric virus. The standard method to introduce foreign genes into plants is the well characterized single-stranded RNA virus, tobacco mosaic virus. "Host cells" can be insect cells which are utilized for the production of large quantities of the polypeptides of the present invention. In a more preferred embodiment, the baculovirus system which provides all the advantages of higher eukaryotic organisms, is utilized. The host cells include, but are not limited to *Spodoptera frugiperda* ovarian cell lines SF9 and SF21 and the *Trichoplusia ni* egg-derived cell line High Five.

The term "transformation" as used herein refers to the introduction of foreign DNA into prokaryotic or eukaryotic cells. Transformation maybe accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, Winter and Milstein 1991). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or F(ab)$_2$ fragments.

The term "reactive" when used in reference to an antibody indicates that the antibody is capable of binding an antigen of interest. For example, a Ves v 4-reactive antibody may bind to one or more epitopes of the polypeptides of the invention, wherein such antibody can be a human IgE or human IgG antibody or a recombinant antibody.

The terms "peptide," "peptide sequence," "amino acid sequence," "polypeptide," and "polypeptide sequence" are used interchangeably herein to refer to at least two amino acids or amino acid analogs, which are covalently linked by a peptide bond or an analog of a peptide bond. The term "peptide" includes oligomers ("oligopeptides") and polymers ("polypeptides") of amino acids or amino acid analogs. The term "peptide" also includes molecules commonly referred to as peptides, which generally contain from about two (2) to about twenty (20) amino acids. The term "peptide" also includes molecules commonly referred to as polypeptides, which generally contain from about twenty (20) to about fifty amino acids (50). The term "peptide" also includes molecules commonly referred to as proteins, which generally contain from about fifty (50) to about three thousand (3000) amino acids. One example of a "polypeptide" or "protein" is the Ves v 4 polypetide, which is of a length of 390 amino acids, as can be seen in FIGS. 2 to 4 and 6 to 8 and in SEQ ID NO. 2. The amino acids of the peptide may be L-amino acids or D-amino acids. A peptide, polypeptide or protein may be synthetic, recombinant or naturally occurring. A synthetic peptide is a peptide produced by artificial means in vitro. A "polypeptide" according to the invention can be the Ves v 4 polypetide and fragments, derivatives and analogs thereof.

The terms "carrier" and "pharmaceutically acceptable carrier" as used herein refer to usually inactive accessory substances into which a pharmaceutical substance (e.g., a polypeptide of the invention, such as the Ves v 4 polypetide and fragments, derivatives and analogs thereof) is suspended. Exemplary carriers include liquid carriers (such as water, saline, culture, medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins. As used herein, a "pharmaceutically acceptable carrier" is intended to include any and all solvents, dispersion media, coatings, antibacterial and antifungal agents, isotonic and adsorption delaying systems, and the like, compatible with the active compound and pharmaceutical administration. The use of such media and agents for pharmaceutically active substances is well known in the art. Supplementary active compounds can also be incorporated into the composition.

DETAILED DESCRIPTION OF THE INVENTION

The invention provides a novel *Vespula* venom protease, termed Ves v 4 that has been identified as *Vespula* venom allergen based on its reactivity to IgE antibodies in sera of individuals who are allergic to *Vespula* venom.

I. Nucleic Acids Encoding the *Vespula* Venom Protease of the Present Invention, and Fragments Thereof, Derivatives and Analogs Thereof In one embodiment, the present invention provides a nucleic acid molecule encoding a novel *Vespula* venom protease, and fragments, derivatives and analogs thereof, all of which are useful in the diagnosis and therapy of vespid venom-specific allergy. The sequence of the nucleic acid encoding the *Vespula* venom protease including 1173 nucleotides is shown in SEQ ID NO:1.

In a specific embodiment, to obtain a nucleic acid encoding the *Vespula* venom protease of the present invention, polymerase chain reaction (PCR) is combined with the rapid amplification of cDNA ends (RACE) techniques well known in the art. Preferably, the printers are based on the nucleic acid sequence for the *Vespula* venom protease of the present invention. Generally, such primers are prepared synthetically. Alternatives to isolating the genomic DNA or cDNA encoding the *Vespula* venom protease of the present invention include, but are not limited to, chemically synthesizing the gene sequence itself from the sequence provided herein. One example of obtaining a nucleic acid encoding the *Vespula* venom protease Ves v 4 is shown in Example 1.

In one embodiment the invention provides a nucleic acid molecule comprising the nucleotide sequence as shown in SEQ ID NO: 1 and nucleic acids hybridizable to the nucleotide sequence as shown in SEQ ID NO: 1 under moderate or high stringency conditions, and fragments, derivatives, mutants and analogs thereof.

In one embodiment the invention provides a nucleic acid molecule comprising the nucleotide sequence as shown in SEQ ID NO: 1 and nucleic acids that are at least 70% identical, preferably more than 80% identical and more preferably more than 90% identical to the nucleotide sequence as shown in SEQ ID NO: 1, and fragments, derivatives, mutants and analogs thereof.

In one embodiment the invention provides a nucleic acid molecule comprising the nucleotide sequence as shown in SEQ ID NO: 1 and nucleic acids hybridizable to the nucleotide sequence as shown in SEQ ID NO: 1 under moderate or high stringency conditions, and nucleic acids that are at least 70% identical, preferably more than 80% identical and more preferably more than 90% identical to the nucleotide sequence as shown in SEQ ID NO: 1, and fragments, derivatives, mutants and analogs thereof.

In one embodiment the invention provides a nucleic acid molecule consisting of the nucleotide sequence as shown in SEQ ID NO: 1.

In one embodiment, the nucleotide sequence encodes the *Vespula* venom protease Ves v 4 or fragments, derivatives and analogs thereof.

In a further embodiment, the nucleotide sequence encodes polypeptide fragments comprising one or more B cell eptiopes of the *Vespula* venom protease Ves v 4, one or more T cell eptiopes of the *Vespula* venom protease Ves v 4 or one or more B" cell eptiopes and one or more T cell eptiopes of the *Vespula* venom protease Ves v 4.

In one embodiment, the invention also provides a nucleic acid, which is a fragment having a length of more than 60 nucleotides of a nucleic acid encoding a polypeptide having a homology of at least 70%, and more preferably 90%, to the amino acid sequence of SEQ ID NO:2, wherein the fragment encodes a polypeptide capable of binding to IgE or IgG from subjects allergic to venom of an insect from the family of Vespidae. Preferably, the nucleic acid is a fragment having a length of more than 129 nucleotides of a nucleic acid encoding a polypeptide having the amino acid sequence of SEQ ID NO: 2, wherein the polynucleotide is selected from the group consisting of nucleotides 64 to 222, 223 to 405, 406 to 570, 571 to 720, 721 to 852, 853 to 1002, and 1003 to 1170 of said nucleic acid, wherein the numbering corresponds to the region encoding said polypeptide. Specifically, said nucleic acid has the nucleotide sequence shown in SEQ ID NO; 1. More preferably, the nucleic acid is a fragment having a length of more than 228 nucleotides of a nucleic acid encoding a polypeptide having the amino acid sequence of SEQ ID NO; 2, wherein the polynucleotide is selected from the group consisting of nucleotides 64 to 405, 406 to 696, 697 to 939, and 940 to 1170 of said nucleic acid. Most preferably, the nucleic acid is a fragment having a length of more than 357 nucleotides of a nucleic acid encoding a polypeptide having the amino acid sequence of SEQ ID NO: 2, wherein the polynucleotide is selected from the group consisting of nucleotides 64 to 444, 445 to 804, and 805 to 1170 of said nucleic acid.

In another embodiment, the invention provides additional fragments of the above mentioned nucleic acid, having a length of more than 60 nucleotides and encoding a polypeptide having a homology of more than 70% to the amino acid sequence of SEQ ID NO:2, wherein the fragment encodes a polypeptide capable of binding to IgE from subjects allergic to venom of an insect from the family of Vespidae, overlapping with fragments from the preceding embodiment. Preferably, the nucleic acid is a fragment having a length of more than 138 nucleotides of a nucleic acid encoding a polypeptide having the amino acid sequence of SEQ ID NO: 2, wherein the polynucleotide is selected from the group consisting of nucleotides 154 to 309, 310 to 480, 481 to 639, 640 to 804, 805 to 945, and 946 to 1089 of said nucleic acid, wherein the numbering corresponds to the region encoding said polypeptide. Specifically, said nucleic acid has the nucleotide sequence shown in SEQ ID NO: 1. More preferably, the nucleic acid is a fragment having a length of more than 267 nucleotides of a nucleic acid encoding a polypeptide having the amino acid sequence of SEQ ID NO: 2, wherein the polynucleotide is selected from the group consisting of nucleotides 274 to 576, 577 to 846, and 847 to 1116 of said nucleic acid. Most preferably, the nucleic acid is a fragment having a length of more than 357 nucleotides of a nucleic acid encoding a polypeptide having the amino acid sequence of SEQ ID NO: 2, wherein the polynucleotide is selected from the group consisting of nucleotides 295 to 711, and 712 to 1071 of said nucleic acid.

In another embodiment, a nucleic acid fragment (oligonucleotide) is provided that comprises at least 39 contiguous nucleotides of the nucleic acid encoding an oligopeptide having a homology of more than 70% to the amino acid sequence of SEQ ID NO: 2, wherein the fragment encodes an oligopeptide capable of stimulating T cells of subjects allergic to Ves v 4. In a preferred embodiment, the fragment is an oligopeptide capable of stimulating T cells of the great majority of subjects allergic to Ves v 4. Preferably, the nucleic acid fragment encodes an oligopeptide having the amino acid sequence of SEQ ID NO: 2, wherein the oligonucleotide is selected from the group consisting of 45 contiguous nucleotides as defined in Tables 2 and 3 of said nucleic acid, wherein the numbering corresponds to the region encoding said polypeptide. Specifically, said nucleic acid has the nucleotide sequence shown in SEQ ID NO: 1.

In another embodiment, the nucleic acid of the invention can be modified by site-directed mutagenesis, wherein the modification preferably affects one or more of the native N-glycosylation sites. The invention also provides a nucleic acid encoding the *Vespula* venom protease, or fragments thereof, which is modified by site-directed mutagenesis. In one specific embodiment, the present invention provides a nucleic acid encoding a Ves v 4 polypeptide of the invention comprising at least one, preferably 2, or 3 mutated glycosylation sites instead of native N-glycosylation sites with Asn-Xaa-Ser/Thr sequences. Most preferably, all 4 putative N-glycosylation sites comprising nucleotides 205 to 213 of SEQ ID NO:1 encoding the peptide sequence Asn-Cys-Thr, nucleotides 238 to 246 of SEQ ID NO:1 encoding the peptide sequence Asn-Cys-Ser, nucleotides 433 to 441 of SEQ ID NO:1 encoding the peptide sequence Asn-Pro-Ser, and nucleotides 646 to 654 of SEQ ID NO:1 encoding the peptide sequence Asn-Asp-Thr, are mutated. In one embodiment, the nucleotide sequence encoding serine residues of the N-glycosylation sites is exchanged by site-directed mutagenesis to a nucleotide sequence encoding alanine residues. In another embodiment, the nucleotide sequence encoding threonine residues of the N-glycosylation sites is exchanged by site-directed mutagenesis to a nucleotide sequence encoding valine residues. In a preferable embodiment, the nucleotide sequence encoding asparagine residues of the N-glycosylation sites is exchanged by site-directed mutagenesis to a nucleotide sequence encoding glutamine residues.

In another embodiment, the nucleic acids of the invention are for use as a medicament. In a further embodiment a nucleic acid comprising or consisting of SEQ ID NO: 1 and fragments, derivatives, mutants and analogs thereof are for use as a medicament. In a more specific embodiment, the nucleic acids of the invention are for use in the treatment of allergy against *Vespula* venom, preferably of allergy against the *Vespula* venom Ves v 4 protease.

In a further embodiment a nucleic acid comprising or consisting of SEQ ID NO: 1 and fragments, derivatives, mutants and analogs thereof are for use in the treatment of allergy against *Vespula* venom, preferably of allergy against the *Vespula* venom Ves v 4 protease.

In another embodiment, the present invention provides a nucleic acid encoding a chimeric or fusion protein, wherein said chimeric or fusion protein preferably comprises one or more polypeptide(s) of the invention. In one embodiment, the chimeric or fusion protein is a Ves v 4 chimeric or fusion protein. As used herein, a Ves v 4 'chimeric protein' or 'fusion protein' comprises a Ves v 4 polypeptide of the invention operatively linked to a non-Ves v 4 polypeptide. A Ves v 4 polypeptide refers to a polypeptide having an amino acid sequence corresponding to Ves v 4 (Vespula venom protease) or fragments thereof, whereas a 'non-Ves v 4 polypeptide' refers to an oligopeptide or polypeptide having an amino acid sequence which is not substantially homologous to the Ves v 4 polypeptides of the invention, e.g. a polypeptide which is different from the Ves v 4 polypeptides and which is derived from the same or different organism. Within the fusion protein, the term 'operatively linked' is intended to indicate that the Ves v 4 polypeptide and the non-Ves v 4 polypeptide are fused in-frame to each other. The non-Ves v 4 polypeptide can be fused to the N-terminus or C-terminus of the Ves v 4 polypeptide. The non-Ves v 4 polypeptide can be selected from the group including, but not limited to a poly-Histidine tag (His tag), glutathione-S-transferase (GST), maltose binding protein (MBP), a chitin binding domain (CBD), β-galactosidase, and an IgG-Fc. In a preferred embodiment, non-Ves v 4 polypeptides that improve solubility of the poypeptides of the invention, e.g., GST or MBP, or simplify purification of the recombinant protein, e.g., a His tag, GST, MBP, CBD or IgG-Fc are employed. For such fusion protein a corresponding affinity column can be used for purification, e.g., a $Ni^{2+}$ glutathione, maltose, or chitin affinity column. For purification of an IgG fusion protein, a protein A or protein G column is suitable. After purification of the protein the non-Ves v 4 polypeptide may be cleaved off chemically or by specific proteases.

Alternatively, it can be beneficial for therapeutic applications to express the polypeptide of the invention linked to a therapeutic polypeptide, e.g. a cytokine. For example, a fusion protein with a cytokine enhancing $T_H1$ and downregulating $T_H2$ responses or inducing class switch to IgG, such as IFN-γ, IL-10, IL-12 or TGF-β, can improve efficiency of desensitisation. If the expression vector is used for gene therapy, it is envisaged to use sequences rich in CpG (unmethylated cytosine guanidine dinucleotides), which promote $T_H1$ responses. Additionally or alternatively, the polypeptide of the invention can be linked to another polypeptide or protein, such as in the form of a fusion protein or as separate proteins expressed by the same vector. Preferably, the further polypeptides or proteins are other vespid venom proteins or fragments thereof.

II. Identification of Nucleic Acid Molecules from the Family Vespidae Hybridizable to the Nucleic Acid Encoding the *Vespula* Venom Protease In another embodiment, the present invention provides methods for isolating nucleic acid molecules from any species of the family Vespidae which are hybridizable under moderate or high stringency conditions to a nucleic acid having the nucleotide sequence shown in SEQ ID NO:1.

For isolating a nucleic acid homologue of the nucleic acid encoding the *Vespula* venom protease of the present invention, one can choose to synthesize several different degenerate primers for use, e.g., in PCR reactions. It is also possible to vary the stringency of hybridization conditions used in priming PCR reactions, to allow for greater or lesser degrees of nucleotide sequence similarity between a homologue of a vespid venom enzyme and the *Vespula* venom protease of the present invention. After successful amplification of a segment of a homologue, that segment may be cloned and sequenced, and utilized as probe to isolate the complete cDNA or genomic clone. This, in turn, will permit the determination of the complete nucleotide sequence, the analysis of its expression, and the production of its protein product for functional analysis, as described herein. In this fashion, additional genes encoding vespid venom enzymes homologous to the *Vespula* venom protease of the present invention, may be identified and expressed.

In another embodiment, genes encoding vespid venom enzymes homologous to the *Vespula* venom protease of the present invention can be isolated from a suitable library by screening with a probe. Useful probes for isolating such genes can be generated from the sequence information provided herein. A suitable library can be constructed by methods known in the art. Preferably, a cDNA library is prepared from cells or tissues that express vespid venom proteins, i.e., cells from the poison gland located near the venom sac. Sometimes, the poison gland is referred to as the acid gland. For example, mRNA or total RNA can be isolated, cDNA is prepared and ligated into an expression vector (e.g., a plasmid or bacteriophage derivative) such that it is capable of being expressed by the host cell into which it is then introduced. Various screening assays can be used then to select for the positive clones. For example, PCR with appropriate primers which can be synthesized based on the nucleic acid sequences provided herein, can be used. PCR is preferred as the amplified sequences can be detected easily, e.g., by ethidium bromide staining. Alternatively, labelled probes derived from the nucleic acid sequences provided herein can be used to screen the colonies. Alternatively, genes encoding vespid venom enzymes homologous to the *Vespula* venom protease of the present invention may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focussing behavior, proteolytic digestion maps, or antigenic properties as known for the *Vespula* venom protease of the present invention. In cases where the recombinant proteins are immunoreactive, e.g., reactive with IgE antibodies from sera of individuals allergic to vespid venom proteins, it is possible to select for positive clones by immunoblot. In another embodiment, the specific catalytic activity of proteases can be used for selection, although bacterially expressed eukaryotic proteins may not fold in an active conformation. Generally, according to the present invention, any method of screening for positive clones can be used.

One embodiment of isolating nucleic acid molecules from any species of the family Vespidae which are hybridizable under moderate or high stringency conditions to a nucleic acid having the nucleotide sequence shown in SEQ ID NO:1 is shown in Example 1.1 and in FIG. 8.

Southern Blotting of a nucleic acid molecule of the invention, such as a Ves v 4 encoding nucleic acid fragment as a probe, with genomic DNA of another species of the family Vespidae as shown in Example 11 and in FIG. 8 can be used to identify nucleic acid molecules from said family that are hybridisable to said nucleic acid molecule of the invention, such as the Ves v 4 encoding nucleic acid fragment.

III. Expression of the *Vespula* Venom Protease, Fragments Thereof or Derivatives Thereof A large number of vector-host systems known in the art may be used. Possible vectors include, but are not limited to, plasmids or modified viruses, but the vector system must be compatible with the host cell used. Potential host-vector systems include, but are not limited to mammalian cell systems infected with virus (e.g., vaccinia virus, adenovirus, etc.), insect cell systems infected with virus (e.g.; baculovirus), microorganisms such as yeast containing yeast vectors, or bacteria transformed with bacteriophages (e.g., lambda derivatives), DNA, plasmid DNA (e.g., various pBR322 derivatives), or cosmid DNA. The vector can be an expression vector. The expression elements of vectors vary in their strengths and specificities. Depending on the host-vector system utilized, any one of a number of suitable transcription and translation elements may be used. In one embodiment, the vector comprises one or more nucleic acid molecule(s) of the invention, wherein the one or more nucleic acid molecule(s) are operationally associated with a promoter.

In an alternative embodiment, a recombinant *Vespula* venom protease of the present invention, or a fragment, derivative or analogue thereof is expressed chromosomally, after integration after the coding sequence by recombination. In this regard, any of a number of amplification systems may be used to achieve high levels of stable gene expression.

The present invention further relates to a host cell comprising said expression vector. This host cell includes, but is not limited to a bacterial cell, a yeast cell, a mammalian cell, an insect cell, or a plant cell. In one embodiment, the host cell comprises a vector comprising one or more nucleic acid molecule(s) of the invention.

Alternatively, a cell-free expression system may be used. The development and optimization of specific methods as well as approaches to overcome a variety of problems associated with any of these expression systems have been published in many articles (for a review, see Schmidt and Hoffman 2002).

In a one embodiment, the invention provides a method for producing the polypeptides of the invention comprising the steps of a) transforming cells with a vector comprising one or more polypeptide(s) of the invention or fragment, derivative and analog thereof to give a transformed host cell, b) culturing said transformed host cells so that the polypeptide(s), fragment, derivative or analog thereof is expressed, and c) recovering the expressed polypeptide(s), fragment, derivative and analog from the culture.

In one embodiment, bacterial expression systems (e.g *E. coli*) are utilized for the production of large quantities of the polypeptides of the present invention. To avoid potential misfolding and segregation of said polypeptides into insoluble aggregates as inclusion bodies upon overproduction, an expression system that secretes the polypeptides into the periplasmatic space can be used to improve solubility of said polypeptides. The periplasmatic space is an oxidizing environment that contains enzymes catalyzing disulfide bonds. Co-overproduction of protein disulfide isomerases may be applied to enhance disulfide bond formation. Other proper folding factors such as peptidyl-prolyl-cis/trans isomerise also have been demonstrated to be helpful in improving solubility. To avoid potential problems in translation, arginine codons AGA and AGG which are rare and inefficiently translated in prokaryotes, can be replaced by site-directed mutagenesis. Alternatively, special strains of E. coli with extra copies of the necessary tRNA genes suitable to circumvent this problem can be selected.

In another embodiment, eukaryotic expression systems including yeast, mammalian, plant, and insect cells are for the production of the polypeptides of the present invention. Eukaryotic cells offer the advantage of being able to perform posttranslational modifications including processing signal sequences, folding, disulfide bond formation, and glycosylation. Among the many types of yeast the methylotrophic Pichia pastoris is capable to produce recombinant proteins in high yield and to add both O- and N-linked carbohydrates. However, as a lower eukaryote it adds only mannose residues, but hyperglycosylation as observed in Saccharomyces cerevisiae occurs less frequently. Mammalian cells are also suitable for the production of the polypeptides of the present invention, but do not produce high yields. In addition, both intact plants and cell lines are suitable for the production of the polypeptides of the present invention. The recombinant polypeptides can be expressed by either transgenic technology or by infection with chimeric virus. The standard method to introduce foreign genes into plants is the well characterized single-stranded RNA virus, tobacco mosaic virus. In a preferred embodiment, insect cells are utilized for the production of large quantities of the polypeptides of the present invention. In a more preferred embodiment, the baculovirus system which provides all the advantages of higher eukaryotic organisms, is utilized. The host cells include, but are not limited to Spodoptera frugiperda ovarian cell lines SF9 and SF21 and the Trichoplusia ni egg-derived cell line High Five.

IV. Ves v 4 Polypeptide and Fragments Thereof

In one embodiment, the invention provides a polypeptide encoded by a nucleic acid comprising the sequence shown in SEQ ID NO: 1 and fragments, derivatives and analogs thereof. In a further embodiment, the invention provides a polypeptide encoded by a nucleic acid consisting of the sequence shown in SEQ ID NO: 1. In the context of the present invention, the terms 'polypeptide' and 'protein' are used interchangeably, without any limitation as to the number of amino acids linked. The polypeptides may also comprise non-naturally occurring amino acids.

In a preferred embodiment, the polypeptide is a full length protease from the venom of an insect from the family Vespidae.

In one embodiment, the polypeptide consists of the amino acid sequence shown in SEQ ID NO:2.

In a further embodiment, the polypeptide of the invention comprises the amino acid sequence as shown in SEQ ID NO:2 and polypeptides that are at least 70% identical, preferably more than 80% identical, more preferably more than 90% identical, more preferably more than 95% identical and most preferably more than 99% identical to the amino sequence as shown in SEQ ID NO: 2, and fragments, derivatives and analogs thereof.

In one embodiment, the polypeptide has an homology of more than 70%, more than 75%, more than 80%, more than 85%, more than 90%, more than 95% or more than 99% to the amino acid sequence of SEQ ID NO: 2. Most preferred is a polypeptide having the amino acid sequence of SEQ ID NO: 2. The Ves v 4 polypeptide having the amino acid sequence of SEQ ID NO: 2 has a predicted molecular weight of 44.4 kDa.

Homology analyses revealed that the amino acid sequence of the Ves v 4 polypeptide differs significantly from amino acid sequences of other insect venom proteases. In the family Apidae consisting of the genera Apis (including the species Apis mellifera, honeybee) and Bombus (bumblebees), the venom serine protease Bom p 4 of Bombus pennsylvanicus with a molecular weight of 27 kDa (Hoffman and Jacobson 1996) shares an amino acid homology of only 18% with Ves v 4, and the venom protease Api m 7 of Apis mellifera with a molecular weight of 39 kDa (Winningham et al 2004) shares an amino acid homology of 35% with Ves v 4. In the subfamily Polistinae of the family Vespidae (vespids), the venom serine protease Pol p 4 of Polistes dominulus with a molecular weight of 27 kDa (Winningham et al 2004) shares an amino acid homology of 35% with Ves v 4. In the subfamily Vespinae of the family Vespidae including the three genera Vespula, Dolichovespula, and Vespa, the venom serine protease magnvesin of Vespa magnifica with a molecular weight of 27.4 kDa (Han et al 2008) shares an amino acid homology of 69% with Ves v 4. From all known insect venom proteases magnevesin shares the highest amino acid homology with Ves v 4. However, both venom proteases exhibit significant differences. The cDNA of magnvesin cloned from the venom sac cDNA library of Vespa magnifica encodes a protein precursor of 305 amino acids and a mature protease of 242 amino acids, whereas the Ves v 4 polypeptide comprises 369 amino acid residues clue to an additional N-terminal CUB domain. This domain mediates protein-protein interactions during development and in interacting protein cascades like the classical complement pathway (Bork and Beckmann 1993).

In one embodiment, the invention provides polypeptide fragments of the Ves v 4 polypeptides of the invention containing one or more B cell epitopes of the Vespula venom protease Ves v 4. In another embodiment, the invention provides T cell epitope-containing polypeptide fragments of the Vespula venom protease Ves v 4 capable of stimulating T cells of subjects allergic to Ves v 4. In a preferred embodiment, the invention provides polypeptide fragments containing one or more T cell epitopes and one or more B cell epitopes of the Vespula venom protease Ves v 4.

In one embodiment, the polypeptide according to the invention is the Vespula venom protease Ves v 4 and fragments, derivatives and analogs thereof, wherein the polypeptide preferably is capable of binding to IgE or IgG from subjects allergic to venom of an insect from the family of Vespidae.

In one embodiment, the polypeptide according to the invention comprises one or more B cell eptiopes of the Vespula venom protease Ves v 4, one or more T cell eptiopes of the Vespula venom protease Ves v 4 or one or more B cell eptiopes and one or more T cell eptiopes of the Vespula venom protease Ves v 4.

Said T cell epitopes can be selected from the group of oligopeptides of 15 contiguous amino acids in length listed in Tables 2 and 3, wherein said T cell epitope is preferably encoded by the group of oligonucleotides listed in Tables 2 and 3, wherein the numbering corresponds to the numbering as defined in SEQ ID NO: 1 and SEQ ID NO: 2, respectively.

Said B cell epitopes can be selected from the group of amino acids and oligopeptides listed in Table 6, wherein the numbering corresponds to the numbering as defined in SEQ ID NO: 2. Such B cell epitopes can be determined as shown in Example 9.

In a further embodiment, the polypeptide preferably is capable of stimulating T cells of subjects allergic to Ves v 4 or of the great majority of subjects allergic to Ves v 4.

Fragments provide important advantages for the development of therapeutic approaches for the treatment of individuals allergic to Ves v 4. For example, recombinant fragments are easier to modify by site-directed mutagenesis than the full-length polypeptide, a fact that allows fast analysis of amino acid residues involved in the formation of B cell epitopes. In particular knowledge of conformational (discontinuous or topographic) epitopes recognized by IgE antibodies is important for the design of novel recombinant Ves v 4 molecules capable of mediating protection in specific immunotherapy with little or no risk of anaphylactic reactions.

In a preferred embodiment, the polypeptide fragments according to the invention, preferably Ves v 4 polyptide fragments, are selected on the basis of their immunological features and structural characteristics. The evaluation of immunological features includes, but is not limited to, analysis of the reactivity of IgE and IgG antibodies obtained from subjects allergic to venom of an insect from the family of Vespidae, with the polypeptide fragment, a predictive analysis of B cell epitopes, and a predictive analysis of T cell epitopes. For the prediction of both linear and conformational B cell epitopes several programs are available (see, e.g., Zhang et al 2008). For the prediction of T cell epitopes an abundance of methods is available (see, e.g., Zhang et al., 2008; Korber et al 2006). In particular four methods including ARB, SMM_align, the method of Sturniolo which is also the basis of TEPITOPE, and a consensus approach have been identified as top performing ones (Zhang et al 2008). The evaluation of structural characteristics include, but is not limited to, analysis of secondary structures (see, e.g., Chou and Fasman 1974) and hydrophilicity-hydrophobicity profiles (see, e.g., Hopp and Woods 1981). Other methods of structural analysis including, but not limited to, X-ray crystallography, mass spectroscopy, and computer modelling may also be used.

In one embodiment of the invention, the polypeptide fragments are between 9-150 amino acids, more preferably between 20-150 amino acids in length. In a specific embodiment, the invention provides a polypeptide fragment having a length of more than 20 amino acid residues of a polypeptide having a homology of at least 70%, and more preferably 90%, to the amino acid sequence as shown in SEQ ID NO: 2, wherein the polypeptide fragment is capable of binding to IgE or IgG from subjects allergic to Ves v 4, and capable of stimulating T cells of subjects allergic to Ves v 4.

Preferably, the polypeptide fragment has a length of more than 43 amino acid residues of a polypeptide having the amino acid sequence of SEQ ID NO: 2, wherein the polypeptide is selected from the group consisting of amino acid residues 22 to 74, 75 to 135, 136 to 190, 191 to 240, 241 to 284, 285 to 334, and 335 to 390 of said polypeptide, wherein the numbering corresponds to the region of said polypeptide having the sequence shown in SEQ ID NO: 2. More preferably, the polypeptide fragment has a length of more than 76 amino acid residues of a polypeptide having the amino acid sequence of SEQ ID NO: 2, wherein the polypeptide is selected from the group consisting of amino acid residues 22 to 135, 136 to 232, 233 to 313, and 314 to 390 of said polypeptide. Most preferably, the polypeptide fragment has a length of more than 119 amino acid residues of a polypeptide having the amino acid sequence of SEQ ID NO: 2, wherein the polypeptide is selected from the group consisting of amino acid residues 22 to 148, 149 to 268, and 269 to 390 of said polypeptide.

In a further embodiment, the invention provides a polypeptide fragment selected from the group of polypeptide fragments listed in Table 1, wherein the amino acid numbering is according to the amino acid numbering as shown in SEQ ID NO: 2. These polypeptide fragments are referred to as "epitope fragments".

In a further embodiment, the invention provides a polypeptide fragment that is encoded by one of the nucleic acid fragments listed in Table 1, wherein the nucleic acid numbering is according to the nucleic acid numbering as shown in SEQ ID NO: 1. These polypeptide fragments are referred to as "epitope fragments".

In another embodiment, the invention provides additional polypeptide fragments overlapping with polypeptide fragments from the preceding embodiment, having a length of more than 20 amino acid residues of a polypeptide having a homology of at least 70%, and more preferably 90%, to the amino acid sequence as shown in SEQ NO: 2, wherein the polypeptide fragment is capable of binding to IgE or IgG from subjects allergic to Ves v 4, and capable of stimulating T cells of subjects allergic to Ves v 4.

Preferably, the polypeptide fragment has a length of more than 46 amino acid residues of a polypeptide having the amino acid sequence as shown in SEQ ID NO: 2, wherein the polypeptide is selected from the group consisting of amino acid residues 52 to 103, 104 to 160, 161 to 213, 214 to 268, 269 to 315, and 316 to 363 of said polypeptide, wherein the numbering corresponds to the region of said polypeptide having the sequence shown in SEQ ID NO: 2. More preferably, the polypeptide fragment has a length of more than 89 amino acid residues of a polypeptide having the amino acid sequence of SEQ ID NO: 2, wherein the polypeptide is selected from the group consisting of amino acid residues 92 to 192, 193 to 282, and 283 to 372 of said polypeptide. Most preferably, the polypeptide fragment has a length of more than 119 amino acid residues of a polypeptide having the amino acid sequence of SEQ ID NO: 2, wherein the polypeptide is selected from the group consisting of amino acid residues 99 to 237, and 238 to 357 of said polypeptide.

In still another embodiment, the invention provides a polypeptide domain of a polypeptide having a homology of at least 70%, and more preferably 90%, to the amino acid sequence as shown in SEQ ID NO: 2, wherein the polypeptide fragment is capable of binding to IgE or IgG from subjects allergic to Ves v 4, and capable of stimulating T cells of subjects allergic to Ves v 4. Preferably, the polypeptide domain has a length of more than 110 amino acid residues of a polypeptide having the amino acid sequence of SEQ ID NO: 2, wherein the polypeptide is selected from the group consisting of amino acid residues 26 to 136 (CUB domain), and 146 to 379 (trypsin-like domain) of said polypeptide, wherein the numbering corresponds to the region of said polypeptide having the sequence shown in SEQ ID NO: 2.

In a preferred embodiment, the invention provides a T-cell epitope-containing oligopeptides of at least 9 amino acids corresponding to a consecutive amino acid sequence within the *Vespula* venom protease Ves v 4, wherein the peptides are capable of stimulating T-cells of subjects allergic to Ves v 4. Such peptides of the invention are preferably immunomodulatory peptides as well in that they induce T-cell anergy when administered to a subject allergic to the *Vespula* venom protease Ves v 4, or otherwise affect the immune response of the subject. Preferably, the amino acid sequence of the T-cell epitope-containing oligopeptide corresponds to a consecutive amino acid sequence of a polypeptide comprising or consisting of the amino acid sequence as shown in SEQ ID NO: 2, wherein the 1-cell epitope-containing oligopeptide is selected from the group consisting of 15 contiguous amino acid residues as defined in Tables 2 and 3 of said polypeptide, wherein the numbering corresponds to the region of said polypeptide.

In a further embodiment, the invention provides a T cell epitope selected from the group of oligopeptides of 15 contiguous amino acids in length listed in Tables 2 and 3, wherein said T cell epitope is preferably encoded by the group of oligonucleotides listed in Tables 2 and 3, wherein the numbering corresponds to the numbering as defined in SEQ ID NO: 1 and SEQ ID NO: 2, respectively.

T-cell stimulating activity can be tested by culturing T-cells obtained from an individual sensitive to the Ves v 4 polypeptide, fragments, and analogs thereof described herein, with the VES v 4 polypeptide, fragments, and analogs thereof, and determining the presence or absence of proliferation by the T-cells in response to the peptide as measured by, for example, uptake of tritriated thymidine. Stimulation indicies for responses by T-cells to peptides useful in methods of the invention can be calculated as the maximum counts per minute (cpm) taken up in response to the peptide divided by the cpm of the control medium. For example, a peptide derived from a protein allergen may have a stimulation index of about 2.0. As a result, a stimulation index of at least 2.0 is generally considered positive for purposes of defining peptides useful as immunotherapeutic agents. Preferred peptides have a stimulation index of at least 2.5, more preferably at least 3.5 and most preferably at least 5.0.

In a further embodiment, the invention provides a B cell epitope selected from the group of amino acids and oligopeptides listed in Table 6, wherein the numbering corresponds to the numbering as defined in SEQ ID NO: 2. Such B cell epitopes can be determined as shown in Example 9.

V. Modification of the N-Glycosylation of the Ves v 4 Polypeptide, Fragments, and Analogs Thereof Sequence analysis of Ves v 4 shows that the protein comprises 4 putative N-glycosylation sites of the sequence Asn-Xaa-Ser/Thr. Depending on the host cell producing the recombinant Ves v 4 polypeptide, the protein is glycosylated (e.g., after expression in insect, yeast, plant or mammalian cells) or non-glycosylated (after expression in bacterial cells). Glycosylation can have profound effects on the binding of specific antibodies. It was shown that carbohydrates can represent IgE epitopes and contribute to observed non-specific cross-reactivity of allergens, e.g., between bee and wasp proteins, due to similar features of the carbohydrate chains. About 30 to 40% of patients with insect venom allergy have IgE antibodies reacting with both honeybee and *Vespula* venom. Apart from true double sensitization, IgE against cross-reactive carbohydrate determinants (CCD) is the most frequent and often only cause for the multiple reactivity and, thereby, for false positive results in assays for the diagnosis of insect venom allergy (Petersen and Mundt 2001; Hancock et al. 2008). Recently, alpha(1,3)-fucosyl residues attached to the innermost GlcNAc of N-glycans of allergens have been identified as prime cross-reactive carbohydrate determinants for insect venom allergens (Hemmer et al. 2004).

In eukaryotes the glycosylation pattern can vary depending on the host cell used (for reviews, see Schmidt and Hoffman 2002) and can thus differ from the glycosylation pattern of natural Ves v 4 isolated from *Vespula* venom. Furthermore, eukaryotic expression systems exhibit drastic differences in their capability of core alpha(1,3)-fucosylation of N-glycan structures (for reviews, see Tomiya et al. 2004). For example, High Five insect cells are capable of modifying N-glycans by core alpha(1,3)-fucosylation. This core fucosylation involves an alpha(1,3)-fucose attachment to the innermost GlcNAc of an N-glycan that may or may not also include an alpha(1,6)-fucose linkage. In contrast, SF9 insect cells do not possess detectable alpha(1,3)-fucosyltransferase activity. N-glycans of recombinant proteins expressed in SF9 cells exhibit only alpha(1,6)-fucose linkages. The absence of core alpha(1,3)-fucosylated N-glycans has also been reported for Ea4 insect cells and the gypsy moth cell line Ld652Y. An alpha(1,3)-fucosyltransferase gene has been identified in the genome of *Drosophila melanogaster* Schneider 2 (S2) insect cells, but it is apparently not active in the S2 cell line. Core alpha(1,3)-fucosylation is also not present in mammalian cells.

In one embodiment, an insect cell expression system is selected which is capable of attaching N-glycans to the recombinant Ves v 4 polypeptide that are identical to the N-glycans of natural Ves v 4 isolated from *Vespula* venom.

In one embodiment, the N-glycosylation of the polypeptide of the invention has been modified, wherein the modified N-glycosylation preferably is selected from the group consisting of absence of detectable core alpha(1,3)-fucosylation, mutated N-glycosylation sites, and absence of N-glycosylation.

In a preferred embodiment, insect cell lines lacking detectable alpha(1,3)-fucosyltransferase activity are utilized for the production of the polypeptides of the present invention that display absence of detectable core alpha(1,3)-fucosylation in order to minimize non-specific cross-reactivity in IgE antibodies in assays for the diagnosis of insect venom allergy.

Alternatively, insect cells with detectable alpha(1,3)-fucosyltransferase activity are utilized as expression system after inhibition of the alpha(1,3)-fucosyltransferase gene by inhibitory RNA or after introduction of a gene encoding an alpha(1,3)-fucosidase (for reviews, see Schmidt and Hoffman 2002). In vitro tests using alpha(1,3)-fucosylated plant glycoproteins (e.g., bromelain) are helpful in identifying sera containing CCD-specific IgE, although a positive result (occurring in 70 to 80% of all double-positive sera) does not reliably exclude true double-sensitization. Reciprocal in vitro inhibition including non-venom inhibitor protein rich in CCDs is the method of choice currently to discriminate between double-sensitization and cross-reactivity. In vitro diagnosis can be markedly improved when recombinant Ves v 4 lacking CCDs are used for testing. The present invention provides polypeptides, preferably Ves v 4 polypeptides, fragments, derivatives and analogs thereof, that lack alpha(1,3)-fucosyl residues and therefore, are suitable to discriminate between double-sensitization and cross-reactivity.

In another preferred embodiment, the polypeptides of the invention, preferably Ves v 4 polypeptides o and fragments thereof are expressed in bacterial cells. Such polypeptides and fragments thereof lack glycosylation. Utilization of the non-glycosylated Ves v 4 polypeptide, fragments, and analogs thereof for diagnostic procedures eliminates false positive results due to cross-reactive carbohydrate determinants (CCD) and can therefore be used to advantage in diagnostic applications.

In still another preferred embodiment, the polypeptides of the invention comprise mutated N-glycosylation sites instead of native N-glycosylation sites. In one specific embodiment, the present invention provides a polypeptide, preferably a Ves v 4 polypeptide of the invention, comprising at least one, preferably 2, or 3 mutated glycosylation sites instead of native N-glycosylation sites with Asn-Xaa-Ser/Thr sequences. Most preferably, all 4 putative N-glycosylation sites comprising amino acid residues 69-71 of SEQ ID NO: 2, amino acid residues 80-82 of SEQ ID NO: 2, amino acid residues 145-147 of SEQ ID NO: 2, and amino acid residues 216-218 of SEQ ID NO: 2, are mutated. In one embodiment, the serine (Ser) residue of the N-glycosylation site is exchanged by an alanine (Ma) residue. In another embodiment, the threonine (Thr) residue of the N-glycosylation sites is exchanged by a valine (Val) residue. In a preferred embodiment, the asparagine (Asn) residue of the N-glycosylation sites is exchanged by a glutamine (Gln) residue (Elbein 1991).

In a further embodiment, the invention provides a method for modification of N-glycosylation of a Ves v 4 polypeptide comprising the steps of a) providing a nucleic acid molecule of the invention or a nucleic acid molecule encoding a polypeptide of the invention, preferably a Ves v 4 polypeptide, or fragments, derivatives and analogs thereof, b) applying site-directed mutagenesis to one or more of the native glycosylation site(s) of said nucleic add molecule to give a modified nucleic acid molecule encoding a polypeptide having modified N-glycosylation.

Said modified N-glycosylation can be selected from the group consisting of absence of detectable core alpha(1,3)-fucosylation, mutated N-glycosylation sites, and absence of N-glycosylation.

VI. Derivatives of the Ves v 4 Polypeptide, Fragments, and Analogs Thereof

Preferably, conservative amino acid substitutions are made at one or more predicted non-essential amino add residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, cine, isoleucine, proline, phenylalanine, methionine, tryptophane), beta-branched side chains (e.g., threonine, valine, isoleucine), and aromatic side chains (e.g., tyrosine, phenylalanine, tryptophane, histidine). Thus, a predicted non-essential amino acid residue in a polypeptide of the invention, preferably in the Ves v 4 polypeptide, fragments, and analogs thereof, is preferably replaced with another amino acid residue from the same side chain family. Alternatively, in another embodiment, mutations can be introduced randomly along all or part of a Ves v 4-coding sequence, to identify mutants that retain activity, including IgE binding capability.

To facilitate purification and potentially increase solubility of the Ves v 4 polypeptide, fragments, and analogs thereof, it is possible to add a suitable non-Ves v 4 polypeptide to the peptide backbone. A "non-Ves v 4 polypeptide" refers to an oligopeptide or polypeptide having an amino acid sequence which is not substantially homologous to the Ves v 4 polypeptides of the invention, e.g. a polypeptide which is different from the Ves v 4 polypeptides and which is derived from the same or different organism. The non-Ves v 4 polypeptide can be fused to the N-terminus or C-terminus of the Ves v 4 polypeptide. The non-Ves v 4 polypeptide can be selected from the group including, but not limited to a poly-Histidine tag (His tag), glutathione-S-transferase (GST), maltose binding protein (MBP), a chitin binding domain (CBD), β-galactosidase, and an IgG-Fc. In a preferred embodiment, non-Ves v 4 polypeptides that improve solubility of the polypeptides of the invention, e.g., GST or MBP, or simplify purification of the recombinant protein, e.g., a His tag, GST, MBP, CBD or IgG-Fc are employed. For such fusion protein a corresponding affinity column can be used for purification, e.g., a $Ni^{2+}$ glutathione, maltose, or chitin affinity column. For purification of an IgG fusion protein, a protein A or protein G column is suitable. After purification of the protein the non-Ves v 4 polypeptide may be cleaved off chemically or by specific proteases. Specific endoprotease cleavage sites can be introduced, if desired, between the Ves v 4 polypeptide and the non-Ves v 4 polypeptide to facilitate isolation of Ves v 4 polypeptides free of irrelevant sequences. In addition, it may be necessary to increase the solubility of the Ves v 4 fragments and analogs thereof by not including hydrophobic regions. Furthermore, it is possible to increase the solubility of the Ves v 4 fragments and analogs thereof by modification with polyethylene glycol (PEG). Substitution of cysteine residues in Ves v 4 fragments and analogs thereof by alanine, or glutamic acid, or alternatively with serine or threonine is another example for increasing the solubility due to inhibition of potential oligomerization.

In one embodiment, the structure of is modified to increase resistance of Ves v 4 polypeptide, fragments and analogs thereof to proteolytic degradation in vivo. For this purpose, amino acid residues of a polypeptide of the invention, preferably the Ves v 4 polypeptide, fragments and analogs thereof, can be substituted by D-amino acids, non-natural amino acids or non-amino acid analogs, or such non-natural amino acids and analogs can be added to produce a modified peptide within the scope of this invention.

To potentially aid proper antigen processing of T-cell epitopes within polypeptides of the invention, preferably the Ves v 4 polypeptide, fragments and analogs thereof, canonical protease sensitive sites can be recombinantly or synthetically engineered between regions, each comprising at least one T-cell epitope. For example, charged amino acid pairs, such as KK or RR, can be introduced between T-cell epitope comprising regions.

Alternatively, it can be beneficial for therapeutic applications to express the polypeptide according to the invention, preferably the Ves v 4 polypeptide, fragments and analogs thereof, linked to a therapeutic polypeptide, e.g. a cytokine. For example, a fusion protein with a cytokine enhancing $T_H1$ and downregulating $T_H2$ responses or inducing class switch to IgG, such as IFN-γ, IL-10, IL-12 or TGF-β, can improve efficiency of desensitisation. If the expression vector is used for gene therapy, it is envisaged to use sequences rich in CpG (unmethylated cytosine guanidine dinucleotides), which promote $T_H1$ responses. Additionally or alternatively, the polypeptide of the invention, preferably the Ves v 4 polypeptide, fragments and analogs thereof, can be linked to another polypeptide or protein, such as in the form of a fusion protein or as separate proteins expressed by the same vector. Preferably, the further polypeptides or proteins are other vespid venom proteins or fragments thereof.

In a further embodiment of the invention, the polypeptide, preferably the Ves v 4 polypeptide is a derivative selected from the group consisting of chimeric or fusion protein, a mutant comprising one or more amino acid substitutions, a mutant comprising one or more amino acid substitutions that increase resistance of the polypeptide to proteolytic degradation and a mutant comprising one or more amino acid substitutions that introduce one or more canonical protease sensitive sites.

In a more specific embodiment, the chimeric or fusion protein comprises a non-Ves v 4 polypeptide selected from the group consisting of poly-Histidine tag (His tag), glutathione-S-transferase (GST), maltose binding protein (MBP), a chitin binding domain (CBD), β-galactosidase, an IgG-Fc, a therapeutic polypeptide, preferably a cytokine, and other vespid venom proteins or fragments thereof.

VII. Hypoallergenic Derivatives of the Ves v 4 Polypeptide, Fragments, and Analogs Thereof In one embodiment, the present invention provides methods for identification and modification via site-directed mutagenesis of those amino acid residues involved in the interaction of the polypeptides of this invention with human IgE or IgG antibodies. In particular, the present invention provides compositions comprising recombinant antibodies wherein each composition is capable of binding to all epitopes recognized by either human IgE or IgG antibodies, including IgG4 antibodies, a method of obtaining such a composition and the use of individual antibodies of such a composition as tools for the design of hypoallergenic molecules, preferably Ves v 4 molecules, for specific immunotherapy (SIT).

In a specific embodiment, antibody compositions capable of binding to all epitopes of the polypeptide of the invention, preferably of the Ves v 4 polypeptide, fragments and analogs thereof that are recognized by human IgE antibodies, are utilized to identify and modify by site-directed mutagenesis those amino acid residues involved in the interaction with allergen-specific human IgE antibodies, thereby eliminating or decreasing the allergenicity of the Ves v 4 polypeptide, fragments and analogs thereof in a structure-based approach. By site-directed mutagenesis of amino acid residues essential for the allergen-IgE antibody interaction, IgE epitopes are eliminated with minimal impairment of the residual surface structure important for a non-IgE immunological response.

In another specific embodiment, antibody compositions capable of binding to all epitopes of the polypeptide of the invention, preferably of the Ves v 4 polypeptide that are recognized by human IgG antibodies, including IgG4 antibodies, are utilized to maintain those structures that mediate an appropriate non IgE response for a long lasting protection after specific immunotherapy (SIT). This rational is based on the recent observation that immune deviation towards T regulatory (Treg) cells is an essential step in successful SIT (for a review, see Jutel et al 2006). Treg cells are defined by their ability to produce high levels of IL-10 and TGF-β and to suppress naive and memory T helper type 1 and 2 responses. There is now clear evidence that IL-10- and/or TGF-β-producing type 1 T regulatory cells are generated in humans during the early course of SIT. Since Treg cells have been shown to differentiate from naive T cells in the periphery upon encountering antigens present at high concentrations, it can be assumed that Treg cells are also induced by high and increasing doses of allergens. Most important is the fact that IL-10 and TGF-β suppress directly or indirectly effector cells of allergic inflammation such as basophils and mast cells, and induce IgG4 from B cells as non-inflammatory immunoglobulin isotypes and suppress IgE production. Based on these observations, antibody compositions capable of binding to all epitopes of the Ves v 4 polypeptide, fragments and analogs thereof that are recognized by human IgG and particularly by human IgG4 antibodies, are utilized to identify and maintain those amino acid residues involved in the interaction with allergen-specific human IgG antibodies.

In the context of the invention, the term "epitope recognized by human IgE (IgE epitope) or human IgG (IgG epitope), including human IgG4 (IgG4 epitope)", relates to the surface area of an allergen that is in contact to these antibodies upon binding to the allergen. It also relates to the surface area of the allergen that is in contact with an antibody construct comprised in the composition of the invention, that overlaps with the first-mentioned IgE epitope or IgG epitope, including IgG4 epitope", so binding of the antibody construct can inhibit binding of the human IgE or IgG, including IgG4; from the sera of patients allergic to the allergen (IgE related epitopes, IgG-related epitopes, IgG4 related epitopes).

In one embodiment, the epitopes overlap by 20% or more, 50% or more, 60% or more, 70% or more, or 80% or more In a further embodiment, the epitopes overlap by 90 or 95% or more or are identical. With reference to the number of epitopes of an allergen, the first-mentioned epitopes and the related epitopes are considered to represent the same epitopes.

For an estimation of the number of antibodies sufficient for binding to all epitopes recognized by human IgE or IgG antibodies, including IgG4 antibodies, on the Ves v 4 polypeptide, it is important to know the approximate number of possible B cell epitopes per allergen. Therefore, methods for estimating the number of B cell epitopes per allergen have been developed. These methods are based on the following parameters:

a) Calculation of the surface of structurally characterized allergens in $A^2$: The solvent accessible surfaces of proteins can be calculated with the aid of POPS (parameter optimized surfaces) according to Fraternali and Cavallo (2002).

b) Surface area of B-cell epitopes in $A^2$: At the moment, one co-crystallization of allergen and antibody is available only, namely for the allergen Bet v 1 and a murine allergen-specific Fab-fragment. The surface area of this discontinuous epitope is 931 $A^2$ (Mirza et al 2000). This correlates well with the area of other B cell epitopes (circa 2×3 nm).

In Table 4, the surface of allergens for which structural data is available in the protein data bank (PDB) was calculated with the aid of a molecule of water. Under the assumption that a B cell epitope takes up an area of 950 $A^2$, the maximal possible number of B cell epitopes for an allergen (without differentiation for IgE or IgG epitopes) was determined. The number calculated in this way is much too high, but can be considered to provide an upper limit for the number of necessary antibody constructs for an allergen. On the basis of this data, an approximate relation between molecular weight and potential B cell epitopes was calculated. The mean value of the upper limit for potential B cell epitopes is approx. 0.5 B cell epitopes per 1 kDa. The polypeptides of the invention, including Ves v 4 polypeptides, fragments, derivatives and analogs thereof, including altered polypeptides or modified allergens, respectively, can comprise or can be crossreactive with the B cell epitopes shown in Table 4.

Table 5 summarizes allergens that have been examined for IgE binding structures with overlapping oligopeptides. Utilizing overlapping oligopeptides (e.g., decapeptides), more potential IgE epitopes are identified than exist in reality, as the majority of IgE epitopes are discontinuous epitopes composed of at least two different areas of the molecule brought together by folding. Different relevant allergens, such as Phospholipase A2 and the birch pollen allergens Bet v1, Bet v3 and Bet v4 exclusively have discontinuous epitopes (Valenta et al 1998). Since the identified linear epitopes probably only form part of these discontinuous epitopes, for estimation of the number of epitopes it is supposed that at least three linear IgE binding epitopes are, as partial structures, involved in forming a discontinuous IgE epitope. Therefore, the number of identified IgE binding peptides has been divided by three and related to the molecular weight of the allergen. A number of 0.06 to 0.19 epitopes per 1 kDa calculated on the basis of linear IgE binding peptides is preferred. The best estimation is possible on the basis of the number of 0.12 IgE epitopes per 1 kDa, which is possibly still too high but could be considered realistic. The preferred compositions correlate well with known data for Bet v 2 (17.4 kDa), which can be bound by three different monoclonal Fab fragments (without differentiating between IgG and IgE epitopes, Valenta et al 1998). Bet v 2 has at least two IgE epitopes, since it can induce in vivo cross-linking of surface bound IgE antibodies. The polypeptides of the invention, including Ves v 4 polypeptides, fragments, derivatives and analogs thereof, including altered polypeptides or modified allergens, respectively, can comprise or can be crossreactive with the IgE epitopes shown in Table 5.

The plurality of Ves v 4-specific monoclonal antibodies can be generated from different sources. Naturally occurring IgE antibodies represent ideal tools for structural analyses of IgE epitopes, but their availability is limited. Cloning and selecting allergen-specific IgE antibodies from the immune repertoire of peripheral blood mononuclear cells of allergic donors is extremely difficult. The low number of IgE-secreting B cells in the peripheral blood of allergic patients (MacKenzie and Dosch 1989) seriously hampers this approach for generating monoclonal IgE antibodies.

Cloning and selecting Ves v 4-specific IgG antibodies, including IgG4 antibodies, from the immune repertoire of peripheral mononuclear cells of allergic donors may be less difficult due to the significantly higher number of IgG-secreting B cells in the peripheral blood of allergic patients as compared to IgE-secreting B cells. Currently, however, the availability of human monoclonal allergen-specific IgG4 antibodies is limited.

In one embodiment, the invention provides a composition comprising one or more antibodies capable of binding to one or more epitope(s) of the polypeptides of the invention, preferably to one or more epitope(s) of the Ves v 4 polypeptides, fragments, analogs and derivatives thereof, wherein the one or more epitope(s) are recognized by human IgE or human IgG antibodies.

Semisynthetic or synthetic immunolibraries (e.g., scFv or Fab format) provide a high degree of variability and, therey, a valuable alternative for generating the required plurality of Ves v 4-specific monoclonal antibody fragments. However, newly generated immunolibraries derived from animals (mammalian species as well as avian species) after immunization with the Ves v 4 polypeptide or fragments thereof provide a significantly higher number of Ves v 4-specific variable antibody domains and, thereby, an increased probability for the selection of the required plurality of Ves v 4-specific high affinity monoclonal antibody fragments. In a preferred embodiment a combination of immunolibraries derived from avian and mammalian species after immunization with the Ves v 4 polypeptide or fragments thereof are used. The phylogenetic difference between avian and mammalian species provides access to a different antibody repertoire than the traditional mammalian antibodies. IgY antibodies recognize other epitopes than mammalian antibodies. Therefore, a combination of immunolibraries from avian and mammalian species provides a significant advantage for generating a plurality of Ves v 4-specific high affinity monoclonal antibodies. If it should—unexpectedly—be found that the combination of all antibodies capable of binding to the Ves v 4 polypeptide is not sufficient to effect essentially complete Inhibition of binding of Ves v 4 to antibodies in a pool serum of patients allergic to said allergen or obtained from said sera, it is recommended to additionally use further antibodies from a different library. Methods for generating immunolibraries are known in the art (e.g., Steinberger et al 1996; Edwards et al 2002; Powers et al 2001; Boel et al 2000). In one embodiment, the invention provides a composition comprising one or more recombinant antibodies capable of binding to one or more epitope(s) of the polypeptides of the invention, preferably to one or more epitope(s) of the Ves v 4 polypeptides, fragments, analogs and derivatives thereof, wherein the one or more epitope(s) are recognized by human IgE or human IgG antibodies.

Each antibody composition is obtainable by a method for generating a composition comprising recombinant antibodies, comprising steps of
a) generating a plurality of allergen-specific antibodies capable of binding to the Ves v 4 polypeptide,
b) combining all generated antibodies and testing whether essentially complete inhibition of binding of the Ves v 4 polypeptide to IgE and IgG antibodies, including IgG4 antibodies; in a pool serum of patients allergic to said allergen or obtained from said serum is achieved,
c) in case essentially complete inhibition is not achieved in step b), steps a) and b) are repeated;
d) in case essentially complete inhibition is achieved, the number of antibodies is reduced to the minimal number of antibodies sufficient for essentially complete inhibition, preferably by a method wherein
  i) groups of the antibodies obtained in step a) are generated, comprising different numbers and combinations of antibodies;
  ii) said groups are tested for essentially complete inhibition of binding of the Ves v 4 polypeptide to IgE and IgG antibodies, including IgG4 antibodies, in a pool serum of patients allergic to said allergen or obtained from said sera;
  iii) wherein, in case one or more group effects essentially complete inhibition in step ii), steps i) and ii) are repeated with subcombinations of the antibodies from said group or groups until the minimal number of antibodies in said group or groups is identified which effects essentially complete inhibition;
  iv) wherein, in case essentially complete inhibition is not achieved in step ii) or iii), steps i), ii) and iii) are repeated with different groups of antibodies; and wherein the group identified in step d), iii) is said composition. It is preferred that the composition comprises the minimal number of antibodies necessary and sufficient for binding to all epitopes recognized by human IgE and IgG antibodies, including IgG4 antibodies; on the Ves v 4 polypeptide Additional antibodies may, however, be added.

In the method of the invention, inhibition of binding of the Ves v 4 polypeptide to IgE can be determined by incubating IgE antibodies in a pool serum of patients allergic to the Ves v 4 polypeptide or antibodies obtained from said serum with human basophils after stripping of said basophils, and with or without preincubation of the Ves v 4 polypeptide with the recombinant antibodies or recombinant antibody fragments or, for comparison, antibodies in a pool serum of patients allergic to said allergen or obtained from said serum, contacting said basophils with said allergen, and detecting release of histamine.

Alternatively, inhibition can be determined by contacting anti IgE antibodies immobilized on a carrier with antibodies in a pool serum of patients allergic to the Ves v 4 polypeptide or obtained from said serum, and, with or without preincubation of labelled Ves v 4 polypeptide with the recombinant antibodies or recombinant antibody fragments or, for comparison, antibodies in a pool serum of patients allergic to said allergen or obtained from said serum, contacting the carrier with said allergen and detecting binding of the labelled Ves v 4 polypeptide to the carrier. For this purpose, the Ves v 4 polypeptide can be labelled with an enzyme, a radioisotope, biotin or a fluorescent marker.

In the method of the invention, inhibition of binding of the Ves v 4 polypeptide to IgG can be determined by contacting anti IgG antibodies immobilized on a carrier with antibodies in a pool serum of patients allergic to the Ves v 4 polypeptide or obtained from said serum, and, with or without preincubation of labelled Ves v 4 polypeptide with the recombinant antibodies or recombinant antibody fragments or, for comparison, antibodies in a pool serum of patients allergic to said allergen or obtained from said serum, contacting the carrier with said allergen and detecting binding of the labelled Ves v 4 polypeptide to the carrier. For this purpose, the Ves v 4 polypeptide can be labelled with an enzyme, a radioisotope, biotin or a fluorescent marker.

In the method of the invention, inhibition of binding of the Ves v 4 polypeptide to IgG4 can be determined by contacting anti IgG4 antibodies immobilized on a carrier with antibodies in a pool serum of patients allergic to the Ves v 4 polypeptide or obtained from said serum, and, with or without preincubation of labelled Ves v 4 polypeptide with the recombinant antibodies or recombinant antibody fragments or, for comparison, antibodies in a pool serum of patients allergic to said allergen or obtained from said serum, contacting the carrier with said allergen and detecting binding of the labelled Ves v 4 polypeptide to the carrier. For this purpose, the Ves v 4 polypeptide can be labelled with an enzyme, a radioisotope, biotin or a fluorescent marker.

The inhibition by recombinant antibodies or recombinant antibody fragments is considered essentially complete if it is comparable to the inhibition by IgE, IgG or IgG4 antibodies in a pool serum of patients allergic to the Ves v 4 polypeptide or obtained from said serum, i.e. if it varies from that inhibition by 20% or less, preferably by 10% or less, or most preferably, by 5% or less.

The pool serum used in the present invention comprises serum from several patients allergic to the Ves v 4 polypeptide. Preferably, said pool serum comprises the antibodies from the sera of at least 5 patients, at least 10 patients or at least 15 patients allergic to said allergen. For IgE inhibition experiments, patients are preferred that are highly sensitized to the allergen. For IgG and IgG4 inhibition experiments, patients after successful SIT are preferred.

IgE antibodies can be obtained from the pool serum, e.g., by affinity chromatography using anti-human IgE antibodies. Preferably, IgG antibodies are removed from the pool serum, e.g. by pre-treatment with a protein A matrix, such as a protein A column. This step, however, is not essential, as sera of allergic patients in all probability only contain relatively low amounts of allergen-specific IgG antibodies, even though the serum level of IgG is about 10.000 times higher than the serum level of IgE. For example, serum obtained from a birch pollen allergic patients which was purified by affinity chromatography on immobilized Bet v 1, did not contain significant quantities of allergen specific IgG antibodies (Ganglberger et al 2000). IgG4 antibodies can also be obtained from the pool serum by affinity chromatography using anti-human IgG4 antibodies.

The individual antibodies of a generated composition are used for structural analyses of IgE and IgG epitopes, including IgG4 epitopes. Since each composition effects essentially complete inhibition of binding of the Ves v 4-polypeptide to patient-derived IgE and IgG antibodies, including IgG4 antibodies, the individual antibodies of each generated composition are capable of identifying all epitopes on the Ves v 4 polypeptide that are accessible for patient-derived IgE and IgG antibodies, including IgG4 antibodies.

According to the present invention the most potent Ves v 4-related hypoallergenic molecule for specificic immunotherapy is an allergen that does not exhibit allergenicity, contains an array of T cell epitopes that is comparable to that of the corresponding natural allergen, and displays a surface structure that is recognized by human IgG and particularly by human IgG4 antibodies with specificity for the corresponding natural allergen. For the design of such a molecule, the individual antibodies of the different antibody compositions are essential to maintain IgG epitopes upon modification of the IgE epitopes by a structure-based approach.

In a preferred embodiment, the invention provides a polypeptide, wherein one or more IgE epitope(s) present on said polypeptide are altered to reduce the allergenicity of said polypeptide to give an altered polypeptide or modified allergen, respectively.

Figure 4:
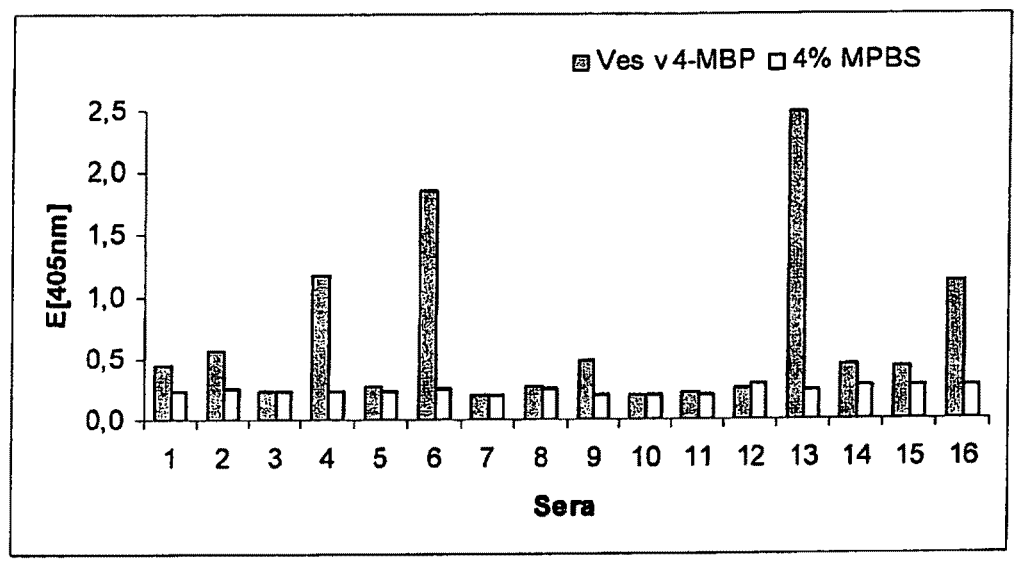
FIG. 4 shows the detection of Ves v 4-MBP produced in *E. coli* with IgE from several sera of yellow jacket venom-allergic individuals, as explained in Example 10.

In a further embodiment, said one or more IgE epitope(s) present on said polypeptide are selected from the group of IgE epitopes listed in Table 4 and Table 5. The immunoreactivity, IgE-reactivity and allergenicity, respectively, of such altered polypeptide or modified allergen can be determined as shown in FIG. 4 and Example 10. In specific embodiments, the present invention provides methods for decreasing the allergenicity (IgE reactivity) of the polypeptides of this invention in a structure-based approach via mutagenesis of IgE epitopes with limited impairment of the residual surface structure important for IgG immunological responses. In a preferred embodiment, the allergenicity of the polypeptides of this invention is reduced by at least 50% while at least 50% of IgG epitopes are maintained. In a more preferred embodiment, the allergenicity of the polypeptides of this invention is reduced by at least 70% while at least 50% of IgG epitopes are maintained. In a most preferred embodiment allergenicity is reduced by at least 90% while at least 50% of IgG epitopes are maintained.

In a further embodiment, the invention provides a method for decreasing the allergenicity of a polypeptide of the invention, preferably of a Ves v 4 polypeptide, or fragments, derivatives and analogs thereof, comprising the steps of a) providing a nucleic acid molecule of the invention or a nucleic acid molecule encoding a polypeptide of the invention or fragments, derivatives and analogs thereof, b) applying site-directed mutagenesis to said nucleic acid molecule so that one or more IgE epitope(s) on the encoded polypeptide is altered to give a modified allergen, and c) determining the reduction in allergenicity of said modified allergen.

For example, IgE epitope(s) present on a given polypeptide or allergen can be determined as shown in Example 10 and in FIG. 4. Such IgE epitope(s) can be selected from the group of IgE epitopes listed in Table 4 and Table 5.

The immunoreactivity, IgE-reactivity and allergenicity, respectively, of such altered polypeptide or modified allergen can be determined as shown in FIG. 4 and Example 10.

In another embodiment, such altered peptides or modified allergens, respectively, can be used in the treatment of allergy or hypersensitivity, respectively, against the *Vespula* venom, preferably of allergy or hypersensitivity against the *Vespula* venom protease Ves v 4, wherein said altered peptides or modified allergens of the invention preferably cause less side effects as compared to the unaltered, wild-type polypeptide or allergen.

VIII. Diagnostic Use of the Ves v 4 Polypeptide, Fragments, Derivatives and Analogs Thereof As used herein, the term diagnostic includes in vitro and in vivo diagnostic assays. Generally, such assays are designed to measure the level of IgE antibodies specific for a given allergen. However, determining the level of allergen-specific antibodies of different isotypes including, but not limited to, antibodies of the IgG and IgA class can also be useful to evaluate the immune status of an allergic patient. For example, a rise in allergen-blocking IgG antibodies, particularly of the IgG4 class (Reid et al 1986), a reduction in the number of mast cells and eosinophils, and a decreased release of mediators (Varney et al 1993) were found to be associated with successful SIT. Therefore, determination of the serum levels of allergen-specific IgE and IgG4 antibodies is useful to analyse the immune status of an allergic patient.

In one embodiment, the invention provides a method for detecting serum IgE or IgG antibodies specific for the polypeptides of the invention, preferably specific for the Ves v 4 polypeptide, or fragments, derivatives and analogs thereof, comprising the step of a) providing serum from an allergic patient, and b) detecting said IgE or IgG antibodies in said serum by a detection method, wherein said detection method is selected from the group consisting of radio-allergosorbent test (RAST), enzyme-linked immunosorbent assays (ELISA), immunoelectrophoresis, immunoblot, immunodotblotting, bead array technology, fluid phase systems, and in vitro mediator release assays (MRA), and wherein the IgG antibodies preferably are IgG4 antibodies.

In a more specific embodiment, said detecting comprises in vitro measuring the ratio of serum IgE and IgG4 antibodies specific for the polypeptides of the invention, preferably specific for the Ves v 4 polypeptide, or fragments, derivatives and analogs thereof, and wherein said method preferably further comprises the step of c) evaluating the success of immunotherapeutical treatment.

Said immunotherapeutical treatment can be the use of the polypeptides of the invention, preferably the Ves v 4 polypetides and fragments thereof for the generation of a medicament for the treatment of allergy against *Vespula* venom, preferably against the *Vespula* venom protease Ves v 4.

In vitro assays for the measurement of allergen-specific serum IgE antibodies or other isotypes such as IgG, and in particular IgG4, include, but are not limited to the radio-allergosorbent test (RAST), various enzyme-linked immunosorbent assays (ELISA) and other IgE-binding techniques such as immunoelectrophoresis, immunoblot, immunodotblotting, bead array technology and various fluid phase systems, and the like. As an alternative to the above listed assay systems, basophil cells derived from patients or from basophil cell lines such as the KU812 can be used for the in vitro measurement of allergen-specific IgE antibodies in serum by in vitro mediator release assays (MRA). The sensitivity and specificity of such assays depend on the availability of pure allergen. In one embodiment, the present invention provides pure Ves v 4 polypeptide, fragments, derivatives and analogs thereof, that are suitable for determining the serum levels of allergen-specific IgE antibodies and other isotypes. The availability of pure Ves v 4 polypeptide, fragments, derivatives and analogs thereof, allows the measurement of serum IgE antibodies or other isotypes that bind specifically to Ves v 4 epitopes. Utilizing such a component resolved allergy test, assessment of sensitization of vespid venom allergic individuals towards Ves v 4 is possible, which in turn will have an impact on the potential immunotherapeutic treatment of these individuals.

In another embodiment, the present invention provides in vitro diagnostic assays on peripheral blood lymphocytes useful for obtaining information on Ves v 4-specific T cell responses, the phenotype of the T cell response, and preferably the T cell epitope(s) of Ves v 4 involved in T cell responses. The immunodominant epitope(s) and the epitope(s) involved in IgE isotype class switch events can be detected, if they are not identical. In particular, the T cell epiotope(s) of Ves v 4 that stimulate proliferation and/or lymphokine secretion of T cells of a phenotype associated with IgE isotype class switching events can be identified for a specific individual, or for a class of individuals who share MHC haplotype or a predominant T cell receptor variable region expression, or both.

In vivo assays for vespid venom allergy generally consist of skin prick sensitivity assays, in which serially diluted amounts of allergen are administered either subcutaneously or intradermally into a patient's skin, and wheel and erythema reactions are detected. Such tests are well known in the art (Biló et al 2005). As with in vitro assays, the availability of pure Ves v 4 allergen greatly increases the value of the results of the in vivo diagnostic assays since cross-reactivity with impurities in extracts prepared from vespid venom sacs can be avoided.

In one embodiment, the invention provides a method for identifying an individual at risk for *Vespula* venom hypersensitivity or allergy, respectively, comprising the step of detecting an immune response raised against one or more of the polypeptides of the invention, preferably against the Ves v 4 polypeptide or fragments; derivatives and analogs thereof.

In a further embodiment said method can be performed as a skin prick sensitivity assay, in which preferably serially diluted amounts of one or more polypeptide(s) of the invention (i.e. the "allergen") is administered preferably either subcutaneously or intradermally into a patient's skin, and preferably wheel and erythema reactions are detected.

In a preferred embodiment, said detection of said immune response is indicative for a risk for *Vespula* venom hypersensitivity. In another preferred embodiment, said polypeptides are for intradermal administration. In another preferred embodiment, said polypeptides are for subcutaneous administration.

In another preferred embodiment, said detection of an immune response is indicative for a risk for hypersensitivity or allergy, respectively, against the polypeptides of the invention, preferably against the Ves v 4 polypeptide, or fragments, derivatives and analogs thereof.

In a further embodiment, the invention provides a kit comprising the following components in one or more containers: a) one or more polypeptide(s) of the invention or fragments, derivatives and analogs thereof, and b) one or more antibodies against said polypeptides, fragments, derivatives and analogs thereof.

IX. Ves v 4-Based Therapeutic Methods

The polypeptides of the invention, and fragments derivatives and analogs thereof are for use as a medicament. In a specific embodiment, the Ves v 4 polypeptide, fragments, derivatives and analogs thereof as well as altered peptides and modified allergens are for use as a medicament.

In one embodiment, the Ves v 4 polypeptide, fragments, derivatives and analogs thereof of the invention are used in specific immunotherapy (SIT) of vespid venom allergy, also referred to as hyposensitization therapy of vespid venom allergy. SIT has proven effective in allergic diseases, particular insect venom allergy. Such therapy may be particularly effective when the allergen or allergens to which the patient is sensitive have been specifically identified and the therapy is targeted to that allergen or those allergens. Therefore, the availability of pure allergen in large quantities is important for specific immunotherapy of allergy.

In one embodiment, the present invention features a method of modulating an immune response by administering the Ves v 4 polypeptide, a fragment, a derivative or an analog thereof to a mammal (such as a human) sensitive to Ves v 4 in a form which results in a decrease in the T cell response of the mammal upon subsequent exposure to the protein allergen. If desired, one or more additional *Vespula* venom polypeptides, or sets of fragments thereof, may also be administered to the subject. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In a specific embodiment, the present invention features a method of modulating an immune response by administering T cell epitope-containing peptides of at least 9 amino acids corresponding to a consecutive amino acid sequence within the *Vespula* venom protease (Ves v 4), to a subject in need thereof in an amount sufficient to inhibit an immune reaction by the subject against the Ves v 4 polypeptide. If desired, T cell epitope-containing peptides of at least 9 amino acids corresponding to a consecutive amino acid sequence within one or more additional *Vespula* venom polypeptides may also be administered to the subject. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

As used herein, a decrease or modification of the T cell response of a mammal sensitive to a protein allergen is defined as non-responsiveness or diminution in symptoms to the protein allergen in the mammal, as determined by standard clinical procedures (see e.g., Varney et al 1991). As referred to herein, a diminution in symptoms to an allergen includes any reduction in the allergic response of a mammal (such as a human) to the allergen following a treatment regimen with a polypeptide as described herein. This diminution in symptoms may be determined subjectively in humans (e.g., the patient fells more comfortable upon exposure to the allergen), or clinically, such as with a standard skin test.

In one embodiment, the polypeptides of the invention and fragments, derivatives and analogs thereof as well as altered peptides and modified allergens are for use in the treatment of allergy against *Vespula* venom.

In another embodiment, the polypeptides of the invention and fragments, derivatives and analogs thereof as well as altered peptides and modified allergens are for use in the treatment of allergy against the *Vespula* venom protease Ves v 4.

In a further embodiment, the polypeptides, or fragments, derivatives and analogs thereof are administered in an amount sufficient to reduce or inhibit an immune reaction against the Ves v 4 polypeptide.

In a further embodiment, the polypeptides or fragments, derivatives and analogs thereof are administered over a period of time in gradually increasing doses.

In a further embodiment, the invention provides a use of the polypeptides of the invention or fragments, derivatives and analogs thereof as well as of altered peptides and modified allergens for the generation of a medicament for the treatment of allergy against the *Vespula* venom, preferably of allergy against the *Vespula* venom protease Ves v 4.

In another embodiment, when altered peptides or modified allergens, respectively, are used in the treatment of allergy or hypersensitivity, respectively, against the *Vespula* venom, preferably of allergy or hypersensitivity against the *Vespula* venom protease Ves v 4, said altered peptides or modified allergens of the invention preferably cause less side effects as compared to the unaltered, wild-type polypeptide or allergen.

The Ves v 4 polypeptide, a fragment, a derivative and an analog thereof can be administered over a period of time in gradually increasing doses effective to reduce the allergic response of the individual to the protein allergen. Examples of routes of administration include parenteral (e.g., intavenous), intradermal, subcutaneous, oral (e.g., sublingual or via inhalation), transdermal (topical), and rectal administrations. The effective amount of the Ves v 4 polypeptide, a fragment, a derivative and an analog thereof will vary according to factors such as the degree of sensitivity of the individual to Ves v 4, the age, sex, and weight of the individual, and the ability of the fragment, derivative, or analog thereof to elicit an antigenic response in the individual. In one embodiment, the amount of Ves v 4 polypeptide administered to an individual corresponds to the amount of Ves v 4 in the venom of vespids that is injected into an individual by a sting. Dosage regimens may be adjusted to provide the optimum therapeutic response. For example, several divided doses may be administered daily.

X. Ves v 4-Based Pharmaceutical Compositions

In one embodiment, the polypeptides of the invention, preferably the Ves v 4 polypeptide, fragments, derivatives and analogs thereof, are incorporated into pharmaceutical compositions suitable for administration. Such compositions typically comprise the Ves v 4 polypeptide, fragments, derivatives or analogs thereof, and a pharmaceutically acceptable carrier. As used herein, a "pharmaceutically acceptable carrier" is intended to include any and all solvents, dispersion media, coatings, antibacterial and antifungal agents, isotonic and adsorption delaying systems, and the like, compatible with the active compound and pharmaceutical administration. The use of such media and agents for pharmaceutically active substances is well known in the art. Supplementary active compounds can also be incorporated into the composition.

In one embodiment, the invention provides a pharmaceutical composition comprising one or more of the polypeptide(s) of the invention and fragments, derivatives and analogs thereof and a pharmaceutically acceptable carrier.

In a further embodiment, the invention provides a pharmaceutical composition comprising one or more of the polypeptide(s) of the invention and fragments, derivatives and analogs thereof and a pharmaceutically acceptable carrier, wherein the one or more polypeptide(s) map the total length of the Ves v 4 polypeptide.

In a further embodiment, the invention provides a pharmaceutical composition comprising one or more of the polypeptide(s) of the invention and fragments, derivatives and analogs thereof and a pharmaceutically acceptable carrier, further comprising one or more additional polypeptide(s) or fragments thereof. Said one or more additional polypeptide(s) or fragments thereof preferably are selected from the group consisting of Ves v 1 polypeptide (phospholipase A1), Ves v 2a polypeptide (hyaluronidase), Ves v 2b polypeptide, Ves v 3 polypeptide (dipeptidylpeptidase), Ves v 5 polypeptide, glycosylated IgE-binding proteins and analogs or derivatives thereof.

In a further embodiment, the invention provides a pharmaceutical composition comprising one or more of the polypeptide(s) of the invention and fragments, derivatives and analogs thereof and a pharmaceutically acceptable carrier, wherein the one or more polypeptide(s) comprises one or more T cell epitope-containing peptides of at least 9 amino acids corresponding to a consecutive amino acid sequence within the *Vespula* venom protease Ves v 4.

The pharmaceutical compositions of the invention, comprising one or more polypeptide(s) of the invention and fragments derivatives and analogs thereof are for use as a medicament. In a specific embodiment, the pharmaceutical compositions of the invention comprising the Ves v 4 polypeptide, fragments, derivatives and analogs thereof are for use as a medicament.

In one embodiment, the pharmaceutical compositions of the invention comprising one or more polypeptide(s) of the invention and fragments, derivatives and analogs thereof are for use in the treatment of allergy against *Vespula* venom, preferably of allergy against the *Vespula* venom protease Ves v 4.

In a further embodiment, the pharmaceutical composition of the invention comprising one or more polypeptide(s) of the invention and fragments, derivatives and analogs thereof are administered in an amount sufficient to reduce or inhibit an immune reaction against the Ves v 4 polypeptide.

In a further embodiment, the pharmaceutical compositions of the invention comprising one or more polypeptide(s) of the invention and fragments, derivatives and analogs thereof are administered over a period of time in gradually increasing doses.

In a further embodiment, the invention provides a use of the pharmaceutical compositions of the invention comprising one or more polypeptide(s) of the invention or fragments, derivatives and analogs thereof for the generation of a medicament for the treatment of allergy against the *Vespula* venom, preferably of allergy against the *Vespula* venom protease Ves v 4.

In another embodiment, the pharmaceutical composition includes an additional polypeptide, e.g., a second, third, fourth, or more *Vespula* venom polypeptide or polypeptides. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In another embodiment, the present invention features a pharmaceutical composition comprising Ves v 4 polypeptide fragments of the invention, preferably between 20-150 amino acids in length, wherein each fragment contains one or more B cell epitopes and one or more T cell epitopes, and a pharmaceutically acceptable carrier. In a preferred embodiment, the composition comprises a set of polypeptide fragments that map the total length of the Ves v 4 polypeptide.

In another embodiment, the pharmaceutical composition includes polypeptide fragments derived from an additional polypeptide, e.g., a second, third, fourth, or more *Vespula* venom polypeptide or polypeptides. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

In another embodiment, the present invention features a pharmaceutical composition comprising T cell epitope containing peptides of at least 9 amino acids corresponding to a consecutive amino acid sequence within the *Vespula* venom protease (Ves v 4) wherein the peptides are capable of stimulating T cells of subjects allergic to Ves v 4. In a preferred embodiment, the composition comprises a set of T cell epitope-containing peptides capable of stimulating T cells of the great majority of subjects allergic to Ves v 4.

In another embodiment, the pharmaceutical composition includes T cell epitope-containing peptides of at least 9 amino acids corresponding to a consecutive amino acid sequence within an additional polypeptide, e.g., a second, third, fourth, or more *Vespula* venom polypeptide or polypeptides. The additional *Vespula* venom polypeptides can include, e.g., the Ves v 1 polypeptide (phospholipase A1), the Ves v 2a polypeptide (hyaluronidase), the Ves v 2b polypeptide, the Ves v 3 polypeptide (dipeptidylpeptidase), the Ves v 5 polypeptide, glycosylated IgE-binding proteins, or analogs or derivatives thereof.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents, antioxidants such as ascorbic acid or sodium bisulfite, chelating agents such as ethylenediaminetetraacetic acid, buffers such as acetates, citrates or phosphates and agents for the adjustment of toxicity such as sodium chloride or dextrose. The pH can be adjusted with acids or bases, such as hydrochloric acid or sodium hydroxide. In many cases, it will be preferable to include isotonic agents, for example, sugars, polyalcohols such as mannitol, sorbitol, sodium chloride in the composition. The composition should be fluid to the extent that easy syringability exists. The proper fluidity can be maintained, for example, by the use of a coating such as lecithin, by the maintenance of the required particle size in the case dispersion and by use of surfactants. The composition must be stable under the conditions of manufacture and storage and must be preserved against the contaminating action of microorganisms such as bacteria and fungi. Prevention of the action of microorganisms can be achieved by various antibacterial and antifungal agents such as parabens, chlorobutanol, phenol, ascorbic acid, thimoseral, and the like. Delayed absorption of the injectable compositions can be achieved by including in the composition an agent such as aluminium monostearate and gelatin. In all cases, the composition must be sterile. Sterile injectable solutions can be prepared by filtered sterilization. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The parenteral preparation can be enclosed in ampoules, disposable syringes or multiple dose vials made of glass or plastic.

Oral compositions generally include an inert diluent or an edible carrier. They can be enclosed in gelatine capsules or compressed into tablets. For the purpose of oral therapeutic administration, the active compound can be incorporated with excipients and used in the form of tablets, troches, or capsules. Oral compositions can also be prepared using a fluid carrier for use as mouthwash, wherein the active compound in the fluid carrier is swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatine; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavouring.

For administration by inhalation, the active compounds are delivered in the form of an aerosol spray from a pressured container or dispenser which contains a suitable propellant, e.g. a gas such as carbon dioxide, or a nebulizer.

For transmucosal or transdermal administration, penetrants appropriate to the barrier to be permeated are used in the formulation. Such penetrants are generally known in the art, and include for transmucosal administration, for example; detergents, bile salts, and fusidic acid derivatives. Transmucosal administration can be accomplished through the use of nasal sprays or suppositories. Suppositories can be prepared using conventional suppository base such as cocoa butter or other glycerides. For transdermal administration, the active compounds are formulated into ointments, salves, gels, or creams as generally known in the art. For rectal delivery the compounds can also be prepared in the form of retention enemas.

In a further embodiment, the active compounds are prepared with carriers that will protect the active compounds against rapid elimination from the body, such as controlled release formulation, including implants and microencapsulated delivery systems. Biodegradable, biocompatible polymers can be used, such as ethylene vinyl acetate, polyanhydrides, polyglycolic acid, collagen, polyorthoesters, and polyacetic acid. Methods for preparation of such formulations will be apparent to those skilled in the art. The materials can also be obtained commercially. Liposomal suspensions can also be used as pharmaceutically acceptable carriers. These can be prepared according to methods known to those skilled in the art.

For oral and parenteral applications it is advantageous to formulate the compositions in dosage unit form for ease of administration and uniformity of dosage. Dosage unit form as used herein refers to physically discrete units suited as unitary dosages for the subject to be treated. Each unit contains a predetermined quantity of the active compound calculated to produce the desired therapeutic effect in association with the included pharmaceutical carrier. The specification for the dosage unit forms of the invention are dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration.

EXAMPLES

Example 1

Cloning of Ves v 4

Materials and Methods cDNA Synthesis

Total RNA was isolated from the separated stinger with attached venom sack and additional glands of yellow jacket (*Vespula vulgaris*) using peqGold TriFast™ (Peqlab Biotechnologie, Erlangen, Germany). SuperScript III Reverse Transcriptase (Invitrogen, Karlsruhe, Germany) was used to synthesize cDNA from the isolated total RNA. RNaseOut™ recombinant ribonuclease inhibitor (0.1 µl) (Invitrogen, Karlsruhe, Germany) was added to the standard 20 µl reaction mix containing 5 µl venom gland RNA. Reverse transcription was performed at 50° C. for 60 minutes. First strand cDNA was used as template for PCR amplification of Api m 5 and Ves v 3 DNA sequences.

Isolation of Ves v 4 Fragment

A fragment of the Ves v 4 ORF was amplified from *Vespula vulgaris* venom gland cDNA with Pfu DNA polymerase (Fermentas, St. Leon-Rot, Germany) using the degenerated primer 5'-NAC DGC KGC YCA YTG-3'. DNA from the PCR reaction was isolated from 1% agarose gels (peqGOLD universal agarose, Peqlab, Erlangen, Germany) using the peqGOLD Gel Extraction Kit (Peqlab). Subcloning for sequencing was done using Zero Blunt TOPO PCR Cloning Kit (Invitrogen) with pCR-Blunt II-TOPO vector. The ligated DNA was transformed into *Escherichia coli* of the strain XL1Blue by electroporation (2 mm cuvettes, EasyJect+; Eurogentec, Seraing, Belgium) and selected on ampicillin agar plates.

Generation of Full-Length Ves v 4

After sequencing of selected subcloned cDNA clones and verification of the sequence, the primer 5'-GGA TGT ACG ATT ATA TCA TCA ATA AG-3' was deduced from the sequence and used for cDNA synthesis as already described. The cDNA was used for 5'RACE employing the 5'/3'RACE Kit, Second Generation (Roche, Grenzach, Germany) according to the recommendations of the manufacturer. Subsequent nested PCR was performed using the primers 5'-CCT TTG TAT CGT TAA TTG GCC ATG-3' and 5'-GTT CTC CAA CAA CAA CTC CTA-3'.

The obtained cDNA fragments were used as basis for further sequence determination. Full length cDNA was then amplified using the forward primer 5"-ATG AAA TTA GAT AAT TTT TTT TTA ATA CTT TAT G-3' and the reverse primer 5'-TTA ATA CGC CTG ACA ATA TAT TTC-3'.

After sequencing of selected full length cDNA clones and verification of the sequence, the clone was used for secondary amplification of the coding region of the mature chain with Pfu DNA polymerase using primers incorporating 5" BamHI and 3' NotI restriction sites as well as a 3" V5 epitope and a 10 fold His-tag. The PCR product was subcloned into the BamHI and NotI digested baculovirus transfer vector pAcGP67-B after restriction digest with the respective enzymes.

Results

Figure 1:
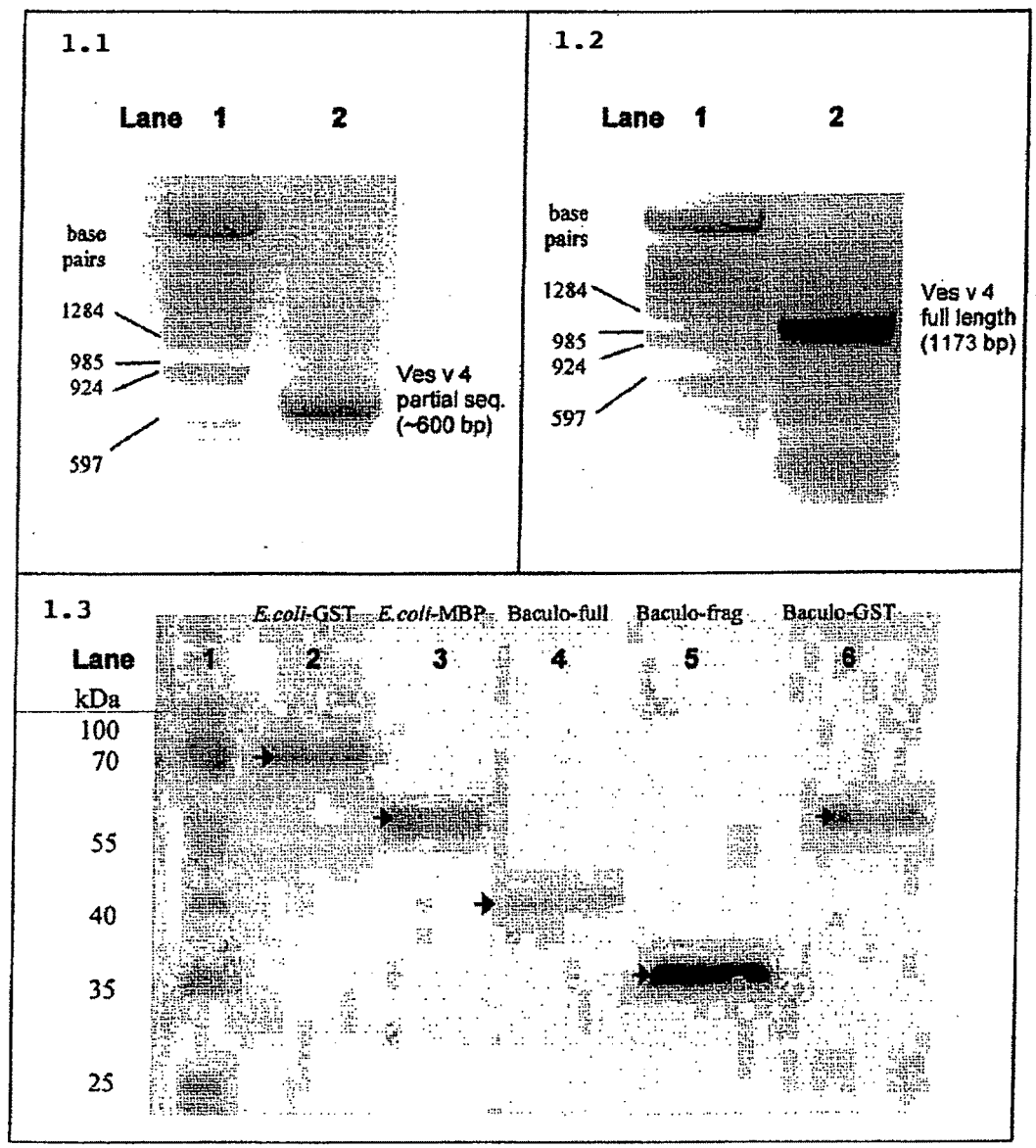
FIG. 1 shows the cloning and expression of Ves v 4, as explained in Example 1 (FIGS. 1A and 1B) and in Examples 2 and 3 (FIG. 1C).

Using degenerated primers, targeting conserved serine protease motifs, a fragment of the Ves v 4 gene was amplified from cDNA as shown in FIG. 1 box A. Depicted is the electrophoretic analysis in 1% agarose gel of the gene fragment derived from PCR with degenerated primers. An approximately 600 base pair fragment (lane 2) was generated, as estimated from comparison with the molecular size marker (Lambda DNA/Eco47I, Fermentas GmbH, St Leon-Rot) in lane 1. The fragment was subsequently used to perform 5'-RACE methods to generate and select a full length clone. The full length clone consists of a 1173 base pair DNA as shown in lane 2 of the electrophoretic analysis in 1% agarose gel in FIG. 1 box B, in comparison to the molecular size standard in lane 1.

The nucleic acid sequence was analysed and is given in SEQ ID NO:1.

Discussion

The full-length cDNA of Ves v 4 of 1173 base pairs (including the stop codon) has been successfully isolated from the stinging apparatus of *Vespula* vulgaris. Sequencing verified the isolation of a new serine protease-like protein containing a N-terminal CUB domain and putative signal peptide sequence, coding for a 390 amino acid long protein (see SEQ ID NO:1 and SEQ ID NO:2).

Example 2

Recombinant Bacterial Expression and Purification of Ves v 4

Materials and Methods

For expression of Ves v 4 in *E. coli*, the cDNA was cloned into the prokaryotic expression vector pMAL-c2x (NEB, Frankfurt, Germany). Expression in XL1 Blue *E. coli* cells and purification of the fusion protein was performed according to the recommendations of the manufacturers.

Results

The gene sequence is used to construct several expression vectors to produce recombinant protein. As an example, FIG. 1 box C shows the analysis of Western blotting and detection of recombinant proteins with anti-V5 antibodies derived from expression in *E. coli* as fusion to the glutathione-S-transferase (GST) domain (lane 2), fusion to the maltose-binding-protein (MBP) domain (lane 3).

Discussion

The full length sequence of Ves v 4 was cloned, sequenced and used for successful expression of the recombinant proteins. The recombinant expression in prokaryotic systems revealed difficulties in obtaining suitable amounts of soluble protein which was subsequently improved by expression as fusion proteins with GST- or MBP-moieties. Purification was simplified by introduction of a His-Tag and metal affinity chromatography.

Example 3

Production of Recombinant Ves v 4 in Sf9 Cells and Purification

Materials and Methods

Production of Recombinant Baculovirus

*Spodoptera frugiperda* cells (Sf9, Invitrogen, Karlsruhe, Germany) were grown at 27° C. in serum-free medium (Express Five SFM, containing 16.5 mM glutamine and 10 µg/ml gentamycin; Invitrogen, Karlsruhe, Germany). Cell density was determined by haemocytometer counts, cell viability was evaluated by staining with Trypan Blue. Recombinant baculovirus was generated by cotransfection of Sf9 cells with BaculoGold bright DNA (BD Pharmingen, Heidelberg, Germany) and the baculovirus transfer vector pAcGP67-B Ves v 4 according to recommendations of the manufacturer. High titer stocks were produced by three rounds of virus amplification and optimal MOI for recombinant protein expression was determined empirically by infection of Sf9 cells in 100 ml suspension flask ($1.5$-$2 \times 10^6$ cells/ml in 20 ml suspension culture) with serial dilutions of high titer virus stock.

Expression in Baculovirus-Infected Sf9 Cells

High titer stocks of recombinant baculovirus containing the Ves v 4-coding DNA were used to infect SF9 cells ($1.5$-$2.0 \times 10^6$ cells per ml) in a 2000 ml suspension flask (400 ml suspension culture). For protein production the cells were incubated at 27° C. and 110 rpm for 72 h.

Protein Purification

The supernatant of baculovirus-infected cells was collected, adjusted to pH 8 and centrifuged at 4000×g for 5 minutes. Supernatants were applied to a nickel-chelating affinity matrix (NTA-agarose, Qiagen, Hilden, Germany). The column was washed with NTA-binding buffer (50 mM sodium phosphate, pH 7.6, 500 mM NaCl) and pre-eluted with NTA-binding buffer containing 20 mM imidazole. The recombinant protein was eluted from the matrix with NTA-binding buffer containing 300 mM imidazole. Purification was confirmed by SDS-PAGE.

Results

The gene sequence is used to construct expression vectors to produce recombinant protein in eukaryotic cells. As an example, FIG. 1 box C shows the analysis of Western blotting and detection of recombinant proteins with anti-V5 antibodies derived from expression in insect cells by the Baculovirus system (lanes 4-6) after separation by 7.5% poly-acryl amide gel electrophoresis (PAGE). For estimation of the molecular size of the proteins a standard marker in lane 1 is used. In FIG. 1 box C lane 4 the recombinant full-length protein with additional V5 and 10×His-Tag is shown. In lane 5 a truncated form without CUB domain is shown. In lane 6 the PAGE analysis of full-length protein with additional GST-domain is shown.

Discussion

The full length sequence of Ves v 4 was cloned, sequenced and used for successful expression of the recombinant proteins. The protein is successfully expressed in eukaryotic expression system, like the Baculovirus system utilizing an insect cell culture. Purification was simplified by introduction of a His-Tag and metal affinity chromatography.

Example 4

Production of Recombinant Ves v 4 in HighFive Cells and Purification

Materials and Methods

Production of Recombinant Baculovirus

*Trichoplusia ni* cells (HighFive, Invitrogen, Karlsruhe, Germany) were grown at 27° C. in serum-free medium (Express Five SFM, containing 16.5 mM glutamine and 10 µg/ml gentamycin; Invitrogen, Karlsruhe, Germany). Cell density was determined by haemocytometer counts, cell viability was evaluated by staining with Trypan Blue. Recombinant baculovirus was generated by cotransfection of HighFive cells with BaculoGold bright DNA (BD Pharmingen, Heidelberg, Germany) and the baculovirus transfer vector pAcGP67-B Ves v 4 according to recommendations of the manufacturer. High titer stocks were produced by three rounds of virus amplification and optimal MOI for recombinant protein expression was determined empirically by infection of High-Five cells in 100 ml suspension flask ($1.5$-$2 \times 10^6$ cells/ml in 20 ml suspension culture) with serial dilutions of high titer virus stock.

Expression in Baculovirus-Infected HighFive Cells

High titer stocks of recombinant baculovirus containing the Ves v 4-coding DNA were used to infect HighFive cells ($1.5$-$2.0 \times 10^6$ cells per ml) in a 2000 ml suspension flask (400 ml suspension culture). For protein production the cells were incubated at 27° C. and 110 rpm for 72 h.

Protein Purification

The supernatant of baculovirus-infected cells was collected, adjusted to pH 8 and centrifuged at 4000×g for 5 minutes. Supernatants were applied to a nickel-chelating affinity matrix (NTA-agarose, Qiagen, Hilden, Germany). The column was washed with NTA-binding buffer (50 mM sodium phosphate, pH 7.6, 500 mM NaCl) and pre-eluted with NTA-binding buffer containing 20 mM imidazole. The recombinant protein was eluted from the matrix with NTA-binding buffer containing 300 mM imidazole. Purification was confirmed by SDS-PAGE.

Results

The gene sequence is used to construct expression vectors to produce recombinant protein in eukaryotic cells, e.g. insect derived (*T. ni*) HighFive cells.

Discussion

The full length sequence of Ves v 4 was cloned, sequenced and used for successful expression of the recombinant proteins in HighFive cells. In comparison with the expression in SF9 cells a different expression yield and glycosylation pattern regarding a(1,3)-fucosylation was found.

Example 5

Analysis of Homologies

Materials and Methods

The nucleic acid sequence of Ves v 4 was used for comparison with other known sequences. An online BLAST search (Altschul et al 1990; Morgulis et al 2008) was performed and sequences suitable for further analysis and alignment identified. The sequences were pairwise aligned using Align-X from the NTI Vector software package (Version 10, Invitrogen Inc) and the degree of sequence identity calculated.

The ClustalW2 multiple sequence alignment programme (Higgins et al 1994; Lopez et al 1997; Larkin et al 2007), available from the EMBL-EBI web site, was used with standard settings to construct a multiple alignment of selected related sequences with Ves v 4.

Results

Four proteins have been selected by identification of sequence similarity to Ves v 4. The nucleic acid and protein sequences of Ves v 4 have been aligned with Magnvesin from *Vespa magnifica* (Han et al 2008), Pol d 4 from *Polistes dominulus* (Winningham et al 2004), Api m 7 from *Apis mellifera* (Winningham et al, 2004) and Bom p 4 from *Bombus pennsylvanicus* (Hoffman and Jacobson 1996). The sequences have been retrieved from public domain sequence databases.

Magnvesin from the venom of the hornet *Vespa magnifica* is a 28 kDa serine protease. A 1250 base pair full-length clone has been identified, coding a proprotein of 305 amino acids. The mature protein length is 242 amino acids. The sequence analysis revealed a N-terminal 48 amino acid domain with high homology to the CUB domain of Ves V 4, not seen in other venom proteases. The pairwise alignment reveals that the homology to Ves v 4 on DNA level, according to the given definition, is 72%, on protein level it is 69%. The pairwise alignment of Ves v 4 with Magnvesin is depicted in FIG. 2.

Pol d 4 is a serine protease from the venom of the European paper wasp. The theoretical molecular weight is 27 kDa. Higher homology in pairwise alignment to Ves v 4 can be found in the C-terminal protease domain and is 46% on DNA level and 35% on protein level for the whole sequence length.

Api m 7 is a protease from the honeybee venom. The theoretical molecular weight is 39 kDa. The sequence shows N-terminal CUB and C-terminal protease domains. The most homology on protein level to Ves v 4 is seen in the protease domain, the difference is less on DNA level. The pairwise homology analysis with Ves v 4 shows 53% DNA level, and 35% on protein level.

Bom p 4 is a serine protease from bumblebee venom. The protein has a theoretical molecular weight of 27 kDa and pairwise sequence alignment analysis shows limited homology to the protease domain. Homology to Ves v 4 on DNA level not known, on protein level it is 18%.

The multiple alignments of all above sequences on protein level are depicted in FIG. 2.

Discussion

Alignment of Ves v 4 sequences to known sequences showed the expected homology to serine proteases from other closely related species. The recently published sequence of Magnvesin from the closely related hymenoptera species *Vespa magnifica* exhibits the highest sequence homology to Ves v 4 of all identified genes.

Example 6

Analysis of Secondary Structural Domains of Ves v 4

Materials and Methods

The online bioinformatics tool SWISS-Model (Arnold et al, 2006) was used to predict the secondary structure of Ves v 4. The protein sequence was used as input with standard settings. In addition, the domain structure was analysed using the online bioinformatics tool InterProScan (Quevillon et al, 2005). As with SWISS-Model the protein sequence was used as input with standard settings.

Results

The result of the SWISS-Model analysis is depicted in FIG. 4. Larger stretches of beta-sheet structures are predicted throughout the protein. In addition, two smaller C-terminal patches of alpha-helical structure were predicted.

The analysis with the InterScanPro tool shows 3 motifs in the Ves v 4 sequence. A putative signal peptide sequence was identified within residues 1-21. Using the SignalP 3.0 server of the Technical University of Denmark (Emanuelsson et al, 2007) this signal peptide prediction has been verified. The second predicted motif is a CUB domain spanning residues 26-136. The third motif represents a serine protease-like domain. This domain includes the residues 146-379. The depiction of the position of predicted domain structures can be found in FIG. 3.

Discussion

The analysis of the secondary structure of Ves v 4 reveals the expected domain of serine proteases, in alignment with the previous sequence homology analysis. In addition a CUB domain was identified, of which the function is unknown.

Example 7

Selection of Ves v 4 Fragments

Materials and Methods

Based on the analysis of the secondary structure of Ves v 4, fragments have been selected to preserve structural motifs, representing possible conformational B cell epitopes and including linear T cell epitopes and covering the range of reactivities. The length of the fragments was selected to enable simplified cloning and expression (approximately 150 and 100 amino acids) or even chemical synthesis of the peptides (approximately 50 amino acid length) and usability for, e.g. different pharmaceutical applications.

Results

The selection of peptide fragments and position in Ves v 4 molecule with the different targeted length is given in Table 1. The positioning of the differently sized fragments is shown in FIGS. 5, 6 and 7.

Discussion

The secondary structure of Ves v 4 provided the basis for the selection of peptide fragments to provide the optimal presentation of B- and T-cell epitopes for diagnosis and therapeutic approaches in insect venom allergy.

Example 8

Analysis of T Cell Epitopes of Ves v 4

Materials and Methods

The analysis of linear T cell epitopes was done using specific weight matrices with the online prediction tool NetMHCII (Morten et al 2007), provided by the Center for Biological Sequence Analysis (CBS) of the Technical University of Denmark with standard settings for all 14 HLA-DR alleles covering the 9 HLA-DR supertypes.

The prediction tool NetMHCIIPAN (Nielsen et al 2008) on the CBS web site was used to predict T cell epitopes in a range of similar HLA-DR alleles using artificial neural networks. For the prediction 15 alleles from DRB1*01xx pool of alleles were used.

Results

The protein sequence of Ves v 4 (SEQ ID NO:2) without signal peptide was used as input for the prediction programme. According to the predicted affinity, putative 15mer T cell peptides were listed and are shown in Tables 2 and 3. Table 2 shows the results from the analysis in regard to the HLA-DR supertypes. Table 3 shows the more detailed results of the analysis within one HLR-DR supertype. Results were limited to peptides with predicted higher affinity to the corresponding MHC I molecules.

Discussion

The results from the prediction of T cell epitopes shows the restriction regarding to human MHC alleles and predicted affinity. The distribution of peptides spans nearly the whole length of the Ves v 4 molecule.

Example 9

Analysis of Linear B Cell Epitopes of Ves v 4

Materials and Methods

The protein sequence of Ves v 4 was used for prediction of linear B cell epitopes employing the online server tool BepiPred 1.0b (Larsen et al 2006). The protein sequence was used as input with standard settings.

Results 13 peptids were predicted by BepiPred to represent linear B cell epitopes. The results are shown in Table 6. The length of the peptides varies from 1-16 residues. The position of the epitopes is given in accordance with the numbering in SEQ ID NO: 2.

Discussion

13 Potential linear B cell epitopes of Ves v 4 have been predicted using BepiPred 1.0b.

Example 10

Immunoreactivity of Ves v 4

Materials and Methods

For assessment of specific IgE immunoreactivity of human sera with purified recombinant Api m 5 and Ves v 3 in ELISA, 384 well microtiter plates (Greiner, Frickenhausen, Germany) were coated with 20 µl of purified recombinant Ves v 4-MBP (20 µg/ml) at 4° C. overnight and blocked with 40 mg/ml MPBS at room temperature. Afterwards human sera were diluted 1:1 with 5 mg/ml BSA in PBS and incubated in a final volume of 20 µl for 4 hours at room temperature. Wells were washed 4 times with PBS before bound IgE was detected with a monoclonal alkaline phosphatase-conjugated mouse anti-human IgE antibody (BD Pharmingen, Heidelberg, Germany) diluted 1:1000. Wells were again washed 4 times with PBS and 50 µl of substrate solution (5 mg/ml 4-nitrophenylphosphate, AppliChem, Darmstadt, Germany) per well were added. After 30 minutes the plates were read at 405 nm. The cutoff was calculated as the mean of the negative controls plus 2 SDs.

Results

The results of the ELISA experiment are shown in FIG. 4. Detection of Ves v 4-MBP produced in *E. coli* with IgE from several sera of yellow jacket venom-allergic individuals.

Discussion 16 patients allergic to wasp venom have been tested for reactivity to Ves v 4. Of this panel 4 patients showed strong reaction towards the MBP-fusion protein which was correctly folded, other 5 patients showed weaker reactivity. In total 56% of the tested patients showed reactivity for Ves v 4-MBP.

Example 11

Identification of Nucleic Acid Molecules from the Family Vespidae Hybridizable to the Nucleic Acid Encoding Ves v 4

Materials and Methods

Fragments of the Ves v 4 ORF were amplified from venom gland cDNA from *Vespula vulgaris* and *Vespula germanica*. 1 µg of the isolated DNA was separated on a 1% agarose gel and blotted to a Hybond-NX nylon membrane (GE Healthcare) by alkaline transfer. After UV-crosslinking and blocking of the membrane with 1% blocking reagent (Roche) the membrane was incubated with the probe at 42° C. overnight.

The probe was generated from DNA from the PCR reaction using *Vespula* vulgaris cDNA was isolated from 1% agarose gels (peqGOLD universal agarose, Peqlab, Erlangen, Germany) using the peqGOLD Gel Extraction Kit (Peqlab). 1 µg of DNA was used for generation of a DIG labelled probe using the DIG DNA Labelling Kit (Roche) according to recommendations of the manufacturer. After washing with 2×SSC buffer, the membrane was blocked again and then incubated with anti-DIG-AP Fab fragments, diluted 1:10000 in 1% blocking reagent for 30 minutes. Visualization of bound Fab fragments was performed with nitrotetrazolium blue and chloride/5-bromo-4-chloro-3-indoyl phosphate according to standard protocols.

Results

The results of the hybridisation experiment under low stringency conditions are shown in FIG. 8. Southern Blot of Ves v 4 fragment with genomic DNA from *Vespula germanica*.

Discussion

As shown in FIG. 8 the probe derived from *Vespula* vulgaris also hybridised to the gene fragment derived from the species *Vespula germanica*, and could be detected. The strong

Example 12

Recombinant Bacterial Expression and Purification of Ves v 4 as a Non-Fusion Protein Materials and Methods For expression of Ves v 4 as a non-fusion protein in *E. coli*, the cDNA was cloned into the prokaryotic expression vector pET22-b(+) (Novagen, Germany) by concomitant deletion f the pelB leader sequence and introduction of a C-terminal 10 fold His-Tag and a V5 epitope. For Expression BL21DE3 *E. coli* cells were used and the insoluble protein was purified under denaturing conditions according to the recommendations of the manufacturers.

Results

Figure 9:
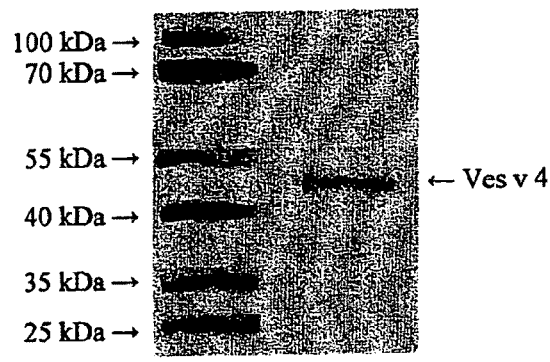
FIG. 9 shows a Western blot of the purified *Vespula vulgaris* venom protease Ves v 4 recombinantly produced in *E. coli* host cells, as explained in Example 12.

The non-fusion protein of Ves v 4 could be obtained in insoluble form from expression in *E. coli*. Purification under denaturating conditions using IMAC resulted in purified protein of the expected molecular weight as proven by Western blotting with an anti-V5 antibody (FIG. 9).

Discussion

The full length sequence of Ves v 4 was cloned, sequenced and used for successful expression of the recombinant non-fusion protein. The recombinant production of the non-fusion protein resulted in insoluble protein and no soluble protein could be observed. Using denaturating conditions, the recombinant protein could be purified via IMAC whereas the protein yield was low.

Example 13

Immunoreactivity of the Recombinant Ves v 4 Non-Fusion Protein

Materials and Methods

For assessment of specific IgE immunoreactivity of human sera with the purified recombinant Ves v 4 non-fusion protein the ELISA procedure described in Example 10 was used.

Results

Figure 10:
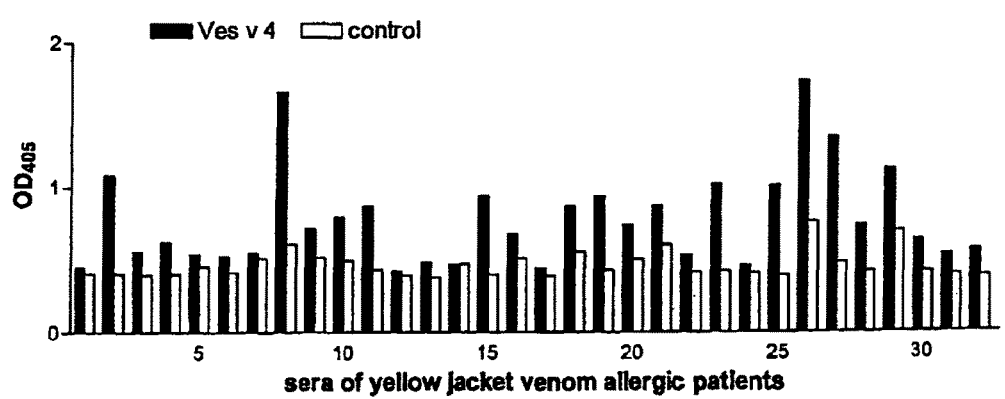
FIG. 10 shows ELISA analysis of IgE immunoreactivity of 32 human sera with the purified recombinant *Vespula vulgaris* venom protease Ves v 4, as explained in Example 13.

From the 32 human sera analysed in the ELISA system, 7 showed specific IgE immunoreactivity with the recombinant Ves v 4 non-fusion protein as shown in FIG. 10.

Discussion

The percentage of specific IgE immunoreactivity with the recombinant Ves v 4 non-fusion protein of 22% is in accordance with the specific IgE immunoreactivity observed for the MBP fusion proteins of Ves v 4.

REFERENCES

Altschul S. F., Gish W., Miller W., Myers E. W. and Lipman D. J. Basic local alignment search tool. J. Mol. Biol. 1990; 215:403-410.

Arnold K. et al. The SWISS-MODEL Workspace: A web-based environment for protein structure homology modelling. [online, last accessed 23 Jan. 2009] http://swissmodel.expasy.org/SWISS-MODEL.html Bioinformatics 2006; 22:195-201.

Asgari S., Zhang G., Zareie R., and Schmidt O. A serine proteinase homolog venom protein from endoparasitoid wasp inhibits melanization of the host hemolymph. Insect Biochem. Mol. Biol. 2003; 33:1017-1024.

Barnard, J. H. Studies of 400 Hymenoptera sting deaths in United States. J. Allergy Clin Immunol 1973; 52:259-264.

Bauer L. et al. Modulation of the allergenic immune response in BALB/c mice by subcutaneous injection of high doses of the dominant T cell epitope from the major birch pollen allergen Bet v 1. Clin. Exp. Immunol. 1997; 107:536-541.

Benjamin D. C. et al. The Antigenic Structure of Proteins: A Reappraisal. Ann. Rev. Immunol. 1984; 2: 67-101.

Bilo, B. M., Rueff, F., Mosbech, H., Bonifazi, F., Oude-Elberink, J. N. G., and the EAACI Interest Group on Insect Venom Hypersensitivity. Diagnosis of Hymenoptera venom allergy. Allergy 2005; 60:1339-1349.

Blank S. et al. Identification and recombinant expression of a novel IgE-reactive 70 kDa carboxylesterase from *Apis mellifera* venom. Submitted, Uniprot entry B2D0J5.

Boel E. et al. Functional human monoclonal antibodies of all isotypes constructed from phage display library-derived single-chain Fv antibody fragments J. Immunol. Meth. 2000; 26: 153-166.

Bork P. and Beckmann, G. The CUB domain: a widespread module in developmentally regulated proteins. J. Mol. Biol. 1993; 231:539-545.

Briner et al. Peripheral T-cell tolerance induced in naive and primed mice by subcutaneous injection of peptides from the major cat allergen Fel d I. Proc. Natl. Acad. Sci. USA 1993; 90:7608-7612.

Carballido J. M. et al. T Cell Epitope Specificity in Human Allergic and Nonallergic Subjects to Bee Venom Phospholipase A2. J. Immunol. 1993; 150:3582-3591

Chou P. Y. and Fasman G. D. Prediction of protein conformation Biochemistry 1974; 13:222-245.

Dhillon M. et al. Mapping human T cell epitopes on phospholipase A2: The major bee-venom allergen. J. Allergy Clin. Immunol. 1992; 90:42-51.

Edwards M. R. et al. Analysis of IgE Antibodies from a Patient with Atopic Dermatitis: Biased V Gene Usage and Evidence for Polyreactive IgE Heavy Chain Complementary-Determining Region 3. J. Immunol 2002; 168: 6305-6313.

Elbein A. D. The Role of N-linked Oligosaccharides in Glycoprotein function. Trends in Biotech 1991; 9:346-352.

Emanuelsson O. et al. Locating proteins in the cell using TargetP, SignalP, and related tools. [online, last accessed 23 Jan. 2009] http://www.cbs.dtu.dk/services/SignalP/ Nature Protocols 2007; 2:953-971.

Finkelman F. D. et al. Lymphokine Control of in vivo Immunoglobulin Isotype Selection Ann. Rev. Immunol. 1990; 8:303-333.

Fraternali F. and Cavallo L. Parameter optimized surfaces (POPS): analysis of interactions and conformational changes in the ribosome. Nucleic Acids Res. 2002; 30:2950-2960.

Ganglberger E. et al. Allergen mimotopes for 3-dimensional epitope search and induction of antibodies inhibiting human IgE. FASEB J. 2000; 14:2177-2184.

Greene A. and Breisch N. L. Avoidance of bee and wasp stings: an entomological perspective. Curr. Opin. Allergy Clin. Immunol. 2005; 5:337-341.

Haim B. et al. Characterization and anticoagulant activity of a proteolytic enzyme from *Vespa orientalis* venom. Toxicon 1999; 37:825-829.

Han J. et al. An anticoagulant serine protease from the wasp venom of *Vespa magnifica*. NCBI nucleic acid database entry EU267370. Toxicon 2008; 51:914-922.

Hancock K. et al. False positive reactivity of recombinant, diagnostic, glycoproteins produced in High Five insect cells: Effect of glycosylation. J. Immunol. Meth. 2008; 330:130-136.

Hemmer W. et al Identification by immunoblot of venom glycoproteins displaying immunoglobulin E-binding N-glycans as cross-reactive allergens in honeybee and yellow jacket venom. Clin. Exp. Allergy 2004; 34:460-469

Higgins D. et al. CLUSTAL W: improving the sensitivity of progressive multiple sequence alignment through sequence weighting, position-specific gap penalties and weight matrix choice. Nucleic Acids Research 1994; 22:4673-4680.

Hoffman, D. R. Allergens in Hymenoptera XIII: isolation and purification of protein components from three species of vespid venoms. J. Allergy Clin. Immunol. 1985; 75:599-605.

Hoffman D. R. and Jacobson R. S. Allergens in Hymenoptera venom XXVII: Bumblebee enom allergy and allergens. UniProtKB database entry Q7M4I3 and Q7M4I6. J Allergy Clin Immunol 1996; 97:812-21.

Hopp T. P and Woods K. R. Prediction of protein antigenic determinants from amino acid sequences. Proc. Natl. Acad. Sci. USA 1981; 78:3824-3828.

Hoyne G. F. et al. Inhibition of T Cell and Antibody Response to House Dust Mite Allergen by Inhalation of the Dominant T Cell Epitope in Naive and Sensitized Mice. J. Exp. Med. 1993; 178:1783-1788.

Jutel M. et al. Mechanism of allergen specific immunotherapy—T-cell tolerance and more. Allergy 2006; 61:796-807.

Karamloo F. et al. Prevention of allergy by a recombinant multi-allergen vaccine with reduced IgE binding and preserved T cell epitopes. Eur. J. Immunol. 2005; 35:3268-3276.

King T. P. Insect venom allergens. Monogr. Allergy 1990; 28: 84-100.

King T. P. (1994) U.S. Pat. No. 5,593,877: p. 1

King T. P. and Spanfort M. D. Structure and biology of stinging insect venom allergens. Int. Arch. Allergy Immunol. 2000; 123:99-106.

Korber B. et al. Immunoinformatics comes of age. PLoS Computational Biology 2006; 2:0484-0492

Larkin M. A. et al. ClustalW and ClustalX version 2. Bioinformatics 2007; 23:2947-2948.

Larsen J. E. P. et al. Improved method for predicting linear B cell epitopes Immunome Research 2006; 2:2.

Lebecque S. et al. Immunologic characterization of monoclonal antibodies that modulate human IgE binding to the major birch pollen allergen Bet v 1. J. Allergy Clin. Immunol. 1997; 99:374-384.

Lopez R. Services Programme and Lloyd A. ClustalW WWW Service at the European Bioinformatics Institute (1997) [online, last accessed 23 Jan. 2009] http://www.ebi.ac.uk/Tools/clustalw2/

MacKenzie T. and Dosch H.-M. Clonal and Molecular Characterization of the Human IgE-Committed B Cell Subset. J. Exp. Med. 1989; 169: 407-430

Mirza O. et al. Dominant Epitopes and Allergic Cross-Reactivity: Complex Formation Between a Fab Fragment of a Monoclonal Murine IgG Antibody and the Major Allergen from Birch Pollen Bet v 1. J. Immunol. 2000; 165:331-338.

Morgulis A et al. Database indexing for production Mega-BLAST searches. Bioinformatics 2008; 15:1757-1764.

Morten N. et al. Prediction of MHC class II binding affinity using SMM-align, a novel stabilization matrix alignment method. NetMHCIII 1.0 Server at CBS [online, last accessed on Jan. 23, 2009] http://www.cbs.dtu.dk/services/NetMHCII/. BMC Bioinformatics 2007; 8:238.

Müller U. et al. Successful immunotherapy with T-cell epitope peptides of bee venom phospholipase A2 induces specific T-cell anergy in patients allergic to bee venom. J. Allergy Clin. Immunol. 1998; 101:747-754.

Niederberger V. et al. Vaccination with genetically engineered allergens prevents progression of allergic disease. Proc. Natl. Acad. Sci. USA 2004; 101:14677-14682.

Nielsen M. et al. Quantitative predictions of peptide binding to any HLA-DR molecule of known sequence: NetMHCII-pan. NetMHCIIpan Server at CBS [online, last accessed on Jan. 23, 2009] http://www.cbs.dtu.dk/services/NetMHCII-pan/ PLoS Comput Biol. 2008; 4(7).

O'Hehir R. E. et al. The Specificity and Regulation of T-Cell Responsiveness to Allergens. Ann. Rev. Immunol. 1991; 6:67-95.

Panjkovich A. and Melo F. Comparison of different melting temperature calculation methods for short DNA sequences. Bioinformatics 2005; 21:711-722

Petersen A., Mundt C. Investigations on the carbohydrate moieties of glycoprotein allergens J. Chromat. B 2001; 756:141-150

Powers D. B. et al. Expression of single-chain Fv-Fc fusions in *Pichia pastoris* J. Immunol. Meth. 2001; 251:123-135.

Quevillon E. et al. InterProScan: protein domains identifier. [online, last accessed 23 Jan. 2009] http://www.ebi.ac.uk/Tools/InterProScan/ Nucleic Acids Res. 2005; 33(Web Server issue):W116-W120

Reid, M. J. et al. Seasonal asthma in northern California: allergic causes and efficacy of immunotherapy. J. Allergy Clin. Immunol. 1986; 78:590-600

Rudensky, et al. Sequence analysis of peptides bound to MHC class II molecules. Nature 1991; 353:622-627.

Sambrook et al, Molecular Cloning: A Laboratory Manual, Cold Spring Harbor Press, NY, 1989; 9.31-9.58, 1989.

Schmidt M. and Hoffman D. R. Expression systems for production of recombinant allergens. Int. Arch. Allergy Immunol. 2002; 128: 264-270.

Steinberger P. et al. Construction of a Combinatorial IgE Library from a Allergic Patient. J. Biol. Chem. 1996; 271: 10967-10972.

Tomiya, N. et al. Comparing N-glycan processing in mammalian cell lines to native and engineered lepidopteran insect cell lines. Glycoconjugate J. 2004; 21: 343-360.

Valenta R. et al. The Immunoglobulin E-Allergen Interaction: A Target for Therapy of Type I Allergic Diseases. Int. Arch. Immunol. 1998; 116: 167-176.

Varney V. A. et al. Usefulness of immunotherapy in patients with severe summer hay fever uncontrolled by antiallergic drugs. British Medical J. 1991; 302: 265-269.

Varney V. A. et al. Influence of grass pollen immunotherapy on cellular infiltration and cytokine mRNA expression during allergen-induced late-phase cutaneous responses. J. Clin. Invest. 1993; 92:644-651.

Wang P. et al. A Systematic Assessment of MHC Class II Peptide Binding Predictions and Evaluation of a Consensus Approach. PloS Comp Biol 2008; 4:1-10.

Wetterwald A. et al. Isotypic and idiotypic characterization of anti-bee venom phospholipase A2 antibodies. Int. Arch. Allergy Appl. Immunol. 1985; 77:195-197.

Winningham K. M. et al. Hymenoptera venom protease allergens. NCBI nucleic acid database entry AY285998.UniProtKB database entry Q7Z269.

Winter G. and Milstein C. Man-made antibodies Nature 1991; 349:93-299 J. Allergy Clin. Immunol. 2004; 114: 928-933.

Yamamoto T. et al. Identification of proteins from venom of the paralytic spider wasp *Cyphonyx dorsalis*. Insect Biochem. Mol. Biol. 2007; 37:278-286.

Zhang, Q. et al. Immune epitope database analysis resource (IEDB-AR) Nucleic Acid Res. 2008; 36:W513-W518.

TABLE 1

Position of peptide fragments

| Fragment | SEQ ID | Position (bp)* | Size (bp) | SEQ ID | Position (aa)** | Size (aa) |
|---|---|---|---|---|---|---|
| ~150 aa epitope fragments | | | | | | |
| F1 | 3 | 64-444 | 381 | 28 | 22-148 | 127 |
| F2 | 4 | 445-804 | 360 | 29 | 149-268 | 120 |
| F3 | 5 | 805-1170 | 366 | 30 | 269-390 | 122 |
| F4 | 6 | 295-711 | 417 | 31 | 99-237 | 139 |
| F5 | 7 | 712-1071 | 360 | 32 | 238-357 | 120 |
| ~100 aa epitope fragments | | | | | | |
| F6 | 8 | 64-405 | 342 | 33 | 22-135 | 114 |
| F7 | 9 | 406-696 | 291 | 34 | 136-232 | 97 |
| F8 | 10 | 697-939 | 243 | 35 | 233-313 | 81 |
| F9 | 11 | 940-1170 | 231 | 36 | 314-390 | 77 |
| F10 | 12 | 274-576 | 299 | 37 | 92-192 | 101 |

TABLE 1-continued

Position of peptide fragments

| Fragment | SEQ ID | Position (bp)* | Size (bp) | SEQ ID | Position (aa)** | Size (aa) |
|---|---|---|---|---|---|---|
| F11 | 13 | 577-846 | 270 | 38 | 193-282 | 90 |
| F12 | 14 | 847-1116 | 270 | 39 | 283-372 | 91 |
| ~50 aa epitope fragments | | | | | | |
| F13 | 15 | 64-222 | 159 | 40 | 22-74 | 53 |
| F14 | 16 | 223-405 | 183 | 41 | 75-135 | 61 |
| F15 | 17 | 406-570 | 165 | 42 | 136-190 | 55 |
| F16 | 18 | 571-720 | 150 | 43 | 191-240 | 50 |
| F17 | 19 | 721-852 | 132 | 44 | 241-284 | 44 |
| F18 | 20 | 853-1002 | 150 | 45 | 285-334 | 50 |
| F19 | 21 | 1003-1170 | 168 | 46 | 335-390 | 56 |
| F20 | 22 | 154-309 | 153 | 47 | 52-103 | 52 |
| F21 | 23 | 310-480 | 171 | 48 | 104-160 | 57 |
| F22 | 24 | 481-639 | 159 | 49 | 161-213 | 53 |
| F23 | 25 | 640-804 | 165 | 50 | 214-268 | 55 |
| F24 | 26 | 805-945 | 141 | 51 | 269-315 | 47 |
| F25 | 27 | 946-1089 | 144 | 52 | 316-363 | 48 |

*According to base pair numbering of SEQ ID NO: 1
**According to amino acid numbering of SEQ ID NO: 2

TABLE 2

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| DRB1*0101 | 53 | 997 | 1041 | 486 | 333 | 347 | 15 |
| | 54 | 1000 | 1044 | 487 | 334 | 348 | 15 |
| | 55 | 1003 | 1047 | 488 | 335 | 349 | 15 |
| | 56 | 1006 | 1050 | 489 | 336 | 350 | 15 |
| | 57 | 1009 | 1053 | 490 | 337 | 351 | 15 |
| | 58 | 478 | 522 | 491 | 160 | 174 | 15 |
| | 59 | 307 | 351 | 492 | 103 | 117 | 15 |
| | 60 | 310 | 354 | 493 | 104 | 118 | 15 |
| | 61 | 304 | 348 | 494 | 102 | 116 | 15 |
| | 62 | 481 | 525 | 495 | 161 | 175 | 15 |
| | 63 | 301 | 345 | 496 | 101 | 115 | 15 |
| | 64 | 487 | 531 | 497 | 163 | 177 | 15 |
| | 65 | 298 | 342 | 498 | 100 | 114 | 15 |
| | 66 | 490 | 534 | 499 | 164 | 178 | 15 |
| | 67 | 484 | 528 | 500 | 162 | 176 | 15 |
| | 68 | 283 | 327 | 501 | 95 | 109 | 15 |
| | 69 | 286 | 330 | 502 | 96 | 110 | 15 |
| | 70 | 280 | 324 | 503 | 94 | 108 | 15 |
| | 71 | 277 | 321 | 504 | 93 | 107 | 15 |
| | 72 | 274 | 318 | 505 | 92 | 106 | 15 |
| | 73 | 469 | 513 | 506 | 157 | 171 | 15 |
| | 74 | 472 | 516 | 507 | 158 | 172 | 15 |
| | 75 | 847 | 891 | 508 | 283 | 297 | 15 |
| | 76 | 466 | 510 | 509 | 156 | 170 | 15 |
| | 77 | 850 | 894 | 510 | 284 | 298 | 15 |
| | 78 | 1012 | 1056 | 511 | 338 | 352 | 15 |
| | 79 | 1015 | 1059 | 512 | 339 | 353 | 15 |
| | 80 | 745 | 789 | 513 | 249 | 263 | 15 |
| | 81 | 475 | 519 | 514 | 159 | 173 | 15 |
| | 82 | 751 | 795 | 515 | 251 | 265 | 15 |
| | 83 | 754 | 798 | 516 | 252 | 266 | 15 |
| | 84 | 748 | 792 | 517 | 250 | 264 | 15 |
| | 85 | 580 | 624 | 518 | 194 | 208 | 15 |
| | 86 | 313 | 357 | 519 | 105 | 119 | 15 |
| | 87 | 757 | 801 | 520 | 253 | 267 | 15 |
| | 88 | 316 | 360 | 521 | 106 | 120 | 15 |
| | 89 | 817 | 861 | 522 | 273 | 287 | 15 |
| | 90 | 505 | 549 | 523 | 169 | 183 | 15 |
| | 91 | 853 | 897 | 524 | 285 | 299 | 15 |
| | 92 | 493 | 537 | 525 | 165 | 179 | 15 |
| | 93 | 841 | 885 | 526 | 281 | 295 | 15 |
| | 94 | 856 | 900 | 527 | 286 | 300 | 15 |
| | 95 | 496 | 540 | 528 | 166 | 180 | 15 |

TABLE 2-continued

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
|  | 96 | 838 | 882 | 529 | 280 | 294 | 15 |
|  | 97 | 583 | 627 | 530 | 195 | 209 | 15 |
|  | 98 | 586 | 630 | 531 | 196 | 210 | 15 |
|  | 99 | 514 | 558 | 532 | 172 | 186 | 15 |
|  | 100 | 589 | 633 | 533 | 197 | 211 | 15 |
|  | 101 | 511 | 555 | 534 | 171 | 185 | 15 |
|  | 102 | 508 | 552 | 535 | 170 | 184 | 15 |
|  | 103 | 460 | 504 | 536 | 154 | 168 | 15 |
|  | 104 | 463 | 507 | 537 | 155 | 169 | 15 |
|  | 105 | 844 | 888 | 538 | 282 | 296 | 15 |
|  | 106 | 289 | 333 | 539 | 97 | 111 | 15 |
|  | 107 | 292 | 336 | 540 | 98 | 112 | 15 |
|  | 108 | 820 | 864 | 541 | 274 | 288 | 15 |
|  | 109 | 808 | 852 | 542 | 270 | 284 | 15 |
|  | 110 | 628 | 672 | 543 | 210 | 224 | 15 |
|  | 111 | 592 | 636 | 544 | 198 | 212 | 15 |
|  | 112 | 631 | 675 | 545 | 211 | 225 | 15 |
|  | 113 | 523 | 567 | 546 | 175 | 189 | 15 |
|  | 114 | 625 | 669 | 547 | 209 | 223 | 15 |
|  | 115 | 811 | 855 | 548 | 271 | 285 | 15 |
|  | 116 | 823 | 867 | 549 | 275 | 289 | 15 |
|  | 117 | 526 | 570 | 550 | 176 | 190 | 15 |
|  | 118 | 517 | 561 | 551 | 173 | 187 | 15 |
|  | 119 | 805 | 849 | 552 | 269 | 283 | 15 |
|  | 120 | 829 | 873 | 553 | 277 | 291 | 15 |
|  | 121 | 919 | 963 | 554 | 307 | 321 | 15 |
|  | 122 | 922 | 966 | 555 | 308 | 322 | 15 |
|  | 123 | 502 | 546 | 556 | 168 | 182 | 15 |
|  | 124 | 697 | 741 | 557 | 233 | 247 | 15 |
|  | 125 | 529 | 573 | 558 | 177 | 191 | 15 |
|  | 126 | 814 | 858 | 559 | 272 | 286 | 15 |
|  | 127 | 532 | 576 | 560 | 178 | 192 | 15 |
|  | 128 | 859 | 903 | 561 | 287 | 301 | 15 |
|  | 129 | 535 | 579 | 562 | 179 | 193 | 15 |
|  | 130 | 520 | 564 | 563 | 174 | 188 | 15 |
|  | 131 | 706 | 750 | 564 | 236 | 250 | 15 |
|  | 132 | 709 | 753 | 565 | 237 | 251 | 15 |
|  | 133 | 916 | 960 | 566 | 306 | 320 | 15 |
|  | 134 | 703 | 747 | 567 | 235 | 249 | 15 |
|  | 135 | 760 | 804 | 568 | 254 | 268 | 15 |
|  | 136 | 700 | 744 | 569 | 234 | 248 | 15 |
|  | 137 | 826 | 870 | 570 | 276 | 290 | 15 |
|  | 138 | 763 | 807 | 571 | 255 | 269 | 15 |
|  | 139 | 913 | 957 | 572 | 305 | 319 | 15 |
|  | 140 | 619 | 663 | 573 | 207 | 221 | 15 |
|  | 141 | 577 | 621 | 574 | 193 | 207 | 15 |
|  | 142 | 622 | 666 | 575 | 208 | 222 | 15 |
|  | 143 | 796 | 840 | 576 | 266 | 280 | 15 |
|  | 144 | 634 | 678 | 577 | 212 | 226 | 15 |
|  | 145 | 637 | 681 | 578 | 213 | 227 | 15 |
|  | 146 | 910 | 954 | 579 | 304 | 318 | 15 |
|  | 147 | 865 | 909 | 580 | 289 | 303 | 15 |
|  | 148 | 862 | 906 | 581 | 288 | 302 | 15 |
|  | 149 | 802 | 846 | 582 | 268 | 282 | 15 |
|  | 150 | 799 | 843 | 583 | 267 | 281 | 15 |
|  | 151 | 541 | 585 | 584 | 181 | 195 | 15 |
|  | 152 | 832 | 876 | 585 | 278 | 292 | 15 |
|  | 153 | 793 | 837 | 586 | 265 | 279 | 15 |
|  | 154 | 928 | 972 | 587 | 310 | 324 | 15 |
|  | 155 | 499 | 543 | 588 | 167 | 181 | 15 |
|  | 156 | 835 | 879 | 589 | 279 | 293 | 15 |
|  | 157 | 1111 | 1155 | 590 | 371 | 385 | 15 |
|  | 158 | 595 | 639 | 591 | 199 | 213 | 15 |
|  | 159 | 925 | 969 | 592 | 309 | 323 | 15 |
|  | 160 | 1108 | 1152 | 593 | 370 | 384 | 15 |
|  | 161 | 538 | 582 | 594 | 180 | 194 | 15 |
|  | 162 | 784 | 828 | 595 | 262 | 276 | 15 |
|  | 163 | 781 | 825 | 596 | 261 | 275 | 15 |
|  | 164 | 457 | 501 | 597 | 153 | 167 | 15 |
|  | 165 | 67 | 111 | 598 | 23 | 37 | 15 |
|  | 166 | 571 | 615 | 599 | 191 | 205 | 15 |
|  | 167 | 544 | 588 | 600 | 182 | 196 | 15 |
|  | 168 | 574 | 618 | 601 | 192 | 206 | 15 |
|  | 169 | 547 | 591 | 602 | 183 | 197 | 15 |

TABLE 2-continued

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 170 | 598 | 642 | 603 | 200 | 214 | 15 |
| | 171 | 871 | 915 | 604 | 291 | 305 | 15 |
| | 172 | 787 | 831 | 605 | 263 | 277 | 15 |
| | 173 | 790 | 834 | 606 | 264 | 278 | 15 |
| | 174 | 208 | 252 | 607 | 70 | 84 | 15 |
| | 175 | 205 | 249 | 608 | 69 | 83 | 15 |
| | 176 | 868 | 912 | 609 | 290 | 304 | 15 |
| | 177 | 1099 | 1143 | 610 | 367 | 381 | 15 |
| | 178 | 1102 | 1146 | 611 | 368 | 382 | 15 |
| | 179 | 874 | 918 | 612 | 292 | 306 | 15 |
| | 180 | 64 | 108 | 613 | 22 | 36 | 15 |
| | 181 | 1105 | 1149 | 614 | 369 | 383 | 15 |
| | 182 | 568 | 612 | 615 | 190 | 204 | 15 |
| | 183 | 415 | 459 | 616 | 139 | 153 | 15 |
| | 184 | 412 | 456 | 617 | 138 | 152 | 15 |
| | 185 | 715 | 759 | 618 | 239 | 253 | 15 |
| | 186 | 451 | 495 | 619 | 151 | 165 | 15 |
| | 187 | 712 | 756 | 620 | 238 | 252 | 15 |
| | 188 | 778 | 822 | 621 | 260 | 274 | 15 |
| | 189 | 409 | 453 | 622 | 137 | 151 | 15 |
| | 190 | 454 | 498 | 623 | 152 | 166 | 15 |
| | 191 | 79 | 123 | 624 | 27 | 41 | 15 |
| | 192 | 418 | 462 | 625 | 140 | 154 | 15 |
| | 193 | 982 | 1026 | 626 | 328 | 342 | 15 |
| | 194 | 202 | 246 | 627 | 68 | 82 | 15 |
| | 195 | 157 | 201 | 628 | 53 | 67 | 15 |
| | 196 | 985 | 1029 | 629 | 329 | 343 | 15 |
| | 197 | 550 | 594 | 630 | 184 | 198 | 15 |
| | 198 | 160 | 204 | 631 | 54 | 68 | 15 |
| | 199 | 154 | 198 | 632 | 52 | 66 | 15 |
| | 200 | 979 | 1023 | 633 | 327 | 341 | 15 |
| | 201 | 163 | 207 | 634 | 55 | 69 | 15 |
| | 202 | 1078 | 1122 | 635 | 360 | 374 | 15 |
| | 203 | 211 | 255 | 636 | 71 | 85 | 15 |
| | 204 | 433 | 477 | 637 | 145 | 159 | 15 |
| | 205 | 430 | 474 | 638 | 144 | 158 | 15 |
| | 206 | 295 | 339 | 639 | 99 | 113 | 15 |
| | 207 | 733 | 777 | 640 | 245 | 259 | 15 |
| | 208 | 976 | 1020 | 641 | 326 | 340 | 15 |
| | 209 | 727 | 771 | 642 | 243 | 257 | 15 |
| | 210 | 1114 | 1158 | 643 | 372 | 386 | 15 |
| | 211 | 730 | 774 | 644 | 244 | 258 | 15 |
| | 212 | 82 | 126 | 645 | 28 | 42 | 15 |
| | 213 | 991 | 1035 | 646 | 331 | 345 | 15 |
| | 214 | 685 | 729 | 647 | 229 | 243 | 15 |
| | 215 | 1081 | 1125 | 648 | 361 | 375 | 15 |
| | 216 | 553 | 597 | 649 | 185 | 199 | 15 |
| | 217 | 973 | 1017 | 650 | 325 | 339 | 15 |
| | 218 | 1117 | 1161 | 651 | 373 | 387 | 15 |
| | 219 | 739 | 783 | 652 | 247 | 261 | 15 |
| DRB1*0301 | 220 | 253 | 297 | 653 | 85 | 99 | 15 |
| | 221 | 250 | 294 | 654 | 84 | 98 | 15 |
| | 222 | 256 | 300 | 655 | 86 | 100 | 15 |
| DRB1*0401 | 223 | 910 | 954 | 656 | 304 | 318 | 15 |
| | 224 | 922 | 966 | 657 | 308 | 322 | 15 |
| | 225 | 916 | 960 | 658 | 306 | 320 | 15 |
| | 226 | 919 | 963 | 659 | 307 | 321 | 15 |
| | 227 | 913 | 957 | 660 | 305 | 319 | 15 |
| | 228 | 106 | 150 | 661 | 36 | 50 | 15 |
| | 229 | 109 | 153 | 662 | 37 | 51 | 15 |
| | 230 | 112 | 156 | 663 | 38 | 52 | 15 |
| | 231 | 115 | 159 | 664 | 39 | 53 | 15 |
| | 232 | 118 | 162 | 665 | 40 | 54 | 15 |
| | 233 | 925 | 969 | 666 | 309 | 323 | 15 |
| | 234 | 928 | 972 | 667 | 310 | 324 | 15 |
| | 235 | 202 | 246 | 668 | 68 | 82 | 15 |
| DRB1*0404 | 236 | 1108 | 1152 | 669 | 370 | 384 | 15 |
| | 237 | 1111 | 1155 | 670 | 371 | 385 | 15 |
| | 238 | 1105 | 1149 | 671 | 369 | 383 | 15 |
| | 239 | 916 | 960 | 672 | 306 | 320 | 15 |
| | 240 | 1102 | 1146 | 673 | 368 | 382 | 15 |
| | 241 | 1030 | 1074 | 674 | 344 | 358 | 15 |
| | 242 | 1033 | 1077 | 675 | 345 | 359 | 15 |
| | 243 | 1099 | 1143 | 676 | 367 | 381 | 15 |

TABLE 2-continued

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 244 | 1036 | 1080 | 677 | 346 | 360 | 15 |
| | 245 | 130 | 174 | 678 | 44 | 58 | 15 |
| | 246 | 136 | 180 | 679 | 46 | 60 | 15 |
| | 247 | 133 | 177 | 680 | 45 | 59 | 15 |
| | 248 | 997 | 1041 | 681 | 333 | 347 | 15 |
| | 249 | 598 | 642 | 682 | 200 | 214 | 15 |
| DRB1*0405 | 250 | 775 | 819 | 683 | 259 | 273 | 15 |
| | 251 | 778 | 822 | 684 | 260 | 274 | 15 |
| | 252 | 787 | 831 | 685 | 263 | 277 | 15 |
| | 253 | 781 | 825 | 686 | 261 | 275 | 15 |
| | 254 | 784 | 828 | 687 | 262 | 276 | 15 |
| | 255 | 793 | 837 | 688 | 265 | 279 | 15 |
| | 256 | 790 | 834 | 689 | 264 | 278 | 15 |
| DRB1*0701 | 257 | 283 | 327 | 690 | 95 | 109 | 15 |
| | 258 | 274 | 318 | 691 | 92 | 106 | 15 |
| | 259 | 277 | 321 | 692 | 93 | 107 | 15 |
| | 260 | 280 | 324 | 693 | 94 | 108 | 15 |
| | 261 | 286 | 330 | 694 | 96 | 110 | 15 |
| | 262 | 793 | 837 | 695 | 265 | 279 | 15 |
| | 263 | 490 | 534 | 696 | 164 | 178 | 15 |
| | 264 | 484 | 528 | 697 | 162 | 176 | 15 |
| | 265 | 799 | 843 | 698 | 267 | 281 | 15 |
| | 266 | 802 | 846 | 699 | 268 | 282 | 15 |
| | 267 | 481 | 525 | 700 | 161 | 175 | 15 |
| | 268 | 796 | 840 | 701 | 266 | 280 | 15 |
| | 269 | 841 | 885 | 702 | 281 | 295 | 15 |
| | 270 | 847 | 891 | 703 | 283 | 297 | 15 |
| | 271 | 838 | 882 | 704 | 280 | 294 | 15 |
| | 272 | 850 | 894 | 705 | 284 | 298 | 15 |
| | 273 | 289 | 333 | 706 | 97 | 111 | 15 |
| | 274 | 292 | 336 | 707 | 98 | 112 | 15 |
| | 275 | 1144 | 1188 | 708 | 382 | 396 | 9 |
| | 276 | 163 | 207 | 709 | 55 | 69 | 15 |
| | 277 | 1087 | 1131 | 710 | 363 | 377 | 15 |
| | 278 | 154 | 198 | 711 | 52 | 66 | 15 |
| | 279 | 1084 | 1128 | 712 | 362 | 376 | 15 |
| | 280 | 160 | 204 | 713 | 54 | 68 | 15 |
| | 281 | 157 | 201 | 714 | 53 | 67 | 15 |
| | 282 | 166 | 210 | 715 | 56 | 70 | 15 |
| | 283 | 553 | 597 | 716 | 185 | 199 | 15 |
| | 284 | 562 | 606 | 717 | 188 | 202 | 15 |
| | 285 | 1006 | 1050 | 718 | 336 | 350 | 15 |
| | 286 | 565 | 609 | 719 | 189 | 203 | 15 |
| | 287 | 493 | 537 | 720 | 165 | 179 | 15 |
| | 288 | 1009 | 1053 | 721 | 337 | 351 | 15 |
| | 289 | 784 | 828 | 722 | 262 | 276 | 15 |
| | 290 | 1003 | 1047 | 723 | 335 | 349 | 15 |
| DRB1*0802 | 291 | 724 | 768 | 724 | 242 | 256 | 15 |
| | 292 | 721 | 765 | 725 | 241 | 255 | 15 |
| | 293 | 727 | 771 | 726 | 243 | 257 | 15 |
| | 294 | 715 | 759 | 727 | 239 | 253 | 15 |
| | 295 | 718 | 762 | 728 | 240 | 254 | 15 |
| | 296 | 730 | 774 | 729 | 244 | 258 | 15 |
| DRB1*0901 | 297 | 922 | 966 | 730 | 308 | 322 | 15 |
| | 298 | 919 | 963 | 731 | 307 | 321 | 15 |
| | 299 | 916 | 960 | 732 | 306 | 320 | 15 |
| | 300 | 913 | 957 | 733 | 305 | 319 | 15 |
| | 301 | 910 | 954 | 734 | 304 | 318 | 15 |
| | 302 | 1111 | 1155 | 735 | 371 | 385 | 15 |
| | 303 | 1114 | 1158 | 736 | 372 | 386 | 15 |
| | 304 | 1117 | 1161 | 737 | 373 | 387 | 15 |
| | 305 | 1120 | 1164 | 738 | 374 | 388 | 15 |
| | 306 | 1123 | 1167 | 739 | 375 | 389 | 15 |
| DRB1*1101 | 307 | 472 | 516 | 740 | 158 | 172 | 15 |
| | 308 | 469 | 513 | 741 | 157 | 171 | 15 |
| | 309 | 463 | 507 | 742 | 155 | 169 | 15 |
| | 310 | 460 | 504 | 743 | 154 | 168 | 15 |
| | 311 | 466 | 510 | 744 | 156 | 170 | 15 |
| | 312 | 409 | 453 | 745 | 137 | 151 | 15 |
| | 313 | 724 | 768 | 746 | 242 | 256 | 15 |
| | 314 | 478 | 522 | 747 | 160 | 174 | 15 |
| | 315 | 721 | 765 | 748 | 241 | 255 | 15 |
| | 316 | 412 | 456 | 749 | 138 | 152 | 15 |
| | 317 | 415 | 459 | 750 | 139 | 153 | 15 |

TABLE 2-continued

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 318 | 718 | 762 | 751 | 240 | 254 | 15 |
| | 319 | 715 | 759 | 752 | 239 | 253 | 15 |
| | 320 | 418 | 462 | 753 | 140 | 154 | 15 |
| | 321 | 421 | 465 | 754 | 141 | 155 | 15 |
| | 322 | 727 | 771 | 755 | 243 | 257 | 15 |
| | 323 | 481 | 525 | 756 | 161 | 175 | 15 |
| | 324 | 484 | 528 | 757 | 162 | 176 | 15 |
| | 325 | 475 | 519 | 758 | 159 | 173 | 15 |
| | 326 | 490 | 534 | 759 | 164 | 178 | 15 |
| | 327 | 487 | 531 | 760 | 163 | 177 | 15 |
| DRB1*1302 | 328 | 1036 | 1080 | 761 | 346 | 360 | 15 |
| | 329 | 1039 | 1083 | 762 | 347 | 361 | 15 |
| | 330 | 715 | 759 | 763 | 239 | 253 | 15 |
| | 331 | 724 | 768 | 764 | 242 | 256 | 15 |
| | 332 | 580 | 624 | 765 | 194 | 208 | 15 |
| | 333 | 721 | 765 | 766 | 241 | 255 | 15 |
| | 334 | 421 | 465 | 767 | 141 | 155 | 15 |
| | 335 | 583 | 627 | 768 | 195 | 209 | 15 |
| | 336 | 718 | 762 | 769 | 240 | 254 | 15 |
| | 337 | 415 | 459 | 770 | 139 | 153 | 15 |
| | 338 | 589 | 633 | 771 | 197 | 211 | 15 |
| | 339 | 409 | 453 | 772 | 137 | 151 | 15 |
| | 340 | 412 | 456 | 773 | 138 | 152 | 15 |
| | 341 | 586 | 630 | 774 | 196 | 210 | 15 |
| | 342 | 727 | 771 | 775 | 243 | 257 | 15 |
| | 343 | 592 | 636 | 776 | 198 | 212 | 15 |
| | 344 | 1033 | 1077 | 777 | 345 | 359 | 15 |
| | 345 | 1030 | 1074 | 778 | 344 | 358 | 15 |
| | 346 | 418 | 462 | 779 | 140 | 154 | 15 |
| | 347 | 1042 | 1086 | 780 | 348 | 362 | 15 |
| | 348 | 733 | 777 | 781 | 245 | 259 | 15 |
| | 349 | 487 | 531 | 782 | 163 | 177 | 15 |
| | 350 | 325 | 369 | 783 | 109 | 123 | 15 |
| | 351 | 1078 | 1122 | 784 | 360 | 374 | 15 |
| | 352 | 1081 | 1125 | 785 | 361 | 375 | 15 |
| | 353 | 1084 | 1128 | 786 | 362 | 376 | 15 |
| | 354 | 490 | 534 | 787 | 164 | 178 | 15 |
| | 355 | 730 | 774 | 788 | 244 | 258 | 15 |
| | 356 | 829 | 873 | 789 | 277 | 291 | 15 |
| | 357 | 427 | 471 | 790 | 143 | 157 | 15 |
| | 358 | 841 | 885 | 791 | 281 | 295 | 15 |
| | 359 | 1087 | 1131 | 792 | 363 | 377 | 15 |
| | 360 | 484 | 528 | 793 | 162 | 176 | 15 |
| | 361 | 481 | 525 | 794 | 161 | 175 | 15 |
| | 362 | 424 | 468 | 795 | 142 | 156 | 15 |
| | 363 | 1045 | 1089 | 796 | 349 | 363 | 15 |
| | 364 | 628 | 672 | 797 | 210 | 224 | 15 |
| | 365 | 847 | 891 | 798 | 283 | 297 | 15 |
| | 366 | 1090 | 1134 | 799 | 364 | 378 | 15 |
| | 367 | 1048 | 1092 | 800 | 350 | 364 | 15 |
| | 368 | 631 | 675 | 801 | 211 | 225 | 15 |
| | 369 | 625 | 669 | 802 | 209 | 223 | 15 |
| | 370 | 595 | 639 | 803 | 199 | 213 | 15 |
| | 371 | 493 | 537 | 804 | 165 | 179 | 15 |
| | 372 | 835 | 879 | 805 | 279 | 293 | 15 |
| | 373 | 832 | 876 | 806 | 278 | 292 | 15 |
| | 374 | 619 | 663 | 807 | 207 | 221 | 15 |
| | 375 | 1027 | 1071 | 808 | 343 | 357 | 15 |
| | 376 | 571 | 615 | 809 | 191 | 205 | 15 |
| | 377 | 328 | 372 | 810 | 110 | 124 | 15 |
| | 378 | 568 | 612 | 811 | 190 | 204 | 15 |
| | 379 | 1024 | 1068 | 812 | 342 | 356 | 15 |
| | 380 | 331 | 375 | 813 | 111 | 125 | 15 |
| | 381 | 178 | 222 | 814 | 60 | 74 | 15 |
| | 382 | 622 | 666 | 815 | 208 | 222 | 15 |
| | 383 | 181 | 225 | 816 | 61 | 75 | 15 |
| | 384 | 577 | 621 | 817 | 193 | 207 | 15 |
| | 385 | 598 | 642 | 818 | 200 | 214 | 15 |
| | 386 | 334 | 378 | 819 | 112 | 126 | 15 |
| | 387 | 337 | 381 | 820 | 113 | 127 | 15 |
| | 388 | 823 | 867 | 821 | 275 | 289 | 15 |
| | 389 | 184 | 228 | 822 | 62 | 76 | 15 |
| | 390 | 187 | 231 | 823 | 63 | 77 | 15 |
| | 391 | 850 | 894 | 824 | 284 | 298 | 15 |

TABLE 2-continued

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 392 | 826 | 870 | 825 | 276 | 290 | 15 |
| | 393 | 853 | 897 | 826 | 285 | 299 | 15 |
| | 394 | 712 | 756 | 827 | 238 | 252 | 15 |
| | 395 | 190 | 234 | 828 | 64 | 78 | 15 |
| | 396 | 817 | 861 | 829 | 273 | 287 | 15 |
| | 397 | 844 | 888 | 830 | 282 | 296 | 15 |
| | 398 | 574 | 618 | 831 | 192 | 206 | 15 |
| | 399 | 478 | 522 | 832 | 160 | 174 | 15 |
| | 400 | 709 | 753 | 833 | 237 | 251 | 15 |
| | 401 | 706 | 750 | 834 | 236 | 250 | 15 |
| | 402 | 1021 | 1065 | 835 | 341 | 355 | 15 |
| | 403 | 343 | 387 | 836 | 115 | 129 | 15 |
| | 404 | 838 | 882 | 837 | 280 | 294 | 15 |
| | 405 | 820 | 864 | 838 | 274 | 288 | 15 |
| | 406 | 739 | 783 | 839 | 247 | 261 | 15 |
| | 407 | 634 | 678 | 840 | 212 | 226 | 15 |
| | 408 | 892 | 936 | 841 | 298 | 312 | 15 |
| | 409 | 637 | 681 | 842 | 213 | 227 | 15 |
| | 410 | 895 | 939 | 843 | 299 | 313 | 15 |
| | 411 | 496 | 540 | 844 | 166 | 180 | 15 |
| | 412 | 307 | 351 | 845 | 103 | 117 | 15 |
| | 413 | 313 | 357 | 846 | 105 | 119 | 15 |
| | 414 | 736 | 780 | 847 | 246 | 260 | 15 |
| | 415 | 310 | 354 | 848 | 104 | 118 | 15 |
| DRB1*1501 | 416 | 1030 | 1074 | 849 | 344 | 358 | 15 |
| | 417 | 1027 | 1071 | 850 | 343 | 357 | 15 |
| | 418 | 1033 | 1077 | 851 | 345 | 359 | 15 |
| | 419 | 1036 | 1080 | 852 | 346 | 360 | 15 |
| | 420 | 1039 | 1083 | 853 | 347 | 361 | 15 |
| | 421 | 865 | 909 | 854 | 289 | 303 | 15 |
| | 422 | 862 | 906 | 855 | 288 | 302 | 15 |
| | 423 | 871 | 915 | 856 | 291 | 305 | 15 |
| | 424 | 868 | 912 | 857 | 290 | 304 | 15 |
| | 425 | 1042 | 1086 | 858 | 348 | 362 | 15 |
| | 426 | 124 | 168 | 859 | 42 | 56 | 15 |
| | 427 | 874 | 918 | 860 | 292 | 306 | 15 |
| | 428 | 718 | 762 | 861 | 240 | 254 | 15 |
| | 429 | 1045 | 1089 | 862 | 349 | 363 | 15 |
| | 430 | 715 | 759 | 863 | 239 | 253 | 15 |
| | 431 | 712 | 756 | 864 | 238 | 252 | 15 |
| | 432 | 580 | 624 | 865 | 194 | 208 | 15 |
| | 433 | 586 | 630 | 866 | 196 | 210 | 15 |
| | 434 | 877 | 921 | 887 | 293 | 307 | 15 |
| | 435 | 589 | 633 | 868 | 197 | 211 | 15 |
| | 436 | 709 | 753 | 869 | 237 | 251 | 15 |
| | 437 | 721 | 765 | 870 | 241 | 255 | 15 |
| | 438 | 583 | 627 | 871 | 195 | 209 | 15 |
| | 439 | 841 | 885 | 872 | 281 | 295 | 15 |
| | 440 | 847 | 891 | 873 | 283 | 297 | 15 |
| | 441 | 706 | 750 | 874 | 236 | 250 | 15 |
| | 442 | 577 | 621 | 875 | 193 | 207 | 15 |
| | 443 | 883 | 927 | 876 | 295 | 309 | 15 |
| | 444 | 889 | 933 | 877 | 297 | 311 | 15 |
| | 445 | 886 | 930 | 878 | 296 | 310 | 15 |
| | 446 | 727 | 771 | 879 | 243 | 257 | 15 |
| | 447 | 859 | 903 | 880 | 287 | 301 | 15 |
| | 448 | 592 | 636 | 881 | 198 | 212 | 15 |
| | 449 | 409 | 453 | 882 | 137 | 151 | 15 |
| | 450 | 838 | 882 | 883 | 280 | 294 | 15 |
| | 451 | 571 | 615 | 884 | 191 | 205 | 15 |
| | 452 | 730 | 774 | 885 | 244 | 258 | 15 |
| | 453 | 574 | 618 | 886 | 192 | 206 | 15 |
| | 454 | 892 | 936 | 887 | 298 | 312 | 15 |
| | 455 | 895 | 939 | 888 | 299 | 313 | 15 |
| | 456 | 850 | 894 | 889 | 284 | 298 | 15 |
| | 457 | 412 | 456 | 890 | 138 | 152 | 15 |
| | 458 | 844 | 888 | 891 | 282 | 296 | 15 |
| DRB4*0101 | 459 | 994 | 1038 | 892 | 332 | 346 | 15 |
| | 460 | 997 | 1041 | 893 | 333 | 347 | 15 |
| | 461 | 1000 | 1044 | 894 | 334 | 348 | 15 |
| | 462 | 1003 | 1047 | 895 | 335 | 349 | 15 |
| | 463 | 991 | 1035 | 896 | 331 | 345 | 15 |
| | 464 | 1006 | 1050 | 897 | 336 | 350 | 15 |
| | 465 | 724 | 768 | 898 | 242 | 256 | 15 |

TABLE 2-continued

T cell epitopes predicted by NetMHCII (only strong and weak binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 466 | 721 | 765 | 899 | 241 | 255 | 15 |
| | 467 | 715 | 759 | 900 | 239 | 253 | 15 |
| | 468 | 718 | 762 | 901 | 240 | 254 | 15 |
| | 469 | 1009 | 1053 | 902 | 337 | 351 | 15 |
| | 470 | 133 | 177 | 903 | 45 | 59 | 15 |
| | 471 | 136 | 180 | 904 | 46 | 60 | 15 |
| | 472 | 127 | 171 | 905 | 43 | 57 | 15 |
| DRB5*0101 | 473 | 1000 | 1044 | 906 | 334 | 348 | 15 |
| | 474 | 997 | 1041 | 907 | 333 | 347 | 15 |
| | 475 | 1003 | 1047 | 908 | 335 | 349 | 15 |
| | 476 | 685 | 729 | 909 | 229 | 243 | 15 |
| | 477 | 1006 | 1050 | 910 | 336 | 350 | 15 |
| | 478 | 1009 | 1053 | 911 | 337 | 351 | 15 |
| | 479 | 688 | 732 | 912 | 230 | 244 | 15 |
| | 480 | 679 | 723 | 913 | 227 | 241 | 15 |
| | 481 | 676 | 720 | 914 | 226 | 240 | 15 |
| | 482 | 673 | 717 | 915 | 225 | 239 | 15 |
| | 483 | 994 | 1038 | 916 | 332 | 346 | 15 |
| | 484 | 691 | 735 | 917 | 231 | 245 | 15 |
| | 485 | 682 | 726 | 918 | 228 | 242 | 15 |

TABLE 3

T cell epitopes predicted by NetMHCIIPAN (only strong binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| DRB1*0101 | 919 | 283 | 327 | 1242 | 95 | 109 | 15 |
| | 920 | 847 | 891 | 1243 | 283 | 297 | 15 |
| | 921 | 487 | 531 | 1244 | 163 | 177 | 15 |
| | 922 | 586 | 630 | 1245 | 196 | 210 | 15 |
| | 923 | 580 | 624 | 1246 | 194 | 208 | 15 |
| | 924 | 508 | 552 | 1247 | 170 | 184 | 15 |
| | 925 | 307 | 351 | 1248 | 103 | 117 | 15 |
| | 926 | 781 | 825 | 1249 | 261 | 275 | 15 |
| | 927 | 1006 | 1050 | 1250 | 336 | 350 | 15 |
| | 928 | 919 | 963 | 1251 | 307 | 321 | 15 |
| | 929 | 469 | 513 | 1252 | 157 | 171 | 15 |
| | 930 | 634 | 678 | 1253 | 212 | 226 | 15 |
| | 931 | 694 | 738 | 1254 | 232 | 246 | 15 |
| | 932 | 163 | 207 | 1255 | 55 | 69 | 15 |
| | 933 | 529 | 573 | 1256 | 177 | 191 | 15 |
| | 934 | 706 | 750 | 1257 | 236 | 250 | 15 |
| | 935 | 835 | 879 | 1258 | 279 | 293 | 15 |
| | 936 | 811 | 855 | 1259 | 271 | 285 | 15 |
| | 937 | 802 | 846 | 1260 | 268 | 282 | 15 |
| | 938 | 295 | 339 | 1261 | 99 | 113 | 15 |
| | 939 | 751 | 795 | 1262 | 251 | 265 | 15 |
| DRB1*0102 | 940 | 283 | 327 | 1262 | 95 | 109 | 15 |
| | 941 | 586 | 630 | 1264 | 196 | 210 | 15 |
| | 942 | 487 | 531 | 1265 | 163 | 177 | 15 |
| | 943 | 847 | 891 | 1266 | 283 | 297 | 15 |
| | 944 | 781 | 825 | 1267 | 261 | 275 | 15 |
| | 945 | 1036 | 1080 | 1268 | 346 | 360 | 15 |
| | 946 | 307 | 351 | 1269 | 103 | 117 | 15 |
| | 947 | 508 | 552 | 1270 | 170 | 184 | 15 |
| | 948 | 574 | 618 | 1271 | 192 | 206 | 15 |
| | 949 | 814 | 858 | 1272 | 272 | 286 | 15 |
| | 950 | 469 | 513 | 1273 | 157 | 171 | 15 |
| | 951 | 475 | 519 | 1274 | 159 | 173 | 15 |
| | 952 | 919 | 963 | 1275 | 307 | 321 | 15 |
| | 953 | 751 | 795 | 1276 | 251 | 265 | 15 |
| | 954 | 634 | 678 | 1277 | 212 | 226 | 15 |
| | 955 | 835 | 879 | 1278 | 279 | 293 | 15 |
| DRB1*0103 | 956 | 487 | 531 | 1279 | 163 | 177 | 15 |
| | 957 | 586 | 630 | 1280 | 196 | 210 | 15 |
| | 958 | 847 | 891 | 1281 | 283 | 297 | 15 |
| | 959 | 283 | 327 | 1282 | 95 | 109 | 15 |
| | 960 | 1006 | 1050 | 1283 | 336 | 350 | 15 |

TABLE 3-continued

T cell epitopes predicted by NetMHCIIPAN (only strong binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 961 | 508 | 552 | 1284 | 170 | 184 | 15 |
| | 962 | 163 | 207 | 1285 | 55 | 69 | 15 |
| | 963 | 307 | 351 | 1286 | 103 | 117 | 15 |
| | 964 | 706 | 750 | 1287 | 236 | 250 | 15 |
| DRB1*0104 | 965 | 586 | 630 | 1288 | 196 | 210 | 15 |
| | 966 | 283 | 327 | 1289 | 95 | 109 | 15 |
| | 967 | 847 | 891 | 1290 | 283 | 297 | 15 |
| | 968 | 487 | 531 | 1291 | 163 | 177 | 15 |
| | 969 | 1036 | 1080 | 1292 | 346 | 360 | 15 |
| | 970 | 307 | 351 | 1293 | 103 | 117 | 15 |
| | 971 | 781 | 825 | 1294 | 261 | 275 | 15 |
| | 972 | 508 | 552 | 1295 | 170 | 184 | 15 |
| | 973 | 811 | 855 | 1296 | 271 | 285 | 15 |
| DRB1*0105 | 974 | 283 | 327 | 1297 | 95 | 109 | 15 |
| | 975 | 847 | 891 | 1298 | 283 | 297 | 15 |
| | 976 | 487 | 531 | 1299 | 163 | 177 | 15 |
| | 977 | 586 | 630 | 1300 | 196 | 210 | 15 |
| | 978 | 580 | 624 | 1301 | 194 | 208 | 15 |
| | 979 | 508 | 552 | 1302 | 170 | 184 | 15 |
| | 980 | 307 | 351 | 1303 | 103 | 117 | 15 |
| | 981 | 781 | 825 | 1304 | 261 | 275 | 15 |
| | 982 | 1006 | 1050 | 1305 | 336 | 350 | 15 |
| | 983 | 919 | 963 | 1306 | 307 | 321 | 15 |
| | 984 | 469 | 513 | 1307 | 157 | 171 | 15 |
| | 985 | 634 | 678 | 1308 | 212 | 226 | 15 |
| | 986 | 694 | 738 | 1309 | 232 | 246 | 15 |
| | 987 | 163 | 207 | 1310 | 55 | 69 | 15 |
| | 988 | 529 | 573 | 1311 | 177 | 191 | 15 |
| | 989 | 706 | 750 | 1312 | 236 | 250 | 15 |
| | 990 | 835 | 879 | 1313 | 279 | 293 | 15 |
| | 991 | 811 | 855 | 1314 | 271 | 285 | 15 |
| | 992 | 802 | 846 | 1315 | 268 | 282 | 15 |
| | 993 | 295 | 339 | 1316 | 99 | 113 | 15 |
| | 994 | 751 | 795 | 1317 | 251 | 265 | 15 |
| DRB1*0106 | 995 | 586 | 630 | 1318 | 196 | 210 | 15 |
| | 996 | 847 | 891 | 1319 | 283 | 297 | 15 |
| | 997 | 283 | 327 | 1320 | 95 | 109 | 15 |
| | 998 | 487 | 531 | 1321 | 163 | 177 | 15 |
| | 999 | 307 | 351 | 1322 | 103 | 117 | 15 |
| | 1000 | 781 | 825 | 1323 | 261 | 275 | 15 |
| | 1001 | 1036 | 1080 | 1324 | 346 | 360 | 15 |
| | 1002 | 469 | 513 | 1325 | 157 | 171 | 15 |
| | 1003 | 508 | 552 | 1326 | 170 | 184 | 15 |
| | 1004 | 574 | 618 | 1327 | 192 | 206 | 15 |
| | 1005 | 814 | 858 | 1328 | 272 | 286 | 15 |
| | 1006 | 835 | 879 | 1329 | 279 | 293 | 15 |
| DRB1*0107 | 1007 | 283 | 327 | 1330 | 95 | 109 | 15 |
| | 1008 | 847 | 891 | 1331 | 283 | 297 | 15 |
| | 1009 | 487 | 531 | 1332 | 163 | 177 | 15 |
| | 1010 | 586 | 630 | 1333 | 196 | 210 | 15 |
| | 1011 | 580 | 624 | 1334 | 194 | 208 | 15 |
| | 1012 | 508 | 552 | 1335 | 170 | 184 | 15 |
| | 1013 | 307 | 351 | 1336 | 103 | 117 | 15 |
| | 1014 | 781 | 825 | 1337 | 261 | 275 | 15 |
| | 1015 | 1006 | 1050 | 1338 | 336 | 350 | 15 |
| | 1016 | 919 | 963 | 1339 | 307 | 321 | 15 |
| | 1017 | 469 | 513 | 1340 | 157 | 171 | 15 |
| | 1018 | 634 | 678 | 1341 | 212 | 226 | 15 |
| | 1019 | 694 | 738 | 1342 | 232 | 246 | 15 |
| | 1020 | 163 | 207 | 1343 | 55 | 69 | 15 |
| | 1021 | 529 | 573 | 1344 | 177 | 191 | 15 |
| | 1022 | 706 | 750 | 1345 | 236 | 250 | 15 |
| | 1023 | 835 | 879 | 1346 | 279 | 293 | 15 |
| | 1024 | 811 | 855 | 1347 | 271 | 285 | 15 |
| | 1025 | 802 | 846 | 1348 | 268 | 282 | 15 |
| | 1026 | 295 | 339 | 1349 | 99 | 113 | 15 |
| | 1027 | 751 | 795 | 1350 | 251 | 265 | 15 |
| DRB1*0108 | 1028 | 283 | 327 | 1351 | 95 | 109 | 15 |
| | 1029 | 847 | 891 | 1352 | 283 | 297 | 15 |
| | 1030 | 487 | 531 | 1353 | 163 | 177 | 15 |
| | 1031 | 586 | 630 | 1354 | 196 | 210 | 15 |
| | 1032 | 580 | 624 | 1355 | 194 | 208 | 15 |
| | 1033 | 508 | 552 | 1356 | 170 | 184 | 15 |
| | 1034 | 307 | 351 | 1357 | 103 | 117 | 15 |

TABLE 3-continued

T cell epitopes predicted by NetMHCIIPAN (only strong binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 1035 | 781 | 825 | 1358 | 261 | 275 | 15 |
| | 1036 | 1006 | 1050 | 1359 | 336 | 350 | 15 |
| | 1037 | 919 | 963 | 1360 | 307 | 321 | 15 |
| | 1038 | 469 | 513 | 1361 | 157 | 171 | 15 |
| | 1039 | 634 | 678 | 1362 | 212 | 226 | 15 |
| | 1040 | 694 | 738 | 1363 | 232 | 246 | 15 |
| | 1041 | 163 | 207 | 1364 | 55 | 69 | 15 |
| | 1042 | 529 | 573 | 1365 | 177 | 191 | 15 |
| | 1043 | 706 | 750 | 1366 | 236 | 250 | 15 |
| | 1044 | 835 | 879 | 1367 | 279 | 293 | 15 |
| | 1045 | 811 | 855 | 1368 | 271 | 285 | 15 |
| | 1046 | 802 | 846 | 1369 | 268 | 282 | 15 |
| | 1047 | 295 | 339 | 1370 | 99 | 113 | 15 |
| | 1048 | 751 | 795 | 1371 | 251 | 265 | 15 |
| DRB1*0109 | 1049 | 283 | 327 | 1372 | 95 | 109 | 15 |
| | 1050 | 847 | 891 | 1373 | 283 | 297 | 15 |
| | 1051 | 586 | 630 | 1374 | 196 | 210 | 15 |
| | 1052 | 487 | 531 | 1375 | 163 | 177 | 15 |
| | 1053 | 1006 | 1050 | 1376 | 336 | 350 | 15 |
| | 1054 | 307 | 351 | 1377 | 103 | 117 | 15 |
| | 1055 | 508 | 552 | 1378 | 170 | 184 | 15 |
| | 1056 | 781 | 825 | 1379 | 261 | 275 | 15 |
| | 1057 | 577 | 621 | 1380 | 193 | 207 | 15 |
| | 1058 | 469 | 513 | 1381 | 157 | 171 | 15 |
| | 1059 | 163 | 207 | 1382 | 55 | 69 | 15 |
| | 1060 | 919 | 963 | 1383 | 307 | 321 | 15 |
| | 1061 | 694 | 738 | 1384 | 232 | 246 | 15 |
| | 1062 | 706 | 750 | 1385 | 236 | 250 | 15 |
| | 1063 | 835 | 879 | 1386 | 279 | 293 | 15 |
| | 1064 | 634 | 678 | 1387 | 212 | 226 | 15 |
| DRB1*0110 | 1065 | 283 | 327 | 1388 | 95 | 109 | 15 |
| | 1066 | 847 | 891 | 1389 | 283 | 297 | 15 |
| | 1067 | 586 | 630 | 1390 | 196 | 210 | 15 |
| | 1068 | 487 | 531 | 1391 | 163 | 177 | 15 |
| | 1069 | 1006 | 1050 | 1392 | 336 | 350 | 15 |
| | 1070 | 580 | 624 | 1393 | 194 | 208 | 15 |
| | 1071 | 508 | 552 | 1394 | 170 | 184 | 15 |
| | 1072 | 307 | 351 | 1395 | 103 | 117 | 15 |
| | 1073 | 781 | 825 | 1396 | 261 | 275 | 15 |
| | 1074 | 919 | 963 | 1397 | 307 | 321 | 15 |
| | 1075 | 163 | 207 | 1398 | 55 | 69 | 15 |
| | 1076 | 694 | 738 | 1399 | 232 | 246 | 15 |
| | 1077 | 469 | 513 | 1400 | 157 | 171 | 15 |
| | 1078 | 802 | 846 | 1401 | 268 | 282 | 15 |
| | 1079 | 634 | 678 | 1402 | 212 | 226 | 15 |
| | 1080 | 706 | 750 | 1403 | 236 | 250 | 15 |
| | 1081 | 835 | 879 | 1404 | 279 | 293 | 15 |
| DRB1*0111 | 1082 | 283 | 327 | 1405 | 95 | 109 | 15 |
| | 1083 | 847 | 891 | 1406 | 283 | 297 | 15 |
| | 1084 | 487 | 531 | 1407 | 163 | 177 | 15 |
| | 1085 | 586 | 630 | 1408 | 196 | 210 | 15 |
| | 1086 | 1006 | 1050 | 1409 | 336 | 350 | 15 |
| | 1087 | 508 | 552 | 1410 | 170 | 184 | 15 |
| | 1088 | 307 | 351 | 1411 | 103 | 117 | 15 |
| | 1089 | 781 | 825 | 1412 | 261 | 275 | 15 |
| | 1090 | 580 | 624 | 1413 | 194 | 208 | 15 |
| | 1091 | 919 | 963 | 1414 | 307 | 321 | 15 |
| | 1092 | 922 | 966 | 1415 | 308 | 322 | 15 |
| | 1093 | 634 | 678 | 1416 | 212 | 226 | 15 |
| | 1094 | 802 | 846 | 1417 | 268 | 282 | 15 |
| | 1095 | 163 | 207 | 1418 | 55 | 69 | 15 |
| | 1096 | 694 | 738 | 1419 | 232 | 246 | 15 |
| | 1097 | 469 | 513 | 1420 | 157 | 171 | 15 |
| | 1098 | 529 | 573 | 1421 | 177 | 191 | 15 |
| DRB1*0112 | 1099 | 283 | 327 | 1422 | 95 | 109 | 15 |
| | 1100 | 847 | 891 | 1423 | 283 | 297 | 15 |
| | 1101 | 487 | 531 | 1424 | 163 | 177 | 15 |
| | 1102 | 586 | 630 | 1425 | 196 | 210 | 15 |
| | 1103 | 580 | 624 | 1426 | 194 | 208 | 15 |
| | 1104 | 508 | 552 | 1427 | 170 | 184 | 15 |
| | 1105 | 307 | 351 | 1428 | 103 | 117 | 15 |
| | 1106 | 781 | 825 | 1429 | 261 | 275 | 15 |
| | 1107 | 1006 | 1050 | 1430 | 336 | 350 | 15 |
| | 1108 | 919 | 963 | 1431 | 307 | 321 | 15 |

TABLE 3-continued

T cell epitopes predicted by NetMHCIIPAN (only strong binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| | 1109 | 469 | 513 | 1432 | 157 | 171 | 15 |
| | 1110 | 634 | 678 | 1433 | 212 | 226 | 15 |
| | 1111 | 694 | 738 | 1434 | 232 | 246 | 15 |
| | 1112 | 163 | 207 | 1435 | 55 | 69 | 15 |
| | 1113 | 529 | 573 | 1436 | 177 | 191 | 15 |
| | 1114 | 706 | 750 | 1437 | 236 | 250 | 15 |
| | 1115 | 835 | 879 | 1438 | 279 | 293 | 15 |
| | 1116 | 811 | 855 | 1439 | 271 | 285 | 15 |
| | 1117 | 802 | 846 | 1440 | 268 | 282 | 15 |
| | 1118 | 295 | 339 | 1441 | 99 | 113 | 15 |
| | 1119 | 751 | 795 | 1442 | 251 | 265 | 15 |
| DRB1*0113 | 1120 | 283 | 327 | 1443 | 95 | 109 | 15 |
| | 1121 | 847 | 891 | 1444 | 283 | 297 | 15 |
| | 1122 | 586 | 630 | 1445 | 196 | 210 | 15 |
| | 1123 | 487 | 531 | 1446 | 163 | 177 | 15 |
| | 1124 | 1006 | 1050 | 1447 | 336 | 350 | 15 |
| | 1125 | 307 | 351 | 1448 | 103 | 117 | 15 |
| | 1126 | 919 | 963 | 1449 | 307 | 321 | 15 |
| | 1127 | 781 | 825 | 1450 | 261 | 275 | 15 |
| | 1128 | 1036 | 1080 | 1451 | 346 | 360 | 15 |
| | 1129 | 784 | 828 | 1452 | 262 | 276 | 15 |
| | 1130 | 577 | 621 | 1453 | 193 | 207 | 15 |
| | 1131 | 508 | 552 | 1454 | 170 | 184 | 15 |
| | 1132 | 469 | 513 | 1455 | 157 | 171 | 15 |
| | 1133 | 802 | 846 | 1456 | 268 | 282 | 15 |
| | 1134 | 163 | 207 | 1457 | 55 | 69 | 15 |
| | 1135 | 835 | 879 | 1458 | 279 | 293 | 15 |
| | 1136 | 694 | 738 | 1459 | 232 | 246 | 15 |
| | 1137 | 634 | 678 | 1460 | 212 | 226 | 15 |
| | 1138 | 340 | 384 | 1461 | 114 | 128 | 15 |
| | 1139 | 811 | 855 | 1462 | 271 | 285 | 15 |
| | 1140 | 85 | 129 | 1463 | 29 | 43 | 15 |
| | 1141 | 529 | 573 | 1464 | 177 | 191 | 15 |
| | 1142 | 748 | 792 | 1465 | 250 | 264 | 15 |
| | 1143 | 124 | 168 | 1466 | 42 | 56 | 15 |
| DRB1*0114 | 1144 | 283 | 327 | 1467 | 95 | 109 | 15 |
| | 1145 | 487 | 531 | 1468 | 163 | 177 | 15 |
| | 1146 | 847 | 891 | 1469 | 283 | 297 | 15 |
| | 1147 | 586 | 630 | 1470 | 196 | 210 | 15 |
| | 1148 | 508 | 552 | 1471 | 170 | 184 | 15 |
| | 1149 | 307 | 351 | 1472 | 103 | 117 | 15 |
| | 1150 | 634 | 678 | 1473 | 212 | 226 | 15 |
| | 1151 | 781 | 825 | 1474 | 261 | 275 | 15 |
| | 1152 | 1006 | 1050 | 1475 | 336 | 350 | 15 |
| | 1153 | 919 | 963 | 1476 | 307 | 321 | 15 |
| | 1154 | 295 | 339 | 1477 | 99 | 113 | 15 |
| | 1155 | 802 | 846 | 1478 | 268 | 282 | 15 |
| | 1156 | 811 | 855 | 1479 | 271 | 285 | 15 |
| | 1157 | 706 | 750 | 1480 | 236 | 250 | 15 |
| | 1158 | 574 | 618 | 1481 | 192 | 206 | 15 |
| | 1159 | 163 | 207 | 1482 | 55 | 69 | 15 |
| | 1160 | 469 | 513 | 1483 | 157 | 171 | 15 |
| | 1161 | 544 | 588 | 1484 | 182 | 196 | 15 |
| | 1162 | 751 | 795 | 1485 | 251 | 265 | 15 |
| DRB1*0115 | 1163 | 847 | 891 | 1486 | 283 | 297 | 15 |
| | 1164 | 283 | 327 | 1487 | 95 | 109 | 15 |
| | 1165 | 586 | 630 | 1488 | 196 | 210 | 15 |
| | 1166 | 487 | 531 | 1489 | 163 | 177 | 15 |
| | 1167 | 1006 | 1050 | 1490 | 336 | 350 | 15 |
| | 1168 | 307 | 351 | 1491 | 103 | 117 | 15 |
| | 1169 | 508 | 552 | 1492 | 170 | 184 | 15 |
| | 1170 | 163 | 207 | 1493 | 55 | 69 | 15 |
| | 1171 | 781 | 825 | 1494 | 261 | 275 | 15 |
| | 1172 | 574 | 618 | 1495 | 192 | 206 | 15 |
| | 1173 | 469 | 513 | 1496 | 157 | 171 | 15 |
| | 1174 | 706 | 750 | 1497 | 236 | 250 | 15 |
| | 1175 | 694 | 738 | 1498 | 232 | 246 | 15 |
| | 1176 | 634 | 678 | 1499 | 212 | 226 | 15 |
| | 1177 | 835 | 879 | 1500 | 279 | 293 | 15 |
| DRB1*0116 | 1178 | 1006 | 1050 | 1501 | 336 | 350 | 15 |
| | 1179 | 847 | 891 | 1502 | 283 | 297 | 15 |
| | 1180 | 283 | 327 | 1503 | 95 | 109 | 15 |
| | 1181 | 85 | 129 | 1504 | 29 | 43 | 15 |
| | 1182 | 163 | 207 | 1505 | 55 | 69 | 15 |

TABLE 3-continued

T cell epitopes predicted by NetMHCIIPAN (only strong binder)

| Allele | SEQ ID | Start No.* nucleic acid | End No.* nucleic acid | SEQ ID | Start No.** amino acid | End No.** amino acid | Length amino acid |
|---|---|---|---|---|---|---|---|
| DRB1*0117 | 1183 | 283 | 327 | 1506 | 95 | 109 | 15 |
|  | 1184 | 847 | 891 | 1507 | 283 | 297 | 15 |
|  | 1185 | 487 | 531 | 1508 | 163 | 177 | 15 |
|  | 1186 | 586 | 630 | 1509 | 196 | 210 | 15 |
|  | 1187 | 1006 | 1050 | 1510 | 336 | 350 | 15 |
|  | 1188 | 580 | 624 | 1511 | 194 | 208 | 15 |
|  | 1189 | 307 | 351 | 1512 | 103 | 117 | 15 |
|  | 1190 | 781 | 825 | 1513 | 261 | 275 | 15 |
|  | 1191 | 508 | 552 | 1514 | 170 | 184 | 15 |
|  | 1192 | 634 | 678 | 1515 | 212 | 226 | 15 |
|  | 1193 | 163 | 207 | 1516 | 55 | 69 | 15 |
|  | 1194 | 919 | 963 | 1517 | 307 | 321 | 15 |
|  | 1195 | 694 | 738 | 1518 | 232 | 246 | 15 |
|  | 1196 | 469 | 513 | 1519 | 157 | 171 | 15 |
|  | 1197 | 706 | 750 | 1520 | 236 | 250 | 15 |
|  | 1198 | 802 | 846 | 1521 | 268 | 282 | 15 |
|  | 1199 | 295 | 339 | 1522 | 99 | 113 | 15 |
|  | 1200 | 529 | 573 | 1523 | 177 | 191 | 15 |
|  | 1201 | 835 | 879 | 1524 | 279 | 293 | 15 |
|  | 1202 | 811 | 855 | 1525 | 271 | 285 | 15 |
|  | 1203 | 751 | 795 | 1526 | 251 | 265 | 15 |
|  | 1204 | 544 | 588 | 1527 | 182 | 196 | 15 |
|  | 1205 | 748 | 792 | 1528 | 250 | 264 | 15 |
| DRB1*0118 | 1206 | 283 | 327 | 1529 | 95 | 109 | 15 |
|  | 1207 | 847 | 891 | 1530 | 283 | 297 | 15 |
|  | 1208 | 487 | 531 | 1531 | 163 | 177 | 15 |
|  | 1209 | 586 | 630 | 1532 | 196 | 210 | 15 |
|  | 1210 | 781 | 825 | 1533 | 261 | 275 | 15 |
|  | 1211 | 508 | 552 | 1534 | 170 | 184 | 15 |
|  | 1212 | 577 | 621 | 1535 | 193 | 207 | 15 |
|  | 1213 | 919 | 963 | 1536 | 307 | 321 | 15 |
|  | 1214 | 307 | 351 | 1537 | 103 | 117 | 15 |
|  | 1215 | 469 | 513 | 1538 | 157 | 171 | 15 |
|  | 1216 | 1006 | 1050 | 1539 | 336 | 350 | 15 |
|  | 1217 | 835 | 879 | 1540 | 279 | 293 | 15 |
|  | 1218 | 706 | 750 | 1541 | 236 | 250 | 15 |
|  | 1219 | 634 | 678 | 1542 | 212 | 226 | 15 |
|  | 1220 | 529 | 573 | 1543 | 177 | 191 | 15 |
| DRB1*0119 | 1221 | 283 | 327 | 1544 | 95 | 109 | 15 |
|  | 1222 | 847 | 891 | 1545 | 283 | 297 | 15 |
|  | 1223 | 487 | 531 | 1546 | 163 | 177 | 15 |
|  | 1224 | 586 | 630 | 1547 | 196 | 210 | 15 |
|  | 1225 | 580 | 624 | 1548 | 194 | 208 | 15 |
|  | 1226 | 508 | 552 | 1549 | 170 | 184 | 15 |
|  | 1227 | 307 | 351 | 1550 | 103 | 117 | 15 |
|  | 1228 | 781 | 825 | 1551 | 261 | 275 | 15 |
|  | 1229 | 1006 | 1050 | 1552 | 336 | 350 | 15 |
|  | 1230 | 919 | 963 | 1553 | 307 | 321 | 15 |
|  | 1231 | 469 | 513 | 1554 | 157 | 171 | 15 |
|  | 1232 | 634 | 678 | 1555 | 212 | 226 | 15 |
|  | 1233 | 694 | 738 | 1556 | 232 | 246 | 15 |
|  | 1234 | 163 | 207 | 1557 | 55 | 69 | 15 |
|  | 1235 | 529 | 573 | 1558 | 177 | 191 | 15 |
|  | 1236 | 706 | 750 | 1559 | 236 | 250 | 15 |
|  | 1237 | 835 | 879 | 1560 | 279 | 293 | 15 |
|  | 1238 | 811 | 855 | 1561 | 271 | 285 | 15 |
|  | 1239 | 802 | 846 | 1562 | 268 | 282 | 15 |
|  | 1240 | 295 | 339 | 1563 | 99 | 113 | 15 |
|  | 1241 | 751 | 795 | 1564 | 251 | 265 | 15 |

*according to numbering SEQ ID NO: 1
**according to numbering SEQ ID NO: 2

TABLE 4

Calculation of putative surface epitopes per protein size ratio

| Antigen | Size | Surface ($A^2$) | Surface epitopes* | Surface epitopes/kDa |
|---|---|---|---|---|
| Amb t 5 | 4.3 kDa | 2438.3 | 2.57 | 0.6 |
| Api m 1 | 16-20 kDa | 7606.4 | 8.0 | 0.4 |
| Api m 2 | 43 kDa | 15905.5 | 16.74 | 0.39 |
| Api m 4 | 3 kDa | 3885.7 | 4.09 | 1.36 |

TABLE 4-continued

Calculation of putative surface epitopes per protein size ratio

| Antigen | Size | Surface ($A^2$) | Surface epitopes* | Surface epitopes/kDa |
|---|---|---|---|---|
| Ara t 8 | 14.2 kDa | 7080.1 | 7.45 | 0.52 |
| Asp f 1 | 16.8 kDa | 16037.6 | 16.88 | 1.0 |
| Asp f 6 | 23.3 kDa | 8793.2 | 9.26 | 0.4 |
| Bet v 1 | 17.4 kDa | 5215.3 | 5.49 | 0.32 |
| Bet v 2 | 14.3 kDa | 6493.9 | 6.84 | 0.48 |
| Bos d 4 | 14.2 kDa | 7246.9 | 7.63 | 0.54 |
| Bos d 5 | 18.2 kDa | 9546.5 | 10.05 | 0.55 |
| Bos d 5 | 18.2 kDa | 9618.4 | 10.12 | 0.56 |
| Der f2 | 15.8 kDa | 7785.2 | 8.19 | 0.52 |
| Der p2 | 16 kDa | 7588.8 | 7.99 | 0.5 |
| Equ c 1 | 20 kDa | 8907.4 | 9.38 | 0.47 |
| Gal d 3 | 75.8 kDa | 15952.9 | 16.79 | 0.22 |
| Gal d 4 | 16.2 kDa | 6951.3 | 7.32 | 0.45 |
| Hev b 8 | 14 kDa | 11982 | 12.61 | 0.9 |
| Mus m 1 | 18.7 kDa | 8943.5 | 9.41 | 0.5 |
| Phl p 1 | 26.1 kDa | 12145.6 | 12.78 | 0.49 |
| Phl p 2 | 10.8 kDa | 6099.5 | 6.42 | 0.59 |
| Phl p 6 | 11.8 kDa | 5429.5 | 5.72 | 0.48 |
| Pru av 1 | 17.7 kDa | 9742.8 | 10.26 | 0.58 |
| Ves v 5 | 25.8 kDa | 11657.1 | 12.27 | 0.47 |
| Zea m14 | 11.7 kDa | 5099.5 | 5.37 | 0.46 |
| | | | Average value | 0.55 +/− 0.23 |

*Estimated IgE epitope area: 950 $Å^2$

TABLE 3

Calculation of the average number of IgE epitopes on allergens

| Antigen | Protein | Organism | Common | PDB code | Size (kDa) | Surface ($Å^2$) | Size/Surface | Possible B-cell epitopes | Identified IgE binding peptides |
|---|---|---|---|---|---|---|---|---|---|
| Alt a 1 | — | *Alt. alternata* | Fungi | — | 15.2 | — | — | — | 2 |
| Ara h 1 | Vicilin | *Arachis hypogaea* | Peanut | — | 67.7 | — | — | — | 21 |
| Ara h 2 | Conglutin | *Arachis hypogaea* | Peanut | — | 17.5 | — | — | — | 10 |
| Asp f 1 | Mitogillin | *Asp. fumigatus* | Fungi | 1AQZ | 16.8 | 16037.6 | 1.0 | 16-17 | 13 |
| Asp f 2 | — | *Asp. fumigatus* | Fungi | — | 31.2 | — | — | — | 9 |
| Asp f 3 | Peroximal protein | *Asp. fumigatus* | Fungi | — | 18.4 | — | — | — | 7 |
| Asp f 13 | Oryzin | *Asp. fumigatus* | Fungi | — | 28.7 | — | — | — | 5 |
| Bet v 1 | PR10 | *Betulla verrucosa* | Birch | 1BV1 | 17.4 | 5215.3 | 3.3 | 5-6 | |
| Bet v 2 | Profilin | *Betulla verrucosa* | Birch | 1CQA | 14.3 | 6493.9 | 2.2 | 6-7 | 3 |
| Bos d 5 | b-Lactoglobulin | *Bos domesticus* | Cow | 1B8E | 18.2 | 9546.5 | 1.9 | 9-10 | 7 |
| Bos d 5 | b-Lactoglobulin | *Bos domesticus* | Cow | 1QG5 | 18.2 | 9618.4 | 1.9 | 9-10 | 7 |
| Cry j 2 | Pectinase | *Cryp. japonica* | Sugi | — | 42.2 | — | — | — | 4 |
| Gal d 5 | Ovomucoid | *Gallus domesticus* | Chicken | — | 20.1 | — | — | — | 9 (8 IgG) |
| Hev b 1 | Elongaton factor | *Hevea brasiliensis* | Latex | — | 14.6 | — | — | — | 8 |
| Hev b 3 | SRPP | *Hevea brasiliensis* | Latex | — | 22.3 | — | — | — | 11 |
| Hev b 5 | — | *Hevea brasiliensis* | Latex | — | 15.9 | — | — | — | 11 |
| Jun a 1 | Pectate lyase | *Juniperus ashei* | Cedar | — | 37.6 | — | — | — | 4 |
| Jun a 3 | — | *Juniperus ashei* | Cedar | — | 21 | — | — | — | 5 |
| Par j 1 | Lipid transfer prot.1 | *Parietaria judaica* | Weed | — | 15 | — | — | — | 5 |
| Par j 2 | Lipid transfer prot.2 | *Parietaria judaica* | Weed | — | 11.3 | — | — | — | 8 |
| Pen n18 | Serine protease | *Pen. notatum* | Fungi | — | 52.4 | — | — | — | 9 |

TABLE 6

Prediction of linear B cell epitopes by BepiPred 1.0b

| Putative B-cell epitope | SEQ ID | Amino acid positions predicted* | Sequence |
|---|---|---|---|
| 1 | 1565 | 22 | T |
| 1 | 1566 | 32.34 | K L K |
| 3 | 1567 | 44-50.52 | P D F P N Y . M |
| 4 | 1568 | 59-61.63 | S A R . N |
| 5 | 1569 | 74-81 | D V P P S S N C |
| 6 | 1570 | 91 | D |

TABLE 6-continued

Prediction of linear B cell epitopes by BepiPred 1.0b

| Putative B-cell epitope | SEQ ID | Amino acid positions predicted* | Sequence |
|---|---|---|---|
| 7  | 1571 | 122-124         | N T Y |
| 8  | 1572 | 143-152.154-159 | W K N P S R I V G G . E T G V N E |
| 9  | 1573 | 212-220         | T W A I N D T K A |
| 10 | 1574 | 234-238         | N Y R P K |
| 11 | 1575 | 328-334.336-344 | A C Q F D S G . P I L W Q N P K S |
| 12 | 1576 | 358-366         | T C A D E A P G V |
| 13 | 1577 | 379-385         | R S T P G E I |

*numbering according to SEQ ID NO. 2

SEQUENCE LISTING

<160> NUMBER OF SEQ ID NOS: 1577

<210> SEQ ID NO 1
<211> LENGTH: 1173
<212> TYPE: DNA
<213> ORGANISM: Vespula vulgaris

<400> SEQUENCE: 1

```
atgaaattag ataatttttt tttaatactt tatgtgctac taagcattat aaaatccaat    60
ggtactatcg atctcaattg tggctacacc caaaaattaa atcagatgt taattattgc   120
gtgtataatc ctgattttcc gaattattac atgggagaac ataattgtcg gtggagtgct   180
aggagcaata ctcgaattaa attgaattgc acagttttcg atgttcctcc gagttcgaat   240
tgttcattgg attttatgaa agtcaaagtc gacgatgaca tcgagtacgt tttctgtgga   300
ttaaattctt ttgcagtgga atcaaatagca tcgaaaatga ctataaaatt ccattcaaga   360
tacaatactt atggaggcaa atttcgatgt aatctcagat cagtcaaaga gaaatgtaga   420
tgtggttgga agaatccgtc gagaatcgta ggcggtgttg aaacaggagt gaatgaatat   480
cctatgatgg ctggtataat acatcttgca acgcgttttc tctattgcgg tgcaactata   540
ataactccgc aacatgtatt aacggctgct cattgcgttg cgaggtataa aaggatttta   600
tatattctag gagttgttgt tggagaacat aatacatggg caattaacga tacaaaggca   660
actcaacttt atcttattga tgatataatc gtacatccga attataggcc aaaattaaac   720
gatttagctg ttataaaatt gcagaagagg ttaaaatatt ctatgagaat tggtccagct   780
tgtcttccgt tctattacat gcagcgaaac tttgtagaca ctgttgttac agctgtagga   840
tggggtctta cgaatttta tggtgtcaag tctgaagttt tgagaaaagt cgatttgcat   900
gtagtttcaa tgaagaaatg cgtcaagtat cactttctgg ctacacctaa gcaactttgt   960
acattcgata tgggaaagga tgcttgccag ttcgacagtg gtggtccaat tttatggcaa  1020
aatccaaaaa gcaaacgtat tttccttctt ggagtcatca attatggaag acatgtgcc   1080
gatgaagctc ctggtgttaa cttgagagtc actagttatt tagattttat tacaagatca  1140
acacctggag aaatatattg tcaggcgtat taa                                1173
```

<210> SEQ ID NO 2

```
<211> LENGTH: 390
<212> TYPE: PRT
<213> ORGANISM: Vespula vulgaris
<220> FEATURE:
<221> NAME/KEY: Signal_sequence
<222> LOCATION: (1)..(21)
<220> FEATURE:
<221> NAME/KEY: CUB_domain
<222> LOCATION: (27)..(135)
<220> FEATURE:
<221> NAME/KEY: Trypsin-like_serine_protease
<222> LOCATION: (141)..(381)

<400> SEQUENCE: 2
```

| Met | Lys | Leu | Asp | Asn | Phe | Phe | Leu | Ile | Leu | Tyr | Val | Leu | Leu | Ser | Ile |
|---|---|---|---|---|---|---|---|---|---|---|---|---|---|---|---|
| 1 | | | | 5 | | | | | 10 | | | | | 15 | |

| Ile | Lys | Ser | Asn | Gly | Thr | Ile | Asp | Leu | Asn | Cys | Gly | Tyr | Thr | Gln | Lys |
|---|---|---|---|---|---|---|---|---|---|---|---|---|---|---|---|
| | | | 20 | | | | | 25 | | | | | 30 | | |

| Leu | Lys | Ser | Asp | Val | Asn | Tyr | Cys | Val | Tyr | Asn | Pro | Asp | Phe | Pro | Asn |
|---|---|---|---|---|---|---|---|---|---|---|---|---|---|---|---|
| | | 35 | | | | | 40 | | | | | 45 | | | |

| Tyr | Tyr | Met | Gly | Glu | His | Asn | Cys | Arg | Trp | Ser | Ala | Arg | Ser | Asn | Thr |
|---|---|---|---|---|---|---|---|---|---|---|---|---|---|---|---|
| | 50 | | | | | 55 | | | | | 60 | | | | |

| Arg | Ile | Lys | Leu | Asn | Cys | Thr | Val | Phe | Asp | Val | Pro | Pro | Ser | Ser | Asn |
|---|---|---|---|---|---|---|---|---|---|---|---|---|---|---|---|
| 65 | | | | | 70 | | | | | 75 | | | | | 80 |

| Cys | Ser | Leu | Asp | Phe | Met | Lys | Val | Lys | Val | Asp | Asp | Ile | Glu | Tyr |
|---|---|---|---|---|---|---|---|---|---|---|---|---|---|---|
| | | | | 85 | | | | | 90 | | | | | 95 |

| Val | Phe | Cys | Gly | Leu | Asn | Ser | Phe | Ala | Val | Glu | Ser | Ile | Ala | Ser | Lys |
|---|---|---|---|---|---|---|---|---|---|---|---|---|---|---|---|
| | | | 100 | | | | | 105 | | | | | 110 | | |

| Met | Thr | Ile | Lys | Phe | His | Ser | Arg | Tyr | Asn | Thr | Tyr | Gly | Gly | Lys | Phe |
|---|---|---|---|---|---|---|---|---|---|---|---|---|---|---|---|
| | | 115 | | | | | 120 | | | | | 125 | | | |

| Arg | Cys | Asn | Leu | Arg | Ser | Val | Lys | Glu | Lys | Cys | Arg | Cys | Gly | Trp | Lys |
|---|---|---|---|---|---|---|---|---|---|---|---|---|---|---|---|
| | 130 | | | | | 135 | | | | | 140 | | | | |

| Asn | Pro | Ser | Arg | Ile | Val | Gly | Gly | Val | Glu | Thr | Gly | Val | Asn | Glu | Tyr |
|---|---|---|---|---|---|---|---|---|---|---|---|---|---|---|---|
| 145 | | | | | 150 | | | | | 155 | | | | | 160 |

| Pro | Met | Met | Ala | Gly | Ile | Ile | His | Leu | Ala | Thr | Arg | Phe | Leu | Tyr | Cys |
|---|---|---|---|---|---|---|---|---|---|---|---|---|---|---|---|
| | | | | 165 | | | | | 170 | | | | | 175 | |

| Gly | Ala | Thr | Ile | Ile | Thr | Pro | Gln | His | Val | Leu | Thr | Ala | Ala | His | Cys |
|---|---|---|---|---|---|---|---|---|---|---|---|---|---|---|---|
| | | | 180 | | | | | 185 | | | | | 190 | | |

| Val | Ala | Arg | Tyr | Lys | Arg | Ile | Leu | Tyr | Ile | Leu | Gly | Val | Val | Gly |
|---|---|---|---|---|---|---|---|---|---|---|---|---|---|---|
| | | 195 | | | | | 200 | | | | | 205 | | |

| Glu | His | Asn | Thr | Trp | Ala | Ile | Asn | Asp | Thr | Lys | Ala | Thr | Gln | Leu | Tyr |
|---|---|---|---|---|---|---|---|---|---|---|---|---|---|---|---|
| | 210 | | | | | 215 | | | | | 220 | | | | |

| Leu | Ile | Asp | Asp | Ile | Ile | Val | His | Pro | Asn | Tyr | Arg | Pro | Lys | Leu | Asn |
|---|---|---|---|---|---|---|---|---|---|---|---|---|---|---|---|
| 225 | | | | | 230 | | | | | 235 | | | | | 240 |

| Asp | Leu | Ala | Val | Ile | Lys | Leu | Gln | Lys | Arg | Leu | Lys | Tyr | Ser | Met | Arg |
|---|---|---|---|---|---|---|---|---|---|---|---|---|---|---|---|
| | | | | 245 | | | | | 250 | | | | | 255 | |

| Ile | Gly | Pro | Ala | Cys | Leu | Pro | Phe | Tyr | Tyr | Met | Gln | Arg | Asn | Phe | Val |
|---|---|---|---|---|---|---|---|---|---|---|---|---|---|---|---|
| | | | 260 | | | | | 265 | | | | | 270 | | |

| Asp | Thr | Val | Val | Thr | Ala | Val | Gly | Trp | Gly | Leu | Thr | Asn | Phe | Tyr | Gly |
|---|---|---|---|---|---|---|---|---|---|---|---|---|---|---|---|
| | | 275 | | | | | 280 | | | | | 285 | | | |

| Val | Lys | Ser | Glu | Val | Leu | Arg | Lys | Val | Asp | Leu | His | Val | Ser | Met |
|---|---|---|---|---|---|---|---|---|---|---|---|---|---|---|
| | 290 | | | | | 295 | | | | | 300 | | | |

| Lys | Lys | Cys | Val | Lys | Tyr | His | Phe | Leu | Ala | Thr | Pro | Lys | Gln | Leu | Cys |
|---|---|---|---|---|---|---|---|---|---|---|---|---|---|---|---|
| 305 | | | | | 310 | | | | | 315 | | | | | 320 |

| Thr | Phe | Asp | Met | Gly | Lys | Asp | Ala | Cys | Gln | Phe | Asp | Ser | Gly | Gly | Pro |
|---|---|---|---|---|---|---|---|---|---|---|---|---|---|---|---|
| | | | | 325 | | | | | 330 | | | | | 335 | |

| Ile | Leu | Trp | Gln | Asn | Pro | Lys | Ser | Lys | Arg | Ile | Phe | Leu | Leu | Gly | Val |
|---|---|---|---|---|---|---|---|---|---|---|---|---|---|---|---|

```
            340             345             350
Ile Asn Tyr Gly Arg Thr Cys Ala Asp Glu Ala Pro Gly Val Asn Leu
        355                 360                 365

Arg Val Thr Ser Tyr Leu Asp Phe Ile Thr Arg Ser Thr Pro Gly Glu
    370                 375                 380

Ile Tyr Cys Gln Ala Tyr
385                 390

<210> SEQ ID NO 3
<211> LENGTH: 381
<212> TYPE: DNA
<213> ORGANISM: Vespula vulgaris

<400> SEQUENCE: 3
actatcgatc tcaattgtgg ctacacccaa aaattaaaat cagatgttaa ttattgcgtg       60
tataatcctg attttccgaa ttattacatg ggagaacata attgtcggtg gagtgctagg      120
agcaatactc gaattaaatt gaattgcaca gttttcgatg ttcctccgag ttcgaattgt      180
tcattggatt ttatgaaagt caaagtcgac gatgacatcg agtacgtttt ctgtggatta      240
aattcttttg cagtggaatc aatagcatcg aaaatgacta taaaattcca ttcaagatac      300
aatacttatg gaggcaaatt tcgatgtaat ctcagatcag tcaaagagaa atgtagatgt      360
ggttggaaga atccgtcgag a                                                381

<210> SEQ ID NO 4
<211> LENGTH: 360
<212> TYPE: DNA
<213> ORGANISM: Vespula vulgaris

<400> SEQUENCE: 4
atcgtaggcg gtgttgaaac aggagtgaat gaatatccta tgatggctgg tataatacat       60
cttgcaacgc gttttctcta ttgcggtgca actataataa ctccgcaaca tgtattaacg      120
gctgctcatt gcgttgcgag gtataaaagg atttttatata ttctaggagt tgttgttgga     180
gaacataata catgggcaat taacgataca aaggcaactc aactttatct tattgatgat      240
ataatcgtac atccgaatta taggccaaaa ttaaacgatt tagctgttat aaaattgcag      300
aagaggttaa aatattctat gagaattggt ccagcttgtc ttccgttcta ttacatgcag      360

<210> SEQ ID NO 5
<211> LENGTH: 366
<212> TYPE: DNA
<213> ORGANISM: Vespula vulgaris

<400> SEQUENCE: 5
cgaaactttg tagacactgt tgttacagct gtaggatggg gtcttacgaa ttttatggt        60 gtcaagtctg aagttttgag aaaagtcgat ttgcatgtag tttcaatgaa gaaatgcgtc      120
aagtatcact ttctggctac acctaagcaa ctttgtacat tcgatatggg aaaggatgct      180
tgccagttcg acagtggtgg tccaattta tggcaaaatc caaaaagcaa acgtattttc       240
cttcttggag tcatcaatta tggaagaaca tgtgccgatg aagctcctgg tgttaacttg      300
agagtcacta gttatttaga ttttattaca agatcaacac tggagaaat atattgtcag       360 gcgtat                                                                 366

<210> SEQ ID NO 6
<211> LENGTH: 417
<212> TYPE: DNA
```

<213> ORGANISM: Vespula vulgaris

<400> SEQUENCE: 6

| | |
|---|---|
| tgtggattaa attcttttgc agtggaatca atagcatcga aaatgactat aaaattccat | 60 |
| tcaagataca atacttatgg aggcaaattt cgatgtaatc tcagatcagt caaagagaaa | 120 |
| tgtagatgtg gttggaagaa tccgtcgaga atcgtaggcg gtgttgaaac aggagtgaat | 180 |
| gaatatccta tgatggctgg tataatacat cttgcaacgc gttttctcta ttgcggtgca | 240 |
| actataataa ctccgcaaca tgtattaacg gctgctcatt gcgttgcgag gtataaaagg | 300 |
| attttatata ttctaggagt tgttgttgga aacataata catgggcaat taacgataca | 360 |
| aaggcaactc aactttatct tattgatgat ataatcgtac atccgaatta taggcca | 417 |

<210> SEQ ID NO 7
<211> LENGTH: 360
<212> TYPE: DNA
<213> ORGANISM: Vespula vulgaris

<400> SEQUENCE: 7

| | |
|---|---|
| aaattaaacg atttagctgt tataaaattg cagaagaggt taaaatattc tatgagaatt | 60 |
| ggtccagctt gtcttccgtt ctattacatg cagcgaaact ttgtagacac tgttgttaca | 120 |
| gctgtaggat ggggtcttac gaattttat ggtgtcaagt ctgaagtttt gagaaaagtc | 180 |
| gatttgcatg tagtttcaat gaagaaatgc gtcaagtatc actttctggc tacacctaag | 240 |
| caactttgta cattcgatat gggaaggat gcttgccagt tcgacagtgg tggtccaatt | 300 |
| ttatggcaaa atccaaaaag caaacgtatt ttccttcttg gagtcatcaa ttatggaaga | 360 |

<210> SEQ ID NO 8
<211> LENGTH: 342
<212> TYPE: DNA
<213> ORGANISM: Vespula vulgaris

<400> SEQUENCE: 8

| | |
|---|---|
| actatcgatc tcaattgtgg ctacacccaa aaattaaaat cagatgttaa ttattgcgtg | 60 |
| tataatcctg attttccgaa ttattacatg ggagaacata attgtcggtg gagtgctagg | 120 |
| agcaatactc gaattaaatt gaattgcaca gttttcgatg ttcctccgag ttcgaattgt | 180 |
| tcattggatt ttatgaaagt caaagtcgac gatgacatcg agtacgtttt ctgtggatta | 240 |
| aattcttttg cagtggaatc aatagcatcg aaaatgacta taaaattcca ttcaagatac | 300 |
| aatacttatg gaggcaaatt tcgatgtaat ctcagatcag tc | 342 |

<210> SEQ ID NO 9
<211> LENGTH: 291
<212> TYPE: DNA
<213> ORGANISM: Vespula vulgaris

<400> SEQUENCE: 9

| | |
|---|---|
| aaagagaaat gtagatgtgg ttggaagaat ccgtcgagaa tcgtaggcgg tgttgaaaca | 60 |
| ggagtgaatg aatatcctat gatggctggt ataatacatc ttgcaacgcg ttttctctat | 120 |
| tgcggtgcaa ctataataac tccgcaacat gtattaacgg ctgctcattg cgttgcgagg | 180 |
| tataaaagga ttttatatat tctaggagtt gttgttggag aacataatac atgggcaatt | 240 |
| aacgatacaa aggcaactca actttatctt attgatgata taatcgtaca t | 291 |

<210> SEQ ID NO 10
<211> LENGTH: 243

```
<212> TYPE: DNA
<213> ORGANISM: Vespula vulgaris

<400> SEQUENCE: 10
ccgaattata ggccaaaatt aaacgattta gctgttataa aattgcagaa gaggttaaaa      60
tattctatga gaattggtcc agcttgtctt ccgttctatt acatgcagcg aaactttgta     120
gacactgttg ttacagctgt aggatggggt cttacgaatt tttatggtgt caagtctgaa     180
gttttgagaa aagtcgattt gcatgtagtt tcaatgaaga aatgcgtcaa gtatcacttt     240
ctg                                                                   243

<210> SEQ ID NO 11
<211> LENGTH: 231
<212> TYPE: DNA
<213> ORGANISM: Vespula vulgaris

<400> SEQUENCE: 11
gctacaccta agcaactttg tacattcgat atgggaaagg atgcttgcca gttcgacagt      60
ggtggtccaa ttttatggca aaatccaaaa agcaaacgta ttttccttct tggagtcatc     120
aattatggaa gaacatgtgc cgatgaagct cctggtgtta acttgagagt cactagttat     180
ttagatttta ttacaagatc aacacctgga gaaatatatt gtcaggcgta t               231

<210> SEQ ID NO 12
<211> LENGTH: 299
<212> TYPE: DNA
<213> ORGANISM: Vespula vulgaris

<400> SEQUENCE: 12
gatgacatcg agtacgt

```
gatatgggaa aggatgcttg ccagttcgac agtggtggtc caattttatg gcaaaatcca      180
aaaagcaaac gtattttcct tcttggagtc atcaattatg gaagaacatg tgccgatgaa      240
gctcctggtg ttaacttgag agtcactagt                                       270

<210> SEQ ID NO 15
<211> LENGTH: 159
<212> TYPE: DNA
<213> ORGANISM: Vespula vulgaris

<400> SEQUENCE: 15
actatcgatc tcaattgtgg ctacacccaa aaattaaaat cagatgttaa ttattgcgtg       60
tataatcctg attttccgaa ttattacatg ggagaacata attgtcggtg gagtgctagg      120
agcaatactc gaattaaatt gaattgcaca gttttcgat                             159

<210> SEQ ID NO 16
<211> LENGTH: 183
<212> TYPE: DNA
<213> ORGANISM: Vespula vulgaris

<400> SEQUENCE: 16
gttcctccga gttcgaattg ttcattggat tttatgaaag tcaaagtcga cgatgacatc       60
gagtacgttt tctgtggatt aaattctttt gcagtggaat caatagcatc gaaaatgact      120
ataaaattcc attcaagata caatacttat ggaggcaaat ttcgatgtaa tctcagatca      180
gtc                                                                    183

<210> SEQ ID NO 17
<211> LENGTH: 165
<212> TYPE: DNA
<213> ORGANISM: Vespula vulgaris

<400> SEQUENCE: 17
aaagagaaat gtagatgtgg ttggaagaat ccgtcgagaa tcgtaggcgg tgttgaaaca       60
ggagtgaatg aatatcctat gatggctggt ataatacatc ttgcaacgcg ttttctctat      120
tgcggtgcaa ctataataac tccgcaacat gtattaacgg ctgct                      165

<210> SEQ ID NO 18
<211> LENGTH: 150
<212> TYPE: DNA
<213> ORGANISM: Vespula vulgaris

<400> SEQUENCE: 18
cattgcgttg cgaggtataa aaggatttta tatattctag gagttgttgt tggagaacat       60
aatacatggg caattaacga tacaaaggca actcaacttt atcttattga tgatataatc      120
gtacatccga attataggcc aaaattaaac                                       150

<210> SEQ ID NO 19
<211> LENGTH: 132
<212> TYPE: DNA
<213> ORGANISM: Vespula vulgaris

<400> SEQUENCE: 19
gatttagctg ttataaaatt gcagaagagg ttaaaatatt ctatgagaat tggtccagct       60
tgtcttccgt tctattacat gcagcgaaac tttgtagaca ctgttgttac agctgtagga      120
tggggtctta cg                                                          132
```

```
<210> SEQ ID NO 20
<211> LENGTH: 150
<212> TYPE: DNA
<213> ORGANISM: Vespula vulgaris

<400> SEQUENCE: 20
aatttttatg gtgtcaagtc tgaagttttg agaaaagtcg atttgcatgt agtttcaatg      60
aagaaatgcg tcaagtatca ctttctggct cacctaagc aactttgtac attcgatatg     120
ggaaaggatg cttgccagtt cgacagtggt                                      150

<210> SEQ ID NO 21
<211> LENGTH: 168
<212> TYPE: DNA
<213> ORGANISM: Vespula vulgaris

<400> SEQUENCE: 21
ggtccaattt tatggcaaaa tccaaaaagc aaacgtattt tccttcttgg agtcatcaat      60
tatggaagaa catgtgccga tgaagctcct ggtgttaact tgagagtcac tagttattta    120
gattttatta caagatcaac acctggagaa atatattgtc aggcgtat                  168

<210> SEQ ID NO 22
<211> LENGTH: 153
<212> TYPE: DNA
<213> ORGANISM: Vespula vulgaris

<400> SEQUENCE: 22
ggagaacata attgtcggtg gagtgctagg agcaatactc gaattaaatt gaattgcaca      60
gttttcgatg ttcctccgag ttcgaattgt tcattggatt ttatgaaagt caaagtcgac    120
gatgacatcg agtacgtttt ctgtggatta aat                                  153

<210> SEQ ID NO 23
<211> LENGTH: 171
<212> TYPE: DNA
<213> ORGANISM: Vespula vulgaris

<400> SEQUENCE: 23
tttgcagtgg aatcaatagc atcgaaaatg actataaaat tccattcaag atacaatact      60
tatggaggca aatttcgatg taatctcaga tcagtcaaag agaaatgtag atgtggttgg    120
aagaatccgt cgagaatcgt aggcggtgtt gaaacaggag tgaatgaata t              171

<210> SEQ ID NO 24
<211> LENGTH: 159
<212> TYPE: DNA
<213> ORGANISM: Vespula vulgaris

<400> SEQUENCE: 24
cctatgatgg ctggtataat acatcttgca acgcgttttc tctattgcgg tgcaactata      60
ataactccgc aacatgtatt aacggctgct cattgcgttg cgaggtataa aaggattta     120 tatattctag gagttgttgt tggagaacat aatacatgg                            159

<210> SEQ ID NO 25
<211> LENGTH: 165
<212> TYPE: DNA
<213> ORGANISM: Vespula vulgaris

<400> SEQUENCE: 25
gcaattaacg atacaaaggc aactcaactt tatcttattg atgatataat cgtacatccg      60
```

```
aattataggc caaaattaaa cgatttagct gttataaaat tgcagaagag gttaaaatat    120
tctatgagaa ttggtccagc ttgtcttccg ttctattaca tgcag                   165
```

<210> SEQ ID NO 26
<211> LENGTH: 141
<212> TYPE: DNA
<213> ORGANISM: Vespula vulgaris

<400> SEQUENCE: 26

```
cgaaactttg tagacactgt tgttacagct gtaggatggg gtcttacgaa tttttatggt    60
gtcaagtctg aagttttgag aaaagtcgat ttgcatgtag tttcaatgaa gaaatgcgtc   120
aagtatcact ttctggctac a                                             141
```

<210> SEQ ID NO 27
<211> LENGTH: 144
<212> TYPE: DNA
<213> ORGANISM: Vespula vulgaris

<400> SEQUENCE: 27

```
cctaagcaac tttgtacatt cgatatggga aaggatgctt gccagttcga cagtggtggt    60
ccaattttat ggcaaaatcc aaaaagcaaa cgtatttttcc ttcttggagt catcaattat   120
ggaagaacat gtgccgatga agct                                          144
```

<210> SEQ ID NO 28
<211> LENGTH: 127
<212> TYPE: PRT
<213> ORGANISM: Vespula vulgaris

<400> SEQUENCE: 28

Thr Ile Asp Leu Asn Cys Gly Tyr Thr Gln Lys Leu Lys Ser Asp Val
1               5                   10                  15

Asn Tyr Cys Val Tyr Asn Pro Asp Phe Pro Asn Tyr Tyr Met Gly Glu
            20                  25                  30

His Asn Cys Arg Trp Ser Ala Arg Ser Asn Thr Arg Ile Lys Leu Asn
        35                  40                  45

Cys Thr Val Phe Asp Val Pro Pro Ser Ser Asn Cys Ser Leu Asp Phe
    50                  55                  60

Met Lys Val Lys Val Asp Asp Asp Ile Glu Tyr Val Phe Cys Gly Leu
65                  70                  75                  80

Asn Ser Phe Ala Val Glu Ser Ile Ala Ser Lys Met Thr Ile Lys Phe
                85                  90                  95

His Ser Arg Tyr Asn Thr Tyr Gly Gly Lys Phe Arg Cys Asn Leu Arg
            100                 105                 110

Ser Val Lys Glu Lys Cys Arg Cys Gly Trp Lys Asn Pro Ser Arg
        115                 120                 125

<210> SEQ ID NO 29
<211> LENGTH: 120
<212> TYPE: PRT
<213> ORGANISM: Vespula vulgaris

<400> SEQUENCE: 29

Ile Val Gly Gly Val Glu Thr Gly Val Asn Glu Tyr Pro Met Met Ala
1               5                   10                  15

Gly Ile Ile His Leu Ala Thr Arg Phe Leu Tyr Cys Gly Ala Thr Ile
            20                  25                  30

Ile Thr Pro Gln His Val Leu Thr Ala Ala His Cys Val Ala Arg Tyr

```
            35                  40                  45
Lys Arg Ile Leu Tyr Ile Leu Gly Val Val Gly Glu His Asn Thr
 50                  55                  60

Trp Ala Ile Asn Asp Thr Lys Ala Thr Gln Leu Tyr Leu Ile Asp Asp
 65                  70                  75                  80

Ile Ile Val His Pro Asn Tyr Arg Pro Lys Leu Asn Asp Leu Ala Val
                 85                  90                  95

Ile Lys Leu Gln Lys Arg Leu Lys Tyr Ser Met Arg Ile Gly Pro Ala
                100                 105                 110

Cys Leu Pro Phe Tyr Tyr Met Gln
            115                 120

<210> SEQ ID NO 30
<211> LENGTH: 122
<212> TYPE: PRT
<213> ORGANISM: Vespula vulgaris

<400> SEQUENCE: 30

Arg Asn Phe Val Asp Thr Val Val Thr Ala Val Gly Trp Gly Leu Thr
 1               5                  10                  15

Asn Phe Tyr Gly Val Lys Ser Glu Val Leu Arg Lys Val Asp Leu His
            20                  25                  30

Val Val Ser Met Lys Lys Cys Val Lys Tyr His Phe Leu Ala Thr Pro
         35                  40                  45

Lys Gln Leu Cys Thr Phe Asp Met Gly Lys Asp Ala Cys Gln Phe Asp
 50                  55                  60

Ser Gly Gly Pro Ile Leu Trp Gln Asn Pro Ser Lys Arg Ile Phe
 65                  70                  75                  80

Leu Leu Gly Val Ile Asn Tyr Gly Arg Thr Cys Ala Asp Glu Ala Pro
                 85                  90                  95

Gly Val Asn Leu Arg Val Thr Ser Tyr Leu Asp Phe Ile Thr Arg Ser
                100                 105                 110

Thr Pro Gly Glu Ile Tyr Cys Gln Ala Tyr
            115                 120

<210> SEQ ID NO 31
<211> LENGTH: 139
<212> TYPE: PRT
<213> ORGANISM: Vespula vulgaris

<400> SEQUENCE: 31

Cys Gly Leu Asn Ser Phe Ala Val Glu Ser Ile Ala Ser Lys Met Thr
 1               5                  10                  15

Ile Lys Phe His Ser Arg Tyr Asn Thr Tyr Gly Gly Lys Phe Arg Cys
            20                  25                  30

Asn Leu Arg Ser Val Lys Glu Lys Cys Arg Cys Gly Trp Lys Asn Pro
         35                  40                  45

Ser Arg Ile Val Gly Gly Val Glu Thr Gly Val Asn Glu Tyr Pro Met
 50                  55                  60

Met Ala Gly Ile Ile His Leu Ala Thr Arg Phe Leu Tyr Cys Gly Ala
 65                  70                  75                  80

Thr Ile Ile Thr Pro Gln His Val Leu Thr Ala Ala His Cys Val Ala
                 85                  90                  95

Arg Tyr Lys Arg Ile Leu Tyr Ile Leu Gly Val Val Gly Glu His
                100                 105                 110

Asn Thr Trp Ala Ile Asn Asp Thr Lys Ala Thr Gln Leu Tyr Leu Ile
```

```
            115                 120                 125
Asp Asp Ile Ile Val His Pro Asn Tyr Arg Pro
    130                 135
```

<210> SEQ ID NO 32
<211> LENGTH: 120
<212> TYPE: PRT
<213> ORGANISM: Vespula vulgaris

<400> SEQUENCE: 32

```
Lys Leu Asn Asp Leu Ala Val Ile Lys Leu Gln Lys Arg Leu Lys Tyr
1               5                   10                  15

Ser Met Arg Ile Gly Pro Ala Cys Leu Pro Phe Tyr Tyr Met Gln Arg
            20                  25                  30

Asn Phe Val Asp Thr Val Val Thr Ala Val Gly Trp Gly Leu Thr Asn
        35                  40                  45

Phe Tyr Gly Val Lys Ser Glu Val Leu Arg Lys Val Asp Leu His Val
    50                  55                  60

Val Ser Met Lys Lys Cys Val Lys Tyr His Phe Leu Ala Thr Pro Lys
65                  70                  75                  80

Gln Leu Cys Thr Phe Asp Met Gly Lys Asp Ala Cys Gln Phe Asp Ser
                85                  90                  95

Gly Gly Pro Ile Leu Trp Gln Asn Pro Lys Ser Lys Arg Ile Phe Leu
            100                 105                 110

Leu Gly Val Ile Asn Tyr Gly Arg
        115                 120
```

<210> SEQ ID NO 33
<211> LENGTH: 114
<212> TYPE: PRT
<213> ORGANISM: Vespula vulgaris

<400> SEQUENCE: 33

```
Thr Ile Asp Leu Asn Cys Gly Tyr Thr Gln Lys Leu Lys Ser Asp Val
1               5                   10                  15

Asn Tyr Cys Val Tyr Asn Pro Asp Phe Pro Asn Tyr Tyr Met Gly Glu
            20                  25                  30

His Asn Cys Arg Trp Ser Ala Arg Ser Asn Thr Arg Ile Lys Leu Asn
        35                  40                  45

Cys Thr Val Phe Asp Val Pro Pro Ser Ser Asn Cys Ser Leu Asp Phe
    50                  55                  60

Met Lys Val Lys Val Asp Asp Asp Ile Glu Tyr Val Phe Cys Gly Leu
65                  70                  75                  80

Asn Ser Phe Ala Val Glu Ser Ile Ala Ser Lys Met Thr Ile Lys Phe
                85                  90                  95

His Ser Arg Tyr Asn Thr Tyr Gly Gly Lys Phe Arg Cys Asn Leu Arg
            100                 105                 110

Ser Val
```

<210> SEQ ID NO 34
<211> LENGTH: 97
<212> TYPE: PRT
<213> ORGANISM: Vespula vulgaris

<400> SEQUENCE: 34

```
Lys Glu Lys Cys Arg Cys Gly Trp Lys Asn Pro Ser Arg Ile Val Gly
1               5                   10                  15
```

```
Gly Val Glu Thr Gly Val Asn Glu Tyr Pro Met Met Ala Gly Ile Ile
            20                  25                  30

His Leu Ala Thr Arg Phe Leu Tyr Cys Gly Ala Thr Ile Ile Thr Pro
        35                  40                  45

Gln His Val Leu Thr Ala Ala His Cys Val Ala Arg Tyr Lys Arg Ile
    50                  55                  60

Leu Tyr Ile Leu Gly Val Val Gly Glu His Asn Thr Trp Ala Ile
65                  70                  75                  80

Asn Asp Thr Lys Ala Thr Gln Leu Tyr Leu Ile Asp Asp Ile Ile Val
                85                  90                  95

His

<210> SEQ ID NO 35
<211> LENGTH: 81
<212> TYPE: PRT
<213> ORGANISM: Vespula vulgaris

<400> SEQUENCE: 35

Pro Asn Tyr Arg Pro Lys Leu Asn Asp Leu Ala Val Ile Lys Leu Gln
1               5                   10                  15

Lys Arg Leu Lys Tyr Ser Met Arg Ile Gly Pro Ala Cys Leu Pro Phe
            20                  25                  30

Tyr Tyr Met Gln Arg Asn Phe Val Asp Thr Val Val Thr Ala Val Gly
        35                  40                  45

Trp Gly Leu Thr Asn Phe Tyr Gly Val Lys Ser Glu Val Leu Arg Lys
    50                  55                  60

Val Asp Leu His Val Val Ser Met Lys Lys Cys Val Lys Tyr His Phe
65                  70                  75                  80

Leu

<210> SEQ ID NO 36
<211> LENGTH: 77
<212> TYPE: PRT
<213> ORGANISM: Vespula vulgaris

<400> SEQUENCE: 36

Ala Thr Pro Lys Gln Leu Cys Thr Phe Asp Met Gly Lys Asp Ala Cys
1               5                   10                  15

Gln Phe Asp Ser Gly Gly Pro Ile Leu Trp Gln Asn Pro Lys Ser Lys
            20                  25                  30

Arg Ile Phe Leu Leu Gly Val Ile Asn Tyr Gly Arg Thr Cys Ala Asp
        35                  40                  45

Glu Ala Pro Gly Val Asn Leu Arg Val Thr Ser Tyr Leu Asp Phe Ile
    50                  55                  60

Thr Arg Ser Thr Pro Gly Glu Ile Tyr Cys Gln Ala Tyr
65                  70                  75

<210> SEQ ID NO 37
<211> LENGTH: 101
<212> TYPE: PRT
<213> ORGANISM: Vespula vulgaris

<400> SEQUENCE: 37

Asp Asp Ile Glu Tyr Val Phe Cys Gly Leu Asn Ser Phe Ala Val Glu
1               5                   10                  15

Ser Ile Ala Ser Lys Met Thr Lys Phe His Ser Arg Tyr Asn Thr
            20                  25                  30
```

```
Tyr Gly Gly Lys Phe Arg Cys Asn Leu Arg Ser Val Lys Glu Lys Cys
            35                  40                  45

Arg Cys Gly Trp Lys Asn Pro Ser Arg Ile Val Gly Val Glu Thr
 50                  55                  60

Gly Val Asn Glu Tyr Pro Met Met Ala Gly Ile Ile His Leu Ala Thr
 65                  70                  75                  80

Arg Phe Leu Tyr Cys Gly Ala Thr Ile Ile Thr Pro Gln His Val Leu
                85                  90                  95

Thr Ala Ala His Cys
            100

<210> SEQ ID NO 38
<211> LENGTH: 90
<212> TYPE: PRT
<213> ORGANISM: Vespula vulgaris

<400> SEQUENCE: 38

Val Ala Arg Tyr Lys Arg Ile Leu Tyr Ile Leu Gly Val Val Gly
 1               5                  10                  15

Glu His Asn Thr Trp Ala Ile Asn Asp Thr Lys Ala Thr Gln Leu Tyr
                20                  25                  30

Leu Ile Asp Asp Ile Ile Val His Pro Asn Tyr Arg Pro Lys Leu Asn
            35                  40                  45

Asp Leu Ala Val Ile Lys Leu Gln Lys Arg Leu Lys Tyr Ser Met Arg
 50                  55                  60

Ile Gly Pro Ala Cys Leu Pro Phe Tyr Met Gln Arg Asn Phe Val
 65                  70                  75                  80

Asp Thr Val Val Thr Ala Val Gly Trp Gly
                85                  90

<210> SEQ ID NO 39
<211> LENGTH: 91
<212> TYPE: PRT
<213> ORGANISM: Vespula vulgaris

<400> SEQUENCE: 39

Leu Thr Asn Phe Tyr Gly Val Lys Ser Glu Val Leu Arg Lys Val Asp
 1               5                  10                  15

Leu His Val Val Ser Met Lys Lys Cys Val Lys Tyr His Phe Leu Ala
                20                  25                  30

Thr Pro Lys Gln Leu Cys Thr Phe Asp Met Gly Lys Asp Ala Cys Gln
            35                  40                  45

Phe Asp Ser Gly Gly Pro Ile Leu Trp Gln Asn Pro Lys Ser Lys Arg
 50                  55                  60

Ile Phe Leu Leu Gly Val Ile Asn Tyr Gly Arg Thr Cys Ala Asp Glu
 65                  70                  75                  80

Ala Pro Gly Val Asn Leu Arg Val Thr Ser Tyr
                85                  90

<210> SEQ ID NO 40
<211> LENGTH: 53
<212> TYPE: PRT
<213> ORGANISM: Vespula vulgaris

<400> SEQUENCE: 40

Thr Ile Asp Leu Asn Cys Gly Tyr Thr Gln Lys Leu Lys Ser Asp Val
 1               5                  10                  15

Asn Tyr Cys Val Tyr Asn Pro Asp Phe Pro Asn Tyr Tyr Met Gly Glu
```

```
                20                  25                  30

His Asn Cys Arg Trp Ser Ala Arg Ser Asn Thr Arg Ile Lys Leu Asn
        35                  40                  45

Cys Thr Val Phe Asp
    50

<210> SEQ ID NO 41
<211> LENGTH: 61
<212> TYPE: PRT
<213> ORGANISM: Vespula vulgaris

<400> SEQUENCE: 41

Val Pro Pro Ser Ser Asn Cys Ser Leu Asp Phe Met Lys Val Lys Val
1               5                   10                  15

Asp Asp Asp Ile Glu Tyr Val Phe Cys Gly Leu Asn Ser Phe Ala Val
                20                  25                  30

Glu Ser Ile Ala Ser Lys Met Thr Ile Lys Phe His Ser Arg Tyr Asn
        35                  40                  45

Thr Tyr Gly Gly Lys Phe Arg Cys Asn Leu Arg Ser Val
    50                  55                  60

<210> SEQ ID NO 42
<211> LENGTH: 55
<212> TYPE: PRT
<213> ORGANISM: Vespula vulgaris

<400> SEQUENCE: 42

Lys Glu Lys Cys Arg Cys Gly Trp Lys Asn Pro Ser Arg Ile Val Gly
1               5                   10                  15

Gly Val Glu Thr Gly Val Asn Glu Tyr Pro Met Met Ala Gly Ile Ile
                20                  25                  30

His Leu Ala Thr Arg Phe Leu Tyr Cys Gly Ala Thr Ile Ile Thr Pro
        35                  40                  45

Gln His Val Leu Thr Ala Ala
    50                  55

<210> SEQ ID NO 43
<211> LENGTH: 50
<212> TYPE: PRT
<213> ORGANISM: Vespula vulgaris

<400> SEQUENCE: 43

His Cys Val Ala Arg Tyr Lys Arg Ile Leu Tyr Ile Leu Gly Val Val
1               5                   10                  15

Val Gly Glu His Asn Thr Trp Ala Ile Asn Asp Thr Lys Ala Thr Gln
                20                  25                  30

Leu Tyr Leu Ile Asp Asp Ile Val His Pro Asn Tyr Arg Pro Lys
        35                  40                  45

Leu Asn
    50

<210> SEQ ID NO 44
<211> LENGTH: 44
<212> TYPE: PRT
<213> ORGANISM: Vespula vulgaris

<400> SEQUENCE: 44

Asp Leu Ala Val Ile Lys Leu Gln Lys Arg Leu Lys Tyr Ser Met Arg
1               5                   10                  15
```

```
Ile Gly Pro Ala Cys Leu Pro Phe Tyr Tyr Met Gln Arg Asn Phe Val
            20                  25                  30

Asp Thr Val Val Thr Ala Val Gly Trp Gly Leu Thr
            35                  40

<210> SEQ ID NO 45
<211> LENGTH: 50
<212> TYPE: PRT
<213> ORGANISM: Vespula vulgaris

<400> SEQUENCE: 45

Asn Phe Tyr Gly Val Lys Ser Glu Val Leu Arg Lys Val Asp Leu His
1               5                   10                  15

Val Val Ser Met Lys Lys Cys Val Lys Tyr His Phe Leu Ala Thr Pro
            20                  25                  30

Lys Gln Leu Cys Thr Phe Asp Met Gly Lys Asp Ala Cys Gln Phe Asp
            35                  40                  45

Ser Gly
    50

<210> SEQ ID NO 46
<211> LENGTH: 56
<212> TYPE: PRT
<213> ORGANISM: Vespula vulgaris

<400> SEQUENCE: 46

Gly Pro Ile Leu Trp Gln Asn Pro Lys Ser Lys Arg Ile Phe Leu Leu
1               5                   10                  15

Gly Val Ile Asn Tyr Gly Arg Thr Cys Ala Asp Glu Ala Pro Gly Val
            20                  25                  30

Asn Leu Arg Val Thr Ser Tyr Leu Asp Phe Ile Thr Arg Ser Thr Pro
            35                  40                  45

Gly Glu Ile Tyr Cys Gln Ala Tyr
    50                  55

<210> SEQ ID NO 47
<211> LENGTH: 52
<212> TYPE: PRT
<213> ORGANISM: Vespula vulgaris

<400> SEQUENCE: 47

Gly Glu His Asn Cys Arg Trp Ser Ala Arg Ser Asn Thr Arg Ile Lys
1               5                   10                  15

Leu Asn Cys Thr Val Phe Asp Val Pro Pro Ser Ser Cys Ser Leu
            20                  25                  30

Asp Phe Met Lys Val Lys Val Asp Asp Ile Glu Tyr Val Phe Cys
            35                  40                  45

Gly Leu Asn Ser
    50

<210> SEQ ID NO 48
<211> LENGTH: 57
<212> TYPE: PRT
<213> ORGANISM: Vespula vulgaris

<400> SEQUENCE: 48

Phe Ala Val Glu Ser Ile Ala Ser Lys Met Thr Ile Lys Phe His Ser
1               5                   10                  15

Arg Tyr Asn Thr Tyr Gly Gly Lys Phe Arg Cys Asn Leu Arg Ser Val
            20                  25                  30
```

```
Lys Glu Lys Cys Arg Cys Gly Trp Lys Asn Pro Ser Arg Ile Val Gly
            35                  40                  45

Gly Val Glu Thr Gly Val Asn Glu Tyr
        50                  55

<210> SEQ ID NO 49
<211> LENGTH: 53
<212> TYPE: PRT
<213> ORGANISM: Vespula vulgaris

<400> SEQUENCE: 49

Pro Met Met Ala Gly Ile Ile His Leu Ala Thr Arg Phe Leu Tyr Cys
1               5                   10                  15

Gly Ala Thr Ile Ile Thr Pro Gln His Val Leu Thr Ala Ala His Cys
            20                  25                  30

Val Ala Arg Tyr Lys Arg Ile Leu Tyr Ile Leu Gly Val Val Val Gly
        35                  40                  45

Glu His Asn Thr Trp
        50

<210> SEQ ID NO 50
<211> LENGTH: 55
<212> TYPE: PRT
<213> ORGANISM: Vespula vulgaris

<400> SEQUENCE: 50

Ala Ile Asn Asp Thr Lys Ala Thr Gln Leu Tyr Leu Ile Asp Asp Ile
1               5                   10                  15

Ile Val His Pro Asn Tyr Arg Pro Lys Leu Asn Asp Leu Ala Val Ile
            20                  25                  30

Lys Leu Gln Lys Arg Leu Lys Tyr Ser Met Arg Ile Gly Pro Ala Cys
        35                  40                  45

Leu Pro Phe Tyr Tyr Met Gln
        50              55

<210> SEQ ID NO 51
<211> LENGTH: 47
<212> TYPE: PRT
<213> ORGANISM: Vespula vulgaris

<400> SEQUENCE: 51

Arg Asn Phe Val Asp Thr Val Val Thr Ala Val Gly Trp Gly Leu Thr
1               5                   10                  15

Asn Phe Tyr Gly Val Lys Ser Glu Val Leu Arg Lys Val Asp Leu His
            20                  25                  30

Val Val Ser Met Lys Lys Cys Val Lys Tyr His Phe Leu Ala Thr
        35                  40                  45

<210> SEQ ID NO 52
<211> LENGTH: 48
<212> TYPE: PRT
<213> ORGANISM: Vespula vulgaris

<400> SEQUENCE: 52

Pro Lys Gln Leu Cys Thr Phe Asp Met Gly Lys Asp Ala Cys Gln Phe
1               5                   10                  15

Asp Ser Gly Gly Pro Ile Leu Trp Gln Asn Pro Lys Ser Lys Arg Ile
            20                  25                  30

Phe Leu Leu Gly Val Ile Asn Tyr Gly Arg Thr Cys Ala Asp Glu Ala
```

<210> SEQ ID NO 53
<211> LENGTH: 45
<212> TYPE: DNA
<213> ORGANISM: Vespula vulgaris

<400> SEQUENCE: 53
agtggtggtc caattttatg gcaaaatcca aaaagcaaac gtatt              45

<210> SEQ ID NO 54
<211> LENGTH: 45
<212> TYPE: DNA
<213> ORGANISM: Vespula vulgaris

<400> SEQUENCE: 54
ggtggtccaa ttttatggca aaatccaaaa agcaaacgta ttttc              45

<210> SEQ ID NO 55
<211> LENGTH: 45
<212> TYPE: DNA
<213> ORGANISM: Vespula vulgaris

<400> SEQUENCE: 55
ggtccaattt tatggcaaaa tccaaaaagc aaacgtattt tcctt              45

<210> SEQ ID NO 56
<211> LENGTH: 45
<212> TYPE: DNA
<213> ORGANISM: Vespula vulgaris

<400> SEQUENCE: 56
ccaattttat ggcaaaatcc aaaaagcaaa cgtattttcc ttctt              45

<210> SEQ ID NO 57
<211> LENGTH: 45
<212> TYPE: DNA
<213> ORGANISM: Vespula vulgaris

<400> SEQUENCE: 57
attttatggc aaaatccaaa agcaaacgt attttccttc ttgga               45

<210> SEQ ID NO 58
<211> LENGTH: 45
<212> TYPE: DNA
<213> ORGANISM: Vespula vulgaris

<400> SEQUENCE: 58
tatcctatga tggctggtat aatacatctt gcaacgcgtt ttctc              45

<210> SEQ ID NO 59
<211> LENGTH: 45
<212> TYPE: DNA
<213> ORGANISM: Vespula vulgaris

<400> SEQUENCE: 59
tcttttgcag tggaatcaat agcatcgaaa atgactataa aattc              45

<210> SEQ ID NO 60
<211> LENGTH: 45
<212> TYPE: DNA
<213> ORGANISM: Vespula vulgaris

<400> SEQUENCE: 60
tttgcagtgg aatcaatagc atcgaaaatg actataaaat tccat          45

<210> SEQ ID NO 61
<211> LENGTH: 45
<212> TYPE: DNA
<213> ORGANISM: Vespula vulgaris

<400> SEQUENCE: 61
aattcttttg cagtggaatc aatagcatcg aaaatgacta taaaa          45

<210> SEQ ID NO 62
<211> LENGTH: 45
<212> TYPE: DNA
<213> ORGANISM: Vespula vulgaris

<400> SEQUENCE: 62
cctatgatgg ctggtataat acatcttgca acgcgttttc tctat          45

<210> SEQ ID NO 63
<211> LENGTH: 45
<212> TYPE: DNA
<213> ORGANISM: Vespula vulgaris

<400> SEQUENCE: 63
ttaaattctt ttgcagtgga atcaatagca tcgaaaatga ctata          45

<210> SEQ ID NO 64
<211> LENGTH: 45
<212> TYPE: DNA
<213> ORGANISM: Vespula vulgaris

<400> SEQUENCE: 64
atggctggta taatacatct tgcaacgcgt tttctctatt gcggt          45

<210> SEQ ID NO 65
<211> LENGTH: 45
<212> TYPE: DNA
<213> ORGANISM: Vespula vulgaris

<400> SEQUENCE: 65
ggattaaatt cttttgcagt ggaatcaata gcatcgaaaa tgact          45

<210> SEQ ID NO 66
<211> LENGTH: 45
<212> TYPE: DNA
<213> ORGANISM: Vespula vulgaris

<400> SEQUENCE: 66
gctggtataa tacatcttgc aacgcgtttt ctctattgcg gtgca          45

<210> SEQ ID NO 67
<211> LENGTH: 45
<212> TYPE: DNA
<213> ORGANISM: Vespula vulgaris

<400> SEQUENCE: 67
atgatggctg gtataataca tcttgcaacg cgttttctct attgc          45

<210> SEQ ID NO 68
<211> LENGTH: 45
<212> TYPE: DNA
<213> ORGANISM: Vespula vulgaris

<400> SEQUENCE: 68
gagtacgttt tctgtggatt aaattctttt gcagtggaat caata        45

<210> SEQ ID NO 69
<211> LENGTH: 45
<212> TYPE: DNA
<213> ORGANISM: Vespula vulgaris

<400> SEQUENCE: 69
tacgttttct gtggattaaa ttcttttgca gtggaatcaa tagca        45

<210> SEQ ID NO 70
<211> LENGTH: 45
<212> TYPE: DNA
<213> ORGANISM: Vespula vulgaris

<400> SEQUENCE: 70
atcgagtacg ttttctgtgg attaaattct tttgcagtgg aatca        45

<210> SEQ ID NO 71
<211> LENGTH: 45
<212> TYPE: DNA
<213> ORGANISM: Vespula vulgaris

<400> SEQUENCE: 71
gacatcgagt acgttttctg tggattaaat tcttttgcag tggaa        45

<210> SEQ ID NO 72
<211> LENGTH: 45
<212> TYPE: DNA
<213> ORGANISM: Vespula vulgaris

<400> SEQUENCE: 72
gatgacatcg agtacgtttt ctgtggatta aattcttttg cagtg        45

<210> SEQ ID NO 73
<211> LENGTH: 45
<212> TYPE: DNA
<213> ORGANISM: Vespula vulgaris

<400> SEQUENCE: 73
gtgaatgaat atcctatgat ggctggtata atacatcttg caacg        45

<210> SEQ ID NO 74
<211> LENGTH: 45
<212> TYPE: DNA
<213> ORGANISM: Vespula vulgaris

<400> SEQUENCE: 74
aatgaatatc ctatgatggc tggtataata catcttgcaa cgcgt        45

<210> SEQ ID NO 75
<211> LENGTH: 45
<212> TYPE: DNA
<213> ORGANISM: Vespula vulgaris

<400> SEQUENCE: 75
cttacgaatt tttatggtgt caagtctgaa gttttgagaa aagtc        45

<210> SEQ ID NO 76
<211> LENGTH: 45
<212> TYPE: DNA
<213> ORGANISM: Vespula vulgaris

<400> SEQUENCE: 76
ggagtgaatg aatatcctat gatggctggt ataatacatc ttgca                    45

<210> SEQ ID NO 77
<211> LENGTH: 45
<212> TYPE: DNA
<213> ORGANISM: Vespula vulgaris

<400> SEQUENCE: 77
acgaattttt atggtgtcaa gtctgaagtt ttgagaaaag tcgat                    45

<210> SEQ ID NO 78
<211> LENGTH: 45
<212> TYPE: DNA
<213> ORGANISM: Vespula vulgaris

<400> SEQUENCE: 78
ttatggcaaa atccaaaaag caaacgtatt ttccttcttg gagtc                    45

<210> SEQ ID NO 79
<211> LENGTH: 45
<212> TYPE: DNA
<213> ORGANISM: Vespula vulgaris

<400> SEQUENCE: 79
tggcaaaatc caaaaagcaa acgtattttc cttcttggag tcatc                    45

<210> SEQ ID NO 80
<211> LENGTH: 45
<212> TYPE: DNA
<213> ORGANISM: Vespula vulgaris

<400> SEQUENCE: 80
aagaggttaa aatattctat gagaattggt ccagcttgtc ttccg                    45

<210> SEQ ID NO 81
<211> LENGTH: 45
<212> TYPE: DNA
<213> ORGANISM: Vespula vulgaris

<400> SEQUENCE: 81
gaatatccta tgatggctgg tataatacat cttgcaacgc gtttt                    45

<210> SEQ ID NO 82
<211> LENGTH: 45
<212> TYPE: DNA
<213> ORGANISM: Vespula vulgaris

<400> SEQUENCE: 82
ttaaaatatt ctatgagaat tggtccagct tgtcttccgt tctat                    45

<210> SEQ ID NO 83
<211> LENGTH: 45
<212> TYPE: DNA
<213> ORGANISM: Vespula vulgaris

<400> SEQUENCE: 83
aaatattcta tgagaattgg tccagcttgt cttccgttct attac                    45

<210> SEQ ID NO 84
<211> LENGTH: 45
<212> TYPE: DNA

<213> ORGANISM: Vespula vulgaris

<400> SEQUENCE: 84
aggttaaaat attctatgag aattggtcca gcttgtcttc cgttc                45

<210> SEQ ID NO 85
<211> LENGTH: 45
<212> TYPE: DNA
<213> ORGANISM: Vespula vulgaris

<400> SEQUENCE: 85
gcgaggtata aaaggatttt atatattcta ggagttgttg ttgga                45

<210> SEQ ID NO 86
<211> LENGTH: 45
<212> TYPE: DNA
<213> ORGANISM: Vespula vulgaris

<400> SEQUENCE: 86
gcagtggaat caatagcatc gaaaatgact ataaaattcc attca                45

<210> SEQ ID NO 87
<211> LENGTH: 45
<212> TYPE: DNA
<213> ORGANISM: Vespula vulgaris

<400> SEQUENCE: 87
tattctatga gaattggtcc agcttgtctt ccgttctatt acatg                45

<210> SEQ ID NO 88
<211> LENGTH: 45
<212> TYPE: DNA
<213> ORGANISM: Vespula vulgaris

<400> SEQUENCE: 88
gtggaatcaa tagcatcgaa aatgactata aaattccatt caaga                45

<210> SEQ ID NO 89
<211> LENGTH: 45
<212> TYPE: DNA
<213> ORGANISM: Vespula vulgaris

<400> SEQUENCE: 89
gacactgttg ttacagctgt aggatggggt cttacgaatt tttat                45

<210> SEQ ID NO 90
<211> LENGTH: 45
<212> TYPE: DNA
<213> ORGANISM: Vespula vulgaris

<400> SEQUENCE: 90
cttgcaacgc gttttctcta ttgcggtgca actataataa ctccg                45

<210> SEQ ID NO 91
<211> LENGTH: 45
<212> TYPE: DNA
<213> ORGANISM: Vespula vulgaris

<400> SEQUENCE: 91
aatttttatg gtgtcaagtc tgaagttttg agaaaagtcg atttg                45

<210> SEQ ID NO 92
<211> LENGTH: 45

<212> TYPE: DNA
<213> ORGANISM: Vespula vulgaris

<400> SEQUENCE: 92
ggtataatac atcttgcaac gcgttttctc tattgcggtg caact         45

<210> SEQ ID NO 93
<211> LENGTH: 45
<212> TYPE: DNA
<213> ORGANISM: Vespula vulgaris

<400> SEQUENCE: 93
tggggtctta cgaattttta tggtgtcaag tctgaagttt tgaga         45

<210> SEQ ID NO 94
<211> LENGTH: 45
<212> TYPE: DNA
<213> ORGANISM: Vespula vulgaris

<400> SEQUENCE: 94
ttttatggtg tcaagtctga agttttgaga aaagtcgatt tgcat         45

<210> SEQ ID NO 95
<211> LENGTH: 45
<212> TYPE: DNA
<213> ORGANISM: Vespula vulgaris

<400> SEQUENCE: 95
ataatacatc ttgcaacgcg ttttctctat tgcggtgcaa ctata         45

<210> SEQ ID NO 96
<211> LENGTH: 45
<212> TYPE: DNA
<213> ORGANISM: Vespula vulgaris

<400> SEQUENCE: 96
ggatggggtc ttacgaattt ttatggtgtc aagtctgaag ttttg         45

<210> SEQ ID NO 97
<211> LENGTH: 45
<212> TYPE: DNA
<213> ORGANISM: Vespula vulgaris

<400> SEQUENCE: 97
aggtataaaa ggatttttata tattctagga gttgttgttg gagaa         45

<210> SEQ ID NO 98
<211> LENGTH: 45
<212> TYPE: DNA
<213> ORGANISM: Vespula vulgaris

<400> SEQUENCE: 98
tataaaagga ttttatatat tctaggagtt gttgttggag aacat         45

<210> SEQ ID NO 99
<211> LENGTH: 45
<212> TYPE: DNA
<213> ORGANISM: Vespula vulgaris

<400> SEQUENCE: 99
cgttttctct attgcggtgc aactataata actccgcaac atgta         45

<210> SEQ ID NO 100

<211> LENGTH: 45
<212> TYPE: DNA
<213> ORGANISM: Vespula vulgaris

<400> SEQUENCE: 100
aaaaggattt tatatattct aggagttgtt gttggagaac ataat            45

<210> SEQ ID NO 101
<211> LENGTH: 45
<212> TYPE: DNA
<213> ORGANISM: Vespula vulgaris

<400> SEQUENCE: 101
acgcgttttc tctattgcgg tgcaactata ataactccgc aacat            45

<210> SEQ ID NO 102
<211> LENGTH: 45
<212> TYPE: DNA
<213> ORGANISM: Vespula vulgaris

<400> SEQUENCE: 102
gcaacgcgtt ttctctattg cggtgcaact ataataactc cgcaa            45

<210> SEQ ID NO 103
<211> LENGTH: 45
<212> TYPE: DNA
<213> ORGANISM: Vespula vulgaris

<400> SEQUENCE: 103
gaaacaggag tgaatgaata tcctatgatg gctggtataa tacat            45

<210> SEQ ID NO 104
<211> LENGTH: 45
<212> TYPE: DNA
<213> ORGANISM: Vespula vulgaris

<400> SEQUENCE: 104
acaggagtga atgaatatcc tatgatggct ggtataatac atctt            45

<210> SEQ ID NO 105
<211> LENGTH: 45
<212> TYPE: DNA
<213> ORGANISM: Vespula vulgaris

<400> SEQUENCE: 105
ggtcttacga atttttatgg tgtcaagtct gaagttttga gaaaa            45

<210> SEQ ID NO 106
<211> LENGTH: 45
<212> TYPE: DNA
<213> ORGANISM: Vespula vulgaris

<400> SEQUENCE: 106
gttttctgtg gattaaattc ttttgcagtg gaatcaatag catcg            45

<210> SEQ ID NO 107
<211> LENGTH: 45
<212> TYPE: DNA
<213> ORGANISM: Vespula vulgaris

<400> SEQUENCE: 107
ttctgtggat taaattcttt tgcagtggaa tcaatagcat cgaaa            45

```
<210> SEQ ID NO 108
<211> LENGTH: 45
<212> TYPE: DNA
<213> ORGANISM: Vespula vulgaris

<400> SEQUENCE: 108
actgttgtta cagctgtagg atggggtctt acgaattttt atggt              45

<210> SEQ ID NO 109
<211> LENGTH: 45
<212> TYPE: DNA
<213> ORGANISM: Vespula vulgaris

<400> SEQUENCE: 109
aactttgtag acactgttgt tacagctgta ggatggggtc ttacg              45

<210> SEQ ID NO 110
<211> LENGTH: 45
<212> TYPE: DNA
<213> ORGANISM: Vespula vulgaris

<400> SEQUENCE: 110
cataatacat gggcaattaa cgatacaaag gcaactcaac tttat              45

<210> SEQ ID NO 111
<211> LENGTH: 45
<212> TYPE: DNA
<213> ORGANISM: Vespula vulgaris

<400> SEQUENCE: 111
aggattttat atattctagg agttgttgtt ggagaacata ataca              45

<210> SEQ ID NO 112
<211> LENGTH: 45
<212> TYPE: DNA
<213> ORGANISM: Vespula vulgaris

<400> SEQUENCE: 112
aatacatggg caattaacga tacaaaggca actcaacttt atctt              45

<210> SEQ ID NO 113
<211> LENGTH: 45
<212> TYPE: DNA
<213> ORGANISM: Vespula vulgaris

<400> SEQUENCE: 113
tattgcggtg caactataat aactccgcaa catgtattaa cggct              45

<210> SEQ ID NO 114
<211> LENGTH: 45
<212> TYPE: DNA
<213> ORGANISM: Vespula vulgaris

<400> SEQUENCE: 114
gaacataata catgggcaat taacgataca aaggcaactc aactt              45

<210> SEQ ID NO 115
<211> LENGTH: 45
<212> TYPE: DNA
<213> ORGANISM: Vespula vulgaris

<400> SEQUENCE: 115
tttgtagaca ctgttgttac agctgtagga tggggtctta cgaat              45
```

<210> SEQ ID NO 116
<211> LENGTH: 45
<212> TYPE: DNA
<213> ORGANISM: Vespula vulgaris

<400> SEQUENCE: 116
gttgttacag ctgtaggatg gggtcttacg aatttttatg gtgtc            45

<210> SEQ ID NO 117
<211> LENGTH: 45
<212> TYPE: DNA
<213> ORGANISM: Vespula vulgaris

<400> SEQUENCE: 117
tgcggtgcaa ctataataac tccgcaacat gtattaacgg ctgct            45

<210> SEQ ID NO 118
<211> LENGTH: 45
<212> TYPE: DNA
<213> ORGANISM: Vespula vulgaris

<400> SEQUENCE: 118
tttctctatt gcggtgcaac tataataact ccgcaacatg tatta            45

<210> SEQ ID NO 119
<211> LENGTH: 45
<212> TYPE: DNA
<213> ORGANISM: Vespula vulgaris

<400> SEQUENCE: 119
cgaaactttg tagacactgt tgttacagct gtaggatggg gtctt            45

<210> SEQ ID NO 120
<211> LENGTH: 45
<212> TYPE: DNA
<213> ORGANISM: Vespula vulgaris

<400> SEQUENCE: 120
acagctgtag gatggggtct tacgaatttt tatggtgtca agtct            45

<210> SEQ ID NO 121
<211> LENGTH: 45
<212> TYPE: DNA
<213> ORGANISM: Vespula vulgaris

<400> SEQUENCE: 121
tgcgtcaagt atcactttct ggctacacct aagcaacttt gtaca            45

<210> SEQ ID NO 122
<211> LENGTH: 45
<212> TYPE: DNA
<213> ORGANISM: Vespula vulgaris

<400> SEQUENCE: 122
gtcaagtatc actttctggc tacacctaag caactttgta cattc            45

<210> SEQ ID NO 123
<211> LENGTH: 45
<212> TYPE: DNA
<213> ORGANISM: Vespula vulgaris

<400> SEQUENCE: 123
catcttgcaa cgcgttttct ctattgcggt gcaactataa taact            45

<210> SEQ ID NO 124
<211> LENGTH: 45
<212> TYPE: DNA
<213> ORGANISM: Vespula vulgaris

<400> SEQUENCE: 124
ccgaattata ggccaaaatt aaacgattta gctgttataa aattg                45

<210> SEQ ID NO 125
<211> LENGTH: 45
<212> TYPE: DNA
<213> ORGANISM: Vespula vulgaris

<400> SEQUENCE: 125
ggtgcaacta taataactcc gcaacatgta ttaacggctg ctcat                45

<210> SEQ ID NO 126
<211> LENGTH: 45
<212> TYPE: DNA
<213> ORGANISM: Vespula vulgaris

<400> SEQUENCE: 126
gtagacactg ttgttacagc tgtaggatgg ggtcttacga atttt                45

<210> SEQ ID NO 127
<211> LENGTH: 45
<212> TYPE: DNA
<213> ORGANISM: Vespula vulgaris

<400> SEQUENCE: 127
gcaactataa taactccgca acatgtatta acggctgctc attgc                45

<210> SEQ ID NO 128
<211> LENGTH: 45
<212> TYPE: DNA
<213> ORGANISM: Vespula vulgaris

<400> SEQUENCE: 128
tatggtgtca agtctgaagt tttgagaaaa gtcgatttgc atgta                45

<210> SEQ ID NO 129
<211> LENGTH: 45
<212> TYPE: DNA
<213> ORGANISM: Vespula vulgaris

<400> SEQUENCE: 129
actataataa ctccgcaaca tgtattaacg gctgctcatt gcgtt                45

<210> SEQ ID NO 130
<211> LENGTH: 45
<212> TYPE: DNA
<213> ORGANISM: Vespula vulgaris

<400> SEQUENCE: 130
ctctattgcg gtgcaactat aataactccg caacatgtat taacg                45

<210> SEQ ID NO 131
<211> LENGTH: 45
<212> TYPE: DNA
<213> ORGANISM: Vespula vulgaris

<400> SEQUENCE: 131
aggccaaaat taaacgattt agctgttata aaattgcaga agagg   45

<210> SEQ ID NO 132
<211> LENGTH: 45
<212> TYPE: DNA
<213> ORGANISM: Vespula vulgaris

<400> SEQUENCE: 132
ccaaaattaa acgatttagc tgttataaaa ttgcagaaga ggtta   45

<210> SEQ ID NO 133
<211> LENGTH: 45
<212> TYPE: DNA
<213> ORGANISM: Vespula vulgaris

<400> SEQUENCE: 133
aaatgcgtca agtatcactt tctggctaca cctaagcaac tttgt   45

<210> SEQ ID NO 134
<211> LENGTH: 45
<212> TYPE: DNA
<213> ORGANISM: Vespula vulgaris

<400> SEQUENCE: 134
tataggccaa aattaaacga tttagctgtt ataaaattgc agaag   45

<210> SEQ ID NO 135
<211> LENGTH: 45
<212> TYPE: DNA
<213> ORGANISM: Vespula vulgaris

<400> SEQUENCE: 135
tctatgagaa ttggtccagc ttgtcttccg ttctattaca tgcag   45

<210> SEQ ID NO 136
<211> LENGTH: 45
<212> TYPE: DNA
<213> ORGANISM: Vespula vulgaris

<400> SEQUENCE: 136
aattataggc caaaattaaa cgatttagct gttataaaat tgcag   45

<210> SEQ ID NO 137
<211> LENGTH: 45
<212> TYPE: DNA
<213> ORGANISM: Vespula vulgaris

<400> SEQUENCE: 137
gttacagctg taggatgggg tcttacgaat ttttatggtg tcaag   45

<210> SEQ ID NO 138
<211> LENGTH: 45
<212> TYPE: DNA
<213> ORGANISM: Vespula vulgaris

<400> SEQUENCE: 138
atgagaattg gtccagcttg tcttccgttc tattacatgc agcga   45

<210> SEQ ID NO 139
<211> LENGTH: 45
<212> TYPE: DNA
<213> ORGANISM: Vespula vulgaris

<400> SEQUENCE: 139
aagaaatgcg tcaagtatca ctttctggct acacctaagc aactt                    45

<210> SEQ ID NO 140
<211> LENGTH: 45
<212> TYPE: DNA
<213> ORGANISM: Vespula vulgaris

<400> SEQUENCE: 140
gttggagaac ataatacatg ggcaattaac gatacaaagg caact                    45

<210> SEQ ID NO 141
<211> LENGTH: 45
<212> TYPE: DNA
<213> ORGANISM: Vespula vulgaris

<400> SEQUENCE: 141
gttgcgaggt ataaaaggat tttatatatt ctaggagttg ttgtt                    45

<210> SEQ ID NO 142
<211> LENGTH: 45
<212> TYPE: DNA
<213> ORGANISM: Vespula vulgaris

<400> SEQUENCE: 142
ggagaacata atacatgggc aattaacgat acaaaggcaa ctcaa                    45

<210> SEQ ID NO 143
<211> LENGTH: 45
<212> TYPE: DNA
<213> ORGANISM: Vespula vulgaris

<400> SEQUENCE: 143
tacatgcagc gaaactttgt agacactgtt gttacagctg tagga                    45

<210> SEQ ID NO 144
<211> LENGTH: 45
<212> TYPE: DNA
<213> ORGANISM: Vespula vulgaris

<400> SEQUENCE: 144
acatgggcaa ttaacgatac aaaggcaact caactttatc ttatt                    45

<210> SEQ ID NO 145
<211> LENGTH: 45
<212> TYPE: DNA
<213> ORGANISM: Vespula vulgaris

<400> SEQUENCE: 145
tgggcaatta acgatacaaa ggcaactcaa ctttatctta ttgat                    45

<210> SEQ ID NO 146
<211> LENGTH: 45
<212> TYPE: DNA
<213> ORGANISM: Vespula vulgaris

<400> SEQUENCE: 146
atgaagaaat gcgtcaagta tcactttctg gctacaccta agcaa                    45

<210> SEQ ID NO 147
<211> LENGTH: 45
<212> TYPE: DNA
<213> ORGANISM: Vespula vulgaris

<400> SEQUENCE: 147
gtcaagtctg aagttttgag aaaagtcgat ttgcatgtag tttca                45

<210> SEQ ID NO 148
<211> LENGTH: 45
<212> TYPE: DNA
<213> ORGANISM: Vespula vulgaris

<400> SEQUENCE: 148
ggtgtcaagt ctgaagtttt gagaaaagtc gatttgcatg tagtt                45

<210> SEQ ID NO 149
<211> LENGTH: 45
<212> TYPE: DNA
<213> ORGANISM: Vespula vulgaris

<400> SEQUENCE: 149
cagcgaaact tgtagacac tgttgttaca gctgtaggat ggggt                 45

<210> SEQ ID NO 150
<211> LENGTH: 45
<212> TYPE: DNA
<213> ORGANISM: Vespula vulgaris

<400> SEQUENCE: 150
atgcagcgaa actttgtaga cactgttgtt acagctgtag gatgg                45

<210> SEQ ID NO 151
<211> LENGTH: 45
<212> TYPE: DNA
<213> ORGANISM: Vespula vulgaris

<400> SEQUENCE: 151
ataactccgc aacatgtatt aacggctgct cattgcgttg cgagg                45

<210> SEQ ID NO 152
<211> LENGTH: 45
<212> TYPE: DNA
<213> ORGANISM: Vespula vulgaris

<400> SEQUENCE: 152
gctgtaggat ggggtcttac gaatttttat ggtgtcaagt ctgaa                45

<210> SEQ ID NO 153
<211> LENGTH: 45
<212> TYPE: DNA
<213> ORGANISM: Vespula vulgaris

<400> SEQUENCE: 153
tattacatgc agcgaaactt gtagacact gttgttacag ctgta                 45

<210> SEQ ID NO 154
<211> LENGTH: 45
<212> TYPE: DNA
<213> ORGANISM: Vespula vulgaris

<400> SEQUENCE: 154
tatcactttc tggctacacc taagcaactt tgtacattcg atatg                45

<210> SEQ ID NO 155
<211> LENGTH: 45
<212> TYPE: DNA
<213> ORGANISM: Vespula vulgaris

```
<400> SEQUENCE: 155
atacatcttg caacgcgttt tctctattgc ggtgcaacta taata            45

<210> SEQ ID NO 156
<211> LENGTH: 45
<212> TYPE: DNA
<213> ORGANISM: Vespula vulgaris

<400> SEQUENCE: 156
gtaggatggg gtcttacgaa tttttatggt gtcaagtctg aagtt            45

<210> SEQ ID NO 157
<211> LENGTH: 45
<212> TYPE: DNA
<213> ORGANISM: Vespula vulgaris

<400> SEQUENCE: 157
actagttatt tagattttat tacaagatca acacctggag aaata            45

<210> SEQ ID NO 158
<211> LENGTH: 45
<212> TYPE: DNA
<213> ORGANISM: Vespula vulgaris

<400> SEQUENCE: 158
attttatata ttctaggagt tgttgttgga gaacataata catgg            45

<210> SEQ ID NO 159
<211> LENGTH: 45
<212> TYPE: DNA
<213> ORGANISM: Vespula vulgaris

<400> SEQUENCE: 159
aagtatcact ttctggctac acctaagcaa ctttgtacat tcgat            45

<210> SEQ ID NO 160
<211> LENGTH: 45
<212> TYPE: DNA
<213> ORGANISM: Vespula vulgaris

<400> SEQUENCE: 160
gtcactagtt atttagattt tattacaaga tcaacacctg gagaa            45

<210> SEQ ID NO 161
<211> LENGTH: 45
<212> TYPE: DNA
<213> ORGANISM: Vespula vulgaris

<400> SEQUENCE: 161
ataataactc cgcaacatgt attaacggct gctcattgcg ttgcg            45

<210> SEQ ID NO 162
<211> LENGTH: 45
<212> TYPE: DNA
<213> ORGANISM: Vespula vulgaris

<400> SEQUENCE: 162
cttccgttct attacatgca gcgaaacttt gtagacactg ttgtt            45

<210> SEQ ID NO 163
<211> LENGTH: 45
<212> TYPE: DNA
```

<213> ORGANISM: Vespula vulgaris

<400> SEQUENCE: 163
tgtcttccgt tctattacat gcagcgaaac tttgtagaca ctgtt        45

<210> SEQ ID NO 164
<211> LENGTH: 45
<212> TYPE: DNA
<213> ORGANISM: Vespula vulgaris

<400> SEQUENCE: 164
gttgaaacag gagtgaatga atatcctatg atggctggta taata        45

<210> SEQ ID NO 165
<211> LENGTH: 45
<212> TYPE: DNA
<213> ORGANISM: Vespula vulgaris

<400> SEQUENCE: 165
atcgatctca attgtggcta cacccaaaaa ttaaaatcag atgtt        45

<210> SEQ ID NO 166
<211> LENGTH: 45
<212> TYPE: DNA
<213> ORGANISM: Vespula vulgaris

<400> SEQUENCE: 166
cattgcgttg cgaggtataa aaggattta tatattctag gagtt        45

<210> SEQ ID NO 167
<211> LENGTH: 45
<212> TYPE: DNA
<213> ORGANISM: Vespula vulgaris

<400> SEQUENCE: 167
actccgcaac atgtattaac ggctgctcat tgcgttgcga ggtat        45

<210> SEQ ID NO 168
<211> LENGTH: 45
<212> TYPE: DNA
<213> ORGANISM: Vespula vulgaris

<400> SEQUENCE: 168
tgcgttgcga ggtataaaag gattttatat attctaggag ttgtt        45

<210> SEQ ID NO 169
<211> LENGTH: 45
<212> TYPE: DNA
<213> ORGANISM: Vespula vulgaris

<400> SEQUENCE: 169
ccgcaacatg tattaacggc tgctcattgc gttgcgaggt ataaa        45

<210> SEQ ID NO 170
<211> LENGTH: 45
<212> TYPE: DNA
<213> ORGANISM: Vespula vulgaris

<400> SEQUENCE: 170
ttatatattc taggagttgt tgttggagaa cataatacat gggca        45

<210> SEQ ID NO 171
<211> LENGTH: 45

<210> SEQ ID NO 171
<211> LENGTH: 45
<212> TYPE: DNA
<213> ORGANISM: Vespula vulgaris

<400> SEQUENCE: 171
tctgaagttt tgagaaaagt cgatttgcat gtagtttcaa tgaag            45

<210> SEQ ID NO 172
<211> LENGTH: 45
<212> TYPE: DNA
<213> ORGANISM: Vespula vulgaris

<400> SEQUENCE: 172
ccgttctatt acatgcagcg aaactttgta gacactgttg ttaca            45

<210> SEQ ID NO 173
<211> LENGTH: 45
<212> TYPE: DNA
<213> ORGANISM: Vespula vulgaris

<400> SEQUENCE: 173
ttctattaca tgcagcgaaa ctttgtagac actgttgtta cagct            45

<210> SEQ ID NO 174
<211> LENGTH: 45
<212> TYPE: DNA
<213> ORGANISM: Vespula vulgaris

<400> SEQUENCE: 174
tgcacagttt tcgatgttcc tccgagttcg aattgttcat tggat            45

<210> SEQ ID NO 175
<211> LENGTH: 45
<212> TYPE: DNA
<213> ORGANISM: Vespula vulgaris

<400> SEQUENCE: 175
aattgcacag ttttcgatgt tcctccgagt tcgaattgtt cattg            45

<210> SEQ ID NO 176
<211> LENGTH: 45
<212> TYPE: DNA
<213> ORGANISM: Vespula vulgaris

<400> SEQUENCE: 176
aagtctgaag ttttgagaaa agtcgatttg catgtagttt caatg            45

<210> SEQ ID NO 177
<211> LENGTH: 45
<212> TYPE: DNA
<213> ORGANISM: Vespula vulgaris

<400> SEQUENCE: 177
aacttgagag tcactagtta tttagatttt attacaagat caaca            45

<210> SEQ ID NO 178
<211> LENGTH: 45
<212> TYPE: DNA
<213> ORGANISM: Vespula vulgaris

<400> SEQUENCE: 178
ttgagagtca ctagttattt agattttatt acaagatcaa cacct            45

<210> SEQ ID NO 179

<210> SEQ ID NO 179
<211> LENGTH: 45
<212> TYPE: DNA
<213> ORGANISM: Vespula vulgaris

<400> SEQUENCE: 179
gaagttttga gaaaagtcga tttgcatgta gtttcaatga agaaa                45

<210> SEQ ID NO 180
<211> LENGTH: 45
<212> TYPE: DNA
<213> ORGANISM: Vespula vulgaris

<400> SEQUENCE: 180
actatcgatc tcaattgtgg ctacacccaa aaattaaaat cagat                45

<210> SEQ ID NO 181
<211> LENGTH: 45
<212> TYPE: DNA
<213> ORGANISM: Vespula vulgaris

<400> SEQUENCE: 181
agagtcacta gttatttaga ttttattaca agatcaacac ctgga                45

<210> SEQ ID NO 182
<211> LENGTH: 45
<212> TYPE: DNA
<213> ORGANISM: Vespula vulgaris

<400> SEQUENCE: 182
gctcattgcg ttgcgaggta taaaaggatt ttatatattc tagga                45

<210> SEQ ID NO 183
<211> LENGTH: 45
<212> TYPE: DNA
<213> ORGANISM: Vespula vulgaris

<400> SEQUENCE: 183
tgtagatgtg gttggaagaa tccgtcgaga atcgtaggcg gtgtt                45

<210> SEQ ID NO 184
<211> LENGTH: 45
<212> TYPE: DNA
<213> ORGANISM: Vespula vulgaris

<400> SEQUENCE: 184
aaatgtagat gtggttggaa gaatccgtcg agaatcgtag gcggt                45

<210> SEQ ID NO 185
<211> LENGTH: 45
<212> TYPE: DNA
<213> ORGANISM: Vespula vulgaris

<400> SEQUENCE: 185
ttaaacgatt tagctgttat aaaattgcag aagaggttaa aatat                45

<210> SEQ ID NO 186
<211> LENGTH: 45
<212> TYPE: DNA
<213> ORGANISM: Vespula vulgaris

<400> SEQUENCE: 186
ggcggtgttg aaacaggagt gaatgaatat cctatgatgg ctggt                45

```
<210> SEQ ID NO 187
<211> LENGTH: 45
<212> TYPE: DNA
<213> ORGANISM: Vespula vulgaris

<400> SEQUENCE: 187
aaattaaacg atttagctgt tataaaattg cagaagaggt taaaa            45

<210> SEQ ID NO 188
<211> LENGTH: 45
<212> TYPE: DNA
<213> ORGANISM: Vespula vulgaris

<400> SEQUENCE: 188
gcttgtcttc cgttctatta catgcagcga aactttgtag acact            45

<210> SEQ ID NO 189
<211> LENGTH: 45
<212> TYPE: DNA
<213> ORGANISM: Vespula vulgaris

<400> SEQUENCE: 189
gagaaatgta gatgtggttg gaagaatccg tcgagaatcg taggc            45

<210> SEQ ID NO 190
<211> LENGTH: 45
<212> TYPE: DNA
<213> ORGANISM: Vespula vulgaris

<400> SEQUENCE: 190
ggtgttgaaa caggagtgaa tgaatatcct atgatggctg gtata            45

<210> SEQ ID NO 191
<211> LENGTH: 45
<212> TYPE: DNA
<213> ORGANISM: Vespula vulgaris

<400> SEQUENCE: 191
tgtggctaca cccaaaaatt aaaatcagat gttaattatt gcgtg            45

<210> SEQ ID NO 192
<211> LENGTH: 45
<212> TYPE: DNA
<213> ORGANISM: Vespula vulgaris

<400> SEQUENCE: 192
agatgtggtt ggaagaatcc gtcgagaatc gtaggcggtg ttgaa            45

<210> SEQ ID NO 193
<211> LENGTH: 45
<212> TYPE: DNA
<213> ORGANISM: Vespula vulgaris

<400> SEQUENCE: 193
gcttgccagt tcgacagtgg tggtccaatt ttatggcaaa atcca            45

<210> SEQ ID NO 194
<211> LENGTH: 45
<212> TYPE: DNA
<213> ORGANISM: Vespula vulgaris

<400> SEQUENCE: 194
ttgaattgca cagttttcga tgttcctccg agttcgaatt gttca            45
```

<210> SEQ ID NO 195
<211> LENGTH: 45
<212> TYPE: DNA
<213> ORGANISM: Vespula vulgaris

<400> SEQUENCE: 195
gaacataatt gtcggtggag tgctaggagc aatactcgaa ttaaa            45

<210> SEQ ID NO 196
<211> LENGTH: 45
<212> TYPE: DNA
<213> ORGANISM: Vespula vulgaris

<400> SEQUENCE: 196
tgccagttcg acagtggtgg tccaatttta tggcaaaatc caaaa            45

<210> SEQ ID NO 197
<211> LENGTH: 45
<212> TYPE: DNA
<213> ORGANISM: Vespula vulgaris

<400> SEQUENCE: 197
caacatgtat taacggctgc tcattgcgtt gcgaggtata aaagg            45

<210> SEQ ID NO 198
<211> LENGTH: 45
<212> TYPE: DNA
<213> ORGANISM: Vespula vulgaris

<400> SEQUENCE: 198
cataattgtc ggtggagtgc taggagcaat actcgaatta aattg            45

<210> SEQ ID NO 199
<211> LENGTH: 45
<212> TYPE: DNA
<213> ORGANISM: Vespula vulgaris

<400> SEQUENCE: 199
ggagaacata attgtcggtg gagtgctagg agcaatactc gaatt            45

<210> SEQ ID NO 200
<211> LENGTH: 45
<212> TYPE: DNA
<213> ORGANISM: Vespula vulgaris

<400> SEQUENCE: 200
gatgcttgcc agttcgacag tggtggtcca attttatggc aaaat            45

<210> SEQ ID NO 201
<211> LENGTH: 45
<212> TYPE: DNA
<213> ORGANISM: Vespula vulgaris

<400> SEQUENCE: 201
aattgtcggt ggagtgctag gagcaatact cgaattaaat tgaat            45

<210> SEQ ID NO 202
<211> LENGTH: 45
<212> TYPE: DNA
<213> ORGANISM: Vespula vulgaris

<400> SEQUENCE: 202
gccgatgaag ctcctggtgt taacttgaga gtcactagtt attta            45

<210> SEQ ID NO 203
<211> LENGTH: 45
<212> TYPE: DNA
<213> ORGANISM: Vespula vulgaris

<400> SEQUENCE: 203
acagttttcg atgttcctcc gagttcgaat tgttcattgg atttt        45

<210> SEQ ID NO 204
<211> LENGTH: 45
<212> TYPE: DNA
<213> ORGANISM: Vespula vulgaris

<400> SEQUENCE: 204
aatccgtcga gaatcgtagg cggtgttgaa acaggagtga atgaa        45

<210> SEQ ID NO 205
<211> LENGTH: 45
<212> TYPE: DNA
<213> ORGANISM: Vespula vulgaris

<400> SEQUENCE: 205
aagaatccgt cgagaatcgt aggcggtgtt gaaacaggag tgaat        45

<210> SEQ ID NO 206
<211> LENGTH: 45
<212> TYPE: DNA
<213> ORGANISM: Vespula vulgaris

<400> SEQUENCE: 206
tgtggattaa attcttttgc agtggaatca atagcatcga aaatg        45

<210> SEQ ID NO 207
<211> LENGTH: 45
<212> TYPE: DNA
<213> ORGANISM: Vespula vulgaris

<400> SEQUENCE: 207
ataaaattgc agaagaggtt aaaatattct atgagaattg gtcca        45

<210> SEQ ID NO 208
<211> LENGTH: 45
<212> TYPE: DNA
<213> ORGANISM: Vespula vulgaris

<400> SEQUENCE: 208
aaggatgctt gccagttcga cagtggtggt ccaattttat ggcaa        45

<210> SEQ ID NO 209
<211> LENGTH: 45
<212> TYPE: DNA
<213> ORGANISM: Vespula vulgaris

<400> SEQUENCE: 209
gctgttataa aattgcagaa gaggttaaaa tattctatga gaatt        45

<210> SEQ ID NO 210
<211> LENGTH: 45
<212> TYPE: DNA
<213> ORGANISM: Vespula vulgaris

<400> SEQUENCE: 210

```
agttatttag attttattac aagatcaaca cctggagaaa tatat          45
```

<210> SEQ ID NO 211
<211> LENGTH: 45
<212> TYPE: DNA
<213> ORGANISM: Vespula vulgaris

<400> SEQUENCE: 211

```
gttataaaat tgcagaagag gttaaaatat tctatgagaa ttggt          45
```

<210> SEQ ID NO 212
<211> LENGTH: 45
<212> TYPE: DNA
<213> ORGANISM: Vespula vulgaris

<400> SEQUENCE: 212

```
ggctacaccc aaaaattaaa atcagatgtt aattattgcg tgtat          45
```

<210> SEQ ID NO 213
<211> LENGTH: 45
<212> TYPE: DNA
<213> ORGANISM: Vespula vulgaris

<400> SEQUENCE: 213

```
ttcgacagtg gtggtccaat tttatggcaa aatccaaaaa gcaaa          45
```

<210> SEQ ID NO 214
<211> LENGTH: 45
<212> TYPE: DNA
<213> ORGANISM: Vespula vulgaris

<400> SEQUENCE: 214

```
ataatcgtac atccgaatta taggccaaaa ttaaacgatt tagct          45
```

<210> SEQ ID NO 215
<211> LENGTH: 45
<212> TYPE: DNA
<213> ORGANISM: Vespula vulgaris

<400> SEQUENCE: 215

```
gatgaagctc ctggtgttaa cttgagagtc actagttatt tagat          45
```

<210> SEQ ID NO 216
<211> LENGTH: 45
<212> TYPE: DNA
<213> ORGANISM: Vespula vulgaris

<400> SEQUENCE: 216

```
catgtattaa cggctgctca ttgcgttgcg aggtataaaa ggatt          45
```

<210> SEQ ID NO 217
<211> LENGTH: 45
<212> TYPE: DNA
<213> ORGANISM: Vespula vulgaris

<400> SEQUENCE: 217

```
ggaaaggatg cttgccagtt cgacagtggt ggtccaattt tatgg          45
```

<210> SEQ ID NO 218
<211> LENGTH: 45
<212> TYPE: DNA
<213> ORGANISM: Vespula vulgaris

<400> SEQUENCE: 218

```
tatttagatt ttattacaag atcaacacct ggagaaatat attgt              45
```

<210> SEQ ID NO 219
<211> LENGTH: 45
<212> TYPE: DNA
<213> ORGANISM: Vespula vulgaris

<400> SEQUENCE: 219

```
ttgcagaaga ggttaaaata ttctatgaga attggtccag cttgt              45
```

<210> SEQ ID NO 220
<211> LENGTH: 45
<212> TYPE: DNA
<213> ORGANISM: Vespula vulgaris

<400> SEQUENCE: 220

```
tttatgaaag tcaaagtcga cgatgacatc gagtacgttt tctgt              45
```

<210> SEQ ID NO 221
<211> LENGTH: 45
<212> TYPE: DNA
<213> ORGANISM: Vespula vulgaris

<400> SEQUENCE: 221

```
gattttatga aagtcaaagt cgacgatgac atcgagtacg ttttc              45
```

<210> SEQ ID NO 222
<211> LENGTH: 45
<212> TYPE: DNA
<213> ORGANISM: Vespula vulgaris

<400> SEQUENCE: 222

```
atgaaagtca aagtcgacga tgacatcgag tacgttttct gtgga              45
```

<210> SEQ ID NO 223
<211> LENGTH: 45
<212> TYPE: DNA
<213> ORGANISM: Vespula vulgaris

<400> SEQUENCE: 223

```
atgaagaaat gcgtcaagta tcactttctg gctacaccta agcaa              45
```

<210> SEQ ID NO 224
<211> LENGTH: 45
<212> TYPE: DNA
<213> ORGANISM: Vespula vulgaris

<400> SEQUENCE: 224

```
gtcaagtatc actttctggc tacacctaag caactttgta cattc              45
```

<210> SEQ ID NO 225
<211> LENGTH: 45
<212> TYPE: DNA
<213> ORGANISM: Vespula vulgaris

<400> SEQUENCE: 225

```
aaatgcgtca agtatcactt tctggctaca cctaagcaac tttgt              45
```

<210> SEQ ID NO 226
<211> LENGTH: 45
<212> TYPE: DNA
<213> ORGANISM: Vespula vulgaris

```
<400> SEQUENCE: 226
tgcgtcaagt atcactttct ggctacacct aagcaacttt gtaca            45

<210> SEQ ID NO 227
<211> LENGTH: 45
<212> TYPE: DNA
<213> ORGANISM: Vespula vulgaris

<400> SEQUENCE: 227
aagaaatgcg tcaagtatca ctttctggct acacctaagc aactt            45

<210> SEQ ID NO 228
<211> LENGTH: 45
<212> TYPE: DNA
<213> ORGANISM: Vespula vulgaris

<400> SEQUENCE: 228
gatgttaatt attgcgtgta taatcctgat tttccgaatt attac            45

<210> SEQ ID NO 229
<211> LENGTH: 45
<212> TYPE: DNA
<213> ORGANISM: Vespula vulgaris

<400> SEQUENCE: 229
gttaattatt gcgtgtataa tcctgatttt ccgaattatt acatg            45

<210> SEQ ID NO 230
<211> LENGTH: 45
<212> TYPE: DNA
<213> ORGANISM: Vespula vulgaris

<400> SEQUENCE: 230
aattattgcg tgtataatcc tgattttccg aattattaca tggga            45

<210> SEQ ID NO 231
<211> LENGTH: 45
<212> TYPE: DNA
<213> ORGANISM: Vespula vulgaris

<400> SEQUENCE: 231
tattgcgtgt ataatcctga ttttccgaat tattacatgg gagaa            45

<210> SEQ ID NO 232
<211> LENGTH: 45
<212> TYPE: DNA
<213> ORGANISM: Vespula vulgaris

<400> SEQUENCE: 232
tgcgtgtata atcctgatttt tccgaattat tacatgggag aacat           45

<210> SEQ ID NO 233
<211> LENGTH: 45
<212> TYPE: DNA
<213> ORGANISM: Vespula vulgaris

<400> SEQUENCE: 233
aagtatcact ttctggctac acctaagcaa ctttgtacat tcgat            45

<210> SEQ ID NO 234
<211> LENGTH: 45
<212> TYPE: DNA
<213> ORGANISM: Vespula vulgaris
```

<400> SEQUENCE: 234
tatcactttc tggctacacc taagcaactt tgtacattcg atatg         45

<210> SEQ ID NO 235
<211> LENGTH: 45
<212> TYPE: DNA
<213> ORGANISM: Vespula vulgaris

<400> SEQUENCE: 235
ttgaattgca cagttttcga tgttcctccg agttcgaatt gttca         45

<210> SEQ ID NO 236
<211> LENGTH: 45
<212> TYPE: DNA
<213> ORGANISM: Vespula vulgaris

<400> SEQUENCE: 236
gtcactagtt atttagattt tattacaaga tcaacacctg gagaa         45

<210> SEQ ID NO 237
<211> LENGTH: 45
<212> TYPE: DNA
<213> ORGANISM: Vespula vulgaris

<400> SEQUENCE: 237
actagttatt tagattttat tacaagatca cacctggag aaata         45

<210> SEQ ID NO 238
<211> LENGTH: 45
<212> TYPE: DNA
<213> ORGANISM: Vespula vulgaris

<400> SEQUENCE: 238
agagtcacta gttatttaga ttttattaca agatcaacac ctgga         45

<210> SEQ ID NO 239
<211> LENGTH: 45
<212> TYPE: DNA
<213> ORGANISM: Vespula vulgaris

<400> SEQUENCE: 239
aaatgcgtca agtatcactt tctggctaca cctaagcaac tttgt         45

<210> SEQ ID NO 240
<211> LENGTH: 45
<212> TYPE: DNA
<213> ORGANISM: Vespula vulgaris

<400> SEQUENCE: 240
ttgagagtca ctagttattt agattttatt acaagatcaa cacct         45

<210> SEQ ID NO 241
<211> LENGTH: 45
<212> TYPE: DNA
<213> ORGANISM: Vespula vulgaris

<400> SEQUENCE: 241
agcaaacgta ttttccttct tggagtcatc aattatggaa gaaca         45

<210> SEQ ID NO 242
<211> LENGTH: 45
<212> TYPE: DNA

<213> ORGANISM: Vespula vulgaris

<400> SEQUENCE: 242
aaacgtattt tccttcttgg agtcatcaat tatggaagaa catgt    45

<210> SEQ ID NO 243
<211> LENGTH: 45
<212> TYPE: DNA
<213> ORGANISM: Vespula vulgaris

<400> SEQUENCE: 243
aacttgagag tcactagtta tttagatttt attacaagat caaca    45

<210> SEQ ID NO 244
<211> LENGTH: 45
<212> TYPE: DNA
<213> ORGANISM: Vespula vulgaris

<400> SEQUENCE: 244
cgtattttcc ttcttggagt catcaattat ggaagaacat gtgcc    45

<210> SEQ ID NO 245
<211> LENGTH: 45
<212> TYPE: DNA
<213> ORGANISM: Vespula vulgaris

<400> SEQUENCE: 245
cctgattttc cgaattatta catgggagaa cataattgtc ggtgg    45

<210> SEQ ID NO 246
<211> LENGTH: 45
<212> TYPE: DNA
<213> ORGANISM: Vespula vulgaris

<400> SEQUENCE: 246
tttccgaatt attacatggg agaacataat tgtcggtgga gtgct    45

<210> SEQ ID NO 247
<211> LENGTH: 45
<212> TYPE: DNA
<213> ORGANISM: Vespula vulgaris

<400> SEQUENCE: 247
gattttccga attattacat gggagaacat aattgtcggt ggagt    45

<210> SEQ ID NO 248
<211> LENGTH: 45
<212> TYPE: DNA
<213> ORGANISM: Vespula vulgaris

<400> SEQUENCE: 248
agtggtggtc caattttatg gcaaaatcca aaaagcaaac gtatt    45

<210> SEQ ID NO 249
<211> LENGTH: 45
<212> TYPE: DNA
<213> ORGANISM: Vespula vulgaris

<400> SEQUENCE: 249
ttatatattc taggagttgt tgttggagaa cataatacat gggca    45

<210> SEQ ID NO 250
<211> LENGTH: 45

<212> TYPE: DNA
<213> ORGANISM: Vespula vulgaris

<400> SEQUENCE: 250
ccagcttgtc ttccgttcta ttacatgcag cgaaactttg tagac        45

<210> SEQ ID NO 251
<211> LENGTH: 45
<212> TYPE: DNA
<213> ORGANISM: Vespula vulgaris

<400> SEQUENCE: 251
gcttgtcttc cgttctatta catgcagcga actttgtag acact        45

<210> SEQ ID NO 252
<211> LENGTH: 45
<212> TYPE: DNA
<213> ORGANISM: Vespula vulgaris

<400> SEQUENCE: 252
ccgttctatt acatgcagcg aaactttgta gacactgttg ttaca        45

<210> SEQ ID NO 253
<211> LENGTH: 45
<212> TYPE: DNA
<213> ORGANISM: Vespula vulgaris

<400> SEQUENCE: 253
tgtcttccgt tctattacat gcagcgaaac tttgtagaca ctgtt        45

<210> SEQ ID NO 254
<211> LENGTH: 45
<212> TYPE: DNA
<213> ORGANISM: Vespula vulgaris

<400> SEQUENCE: 254
cttccgttct attacatgca gcgaaacttt gtagacactg ttgtt        45

<210> SEQ ID NO 255
<211> LENGTH: 45
<212> TYPE: DNA
<213> ORGANISM: Vespula vulgaris

<400> SEQUENCE: 255
tattacatgc agcgaaactt tgtagacact gttgttacag ctgta        45

<210> SEQ ID NO 256
<211> LENGTH: 45
<212> TYPE: DNA
<213> ORGANISM: Vespula vulgaris

<400> SEQUENCE: 256
ttctattaca tgcagcgaaa ctttgtagac actgttgtta cagct        45

<210> SEQ ID NO 257
<211> LENGTH: 45
<212> TYPE: DNA
<213> ORGANISM: Vespula vulgaris

<400> SEQUENCE: 257
gagtacgttt tctgtggatt aaattctttt gcagtggaat caata        45

<210> SEQ ID NO 258

<210> SEQ ID NO 258
<211> LENGTH: 45
<212> TYPE: DNA
<213> ORGANISM: Vespula vulgaris

<400> SEQUENCE: 258
gatgacatcg agtacgtttt ctgtggatta aattcttttg cagtg         45

<210> SEQ ID NO 259
<211> LENGTH: 45
<212> TYPE: DNA
<213> ORGANISM: Vespula vulgaris

<400> SEQUENCE: 259
gacatcgagt acgttttctg tggattaaat tcttttgcag tggaa         45

<210> SEQ ID NO 260
<211> LENGTH: 45
<212> TYPE: DNA
<213> ORGANISM: Vespula vulgaris

<400> SEQUENCE: 260
atcgagtacg ttttctgtgg attaaattct tttgcagtgg aatca         45

<210> SEQ ID NO 261
<211> LENGTH: 45
<212> TYPE: DNA
<213> ORGANISM: Vespula vulgaris

<400> SEQUENCE: 261
tacgttttct gtggattaaa ttcttttgca gtggaatcaa tagca         45

<210> SEQ ID NO 262
<211> LENGTH: 45
<212> TYPE: DNA
<213> ORGANISM: Vespula vulgaris

<400> SEQUENCE: 262
tattacatgc agcgaaactt tgtagacact gttgttacag ctgta         45

<210> SEQ ID NO 263
<211> LENGTH: 45
<212> TYPE: DNA
<213> ORGANISM: Vespula vulgaris

<400> SEQUENCE: 263
gctggtataa tacatcttgc aacgcgtttt ctctattgcg gtgca         45

<210> SEQ ID NO 264
<211> LENGTH: 45
<212> TYPE: DNA
<213> ORGANISM: Vespula vulgaris

<400> SEQUENCE: 264
atgatggctg gtataataca tcttgcaacg cgttttctct attgc         45

<210> SEQ ID NO 265
<211> LENGTH: 45
<212> TYPE: DNA
<213> ORGANISM: Vespula vulgaris

<400> SEQUENCE: 265
atgcagcgaa actttgtaga cactgttgtt acagctgtag gatgg         45

<210> SEQ ID NO 266
<211> LENGTH: 45
<212> TYPE: DNA
<213> ORGANISM: Vespula vulgaris

<400> SEQUENCE: 266
cagcgaaact tgtagacac tgttgttaca gctgtaggat ggggt                45

<210> SEQ ID NO 267
<211> LENGTH: 45
<212> TYPE: DNA
<213> ORGANISM: Vespula vulgaris

<400> SEQUENCE: 267
cctatgatgg ctggtataat acatcttgca acgcgttttc tctat                45

<210> SEQ ID NO 268
<211> LENGTH: 45
<212> TYPE: DNA
<213> ORGANISM: Vespula vulgaris

<400> SEQUENCE: 268
tacatgcagc gaaactttgt agacactgtt gttacagctg tagga                45

<210> SEQ ID NO 269
<211> LENGTH: 45
<212> TYPE: DNA
<213> ORGANISM: Vespula vulgaris

<400> SEQUENCE: 269
tggggtctta cgaattttta tggtgtcaag tctgaagttt tgaga                45

<210> SEQ ID NO 270
<211> LENGTH: 45
<212> TYPE: DNA
<213> ORGANISM: Vespula vulgaris

<400> SEQUENCE: 270
cttacgaatt tttatggtgt caagtctgaa gttttgagaa aagtc                45

<210> SEQ ID NO 271
<211> LENGTH: 45
<212> TYPE: DNA
<213> ORGANISM: Vespula vulgaris

<400> SEQUENCE: 271
ggatggggtc ttacgaattt ttatggtgtc aagtctgaag ttttg                45

<210> SEQ ID NO 272
<211> LENGTH: 45
<212> TYPE: DNA
<213> ORGANISM: Vespula vulgaris

<400> SEQUENCE: 272
acgaattttt atggtgtcaa gtctgaagtt ttgagaaaag tcgat                45

<210> SEQ ID NO 273
<211> LENGTH: 45
<212> TYPE: DNA
<213> ORGANISM: Vespula vulgaris

<400> SEQUENCE: 273
gttttctgtg gattaaattc ttttgcagtg gaatcaatag catcg                45

<210> SEQ ID NO 274
<211> LENGTH: 45
<212> TYPE: DNA
<213> ORGANISM: Vespula vulgaris

<400> SEQUENCE: 274
ttctgtggat taaattcttt tgcagtggaa tcaatagcat cgaaa    45

<210> SEQ ID NO 275
<211> LENGTH: 30
<212> TYPE: DNA
<213> ORGANISM: Vespula vulgaris

<400> SEQUENCE: 275
cctggagaaa tatattgtca ggcgtattaa    30

<210> SEQ ID NO 276
<211> LENGTH: 45
<212> TYPE: DNA
<213> ORGANISM: Vespula vulgaris

<400> SEQUENCE: 276
aattgtcggt ggagtgctag gagcaatact cgaattaaat tgaat    45

<210> SEQ ID NO 277
<211> LENGTH: 45
<212> TYPE: DNA
<213> ORGANISM: Vespula vulgaris

<400> SEQUENCE: 277
gctcctggtg ttaacttgag agtcactagt tatttagatt ttatt    45

<210> SEQ ID NO 278
<211> LENGTH: 45
<212> TYPE: DNA
<213> ORGANISM: Vespula vulgaris

<400> SEQUENCE: 278
ggagaacata attgtcggtg gagtgctagg agcaatactc gaatt    45

<210> SEQ ID NO 279
<211> LENGTH: 45
<212> TYPE: DNA
<213> ORGANISM: Vespula vulgaris

<400> SEQUENCE: 279
gaagctcctg gtgttaactt gagagtcact agttatttag atttt    45

<210> SEQ ID NO 280
<211> LENGTH: 45
<212> TYPE: DNA
<213> ORGANISM: Vespula vulgaris

<400> SEQUENCE: 280
cataattgtc ggtggagtgc taggagcaat actcgaatta aattg    45

<210> SEQ ID NO 281
<211> LENGTH: 45
<212> TYPE: DNA
<213> ORGANISM: Vespula vulgaris

<400> SEQUENCE: 281
gaacataatt gtcggtggag tgctaggagc aatactcgaa ttaaa    45

<210> SEQ ID NO 282
<211> LENGTH: 45
<212> TYPE: DNA
<213> ORGANISM: Vespula vulgaris

<400> SEQUENCE: 282
tgtcggtgga gtgctaggag caatactcga attaaattga attgc               45

<210> SEQ ID NO 283
<211> LENGTH: 45
<212> TYPE: DNA
<213> ORGANISM: Vespula vulgaris

<400> SEQUENCE: 283
catgtattaa cggctgctca ttgcgttgcg aggtataaaa ggatt               45

<210> SEQ ID NO 284
<211> LENGTH: 45
<212> TYPE: DNA
<213> ORGANISM: Vespula vulgaris

<400> SEQUENCE: 284
acggctgctc attgcgttgc gaggtataaa aggattttat atatt               45

<210> SEQ ID NO 285
<211> LENGTH: 45
<212> TYPE: DNA
<213> ORGANISM: Vespula vulgaris

<400> SEQUENCE: 285
ccaattttat ggcaaaatcc aaaaagcaaa cgtattttcc ttctt               45

<210> SEQ ID NO 286
<211> LENGTH: 45
<212> TYPE: DNA
<213> ORGANISM: Vespula vulgaris

<400> SEQUENCE: 286
gctgctcatt gcgttgcgag gtataaaagg attttatata ttcta               45

<210> SEQ ID NO 287
<211> LENGTH: 45
<212> TYPE: DNA
<213> ORGANISM: Vespula vulgaris

<400> SEQUENCE: 287
ggtataatac atcttgcaac gcgttttctc tattgcggtg caact               45

<210> SEQ ID NO 288
<211> LENGTH: 45
<212> TYPE: DNA
<213> ORGANISM: Vespula vulgaris

<400> SEQUENCE: 288
attttatggc aaaatccaaa aagcaaacgt attttccttc ttgga               45

<210> SEQ ID NO 289
<211> LENGTH: 45
<212> TYPE: DNA
<213> ORGANISM: Vespula vulgaris

<400> SEQUENCE: 289
cttccgttct attacatgca gcgaaacttt gtagacactg ttgtt                45

<210> SEQ ID NO 290
<211> LENGTH: 45
<212> TYPE: DNA
<213> ORGANISM: Vespula vulgaris

<400> SEQUENCE: 290
ggtccaattt tatggcaaaa tccaaaaagc aaacgtattt tcctt                45

<210> SEQ ID NO 291
<211> LENGTH: 45
<212> TYPE: DNA
<213> ORGANISM: Vespula vulgaris

<400> SEQUENCE: 291
ttagctgtta taaaattgca gaagaggtta aatattcta tgaga                 45

<210> SEQ ID NO 292
<211> LENGTH: 45
<212> TYPE: DNA
<213> ORGANISM: Vespula vulgaris

<400> SEQUENCE: 292
gatttagctg ttataaaatt gcagaagagg ttaaatatt ctatg                 45

<210> SEQ ID NO 293
<211> LENGTH: 45
<212> TYPE: DNA
<213> ORGANISM: Vespula vulgaris

<400> SEQUENCE: 293
gctgttataa aattgcagaa gaggttaaaa tattctatga gaatt                45

<210> SEQ ID NO 294
<211> LENGTH: 45
<212> TYPE: DNA
<213> ORGANISM: Vespula vulgaris

<400> SEQUENCE: 294
ttaaacgatt tagctgttat aaaattgcag aagaggttaa aatat                45

<210> SEQ ID NO 295
<211> LENGTH: 45
<212> TYPE: DNA
<213> ORGANISM: Vespula vulgaris

<400> SEQUENCE: 295
aacgatttag ctgttataaa attgcagaag aggttaaaat attct                45

<210> SEQ ID NO 296
<211> LENGTH: 45
<212> TYPE: DNA
<213> ORGANISM: Vespula vulgaris

<400> SEQUENCE: 296
gttataaaat tgcagaagag gttaaaatat tctatgagaa ttggt                45

<210> SEQ ID NO 297
<211> LENGTH: 45
<212> TYPE: DNA
<213> ORGANISM: Vespula vulgaris

<400> SEQUENCE: 297
gtcaagtatc actttctggc tacacctaag caactttgta cattc 45

<210> SEQ ID NO 298
<211> LENGTH: 45
<212> TYPE: DNA
<213> ORGANISM: Vespula vulgaris

<400> SEQUENCE: 298
tgcgtcaagt atcactttct ggctacacct aagcaacttt gtaca 45

<210> SEQ ID NO 299
<211> LENGTH: 45
<212> TYPE: DNA
<213> ORGANISM: Vespula vulgaris

<400> SEQUENCE: 299
aaatgcgtca agtatcactt tctggctaca cctaagcaac tttgt 45

<210> SEQ ID NO 300
<211> LENGTH: 45
<212> TYPE: DNA
<213> ORGANISM: Vespula vulgaris

<400> SEQUENCE: 300
aagaaatgcg tcaagtatca ctttctggct acacctaagc aactt 45

<210> SEQ ID NO 301
<211> LENGTH: 45
<212> TYPE: DNA
<213> ORGANISM: Vespula vulgaris

<400> SEQUENCE: 301
atgaagaaat gcgtcaagta tcactttctg gctacaccta agcaa 45

<210> SEQ ID NO 302
<211> LENGTH: 45
<212> TYPE: DNA
<213> ORGANISM: Vespula vulgaris

<400> SEQUENCE: 302
actagttatt tagattttat tacaagatca cacctggag aaata 45

<210> SEQ ID NO 303
<211> LENGTH: 45
<212> TYPE: DNA
<213> ORGANISM: Vespula vulgaris

<400> SEQUENCE: 303
agttatttag attttattac aagatcaaca cctggagaaa tatat 45

<210> SEQ ID NO 304
<211> LENGTH: 45
<212> TYPE: DNA
<213> ORGANISM: Vespula vulgaris

<400> SEQUENCE: 304
tatttagatt ttattacaag atcaacacct ggagaaatat attgt 45

<210> SEQ ID NO 305
<211> LENGTH: 45
<212> TYPE: DNA
<213> ORGANISM: Vespula vulgaris

<400> SEQUENCE: 305
ttagatttta ttacaagatc aacacctgga gaaatatatt gtcag					45

<210> SEQ ID NO 306
<211> LENGTH: 45
<212> TYPE: DNA
<213> ORGANISM: Vespula vulgaris

<400> SEQUENCE: 306
gattttatta caagatcaac acctggagaa atatattgtc aggcg					45

<210> SEQ ID NO 307
<211> LENGTH: 45
<212> TYPE: DNA
<213> ORGANISM: Vespula vulgaris

<400> SEQUENCE: 307
aatgaatatc ctatgatggc tggtataata catcttgcaa cgcgt					45

<210> SEQ ID NO 308
<211> LENGTH: 45
<212> TYPE: DNA
<213> ORGANISM: Vespula vulgaris

<400> SEQUENCE: 308
gtgaatgaat atcctatgat ggctggtata atacatcttg caacg					45

<210> SEQ ID NO 309
<211> LENGTH: 45
<212> TYPE: DNA
<213> ORGANISM: Vespula vulgaris

<400> SEQUENCE: 309
acaggagtga atgaatatcc tatgatggct ggtataatac atctt					45

<210> SEQ ID NO 310
<211> LENGTH: 45
<212> TYPE: DNA
<213> ORGANISM: Vespula vulgaris

<400> SEQUENCE: 310
gaaacaggag tgaatgaata tcctatgatg gctggtataa tacat					45

<210> SEQ ID NO 311
<211> LENGTH: 45
<212> TYPE: DNA
<213> ORGANISM: Vespula vulgaris

<400> SEQUENCE: 311
ggagtgaatg aatatcctat gatggctggt ataatacatc ttgca					45

<210> SEQ ID NO 312
<211> LENGTH: 45
<212> TYPE: DNA
<213> ORGANISM: Vespula vulgaris

<400> SEQUENCE: 312
gagaaatgta gatgtggttg gaagaatccg tcgagaatcg taggc					45

<210> SEQ ID NO 313
<211> LENGTH: 45
<212> TYPE: DNA
<213> ORGANISM: Vespula vulgaris -continued

<400> SEQUENCE: 313
ttagctgtta taaaattgca gaagaggtta aatattcta tgaga                45

<210> SEQ ID NO 314
<211> LENGTH: 45
<212> TYPE: DNA
<213> ORGANISM: Vespula vulgaris

<400> SEQUENCE: 314
tatcctatga tggctggtat aatacatctt gcaacgcgtt ttctc                45

<210> SEQ ID NO 315
<211> LENGTH: 45
<212> TYPE: DNA
<213> ORGANISM: Vespula vulgaris

<400> SEQUENCE: 315
gatttagctg ttataaaatt gcagaagagg ttaaaatatt ctatg                45

<210> SEQ ID NO 316
<211> LENGTH: 45
<212> TYPE: DNA
<213> ORGANISM: Vespula vulgaris

<400> SEQUENCE: 316
aaatgtagat gtggttggaa gaatccgtcg agaatcgtag gcggt                45

<210> SEQ ID NO 317
<211> LENGTH: 45
<212> TYPE: DNA
<213> ORGANISM: Vespula vulgaris

<400> SEQUENCE: 317
tgtagatgtg gttggaagaa tccgtcgaga atcgtaggcg gtgtt                45

<210> SEQ ID NO 318
<211> LENGTH: 45
<212> TYPE: DNA
<213> ORGANISM: Vespula vulgaris

<400> SEQUENCE: 318
aacgatttag ctgttataaa attgcagaag aggttaaaat attct                45

<210> SEQ ID NO 319
<211> LENGTH: 45
<212> TYPE: DNA
<213> ORGANISM: Vespula vulgaris

<400> SEQUENCE: 319
ttaaacgatt tagctgttat aaaattgcag aaggttaa aatat                45

<210> SEQ ID NO 320
<211> LENGTH: 45
<212> TYPE: DNA
<213> ORGANISM: Vespula vulgaris

<400> SEQUENCE: 320
agatgtggtt ggaagaatcc gtcgagaatc gtaggcggtg ttgaa                45

<210> SEQ ID NO 321
<211> LENGTH: 45
<212> TYPE: DNA

<213> ORGANISM: Vespula vulgaris

<400> SEQUENCE: 321
tgtggttgga agaatccgtc gagaatcgta

```
<212> TYPE: DNA
<213> ORGANISM: Vespula vulgaris

<400> SEQUENCE: 329
attttccttc ttggagtcat caattatgga agaacatgtg ccgat              45

<210> SEQ ID NO 330
<211> LENGTH: 45
<212> TYPE: DNA
<213> ORGANISM: Vespula vulgaris

<400> SEQUENCE: 330
ttaaacgatt tagctgttat aaaattgcag aagaggttaa aatat              45

<210> SEQ ID NO 331
<211> LENGTH: 45
<212> TYPE: DNA
<213> ORGANISM: Vespula vulgaris

<400> SEQUENCE: 331
ttagctgtta taaaattgca gaagaggtta aatattcta tgaga               45

<210> SEQ ID NO 332
<211> LENGTH: 45
<212> TYPE: DNA
<213> ORGANISM: Vespula vulgaris

<400> SEQUENCE: 332
gcgaggtata aaaggatttt atatattcta ggagttgttg ttgga              45

<210> SEQ ID NO 333
<211> LENGTH: 45
<212> TYPE: DNA
<213> ORGANISM: Vespula vulgaris

<400> SEQUENCE: 333
gatttagctg ttataaaatt gcagaagagg ttaaaatatt ctatg              45

<210> SEQ ID NO 334
<211> LENGTH: 45
<212> TYPE: DNA
<213> ORGANISM: Vespula vulgaris

<400> SEQUENCE: 334
tgtggttgga agaatccgtc gagaatcgta ggcggtgttg aaaca              45

<210> SEQ ID NO 335
<211> LENGTH: 45
<212> TYPE: DNA
<213> ORGANISM: Vespula vulgaris

<400> SEQUENCE: 335
aggtataaaa ggattttata tattctagga gttgttgttg gagaa              45

<210> SEQ ID NO 336
<211> LENGTH: 45
<212> TYPE: DNA
<213> ORGANISM: Vespula vulgaris

<400> SEQUENCE: 336
aacgatttag ctgttataaa attgcagaag aggttaaaat attct              45

<210> SEQ ID NO 337
```

<210> SEQ ID NO 337
<211> LENGTH: 45
<212> TYPE: DNA
<213> ORGANISM: Vespula vulgaris

<400> SEQUENCE: 337
tgtagatgtg gttggaagaa tccgtcgaga atcgtaggcg gtgtt           45

<210> SEQ ID NO 338
<211> LENGTH: 45
<212> TYPE: DNA
<213> ORGANISM: Vespula vulgaris

<400> SEQUENCE: 338
aaaaggattt tatatattct aggagttgtt gttggagaac ataat           45

<210> SEQ ID NO 339
<211> LENGTH: 45
<212> TYPE: DNA
<213> ORGANISM: Vespula vulgaris

<400> SEQUENCE: 339
gagaaatgta gatgtggttg aagaatccg tcgagaatcg taggc            45

<210> SEQ ID NO 340
<211> LENGTH: 45
<212> TYPE: DNA
<213> ORGANISM: Vespula vulgaris

<400> SEQUENCE: 340
aaatgtagat gtggttggaa gaatccgtcg agaatcgtag gcggt           45

<210> SEQ ID NO 341
<211> LENGTH: 45
<212> TYPE: DNA
<213> ORGANISM: Vespula vulgaris

<400> SEQUENCE: 341
tataaaagga ttttatatat tctaggagtt gttgttggag aacat           45

<210> SEQ ID NO 342
<211> LENGTH: 45
<212> TYPE: DNA
<213> ORGANISM: Vespula vulgaris

<400> SEQUENCE: 342
gctgttataa aattgcagaa gaggttaaaa tattctatga gaatt           45

<210> SEQ ID NO 343
<211> LENGTH: 45
<212> TYPE: DNA
<213> ORGANISM: Vespula vulgaris

<400> SEQUENCE: 343
aggattttat atattctagg agttgttgtt ggagaacata ataca           45

<210> SEQ ID NO 344
<211> LENGTH: 45
<212> TYPE: DNA
<213> ORGANISM: Vespula vulgaris

<400> SEQUENCE: 344
aaacgtattt tccttcttgg agtcatcaat tatggaagaa catgt           45

```
<210> SEQ ID NO 345
<211> LENGTH: 45
<212> TYPE: DNA
<213> ORGANISM: Vespula vulgaris

<400> SEQUENCE: 345
agcaaacgta ttttccttct tggagtcatc aattatggaa gaaca              45

<210> SEQ ID NO 346
<211> LENGTH: 45
<212> TYPE: DNA
<213> ORGANISM: Vespula vulgaris

<400> SEQUENCE: 346
agatgtggtt ggaagaatcc gtcgagaatc gtaggcggtg ttgaa              45

<210> SEQ ID NO 347
<211> LENGTH: 45
<212> TYPE: DNA
<213> ORGANISM: Vespula vulgaris

<400> SEQUENCE: 347
ttccttcttg gagtcatcaa ttatggaaga acatgtgccg atgaa              45

<210> SEQ ID NO 348
<211> LENGTH: 45
<212> TYPE: DNA
<213> ORGANISM: Vespula vulgaris

<400> SEQUENCE: 348
ataaaattgc agaagaggtt aaatattct atgagaattg gtcca               45

<210> SEQ ID NO 349
<211> LENGTH: 45
<212> TYPE: DNA
<213> ORGANISM: Vespula vulgaris

<400> SEQUENCE: 349
atggctggta taatacatct tgcaacgcgt tttctctatt gcggt              45

<210> SEQ ID NO 350
<211> LENGTH: 45
<212> TYPE: DNA
<213> ORGANISM: Vespula vulgaris

<400> SEQUENCE: 350
atagcatcga aaatgactat aaaattccat tcaagataca atact              45

<210> SEQ ID NO 351
<211> LENGTH: 45
<212> TYPE: DNA
<213> ORGANISM: Vespula vulgaris

<400> SEQUENCE: 351
gccgatgaag ctcctggtgt taacttgaga gtcactagtt attta              45

<210> SEQ ID NO 352
<211> LENGTH: 45
<212> TYPE: DNA
<213> ORGANISM: Vespula vulgaris

<400> SEQUENCE: 352
gatgaagctc ctggtgttaa cttgagagtc actagttatt tagat              45
```

<210> SEQ ID NO 353
<211> LENGTH: 45
<212> TYPE: DNA
<213> ORGANISM: Vespula vulgaris

<400> SEQUENCE: 353
gaagctcctg gtgttaactt gagagtcact agttatttag atttt              45

<210> SEQ ID NO 354
<211> LENGTH: 45
<212> TYPE: DNA
<213> ORGANISM: Vespula vulgaris

<400> SEQUENCE: 354
gctggtataa tacatcttgc aacgcgtttt ctctattgcg gtgca              45

<210> SEQ ID NO 355
<211> LENGTH: 45
<212> TYPE: DNA
<213> ORGANISM: Vespula vulgaris

<400> SEQUENCE: 355
gttataaaat tgcagaagag gttaaaatat tctatgagaa ttggt              45

<210> SEQ ID NO 356
<211> LENGTH: 45
<212> TYPE: DNA
<213> ORGANISM: Vespula vulgaris

<400> SEQUENCE: 356
acagctgtag gatggggtct tacgaatttt tatggtgtca agtct              45

<210> SEQ ID NO 357
<211> LENGTH: 45
<212> TYPE: DNA
<213> ORGANISM: Vespula vulgaris

<400> SEQUENCE: 357
tggaagaatc cgtcgagaat cgtaggcggt gttgaaacag gagtg              45

<210> SEQ ID NO 358
<211> LENGTH: 45
<212> TYPE: DNA
<213> ORGANISM: Vespula vulgaris

<400> SEQUENCE: 358
tggggtctta cgaatttta tggtgtcaag tctgaagttt tgaga              45

<210> SEQ ID NO 359
<211> LENGTH: 45
<212> TYPE: DNA
<213> ORGANISM: Vespula vulgaris

<400> SEQUENCE: 359
gctcctggtg ttaacttgag agtcactagt tatttagatt ttatt              45

<210> SEQ ID NO 360
<211> LENGTH: 45
<212> TYPE: DNA
<213> ORGANISM: Vespula vulgaris

<400> SEQUENCE: 360
atgatggctg gtataataca tcttgcaacg cgttttctct attgc              45

```
<210> SEQ ID NO 361
<211> LENGTH: 45
<212> TYPE: DNA
<213> ORGANISM: Vespula vulgaris

<400> SEQUENCE: 361
cctatgatgg ctggtataat acatcttgca acgcgttttc tctat            45

<210> SEQ ID NO 362
<211> LENGTH: 45
<212> TYPE: DNA
<213> ORGANISM: Vespula vulgaris

<400> SEQUENCE: 362
ggttggaaga atccgtcgag aatcgtaggc ggtgttgaaa cagga            45

<210> SEQ ID NO 363
<211> LENGTH: 45
<212> TYPE: DNA
<213> ORGANISM: Vespula vulgaris

<400> SEQUENCE: 363
cttcttggag tcatcaatta tggaagaaca tgtgccgatg aagct            45

<210> SEQ ID NO 364
<211> LENGTH: 45
<212> TYPE: DNA
<213> ORGANISM: Vespula vulgaris

<400> SEQUENCE: 364
cataatacat gggcaattaa cgatacaaag gcaactcaac tttat            45

<210> SEQ ID NO 365
<211> LENGTH: 45
<212> TYPE: DNA
<213> ORGANISM: Vespula vulgaris

<400> SEQUENCE: 365
cttacgaatt tttatggtgt caagtctgaa gttttgagaa aagtc            45

<210> SEQ ID NO 366
<211> LENGTH: 45
<212> TYPE: DNA
<213> ORGANISM: Vespula vulgaris

<400> SEQUENCE: 366
cctggtgtta acttgagagt cactagttat ttagatttta ttaca            45

<210> SEQ ID NO 367
<211> LENGTH: 45
<212> TYPE: DNA
<213> ORGANISM: Vespula vulgaris

<400> SEQUENCE: 367
cttggagtca tcaattatgg aagaacatgt gccgatgaag ctcct            45

<210> SEQ ID NO 368
<211> LENGTH: 45
<212> TYPE: DNA
<213> ORGANISM: Vespula vulgaris

<400> SEQUENCE: 368
```
aatacatggg caattaacga tacaaaggca actcaacttt atctt    45

<210> SEQ ID NO 369
<211> LENGTH: 45
<212> TYPE: DNA
<213> ORGANISM: Vespula vulgaris

<400> SEQUENCE: 369
gaacataata catgggcaat taacgataca aggcaactc aactt    45

<210> SEQ ID NO 370
<211> LENGTH: 45
<212> TYPE: DNA
<213> ORGANISM: Vespula vulgaris

<400> SEQUENCE: 370
attttatata ttctaggagt tgttgttgga gaacataata catgg    45

<210> SEQ ID NO 371
<211> LENGTH: 45
<212> TYPE: DNA
<213> ORGANISM: Vespula vulgaris

<400> SEQUENCE: 371
ggtataatac atcttgcaac gcgttttctc tattgcggtg caact    45

<210> SEQ ID NO 372
<211> LENGTH: 45
<212> TYPE: DNA
<213> ORGANISM: Vespula vulgaris

<400> SEQUENCE: 372
gtaggatggg gtcttacgaa tttttatggt gtcaagtctg aagtt    45

<210> SEQ ID NO 373
<211> LENGTH: 45
<212> TYPE: DNA
<213> ORGANISM: Vespula vulgaris

<400> SEQUENCE: 373
gctgtaggat ggggtcttac gaattttat ggtgtcaagt ctgaa    45

<210> SEQ ID NO 374
<211> LENGTH: 45
<212> TYPE: DNA
<213> ORGANISM: Vespula vulgaris

<400> SEQUENCE: 374
gttggagaac ataatacatg gcaattaac gatacaaagg caact    45

<210> SEQ ID NO 375
<211> LENGTH: 45
<212> TYPE: DNA
<213> ORGANISM: Vespula vulgaris

<400> SEQUENCE: 375
aaaagcaaac gtattttcct tcttggagtc atcaattatg gaaga    45

<210> SEQ ID NO 376
<211> LENGTH: 45
<212> TYPE: DNA
<213> ORGANISM: Vespula vulgaris

<400> SEQUENCE: 376
cattgcgttg cgaggtataa aaggatttta tatattctag gagtt            45

<210> SEQ ID NO 377
<211> LENGTH: 45
<212> TYPE: DNA
<213> ORGANISM: Vespula vulgaris

<400> SEQUENCE: 377
gcatcgaaaa tgactataaa attccattca agatacaata cttat            45

<210> SEQ ID NO 378
<211> LENGTH: 45
<212> TYPE: DNA
<213> ORGANISM: Vespula vulgaris

<400> SEQUENCE: 378
gctcattgcg ttgcgaggta taaaaggatt ttatatattc tagga            45

<210> SEQ ID NO 379
<211> LENGTH: 45
<212> TYPE: DNA
<213> ORGANISM: Vespula vulgaris

<400> SEQUENCE: 379
ccaaaaagca aacgtatttt ccttcttgga gtcatcaatt atgga            45

<210> SEQ ID NO 380
<211> LENGTH: 45
<212> TYPE: DNA
<213> ORGANISM: Vespula vulgaris

<400> SEQUENCE: 380
tcgaaaatga ctataaaatt ccattcaaga tacaatactt atgga            45

<210> SEQ ID NO 381
<211> LENGTH: 45
<212> TYPE: DNA
<213> ORGANISM: Vespula vulgaris

<400> SEQUENCE: 381
gctaggagca atactcgaat taaattgaat tgcacagttt tcgat            45

<210> SEQ ID NO 382
<211> LENGTH: 45
<212> TYPE: DNA
<213> ORGANISM: Vespula vulgaris

<400> SEQUENCE: 382
ggagaacata atacatgggc aattaacgat acaaaggcaa ctcaa            45

<210> SEQ ID NO 383
<211> LENGTH: 45
<212> TYPE: DNA
<213> ORGANISM: Vespula vulgaris

<400> SEQUENCE: 383
aggagcaata ctcgaattaa attgaattgc acagttttcg atgtt            45

<210> SEQ ID NO 384
<211> LENGTH: 45
<212> TYPE: DNA
<213> ORGANISM: Vespula vulgaris

```
<400> SEQUENCE: 384
gttgcgaggt ataaaaggat tttatatatt ctaggagttg ttgtt           45

<210> SEQ ID NO 385
<211> LENGTH: 45
<212> TYPE: DNA
<213> ORGANISM: Vespula vulgaris

<400> SEQUENCE: 385
ttatatattc taggagttgt tgttggagaa cataatacat gggca           45

<210> SEQ ID NO 386
<211> LENGTH: 45
<212> TYPE: DNA
<213> ORGANISM: Vespula vulgaris

<400> SEQUENCE: 386
aaaatgacta taaaattcca ttcaagatac aatacttatg gaggc           45

<210> SEQ ID NO 387
<211> LENGTH: 45
<212> TYPE: DNA
<213> ORGANISM: Vespula vulgaris

<400> SEQUENCE: 387
atgactataa aattccattc aagatacaat acttatggag gcaaa           45

<210> SEQ ID NO 388
<211> LENGTH: 45
<212> TYPE: DNA
<213> ORGANISM: Vespula vulgaris

<400> SEQUENCE: 388
gttgttacag ctgtaggatg gggtcttacg aatttttatg gtgtc           45

<210> SEQ ID NO 389
<211> LENGTH: 45
<212> TYPE: DNA
<213> ORGANISM: Vespula vulgaris

<400> SEQUENCE: 389
agcaatactc gaattaaatt gaattgcaca gttttcgatg ttcct           45

<210> SEQ ID NO 390
<211> LENGTH: 45
<212> TYPE: DNA
<213> ORGANISM: Vespula vulgaris

<400> SEQUENCE: 390
aatactcgaa ttaaattgaa ttgcacagtt tcgatgttc ctccg            45

<210> SEQ ID NO 391
<211> LENGTH: 45
<212> TYPE: DNA
<213> ORGANISM: Vespula vulgaris

<400> SEQUENCE: 391
acgaattttt atggtgtcaa gtctgaagtt ttgagaaaag tcgat           45

<210> SEQ ID NO 392
<211> LENGTH: 45
<212> TYPE: DNA
<213> ORGANISM: Vespula vulgaris
```

<210> SEQ ID NO 393
<211> LENGTH: 45
<212> TYPE: DNA
<213> ORGANISM: Vespula vulgaris

<400> SEQUENCE: 393 aattttatg gtgtcaagtc tgaagttttg agaaaagtcg atttg 45

<210> SEQ ID NO 394
<211> LENGTH: 45
<212> TYPE: DNA
<213> ORGANISM: Vespula vulgaris

<400> SEQUENCE: 394
aaattaaacg atttagctgt tataaaattg cagaagaggt taaaa 45

<210> SEQ ID NO 395
<211> LENGTH: 45
<212> TYPE: DNA
<213> ORGANISM: Vespula vulgaris

<400> SEQUENCE: 395
actcgaatta aattgaattg cacagttttc gatgttcctc cgagt 45

<210> SEQ ID NO 396
<211> LENGTH: 45
<212> TYPE: DNA
<213> ORGANISM: Vespula vulgaris

<400> SEQUENCE: 396
gacactgttg ttacagctgt aggatggggt cttacgaatt tttat 45

<210> SEQ ID NO 397
<211> LENGTH: 45
<212> TYPE: DNA
<213> ORGANISM: Vespula vulgaris

<400> SEQUENCE: 397
ggtcttacga atttttatgg tgtcaagtct gaagttttga gaaaa 45

<210> SEQ ID NO 398
<211> LENGTH: 45
<212> TYPE: DNA
<213> ORGANISM: Vespula vulgaris

<400> SEQUENCE: 398
tgcgttgcga ggtataaaag gattttatat attctaggag ttgtt 45

<210> SEQ ID NO 399
<211> LENGTH: 45
<212> TYPE: DNA
<213> ORGANISM: Vespula vulgaris

<400> SEQUENCE: 399
tatcctatga tggctggtat aatacatctt gcaacgcgtt ttctc 45

<210> SEQ ID NO 400
<211> LENGTH: 45
<212> TYPE: DNA

<400> SEQUENCE: 392
gttacagctg taggatgggg tcttacgaat ttttatggtg tcaag 45

<213> ORGANISM: Vespula vulgaris

<400> SEQUENCE: 400
ccaaaattaa acgatttagc tgttataaaa ttgcagaaga ggtta                         45

<210> SEQ ID NO 401
<211> LENGTH: 45
<212> TYPE: DNA
<213> ORGANISM: Vespula vulgaris

<400> SEQUENCE: 401
aggccaaaat taaacgattt agctgttata aaattgcaga agagg                         45

<210> SEQ ID NO 402
<211> LENGTH: 45
<212> TYPE: DNA
<213> ORGANISM: Vespula vulgaris

<400> SEQUENCE: 402
aatccaaaaa gcaaacgtat tttccttctt ggagtcatca attat                         45

<210> SEQ ID NO 403
<211> LENGTH: 45
<212> TYPE: DNA
<213> ORGANISM: Vespula vulgaris

<400> SEQUENCE: 403
ataaaattcc attcaagata caatacttat ggaggcaaat ttcga                         45

<210> SEQ ID NO 404
<211> LENGTH: 45
<212> TYPE: DNA
<213> ORGANISM: Vespula vulgaris

<400> SEQUENCE: 404
ggatggggtc ttacgaattt ttatggtgtc aagtctgaag ttttg                         45

<210> SEQ ID NO 405
<211> LENGTH: 45
<212> TYPE: DNA
<213> ORGANISM: Vespula vulgaris

<400> SEQUENCE: 405
actgttgtta cagctgtagg atggggtctt acgaattttt atggt                         45

<210> SEQ ID NO 406
<211> LENGTH: 45
<212> TYPE: DNA
<213> ORGANISM: Vespula vulgaris

<400> SEQUENCE: 406
ttgcagaaga ggttaaaata ttctatgaga attggtccag cttgt                         45

<210> SEQ ID NO 407
<211> LENGTH: 45
<212> TYPE: DNA
<213> ORGANISM: Vespula vulgaris

<400> SEQUENCE: 407
acatgggcaa ttaacgatac aaaggcaact caactttatc ttatt                         45

<210> SEQ ID NO 408
<211> LENGTH: 45

```
<212> TYPE: DNA
<213> ORGANISM: Vespula vulgaris

<400> SEQUENCE: 408
gatttgcatg tagtttcaat gaagaaatgc gtcaagtatc acttt          45

<210> SEQ ID NO 409
<211> LENGTH: 45
<212> TYPE: DNA
<213> ORGANISM: Vespula vulgaris

<400> SEQUENCE: 409
tgggcaatta acgatacaaa ggcaactcaa ctttatctta ttgat          45

<210> SEQ ID NO 410
<211> LENGTH: 45
<212> TYPE: DNA
<213> ORGANISM: Vespula vulgaris

<400> SEQUENCE: 410
ttgcatgtag tttcaatgaa gaaatgcgtc aagtatcact ttctg          45

<210> SEQ ID NO 411
<211> LENGTH: 45
<212> TYPE: DNA
<213> ORGANISM: Vespula vulgaris

<400> SEQUENCE: 411
ataatacatc ttgcaacgcg ttttctctat tgcggtgcaa ctata          45

<210> SEQ ID NO 412
<211> LENGTH: 45
<212> TYPE: DNA
<213> ORGANISM: Vespula vulgaris

<400> SEQUENCE: 412
tcttttgcag tggaatcaat agcatcgaaa atgactataa aattc          45

<210> SEQ ID NO 413
<211> LENGTH: 45
<212> TYPE: DNA
<213> ORGANISM: Vespula vulgaris

<400> SEQUENCE: 413
gcagtggaat caatagcatc gaaaatgact ataaaattcc attca          45

<210> SEQ ID NO 414
<211> LENGTH: 45
<212> TYPE: DNA
<213> ORGANISM: Vespula vulgaris

<400> SEQUENCE: 414
aaattgcaga agaggttaaa atattctatg agaattggtc cagct          45

<210> SEQ ID NO 415
<211> LENGTH: 45
<212> TYPE: DNA
<213> ORGANISM: Vespula vulgaris

<400> SEQUENCE: 415
tttgcagtgg aatcaatagc atcgaaaatg actataaaat tccat          45

<210> SEQ ID NO 416
```

<210> SEQ ID NO 416
<211> LENGTH: 45
<212> TYPE: DNA
<213> ORGANISM: Vespula vulgaris

<400> SEQUENCE: 416
agcaaacgta ttttccttct tggagtcatc aattatggaa gaaca     45

<210> SEQ ID NO 417
<211> LENGTH: 45
<212> TYPE: DNA
<213> ORGANISM: Vespula vulgaris

<400> SEQUENCE: 417
aaaagcaaac gtatttttcct tcttggagtc atcaattatg gaaga     45

<210> SEQ ID NO 418
<211> LENGTH: 45
<212> TYPE: DNA
<213> ORGANISM: Vespula vulgaris

<400> SEQUENCE: 418
aaacgtattt tccttcttgg agtcatcaat tatggaagaa catgt     45

<210> SEQ ID NO 419
<211> LENGTH: 45
<212> TYPE: DNA
<213> ORGANISM: Vespula vulgaris

<400> SEQUENCE: 419
cgtattttcc ttcttggagt catcaattat ggaagaacat gtgcc     45

<210> SEQ ID NO 420
<211> LENGTH: 45
<212> TYPE: DNA
<213> ORGANISM: Vespula vulgaris

<400> SEQUENCE: 420
attttccttc ttggagtcat caattatgga agaacatgtg ccgat     45

<210> SEQ ID NO 421
<211> LENGTH: 45
<212> TYPE: DNA
<213> ORGANISM: Vespula vulgaris

<400> SEQUENCE: 421
gtcaagtctg aagttttgag aaaagtcgat ttgcatgtag tttca     45

<210> SEQ ID NO 422
<211> LENGTH: 45
<212> TYPE: DNA
<213> ORGANISM: Vespula vulgaris

<400> SEQUENCE: 422
ggtgtcaagt ctgaagtttt gagaaaagtc gatttgcatg tagtt     45

<210> SEQ ID NO 423
<211> LENGTH: 45
<212> TYPE: DNA
<213> ORGANISM: Vespula vulgaris

<400> SEQUENCE: 423
tctgaagttt tgagaaaagt cgatttgcat gtagtttcaa tgaag     45

```
<210> SEQ ID NO 424
<211> LENGTH: 45
<212> TYPE: DNA
<213> ORGANISM: Vespula vulgaris

<400> SEQUENCE: 424
aagtctgaag ttttgagaaa agtcgatttg catgtagttt caatg              45

<210> SEQ ID NO 425
<211> LENGTH: 45
<212> TYPE: DNA
<213> ORGANISM: Vespula vulgaris

<400> SEQUENCE: 425
ttccttcttg gagtcatcaa ttatggaaga acatgtgccg atgaa              45

<210> SEQ ID NO 426
<211> LENGTH: 45
<212> TYPE: DNA
<213> ORGANISM: Vespula vulgaris

<400> SEQUENCE: 426
tataatcctg attttccgaa ttattacatg ggagaacata attgt              45

<210> SEQ ID NO 427
<211> LENGTH: 45
<212> TYPE: DNA
<213> ORGANISM: Vespula vulgaris

<400> SEQUENCE: 427
gaagttttga gaaaagtcga tttgcatgta gtttcaatga agaaa              45

<210> SEQ ID NO 428
<211> LENGTH: 45
<212> TYPE: DNA
<213> ORGANISM: Vespula vulgaris

<400> SEQUENCE: 428
aacgatttag ctgttataaa attgcagaag aggttaaaat attct              45

<210> SEQ ID NO 429
<211> LENGTH: 45
<212> TYPE: DNA
<213> ORGANISM: Vespula vulgaris

<400> SEQUENCE: 429
cttcttggag tcatcaatta tggaagaaca tgtgccgatg aagct              45

<210> SEQ ID NO 430
<211> LENGTH: 45
<212> TYPE: DNA
<213> ORGANISM: Vespula vulgaris

<400> SEQUENCE: 430
ttaaacgatt tagctgttat aaaattgcag aagaggttaa aatat              45

<210> SEQ ID NO 431
<211> LENGTH: 45
<212> TYPE: DNA
<213> ORGANISM: Vespula vulgaris

<400> SEQUENCE: 431
aaattaaacg atttagctgt tataaaattg cagaagaggt taaaa              45
```

<210> SEQ ID NO 432
<211> LENGTH: 45
<212> TYPE: DNA
<213> ORGANISM: Vespula vulgaris

<400> SEQUENCE: 432
gcgaggtata aaaggatttt atatattcta ggagttgttg ttgga                           45

<210> SEQ ID NO 433
<211> LENGTH: 45
<212> TYPE: DNA
<213> ORGANISM: Vespula vulgaris

<400> SEQUENCE: 433
tataaaagga ttttatatat tctaggagtt gttgttggag aacat                           45

<210> SEQ ID NO 434
<211> LENGTH: 45
<212> TYPE: DNA
<213> ORGANISM: Vespula vulgaris

<400> SEQUENCE: 434
gttttgagaa aagtcgattt gcatgtagtt tcaatgaaga aatgc                           45

<210> SEQ ID NO 435
<211> LENGTH: 45
<212> TYPE: DNA
<213> ORGANISM: Vespula vulgaris

<400> SEQUENCE: 435
aaaaggattt tatatattct aggagttgtt gttggagaac ataat                           45

<210> SEQ ID NO 436
<211> LENGTH: 45
<212> TYPE: DNA
<213> ORGANISM: Vespula vulgaris

<400> SEQUENCE: 436
ccaaaattaa acgatttagc tgttataaaa ttgcagaaga ggtta                           45

<210> SEQ ID NO 437
<211> LENGTH: 45
<212> TYPE: DNA
<213> ORGANISM: Vespula vulgaris

<400> SEQUENCE: 437
gatttagctg ttataaaatt gcagaagagg ttaaaatatt ctatg                           45

<210> SEQ ID NO 438
<211> LENGTH: 45
<212> TYPE: DNA
<213> ORGANISM: Vespula vulgaris

<400> SEQUENCE: 438
aggtataaaa ggattttata tattctagga gttgttgttg agaa                            45

<210> SEQ ID NO 439
<211> LENGTH: 45
<212> TYPE: DNA
<213> ORGANISM: Vespula vulgaris

<400> SEQUENCE: 439
tggggtctta cgaatttta tggtgtcaag tctgaagttt tgaga                            45

<210> SEQ ID NO 440
<211> LENGTH: 45
<212> TYPE: DNA
<213> ORGANISM: Vespula vulgaris

<400> SEQUENCE: 440
cttacgaatt tttatggtgt caagtctgaa gttttgagaa aagtc                45

<210> SEQ ID NO 441
<211> LENGTH: 45
<212> TYPE: DNA
<213> ORGANISM: Vespula vulgaris

<400> SEQUENCE: 441
aggccaaaat taaacgattt agctgttata aaattgcaga agagg                45

<210> SEQ ID NO 442
<211> LENGTH: 45
<212> TYPE: DNA
<213> ORGANISM: Vespula vulgaris

<400> SEQUENCE: 442
gttgcgaggt ataaaaggat tttatatatt ctaggagttg ttgtt                45

<210> SEQ ID NO 443
<211> LENGTH: 45
<212> TYPE: DNA
<213> ORGANISM: Vespula vulgaris

<400> SEQUENCE: 443
agaaaagtcg atttgcatgt agtttcaatg aagaaatgcg tcaag                45

<210> SEQ ID NO 444
<211> LENGTH: 45
<212> TYPE: DNA
<213> ORGANISM: Vespula vulgaris

<400> SEQUENCE: 444
gtcgatttgc atgtagtttc aatgaagaaa tgcgtcaagt atcac                45

<210> SEQ ID NO 445
<211> LENGTH: 45
<212> TYPE: DNA
<213> ORGANISM: Vespula vulgaris

<400> SEQUENCE: 445
aaagtcgatt tgcatgtagt ttcaatgaag aaatgcgtca agtat                45

<210> SEQ ID NO 446
<211> LENGTH: 45
<212> TYPE: DNA
<213> ORGANISM: Vespula vulgaris

<400> SEQUENCE: 446
gctgttataa aattgcagaa gaggttaaaa tattctatga gaatt                45

<210> SEQ ID NO 447
<211> LENGTH: 45
<212> TYPE: DNA
<213> ORGANISM: Vespula vulgaris

<400> SEQUENCE: 447

```
tatggtgtca agtctgaagt tttgagaaaa gtcgatttgc atgta              45

<210> SEQ ID NO 448
<211> LENGTH: 45
<212> TYPE: DNA
<213> ORGANISM: Vespula vulgaris

<400> SEQUENCE: 448
aggattttat atattctagg agttgttgtt ggagaacata ataca              45

<210> SEQ ID NO 449
<211> LENGTH: 45
<212> TYPE: DNA
<213> ORGANISM: Vespula vulgaris

<400> SEQUENCE: 449
gagaaatgta gatgtggttg gaagaatccg tcgagaatcg taggc              45

<210> SEQ ID NO 450
<211> LENGTH: 45
<212> TYPE: DNA
<213> ORGANISM: Vespula vulgaris

<400> SEQUENCE: 450
ggatggggtc ttacgaattt ttatggtgtc aagtctgaag ttttg              45

<210> SEQ ID NO 451
<211> LENGTH: 45
<212> TYPE: DNA
<213> ORGANISM: Vespula vulgaris

<400> SEQUENCE: 451
cattgcgttg cgaggtataa aaggatttta tatattctag gagtt              45

<210> SEQ ID NO 452
<211> LENGTH: 45
<212> TYPE: DNA
<213> ORGANISM: Vespula vulgaris

<400> SEQUENCE: 452
gttataaaat tgcagaagag gttaaaatat tctatgagaa ttggt              45

<210> SEQ ID NO 453
<211> LENGTH: 45
<212> TYPE: DNA
<213> ORGANISM: Vespula vulgaris

<400> SEQUENCE: 453
tgcgttgcga ggtataaaag gattttatat attctaggag ttgtt              45

<210> SEQ ID NO 454
<211> LENGTH: 45
<212> TYPE: DNA
<213> ORGANISM: Vespula vulgaris

<400> SEQUENCE: 454
gatttgcatg tagtttcaat gaagaaatgc gtcaagtatc acttt              45

<210> SEQ ID NO 455
<211> LENGTH: 45
<212> TYPE: DNA
<213> ORGANISM: Vespula vulgaris

<400> SEQUENCE: 455
```

-continued

```
ttgcatgtag tttcaatgaa gaaatgcgtc aagtatcact ttctg          45

<210> SEQ ID NO 456
<211> LENGTH: 45
<212> TYPE: DNA
<213> ORGANISM: Vespula vulgaris

<400> SEQUENCE: 456
acgaattttt atggtgtcaa gtctgaagtt ttgagaaaag tcgat          45

<210> SEQ ID NO 457
<211> LENGTH: 45
<212> TYPE: DNA
<213> ORGANISM: Vespula vulgaris

<400> SEQUENCE: 457
aaatgtagat gtggttggaa gaatccgtcg agaatcgtag gcggt          45

<210> SEQ ID NO 458
<211> LENGTH: 45
<212> TYPE: DNA
<213> ORGANISM: Vespula vulgaris

<400> SEQUENCE: 458
ggtcttacga atttttatgg tgtcaagtct gaagttttga gaaaa          45

<210> SEQ ID NO 459
<211> LENGTH: 45
<212> TYPE: DNA
<213> ORGANISM: Vespula vulgaris

<400> SEQUENCE: 459
gacagtggtg gtccaatttt atggcaaaat ccaaaaagca aacgt          45

<210> SEQ ID NO 460
<211> LENGTH: 45
<212> TYPE: DNA
<213> ORGANISM: Vespula vulgaris

<400> SEQUENCE: 460
agtggtggtc caattttatg gcaaaatcca aaagcaaac gtatt          45

<210> SEQ ID NO 461
<211> LENGTH: 45
<212> TYPE: DNA
<213> ORGANISM: Vespula vulgaris

<400> SEQUENCE: 461
ggtggtccaa ttttatggca aaatccaaaa agcaaacgta ttttc          45

<210> SEQ ID NO 462
<211> LENGTH: 45
<212> TYPE: DNA
<213> ORGANISM: Vespula vulgaris

<400> SEQUENCE: 462
ggtccaattt tatggcaaaa tccaaaaagc aaacgtattt tcctt          45

<210> SEQ ID NO 463
<211> LENGTH: 45
<212> TYPE: DNA
<213> ORGANISM: Vespula vulgaris
```

-continued

<400> SEQUENCE: 463
ttcgacagtg gtggtccaat tttatggcaa aatccaaaaa gcaaa                    45

<210> SEQ ID NO 464
<211> LENGTH: 45
<212> TYPE: DNA
<213> ORGANISM: Vespula vulgaris

<400> SEQUENCE: 464
ccaattttat ggcaaaatcc aaaaagcaaa cgtatttcc ttctt                     45

<210> SEQ ID NO 465
<211> LENGTH: 45
<212> TYPE: DNA
<213> ORGANISM: Vespula vulgaris

<400> SEQUENCE: 465
ttagctgtta taaaattgca gaagaggtta aatattcta tgaga                     45

<210> SEQ ID NO 466
<211> LENGTH: 45
<212> TYPE: DNA
<213> ORGANISM: Vespula vulgaris

<400> SEQUENCE: 466
gatttagctg ttataaaatt gcagaagagg ttaaatatt ctatg                     45

<210> SEQ ID NO 467
<211> LENGTH: 45
<212> TYPE: DNA
<213> ORGANISM: Vespula vulgaris

<400> SEQUENCE: 467
ttaaacgatt tagctgttat aaaattgcag aagaggttaa aatat                    45

<210> SEQ ID NO 468
<211> LENGTH: 45
<212> TYPE: DNA
<213> ORGANISM: Vespula vulgaris

<400> SEQUENCE: 468
aacgatttag ctgttataaa attgcagaag aggttaaaat attct                    45

<210> SEQ ID NO 469
<211> LENGTH: 45
<212> TYPE: DNA
<213> ORGANISM: Vespula vulgaris

<400> SEQUENCE: 469
attttatggc aaaatccaaa aagcaaacgt attttccttc ttgga                    45

<210> SEQ ID NO 470
<211> LENGTH: 45
<212> TYPE: DNA
<213> ORGANISM: Vespula vulgaris

<400> SEQUENCE: 470
gattttccga attattacat gggagaacat aattgtcggt ggagt                    45

<210> SEQ ID NO 471
<211> LENGTH: 45
<212> TYPE: DNA
<213> ORGANISM: Vespula vulgaris -continued

<400> SEQUENCE: 471
tttccgaatt attacatggg agaacataat tgtcggtgga gtgct          45

<210> SEQ ID NO 472
<211> LENGTH: 45
<212> TYPE: DNA
<213> ORGANISM: Vespula vulgaris

<400> SEQUENCE: 472
aatcctgatt ttccgaatta ttacatggga gaacataatt gtcgg          45

<210> SEQ ID NO 473
<211> LENGTH: 45
<212> TYPE: DNA
<213> ORGANISM: Vespula vulgaris

<400> SEQUENCE: 473
ggtggtccaa ttttatggca aaatccaaaa agcaaacgta ttttc          45

<210> SEQ ID NO 474
<211> LENGTH: 45
<212> TYPE: DNA
<213> ORGANISM: Vespula vulgaris

<400> SEQUENCE: 474
agtggtggtc caattttatg gcaaaatcca aaagcaaac gtatt           45

<210> SEQ ID NO 475
<211> LENGTH: 45
<212> TYPE: DNA
<213> ORGANISM: Vespula vulgaris

<400> SEQUENCE: 475
ggtccaattt tatggcaaaa tccaaaaagc aaacgtattt tcctt          45

<210> SEQ ID NO 476
<211> LENGTH: 45
<212> TYPE: DNA
<213> ORGANISM: Vespula vulgaris

<400> SEQUENCE: 476
ataatcgtac atccgaatta taggccaaaa ttaaacgatt tagct          45

<210> SEQ ID NO 477
<211> LENGTH: 45
<212> TYPE: DNA
<213> ORGANISM: Vespula vulgaris

<400> SEQUENCE: 477
ccaattttat ggcaaaatcc aaaaagcaaa cgtattttcc ttctt          45

<210> SEQ ID NO 478
<211> LENGTH: 45
<212> TYPE: DNA
<213> ORGANISM: Vespula vulgaris

<400> SEQUENCE: 478
attttatggc aaaatccaaa agcaaacgt attttccttc ttgga           45

<210> SEQ ID NO 479
<211> LENGTH: 45
<212> TYPE: DNA

<213> ORGANISM: Vespula vulgaris

<400> SEQUENCE: 479
atcgtacatc cgaattatag gccaaaatta aacgatttag ctgtt    45

<210> SEQ ID NO 480
<211> LENGTH: 45
<212> TYPE: DNA
<213> ORGANISM: Vespula vulgaris

<400> SEQUENCE: 480
gatgatataa tcgtacatcc gaattatagg ccaaaattaa acgat    45

<210> SEQ ID NO 481
<211> LENGTH: 45
<212> TYPE: DNA
<213> ORGANISM: Vespula vulgaris

<400> SEQUENCE: 481
attgatgata taatcgtaca tccgaattat aggccaaaat taaac    45

<210> SEQ ID NO 482
<211> LENGTH: 45
<212> TYPE: DNA
<213> ORGANISM: Vespula vulgaris

<400> SEQUENCE: 482
cttattgatg atataatcgt acatccgaat tataggccaa aatta    45

<210> SEQ ID NO 483
<211> LENGTH: 45
<212> TYPE: DNA
<213> ORGANISM: Vespula vulgaris

<400> SEQUENCE: 483
gacagtggtg gtccaatttt atggcaaaat ccaaaaagca aacgt    45

<210> SEQ ID NO 484
<211> LENGTH: 45
<212> TYPE: DNA
<213> ORGANISM: Vespula vulgaris

<400> SEQUENCE: 484
gtacatccga attataggcc aaaattaaac gatttagctg ttata    45

<210> SEQ ID NO 485
<211> LENGTH: 45
<212> TYPE: DNA
<213> ORGANISM: Vespula vulgaris

<400> SEQUENCE: 485
gatataatcg tacatccgaa ttataggcca aaattaaacg attta    45

<210> SEQ ID NO 486
<211> LENGTH: 15
<212> TYPE: PRT
<213> ORGANISM: Vespula vulgaris

<400> SEQUENCE: 486

Ser Gly Gly Pro Ile Leu Trp Gln Asn Pro Lys Ser Lys Arg Ile
1               5                   10                  15

<210> SEQ ID NO 487

```
<211> LENGTH: 15
<212> TYPE: PRT
<213> ORGANISM: Vespula vulgaris

<400> SEQUENCE: 487

Gly Gly Pro Ile Leu Trp Gln Asn Pro Lys Ser Lys Arg Ile Phe
1               5                   10                  15

<210> SEQ ID NO 488
<211> LENGTH: 15
<212> TYPE: PRT
<213> ORGANISM: Vespula vulgaris

<400> SEQUENCE: 488

Gly Pro Ile Leu Trp Gln Asn Pro Lys Ser Lys Arg Ile Phe Leu
1               5                   10                  15

<210> SEQ ID NO 489
<211> LENGTH: 15
<212> TYPE: PRT
<213> ORGANISM: Vespula vulgaris

<400> SEQUENCE: 489

Pro Ile Leu Trp Gln Asn Pro Lys Ser Lys Arg Ile Phe Leu Leu
1               5                   10                  15

<210> SEQ ID NO 490
<211> LENGTH: 15
<212> TYPE: PRT
<213> ORGANISM: Vespula vulgaris

<400> SEQUENCE: 490

Ile Leu Trp Gln Asn Pro Lys Ser Lys Arg Ile Phe Leu Leu Gly
1               5                   10                  15

<210> SEQ ID NO 491
<211> LENGTH: 15
<212> TYPE: PRT
<213> ORGANISM: Vespula vulgaris

<400> SEQUENCE: 491

Tyr Pro Met Met Ala Gly Ile Ile His Leu Ala Thr Arg Phe Leu
1               5                   10                  15

<210> SEQ ID NO 492
<211> LENGTH: 15
<212> TYPE: PRT
<213> ORGANISM: Vespula vulgaris

<400> SEQUENCE: 492

Ser Phe Ala Val Glu Ser Ile Ala Ser Lys Met Thr Ile Lys Phe
1               5                   10                  15

<210> SEQ ID NO 493
<211> LENGTH: 15
<212> TYPE: PRT
<213> ORGANISM: Vespula vulgaris

<400> SEQUENCE: 493

Phe Ala Val Glu Ser Ile Ala Ser Lys Met Thr Ile Lys Phe His
1               5                   10                  15

<210> SEQ ID NO 494
<211> LENGTH: 15
<212> TYPE: PRT
```

<213> ORGANISM: Vespula vulgaris

<400> SEQUENCE: 494

Asn Ser Phe Ala Val Glu Ser Ile Ala Ser Lys Met Thr Ile Lys
1               5                   10                  15

<210> SEQ ID NO 495
<211> LENGTH: 15
<212> TYPE: PRT
<213> ORGANISM: Vespula vulgaris

<400> SEQUENCE: 495

Pro Met Met Ala Gly Ile Ile His Leu Ala Thr Arg Phe Leu Tyr
1               5                   10                  15

<210> SEQ ID NO 496
<211> LENGTH: 15
<212> TYPE: PRT
<213> ORGANISM: Vespula vulgaris

<400> SEQUENCE: 496

Leu Asn Ser Phe Ala Val Glu Ser Ile Ala Ser Lys Met Thr Ile
1               5                   10                  15

<210> SEQ ID NO 497
<211> LENGTH: 15
<212> TYPE: PRT
<213> ORGANISM: Vespula vulgaris

<400> SEQUENCE: 497

Met Ala Gly Ile Ile His Leu Ala Thr Arg Phe Leu Tyr Cys Gly
1               5                   10                  15

<210> SEQ ID NO 498
<211> LENGTH: 15
<212> TYPE: PRT
<213> ORGANISM: Vespula vulgaris

<400> SEQUENCE: 498

Gly Leu Asn Ser Phe Ala Val Glu Ser Ile Ala Ser Lys Met Thr
1               5                   10                  15

<210> SEQ ID NO 499
<211> LENGTH: 15
<212> TYPE: PRT
<213> ORGANISM: Vespula vulgaris

<400> SEQUENCE: 499

Ala Gly Ile Ile His Leu Ala Thr Arg Phe Leu Tyr Cys Gly Ala
1               5                   10                  15

<210> SEQ ID NO 500
<211> LENGTH: 15
<212> TYPE: PRT
<213> ORGANISM: Vespula vulgaris

<400> SEQUENCE: 500

Met Met Ala Gly Ile Ile His Leu Ala Thr Arg Phe Leu Tyr Cys
1               5                   10                  15

<210> SEQ ID NO 501
<211> LENGTH: 15
<212> TYPE: PRT
<213> ORGANISM: Vespula vulgaris

<400> SEQUENCE: 501

Glu Tyr Val Phe Cys Gly Leu Asn Ser Phe Ala Val Glu Ser Ile
1               5                   10                  15

<210> SEQ ID NO 502
<211> LENGTH: 15
<212> TYPE: PRT
<213> ORGANISM: Vespula vulgaris

<400> SEQUENCE: 502

Tyr Val Phe Cys Gly Leu Asn Ser Phe Ala Val Glu Ser Ile Ala
1               5                   10                  15

<210> SEQ ID NO 503
<211> LENGTH: 15
<212> TYPE: PRT
<213> ORGANISM: Vespula vulgaris

<400> SEQUENCE: 503

Ile Glu Tyr Val Phe Cys Gly Leu Asn Ser Phe Ala Val Glu Ser
1               5                   10                  15

<210> SEQ ID NO 504
<211> LENGTH: 15
<212> TYPE: PRT
<213> ORGANISM: Vespula vulgaris

<400> SEQUENCE: 504

Asp Ile Glu Tyr Val Phe Cys Gly Leu Asn Ser Phe Ala Val Glu
1               5                   10                  15

<210> SEQ ID NO 505
<211> LENGTH: 15
<212> TYPE: PRT
<213> ORGANISM: Vespula vulgaris

<400> SEQUENCE: 505

Asp Asp Ile Glu Tyr Val Phe Cys Gly Leu Asn Ser Phe Ala Val
1               5                   10                  15

<210> SEQ ID NO 506
<211> LENGTH: 15
<212> TYPE: PRT
<213> ORGANISM: Vespula vulgaris

<400> SEQUENCE: 506

Val Asn Glu Tyr Pro Met Met Ala Gly Ile Ile His Leu Ala Thr
1               5                   10                  15

<210> SEQ ID NO 507
<211> LENGTH: 15
<212> TYPE: PRT
<213> ORGANISM: Vespula vulgaris

<400> SEQUENCE: 507

Asn Glu Tyr Pro Met Met Ala Gly Ile Ile His Leu Ala Thr Arg
1               5                   10                  15

<210> SEQ ID NO 508
<211> LENGTH: 15
<212> TYPE: PRT
<213> ORGANISM: Vespula vulgaris

<400> SEQUENCE: 508

```
Leu Thr Asn Phe Tyr Gly Val Lys Ser Glu Val Leu Arg Lys Val
1               5                   10                  15
```

<210> SEQ ID NO 509
<211> LENGTH: 15
<212> TYPE: PRT
<213> ORGANISM: Vespula vulgaris

<400> SEQUENCE: 509

```
Gly Val Asn Glu Tyr Pro Met Met Ala Gly Ile Ile His Leu Ala
1               5                   10                  15
```

<210> SEQ ID NO 510
<211> LENGTH: 15
<212> TYPE: PRT
<213> ORGANISM: Vespula vulgaris

<400> SEQUENCE: 510

```
Thr Asn Phe Tyr Gly Val Lys Ser Glu Val Leu Arg Lys Val Asp
1               5                   10                  15
```

<210> SEQ ID NO 511
<211> LENGTH: 15
<212> TYPE: PRT
<213> ORGANISM: Vespula vulgaris

<400> SEQUENCE: 511

```
Leu Trp Gln Asn Pro Lys Ser Lys Arg Ile Phe Leu Leu Gly Val
1               5                   10                  15
```

<210> SEQ ID NO 512
<211> LENGTH: 15
<212> TYPE: PRT
<213> ORGANISM: Vespula vulgaris

<400> SEQUENCE: 512

```
Trp Gln Asn Pro Lys Ser Lys Arg Ile Phe Leu Leu Gly Val Ile
1               5                   10                  15
```

<210> SEQ ID NO 513
<211> LENGTH: 15
<212> TYPE: PRT
<213> ORGANISM: Vespula vulgaris

<400> SEQUENCE: 513

```
Lys Arg Leu Lys Tyr Ser Met Arg Ile Gly Pro Ala Cys Leu Pro
1               5                   10                  15
```

<210> SEQ ID NO 514
<211> LENGTH: 15
<212> TYPE: PRT
<213> ORGANISM: Vespula vulgaris

<400> SEQUENCE: 514

```
Glu Tyr Pro Met Met Ala Gly Ile Ile His Leu Ala Thr Arg Phe
1               5                   10                  15
```

<210> SEQ ID NO 515
<211> LENGTH: 15
<212> TYPE: PRT
<213> ORGANISM: Vespula vulgaris

<400> SEQUENCE: 515

```
Leu Lys Tyr Ser Met Arg Ile Gly Pro Ala Cys Leu Pro Phe Tyr
1               5                   10                  15
```

<210> SEQ ID NO 516
<211> LENGTH: 15
<212> TYPE: PRT
<213> ORGANISM: Vespula vulgaris

<400> SEQUENCE: 516

Lys Tyr Ser Met Arg Ile Gly Pro Ala Cys Leu Pro Phe Tyr Tyr
1               5                   10                  15

<210> SEQ ID NO 517
<211> LENGTH: 15
<212> TYPE: PRT
<213> ORGANISM: Vespula vulgaris

<400> SEQUENCE: 517

Arg Leu Lys Tyr Ser Met Arg Ile Gly Pro Ala Cys Leu Pro Phe
1               5                   10                  15

<210> SEQ ID NO 518
<211> LENGTH: 15
<212> TYPE: PRT
<213> ORGANISM: Vespula vulgaris

<400> SEQUENCE: 518

Ala Arg Tyr Lys Arg Ile Leu Tyr Ile Leu Gly Val Val Val Gly
1               5                   10                  15

<210> SEQ ID NO 519
<211> LENGTH: 15
<212> TYPE: PRT
<213> ORGANISM: Vespula vulgaris

<400> SEQUENCE: 519

Ala Val Glu Ser Ile Ala Ser Lys Met Thr Ile Lys Phe His Ser
1               5                   10                  15

<210> SEQ ID NO 520
<211> LENGTH: 15
<212> TYPE: PRT
<213> ORGANISM: Vespula vulgaris

<400> SEQUENCE: 520

Tyr Ser Met Arg Ile Gly Pro Ala Cys Leu Pro Phe Tyr Tyr Met
1               5                   10                  15

<210> SEQ ID NO 521
<211> LENGTH: 15
<212> TYPE: PRT
<213> ORGANISM: Vespula vulgaris

<400> SEQUENCE: 521

Val Glu Ser Ile Ala Ser Lys Met Thr Ile Lys Phe His Ser Arg
1               5                   10                  15

<210> SEQ ID NO 522
<211> LENGTH: 15
<212> TYPE: PRT
<213> ORGANISM: Vespula vulgaris

<400> SEQUENCE: 522

Asp Thr Val Val Thr Ala Val Gly Trp Gly Leu Thr Asn Phe Tyr
1               5                   10                  15

```
<210> SEQ ID NO 523
<211> LENGTH: 15
<212> TYPE: PRT
<213> ORGANISM: Vespula vulgaris

<400> SEQUENCE: 523

Leu Ala Thr Arg Phe Leu Tyr Cys Gly Ala Thr Ile Ile Thr Pro
1               5                   10                  15

<210> SEQ ID NO 524
<211> LENGTH: 15
<212> TYPE: PRT
<213> ORGANISM: Vespula vulgaris

<400> SEQUENCE: 524

Asn Phe Tyr Gly Val Lys Ser Glu Val Leu Arg Lys Val Asp Leu
1               5                   10                  15

<210> SEQ ID NO 525
<211> LENGTH: 15
<212> TYPE: PRT
<213> ORGANISM: Vespula vulgaris

<400> SEQUENCE: 525

Gly Ile Ile His Leu Ala Thr Arg Phe Leu Tyr Cys Gly Ala Thr
1               5                   10                  15

<210> SEQ ID NO 526
<211> LENGTH: 15
<212> TYPE: PRT
<213> ORGANISM: Vespula vulgaris

<400> SEQUENCE: 526

Trp Gly Leu Thr Asn Phe Tyr Gly Val Lys Ser Glu Val Leu Arg
1               5                   10                  15

<210> SEQ ID NO 527
<211> LENGTH: 15
<212> TYPE: PRT
<213> ORGANISM: Vespula vulgaris

<400> SEQUENCE: 527

Phe Tyr Gly Val Lys Ser Glu Val Leu Arg Lys Val Asp Leu His
1               5                   10                  15

<210> SEQ ID NO 528
<211> LENGTH: 15
<212> TYPE: PRT
<213> ORGANISM: Vespula vulgaris

<400> SEQUENCE: 528

Ile Ile His Leu Ala Thr Arg Phe Leu Tyr Cys Gly Ala Thr Ile
1               5                   10                  15

<210> SEQ ID NO 529
<211> LENGTH: 15
<212> TYPE: PRT
<213> ORGANISM: Vespula vulgaris

<400> SEQUENCE: 529

Gly Trp Gly Leu Thr Asn Phe Tyr Gly Val Lys Ser Glu Val Leu
1               5                   10                  15

<210> SEQ ID NO 530
<211> LENGTH: 15
```

```
<212> TYPE: PRT
<213> ORGANISM: Vespula vulgaris

<400> SEQUENCE: 530

Arg Tyr Lys Arg Ile Leu Tyr Ile Leu Gly Val Val Gly Glu
1               5                   10                  15

<210> SEQ ID NO 531
<211> LENGTH: 15
<212> TYPE: PRT
<213> ORGANISM: Vespula vulgaris

<400> SEQUENCE: 531

Tyr Lys Arg Ile Leu Tyr Ile Leu Gly Val Val Gly Glu His
1               5                   10                  15

<210> SEQ ID NO 532
<211> LENGTH: 15
<212> TYPE: PRT
<213> ORGANISM: Vespula vulgaris

<400> SEQUENCE: 532

Arg Phe Leu Tyr Cys Gly Ala Thr Ile Ile Thr Pro Gln His Val
1               5                   10                  15

<210> SEQ ID NO 533
<211> LENGTH: 15
<212> TYPE: PRT
<213> ORGANISM: Vespula vulgaris

<400> SEQUENCE: 533

Lys Arg Ile Leu Tyr Ile Leu Gly Val Val Gly Glu His Asn
1               5                   10                  15

<210> SEQ ID NO 534
<211> LENGTH: 15
<212> TYPE: PRT
<213> ORGANISM: Vespula vulgaris

<400> SEQUENCE: 534

Thr Arg Phe Leu Tyr Cys Gly Ala Thr Ile Ile Thr Pro Gln His
1               5                   10                  15

<210> SEQ ID NO 535
<211> LENGTH: 15
<212> TYPE: PRT
<213> ORGANISM: Vespula vulgaris

<400> SEQUENCE: 535

Ala Thr Arg Phe Leu Tyr Cys Gly Ala Thr Ile Ile Thr Pro Gln
1               5                   10                  15

<210> SEQ ID NO 536
<211> LENGTH: 15
<212> TYPE: PRT
<213> ORGANISM: Vespula vulgaris

<400> SEQUENCE: 536

Glu Thr Gly Val Asn Glu Tyr Pro Met Met Ala Gly Ile Ile His
1               5                   10                  15

<210> SEQ ID NO 537
<211> LENGTH: 15
<212> TYPE: PRT
<213> ORGANISM: Vespula vulgaris
```

<400> SEQUENCE: 537

Thr Gly Val Asn Glu Tyr Pro Met Met Ala Gly Ile Ile His Leu
1               5                   10                  15

<210> SEQ ID NO 538
<211> LENGTH: 15
<212> TYPE: PRT
<213> ORGANISM: Vespula vulgaris

<400> SEQUENCE: 538

Gly Leu Thr Asn Phe Tyr Gly Val Lys Ser Glu Val Leu Arg Lys
1               5                   10                  15

<210> SEQ ID NO 539
<211> LENGTH: 15
<212> TYPE: PRT
<213> ORGANISM: Vespula vulgaris

<400> SEQUENCE: 539

Val Phe Cys Gly Leu Asn Ser Phe Ala Val Glu Ser Ile Ala Ser
1               5                   10                  15

<210> SEQ ID NO 540
<211> LENGTH: 15
<212> TYPE: PRT
<213> ORGANISM: Vespula vulgaris

<400> SEQUENCE: 540

Phe Cys Gly Leu Asn Ser Phe Ala Val Glu Ser Ile Ala Ser Lys
1               5                   10                  15

<210> SEQ ID NO 541
<211> LENGTH: 15
<212> TYPE: PRT
<213> ORGANISM: Vespula vulgaris

<400> SEQUENCE: 541

Thr Val Val Thr Ala Val Gly Trp Gly Leu Thr Asn Phe Tyr Gly
1               5                   10                  15

<210> SEQ ID NO 542
<211> LENGTH: 15
<212> TYPE: PRT
<213> ORGANISM: Vespula vulgaris

<400> SEQUENCE: 542

Asn Phe Val Asp Thr Val Thr Ala Val Gly Trp Gly Leu Thr
1               5                   10                  15

<210> SEQ ID NO 543
<211> LENGTH: 15
<212> TYPE: PRT
<213> ORGANISM: Vespula vulgaris

<400> SEQUENCE: 543

His Asn Thr Trp Ala Ile Asn Asp Thr Lys Ala Thr Gln Leu Tyr
1               5                   10                  15

<210> SEQ ID NO 544
<211> LENGTH: 15
<212> TYPE: PRT
<213> ORGANISM: Vespula vulgaris

<400> SEQUENCE: 544

```
Arg Ile Leu Tyr Ile Leu Gly Val Val Gly Glu His Asn Thr
1               5                   10                  15

<210> SEQ ID NO 545
<211> LENGTH: 15
<212> TYPE: PRT
<213> ORGANISM: Vespula vulgaris

<400> SEQUENCE: 545

Asn Thr Trp Ala Ile Asn Asp Thr Lys Ala Thr Gln Leu Tyr Leu
1               5                   10                  15

<210> SEQ ID NO 546
<211> LENGTH: 15
<212> TYPE: PRT
<213> ORGANISM: Vespula vulgaris

<400> SEQUENCE: 546

Tyr Cys Gly Ala Thr Ile Ile Thr Pro Gln His Val Leu Thr Ala
1               5                   10                  15

<210> SEQ ID NO 547
<211> LENGTH: 15
<212> TYPE: PRT
<213> ORGANISM: Vespula vulgaris

<400> SEQUENCE: 547

Glu His Asn Thr Trp Ala Ile Asn Asp Thr Lys Ala Thr Gln Leu
1               5                   10                  15

<210> SEQ ID NO 548
<211> LENGTH: 15
<212> TYPE: PRT
<213> ORGANISM: Vespula vulgaris

<400> SEQUENCE: 548

Phe Val Asp Thr Val Val Thr Ala Val Gly Trp Gly Leu Thr Asn
1               5                   10                  15

<210> SEQ ID NO 549
<211> LENGTH: 15
<212> TYPE: PRT
<213> ORGANISM: Vespula vulgaris

<400> SEQUENCE: 549

Val Val Thr Ala Val Gly Trp Gly Leu Thr Asn Phe Tyr Gly Val
1               5                   10                  15

<210> SEQ ID NO 550
<211> LENGTH: 15
<212> TYPE: PRT
<213> ORGANISM: Vespula vulgaris

<400> SEQUENCE: 550

Cys Gly Ala Thr Ile Ile Thr Pro Gln His Val Leu Thr Ala Ala
1               5                   10                  15

<210> SEQ ID NO 551
<211> LENGTH: 15
<212> TYPE: PRT
<213> ORGANISM: Vespula vulgaris

<400> SEQUENCE: 551

Phe Leu Tyr Cys Gly Ala Thr Ile Ile Thr Pro Gln His Val Leu
```

```
                    1               5              10              15

<210> SEQ ID NO 552
<211> LENGTH: 15
<212> TYPE: PRT
<213> ORGANISM: Vespula vulgaris

<400> SEQUENCE: 552

Arg Asn Phe Val Asp Thr Val Val Thr Ala Val Gly Trp Gly Leu
1               5                  10                  15

<210> SEQ ID NO 553
<211> LENGTH: 15
<212> TYPE: PRT
<213> ORGANISM: Vespula vulgaris

<400> SEQUENCE: 553

Thr Ala Val Gly Trp Gly Leu Thr Asn Phe Tyr Gly Val Lys Ser
1               5                  10                  15

<210> SEQ ID NO 554
<211> LENGTH: 15
<212> TYPE: PRT
<213> ORGANISM: Vespula vulgaris

<400> SEQUENCE: 554

Cys Val Lys Tyr His Phe Leu Ala Thr Pro Lys Gln Leu Cys Thr
1               5                  10                  15

<210> SEQ ID NO 555
<211> LENGTH: 15
<212> TYPE: PRT
<213> ORGANISM: Vespula vulgaris

<400> SEQUENCE: 555

Val Lys Tyr His Phe Leu Ala Thr Pro Lys Gln Leu Cys Thr Phe
1               5                  10                  15

<210> SEQ ID NO 556
<211> LENGTH: 15
<212> TYPE: PRT
<213> ORGANISM: Vespula vulgaris

<400> SEQUENCE: 556

His Leu Ala Thr Arg Phe Leu Tyr Cys Gly Ala Thr Ile Ile Thr
1               5                  10                  15

<210> SEQ ID NO 557
<211> LENGTH: 15
<212> TYPE: PRT
<213> ORGANISM: Vespula vulgaris

<400> SEQUENCE: 557

Pro Asn Tyr Arg Pro Lys Leu Asn Asp Leu Ala Val Ile Lys Leu
1               5                  10                  15

<210> SEQ ID NO 558
<211> LENGTH: 15
<212> TYPE: PRT
<213> ORGANISM: Vespula vulgaris

<400> SEQUENCE: 558

Gly Ala Thr Ile Ile Thr Pro Gln His Val Leu Thr Ala Ala His
1               5                  10                  15
```

<210> SEQ ID NO 559
<211> LENGTH: 15
<212> TYPE: PRT
<213> ORGANISM: Vespula vulgaris

<400> SEQUENCE: 559

Val Asp Thr Val Val Thr Ala Val Gly Trp Gly Leu Thr Asn Phe
1               5                   10                  15

<210> SEQ ID NO 560
<211> LENGTH: 15
<212> TYPE: PRT
<213> ORGANISM: Vespula vulgaris

<400> SEQUENCE: 560

Ala Thr Ile Ile Thr Pro Gln His Val Leu Thr Ala Ala His Cys
1               5                   10                  15

<210> SEQ ID NO 561
<211> LENGTH: 15
<212> TYPE: PRT
<213> ORGANISM: Vespula vulgaris

<400> SEQUENCE: 561

Tyr Gly Val Lys Ser Glu Val Leu Arg Lys Val Asp Leu His Val
1               5                   10                  15

<210> SEQ ID NO 562
<211> LENGTH: 15
<212> TYPE: PRT
<213> ORGANISM: Vespula vulgaris

<400> SEQUENCE: 562

Thr Ile Ile Thr Pro Gln His Val Leu Thr Ala Ala His Cys Val
1               5                   10                  15

<210> SEQ ID NO 563
<211> LENGTH: 15
<212> TYPE: PRT
<213> ORGANISM: Vespula vulgaris

<400> SEQUENCE: 563

Leu Tyr Cys Gly Ala Thr Ile Ile Thr Pro Gln His Val Leu Thr
1               5                   10                  15

<210> SEQ ID NO 564
<211> LENGTH: 15
<212> TYPE: PRT
<213> ORGANISM: Vespula vulgaris

<400> SEQUENCE: 564

Arg Pro Lys Leu Asn Asp Leu Ala Val Ile Lys Leu Gln Lys Arg
1               5                   10                  15

<210> SEQ ID NO 565
<211> LENGTH: 15
<212> TYPE: PRT
<213> ORGANISM: Vespula vulgaris

<400> SEQUENCE: 565

Pro Lys Leu Asn Asp Leu Ala Val Ile Lys Leu Gln Lys Arg Leu
1               5                   10                  15

<210> SEQ ID NO 566

```
<211> LENGTH: 15
<212> TYPE: PRT
<213> ORGANISM: Vespula vulgaris

<400> SEQUENCE: 566

Lys Cys Val Lys Tyr His Phe Leu Ala Thr Pro Lys Gln Leu Cys
1               5                   10                  15

<210> SEQ ID NO 567
<211> LENGTH: 15
<212> TYPE: PRT
<213> ORGANISM: Vespula vulgaris

<400> SEQUENCE: 567

Tyr Arg Pro Lys Leu Asn Asp Leu Ala Val Ile Lys Leu Gln Lys
1               5                   10                  15

<210> SEQ ID NO 568
<211> LENGTH: 15
<212> TYPE: PRT
<213> ORGANISM: Vespula vulgaris

<400> SEQUENCE: 568

Ser Met Arg Ile Gly Pro Ala Cys Leu Pro Phe Tyr Tyr Met Gln
1               5                   10                  15

<210> SEQ ID NO 569
<211> LENGTH: 15
<212> TYPE: PRT
<213> ORGANISM: Vespula vulgaris

<400> SEQUENCE: 569

Asn Tyr Arg Pro Lys Leu Asn Asp Leu Ala Val Ile Lys Leu Gln
1               5                   10                  15

<210> SEQ ID NO 570
<211> LENGTH: 15
<212> TYPE: PRT
<213> ORGANISM: Vespula vulgaris

<400> SEQUENCE: 570

Val Thr Ala Val Gly Trp Gly Leu Thr Asn Phe Tyr Gly Val Lys
1               5                   10                  15

<210> SEQ ID NO 571
<211> LENGTH: 15
<212> TYPE: PRT
<213> ORGANISM: Vespula vulgaris

<400> SEQUENCE: 571

Met Arg Ile Gly Pro Ala Cys Leu Pro Phe Tyr Tyr Met Gln Arg
1               5                   10                  15

<210> SEQ ID NO 572
<211> LENGTH: 15
<212> TYPE: PRT
<213> ORGANISM: Vespula vulgaris

<400> SEQUENCE: 572

Lys Lys Cys Val Lys Tyr His Phe Leu Ala Thr Pro Lys Gln Leu
1               5                   10                  15

<210> SEQ ID NO 573
<211> LENGTH: 15
<212> TYPE: PRT
```

<213> ORGANISM: Vespula vulgaris

<400> SEQUENCE: 573

Val Gly Glu His Asn Thr Trp Ala Ile Asn Asp Thr Lys Ala Thr
1               5                   10                  15

<210> SEQ ID NO 574
<211> LENGTH: 15
<212> TYPE: PRT
<213> ORGANISM: Vespula vulgaris

<400> SEQUENCE: 574

Val Ala Arg Tyr Lys Arg Ile Leu Tyr Ile Leu Gly Val Val Val
1               5                   10                  15

<210> SEQ ID NO 575
<211> LENGTH: 15
<212> TYPE: PRT
<213> ORGANISM: Vespula vulgaris

<400> SEQUENCE: 575

Gly Glu His Asn Thr Trp Ala Ile Asn Asp Thr Lys Ala Thr Gln
1               5                   10                  15

<210> SEQ ID NO 576
<211> LENGTH: 15
<212> TYPE: PRT
<213> ORGANISM: Vespula vulgaris

<400> SEQUENCE: 576

Tyr Met Gln Arg Asn Phe Val Asp Thr Val Val Thr Ala Val Gly
1               5                   10                  15

<210> SEQ ID NO 577
<211> LENGTH: 15
<212> TYPE: PRT
<213> ORGANISM: Vespula vulgaris

<400> SEQUENCE: 577

Thr Trp Ala Ile Asn Asp Thr Lys Ala Thr Gln Leu Tyr Leu Ile
1               5                   10                  15

<210> SEQ ID NO 578
<211> LENGTH: 15
<212> TYPE: PRT
<213> ORGANISM: Vespula vulgaris

<400> SEQUENCE: 578

Trp Ala Ile Asn Asp Thr Lys Ala Thr Gln Leu Tyr Leu Ile Asp
1               5                   10                  15

<210> SEQ ID NO 579
<211> LENGTH: 15
<212> TYPE: PRT
<213> ORGANISM: Vespula vulgaris

<400> SEQUENCE: 579

Met Lys Lys Cys Val Lys Tyr His Phe Leu Ala Thr Pro Lys Gln
1               5                   10                  15

<210> SEQ ID NO 580
<211> LENGTH: 15
<212> TYPE: PRT
<213> ORGANISM: Vespula vulgaris

```
<400> SEQUENCE: 580

Val Lys Ser Glu Val Leu Arg Lys Val Asp Leu His Val Val Ser
1               5                   10                  15

<210> SEQ ID NO 581
<211> LENGTH: 15
<212> TYPE: PRT
<213> ORGANISM: Vespula vulgaris

<400> SEQUENCE: 581

Gly Val Lys Ser Glu Val Leu Arg Lys Val Asp Leu His Val Val
1               5                   10                  15

<210> SEQ ID NO 582
<211> LENGTH: 15
<212> TYPE: PRT
<213> ORGANISM: Vespula vulgaris

<400> SEQUENCE: 582

Gln Arg Asn Phe Val Asp Thr Val Val Thr Ala Val Gly Trp Gly
1               5                   10                  15

<210> SEQ ID NO 583
<211> LENGTH: 15
<212> TYPE: PRT
<213> ORGANISM: Vespula vulgaris

<400> SEQUENCE: 583

Met Gln Arg Asn Phe Val Asp Thr Val Val Thr Ala Val Gly Trp
1               5                   10                  15

<210> SEQ ID NO 584
<211> LENGTH: 15
<212> TYPE: PRT
<213> ORGANISM: Vespula vulgaris

<400> SEQUENCE: 584

Ile Thr Pro Gln His Val Leu Thr Ala Ala His Cys Val Ala Arg
1               5                   10                  15

<210> SEQ ID NO 585
<211> LENGTH: 15
<212> TYPE: PRT
<213> ORGANISM: Vespula vulgaris

<400> SEQUENCE: 585

Ala Val Gly Trp Gly Leu Thr Asn Phe Tyr Gly Val Lys Ser Glu
1               5                   10                  15

<210> SEQ ID NO 586
<211> LENGTH: 15
<212> TYPE: PRT
<213> ORGANISM: Vespula vulgaris

<400> SEQUENCE: 586

Tyr Tyr Met Gln Arg Asn Phe Val Asp Thr Val Val Thr Ala Val
1               5                   10                  15

<210> SEQ ID NO 587
<211> LENGTH: 15
<212> TYPE: PRT
<213> ORGANISM: Vespula vulgaris

<400> SEQUENCE: 587
```

```
Tyr His Phe Leu Ala Thr Pro Lys Gln Leu Cys Thr Phe Asp Met
1               5                   10                  15

<210> SEQ ID NO 588
<211> LENGTH: 15
<212> TYPE: PRT
<213> ORGANISM: Vespula vulgaris

<400> SEQUENCE: 588

Ile His Leu Ala Thr Arg Phe Leu Tyr Cys Gly Ala Thr Ile Ile
1               5                   10                  15

<210> SEQ ID NO 589
<211> LENGTH: 15
<212> TYPE: PRT
<213> ORGANISM: Vespula vulgaris

<400> SEQUENCE: 589

Val Gly Trp Gly Leu Thr Asn Phe Tyr Gly Val Lys Ser Glu Val
1               5                   10                  15

<210> SEQ ID NO 590
<211> LENGTH: 15
<212> TYPE: PRT
<213> ORGANISM: Vespula vulgaris

<400> SEQUENCE: 590

Thr Ser Tyr Leu Asp Phe Ile Thr Arg Ser Thr Pro Gly Glu Ile
1               5                   10                  15

<210> SEQ ID NO 591
<211> LENGTH: 15
<212> TYPE: PRT
<213> ORGANISM: Vespula vulgaris

<400> SEQUENCE: 591

Ile Leu Tyr Ile Leu Gly Val Val Val Gly Glu His Asn Thr Trp
1               5                   10                  15

<210> SEQ ID NO 592
<211> LENGTH: 15
<212> TYPE: PRT
<213> ORGANISM: Vespula vulgaris

<400> SEQUENCE: 592

Lys Tyr His Phe Leu Ala Thr Pro Lys Gln Leu Cys Thr Phe Asp
1               5                   10                  15

<210> SEQ ID NO 593
<211> LENGTH: 15
<212> TYPE: PRT
<213> ORGANISM: Vespula vulgaris

<400> SEQUENCE: 593

Val Thr Ser Tyr Leu Asp Phe Ile Thr Arg Ser Thr Pro Gly Glu
1               5                   10                  15

<210> SEQ ID NO 594
<211> LENGTH: 15
<212> TYPE: PRT
<213> ORGANISM: Vespula vulgaris

<400> SEQUENCE: 594

Ile Ile Thr Pro Gln His Val Leu Thr Ala Ala His Cys Val Ala
1               5                   10                  15
```

<210> SEQ ID NO 595
<211> LENGTH: 15
<212> TYPE: PRT
<213> ORGANISM: Vespula vulgaris

<400> SEQUENCE: 595

Leu Pro Phe Tyr Tyr Met Gln Arg Asn Phe Val Asp Thr Val Val
1               5                   10                  15

<210> SEQ ID NO 596
<211> LENGTH: 15
<212> TYPE: PRT
<213> ORGANISM: Vespula vulgaris

<400> SEQUENCE: 596

Cys Leu Pro Phe Tyr Tyr Met Gln Arg Asn Phe Val Asp Thr Val
1               5                   10                  15

<210> SEQ ID NO 597
<211> LENGTH: 15
<212> TYPE: PRT
<213> ORGANISM: Vespula vulgaris

<400> SEQUENCE: 597

Val Glu Thr Gly Val Asn Glu Tyr Pro Met Met Ala Gly Ile Ile
1               5                   10                  15

<210> SEQ ID NO 598
<211> LENGTH: 15
<212> TYPE: PRT
<213> ORGANISM: Vespula vulgaris

<400> SEQUENCE: 598

Ile Asp Leu Asn Cys Gly Tyr Thr Gln Lys Leu Lys Ser Asp Val
1               5                   10                  15

<210> SEQ ID NO 599
<211> LENGTH: 15
<212> TYPE: PRT
<213> ORGANISM: Vespula vulgaris

<400> SEQUENCE: 599

His Cys Val Ala Arg Tyr Lys Arg Ile Leu Tyr Ile Leu Gly Val
1               5                   10                  15

<210> SEQ ID NO 600
<211> LENGTH: 15
<212> TYPE: PRT
<213> ORGANISM: Vespula vulgaris

<400> SEQUENCE: 600

Thr Pro Gln His Val Leu Thr Ala Ala His Cys Val Ala Arg Tyr
1               5                   10                  15

<210> SEQ ID NO 601
<211> LENGTH: 15
<212> TYPE: PRT
<213> ORGANISM: Vespula vulgaris

<400> SEQUENCE: 601

Cys Val Ala Arg Tyr Lys Arg Ile Leu Tyr Ile Leu Gly Val Val
1               5                   10                  15

<210> SEQ ID NO 602
<211> LENGTH: 15
<212> TYPE: PRT
<213> ORGANISM: Vespula vulgaris

<400> SEQUENCE: 602

Pro Gln His Val Leu Thr Ala Ala His Cys Val Ala Arg Tyr Lys
1 5 10 15

<210> SEQ ID NO 603
<211> LENGTH: 15
<212> TYPE: PRT
<213> ORGANISM: Vespula vulgaris

<400> SEQUENCE: 603

Leu Tyr Ile Leu Gly Val Val Val Gly Glu His Asn Thr Trp Ala
1 5 10 15 

<210> SEQ ID NO 604
<211> LENGTH: 15
<212> TYPE: PRT
<213> ORGANISM: Vespula vulgaris

<400> SEQUENCE: 604

Ser Glu Val Leu Arg Lys Val Asp Leu His Val Val Ser Met Lys
1 5 10 15

<210> SEQ ID NO 605
<211> LENGTH: 15
<212> TYPE: PRT
<213> ORGANISM: Vespula vulgaris

<400> SEQUENCE: 605

Pro Phe Tyr Tyr Met Gln Arg Asn Phe Val Asp Thr Val Val Thr
1 5 10 15

<210> SEQ ID NO 606
<211> LENGTH: 15
<212> TYPE: PRT
<213> ORGANISM: Vespula vulgaris

<400> SEQUENCE: 606

Phe Tyr Tyr Met Gln Arg Asn Phe Val Asp Thr Val Val Thr Ala
1 5 10 15

<210> SEQ ID NO 607
<211> LENGTH: 15
<212> TYPE: PRT
<213> ORGANISM: Vespula vulgaris

<400> SEQUENCE: 607

Cys Thr Val Phe Asp Val Pro Pro Ser Ser Asn Cys Ser Leu Asp
1 5 10 15

<210> SEQ ID NO 608
<211> LENGTH: 15
<212> TYPE: PRT
<213> ORGANISM: Vespula vulgaris

<400> SEQUENCE: 608

Asn Cys Thr Val Phe Asp Val Pro Pro Ser Ser Asn Cys Ser Leu
1 5 10 15

<210> SEQ ID NO 609
<211> LENGTH: 15
```
<212> TYPE: PRT
<213> ORGANISM: Vespula vulgaris

<400> SEQUENCE: 609

Lys Ser Glu Val Leu Arg Lys Val Asp Leu His Val Val Ser Met
1               5                   10                  15

<210> SEQ ID NO 610
<211> LENGTH: 15
<212> TYPE: PRT
<213> ORGANISM: Vespula vulgaris

<400> SEQUENCE: 610

Asn Leu Arg Val Thr Ser Tyr Leu Asp Phe Ile Thr Arg Ser Thr
1               5                   10                  15

<210> SEQ ID NO 611
<211> LENGTH: 15
<212> TYPE: PRT
<213> ORGANISM: Vespula vulgaris

<400> SEQUENCE: 611

Leu Arg Val Thr Ser Tyr Leu Asp Phe Ile Thr Arg Ser Thr Pro
1               5                   10                  15

<210> SEQ ID NO 612
<211> LENGTH: 15
<212> TYPE: PRT
<213> ORGANISM: Vespula vulgaris

<400> SEQUENCE: 612

Glu Val Leu Arg Lys Val Asp Leu His Val Val Ser Met Lys Lys
1               5                   10                  15

<210> SEQ ID NO 613
<211> LENGTH: 15
<212> TYPE: PRT
<213> ORGANISM: Vespula vulgaris

<400> SEQUENCE: 613

Thr Ile Asp Leu Asn Cys Gly Tyr Thr Gln Lys Leu Lys Ser Asp
1               5                   10                  15

<210> SEQ ID NO 614
<211> LENGTH: 15
<212> TYPE: PRT
<213> ORGANISM: Vespula vulgaris

<400> SEQUENCE: 614

Arg Val Thr Ser Tyr Leu Asp Phe Ile Thr Arg Ser Thr Pro Gly
1               5                   10                  15

<210> SEQ ID NO 615
<211> LENGTH: 15
<212> TYPE: PRT
<213> ORGANISM: Vespula vulgaris

<400> SEQUENCE: 615

Ala His Cys Val Ala Arg Tyr Lys Arg Ile Leu Tyr Ile Leu Gly
1               5                   10                  15

<210> SEQ ID NO 616
<211> LENGTH: 15
<212> TYPE: PRT
<213> ORGANISM: Vespula vulgaris
```

<400> SEQUENCE: 616

Cys Arg Cys Gly Trp Lys Asn Pro Ser Arg Ile Val Gly Gly Val
1               5                   10                  15

<210> SEQ ID NO 617
<211> LENGTH: 15
<212> TYPE: PRT
<213> ORGANISM: Vespula vulgaris

<400> SEQUENCE: 617

Lys Cys Arg Cys Gly Trp Lys Asn Pro Ser Arg Ile Val Gly Gly
1               5                   10                  15

<210> SEQ ID NO 618
<211> LENGTH: 15
<212> TYPE: PRT
<213> ORGANISM: Vespula vulgaris

<400> SEQUENCE: 618

Leu Asn Asp Leu Ala Val Ile Lys Leu Gln Lys Arg Leu Lys Tyr
1               5                   10                  15

<210> SEQ ID NO 619
<211> LENGTH: 15
<212> TYPE: PRT
<213> ORGANISM: Vespula vulgaris

<400> SEQUENCE: 619

Gly Gly Val Glu Thr Gly Val Asn Glu Tyr Pro Met Met Ala Gly
1               5                   10                  15

<210> SEQ ID NO 620
<211> LENGTH: 15
<212> TYPE: PRT
<213> ORGANISM: Vespula vulgaris

<400> SEQUENCE: 620

Lys Leu Asn Asp Leu Ala Val Ile Lys Leu Gln Lys Arg Leu Lys
1               5                   10                  15

<210> SEQ ID NO 621
<211> LENGTH: 15
<212> TYPE: PRT
<213> ORGANISM: Vespula vulgaris

<400> SEQUENCE: 621

Ala Cys Leu Pro Phe Tyr Tyr Met Gln Arg Asn Phe Val Asp Thr
1               5                   10                  15

<210> SEQ ID NO 622
<211> LENGTH: 15
<212> TYPE: PRT
<213> ORGANISM: Vespula vulgaris

<400> SEQUENCE: 622

Glu Lys Cys Arg Cys Gly Trp Lys Asn Pro Ser Arg Ile Val Gly
1               5                   10                  15

<210> SEQ ID NO 623
<211> LENGTH: 15
<212> TYPE: PRT
<213> ORGANISM: Vespula vulgaris

<400> SEQUENCE: 623

```
Gly Val Glu Thr Gly Val Asn Glu Tyr Pro Met Met Ala Gly Ile
1               5                   10                  15

<210> SEQ ID NO 624
<211> LENGTH: 15
<212> TYPE: PRT
<213> ORGANISM: Vespula vulgaris

<400> SEQUENCE: 624

Cys Gly Tyr Thr Gln Lys Leu Lys Ser Asp Val Asn Tyr Cys Val
1               5                   10                  15

<210> SEQ ID NO 625
<211> LENGTH: 15
<212> TYPE: PRT
<213> ORGANISM: Vespula vulgaris

<400> SEQUENCE: 625

Arg Cys Gly Trp Lys Asn Pro Ser Arg Ile Val Gly Gly Val Glu
1               5                   10                  15

<210> SEQ ID NO 626
<211> LENGTH: 15
<212> TYPE: PRT
<213> ORGANISM: Vespula vulgaris

<400> SEQUENCE: 626

Ala Cys Gln Phe Asp Ser Gly Gly Pro Ile Leu Trp Gln Asn Pro
1               5                   10                  15

<210> SEQ ID NO 627
<211> LENGTH: 15
<212> TYPE: PRT
<213> ORGANISM: Vespula vulgaris

<400> SEQUENCE: 627

Leu Asn Cys Thr Val Phe Asp Val Pro Pro Ser Ser Asn Cys Ser
1               5                   10                  15

<210> SEQ ID NO 628
<211> LENGTH: 15
<212> TYPE: PRT
<213> ORGANISM: Vespula vulgaris

<400> SEQUENCE: 628

Glu His Asn Cys Arg Trp Ser Ala Arg Ser Asn Thr Arg Ile Lys
1               5                   10                  15

<210> SEQ ID NO 629
<211> LENGTH: 15
<212> TYPE: PRT
<213> ORGANISM: Vespula vulgaris

<400> SEQUENCE: 629

Cys Gln Phe Asp Ser Gly Gly Pro Ile Leu Trp Gln Asn Pro Lys
1               5                   10                  15

<210> SEQ ID NO 630
<211> LENGTH: 15
<212> TYPE: PRT
<213> ORGANISM: Vespula vulgaris

<400> SEQUENCE: 630

Gln His Val Leu Thr Ala Ala His Cys Val Ala Arg Tyr Lys Arg
```

-continued

```
1               5                   10                  15

<210> SEQ ID NO 631
<211> LENGTH: 15
<212> TYPE: PRT
<213> ORGANISM: Vespula vulgaris

<400> SEQUENCE: 631

His Asn Cys Arg Trp Ser Ala Arg Ser Asn Thr Arg Ile Lys Leu
1               5                   10                  15

<210> SEQ ID NO 632
<211> LENGTH: 15
<212> TYPE: PRT
<213> ORGANISM: Vespula vulgaris

<400> SEQUENCE: 632

Gly Glu His Asn Cys Arg Trp Ser Ala Arg Ser Asn Thr Arg Ile
1               5                   10                  15

<210> SEQ ID NO 633
<211> LENGTH: 15
<212> TYPE: PRT
<213> ORGANISM: Vespula vulgaris

<400> SEQUENCE: 633

Asp Ala Cys Gln Phe Asp Ser Gly Gly Pro Ile Leu Trp Gln Asn
1               5                   10                  15

<210> SEQ ID NO 634
<211> LENGTH: 15
<212> TYPE: PRT
<213> ORGANISM: Vespula vulgaris

<400> SEQUENCE: 634

Asn Cys Arg Trp Ser Ala Arg Ser Asn Thr Arg Ile Lys Leu Asn
1               5                   10                  15

<210> SEQ ID NO 635
<211> LENGTH: 15
<212> TYPE: PRT
<213> ORGANISM: Vespula vulgaris

<400> SEQUENCE: 635

Ala Asp Glu Ala Pro Gly Val Asn Leu Arg Val Thr Ser Tyr Leu
1               5                   10                  15

<210> SEQ ID NO 636
<211> LENGTH: 15
<212> TYPE: PRT
<213> ORGANISM: Vespula vulgaris

<400> SEQUENCE: 636

Thr Val Phe Asp Val Pro Pro Ser Ser Asn Cys Ser Leu Asp Phe
1               5                   10                  15

<210> SEQ ID NO 637
<211> LENGTH: 15
<212> TYPE: PRT
<213> ORGANISM: Vespula vulgaris

<400> SEQUENCE: 637

Asn Pro Ser Arg Ile Val Gly Gly Val Glu Thr Gly Val Asn Glu
1               5                   10                  15
```

```
<210> SEQ ID NO 638
<211> LENGTH: 15
<212> TYPE: PRT
<213> ORGANISM: Vespula vulgaris

<400> SEQUENCE: 638

Lys Asn Pro Ser Arg Ile Val Gly Gly Val Glu Thr Gly Val Asn
1               5                   10                  15

<210> SEQ ID NO 639
<211> LENGTH: 15
<212> TYPE: PRT
<213> ORGANISM: Vespula vulgaris

<400> SEQUENCE: 639

Cys Gly Leu Asn Ser Phe Ala Val Glu Ser Ile Ala Ser Lys Met
1               5                   10                  15

<210> SEQ ID NO 640
<211> LENGTH: 15
<212> TYPE: PRT
<213> ORGANISM: Vespula vulgaris

<400> SEQUENCE: 640

Ile Lys Leu Gln Lys Arg Leu Lys Tyr Ser Met Arg Ile Gly Pro
1               5                   10                  15

<210> SEQ ID NO 641
<211> LENGTH: 15
<212> TYPE: PRT
<213> ORGANISM: Vespula vulgaris

<400> SEQUENCE: 641

Lys Asp Ala Cys Gln Phe Asp Ser Gly Gly Pro Ile Leu Trp Gln
1               5                   10                  15

<210> SEQ ID NO 642
<211> LENGTH: 15
<212> TYPE: PRT
<213> ORGANISM: Vespula vulgaris

<400> SEQUENCE: 642

Ala Val Ile Lys Leu Gln Lys Arg Leu Lys Tyr Ser Met Arg Ile
1               5                   10                  15

<210> SEQ ID NO 643
<211> LENGTH: 15
<212> TYPE: PRT
<213> ORGANISM: Vespula vulgaris

<400> SEQUENCE: 643

Ser Tyr Leu Asp Phe Ile Thr Arg Ser Thr Pro Gly Glu Ile Tyr
1               5                   10                  15

<210> SEQ ID NO 644
<211> LENGTH: 15
<212> TYPE: PRT
<213> ORGANISM: Vespula vulgaris

<400> SEQUENCE: 644

Val Ile Lys Leu Gln Lys Arg Leu Lys Tyr Ser Met Arg Ile Gly
1               5                   10                  15

<210> SEQ ID NO 645
```

```
<211> LENGTH: 15
<212> TYPE: PRT
<213> ORGANISM: Vespula vulgaris

<400> SEQUENCE: 645

Gly Tyr Thr Gln Lys Leu Lys Ser Asp Val Asn Tyr Cys Val Tyr
1               5                   10                  15

<210> SEQ ID NO 646
<211> LENGTH: 15
<212> TYPE: PRT
<213> ORGANISM: Vespula vulgaris

<400> SEQUENCE: 646

Phe Asp Ser Gly Gly Pro Ile Leu Trp Gln Asn Pro Lys Ser Lys
1               5                   10                  15

<210> SEQ ID NO 647
<211> LENGTH: 15
<212> TYPE: PRT
<213> ORGANISM: Vespula vulgaris

<400> SEQUENCE: 647

Ile Ile Val His Pro Asn Tyr Arg Pro Lys Leu Asn Asp Leu Ala
1               5                   10                  15

<210> SEQ ID NO 648
<211> LENGTH: 15
<212> TYPE: PRT
<213> ORGANISM: Vespula vulgaris

<400> SEQUENCE: 648

Asp Glu Ala Pro Gly Val Asn Leu Arg Val Thr Ser Tyr Leu Asp
1               5                   10                  15

<210> SEQ ID NO 649
<211> LENGTH: 15
<212> TYPE: PRT
<213> ORGANISM: Vespula vulgaris

<400> SEQUENCE: 649

His Val Leu Thr Ala Ala His Cys Val Ala Arg Tyr Lys Arg Ile
1               5                   10                  15

<210> SEQ ID NO 650
<211> LENGTH: 15
<212> TYPE: PRT
<213> ORGANISM: Vespula vulgaris

<400> SEQUENCE: 650

Gly Lys Asp Ala Cys Gln Phe Asp Ser Gly Gly Pro Ile Leu Trp
1               5                   10                  15

<210> SEQ ID NO 651
<211> LENGTH: 15
<212> TYPE: PRT
<213> ORGANISM: Vespula vulgaris

<400> SEQUENCE: 651

Tyr Leu Asp Phe Ile Thr Arg Ser Thr Pro Gly Glu Ile Tyr Cys
1               5                   10                  15

<210> SEQ ID NO 652
<211> LENGTH: 15
<212> TYPE: PRT
```

<213> ORGANISM: Vespula vulgaris

<400> SEQUENCE: 652

```
Leu Gln Lys Arg Leu Lys Tyr Ser Met Arg Ile Gly Pro Ala Cys
1               5                   10                  15
```

<210> SEQ ID NO 653
<211> LENGTH: 15
<212> TYPE: PRT
<213> ORGANISM: Vespula vulgaris

<400> SEQUENCE: 653

```
Phe Met Lys Val Lys Val Asp Asp Ile Glu Tyr Val Phe Cys
1               5                   10                  15
```

<210> SEQ ID NO 654
<211> LENGTH: 15
<212> TYPE: PRT
<213> ORGANISM: Vespula vulgaris

<400> SEQUENCE: 654

```
Asp Phe Met Lys Val Lys Val Asp Asp Ile Glu Tyr Val Phe
1               5                   10                  15
```

<210> SEQ ID NO 655
<211> LENGTH: 15
<212> TYPE: PRT
<213> ORGANISM: Vespula vulgaris

<400> SEQUENCE: 655

```
Met Lys Val Lys Val Asp Asp Ile Glu Tyr Val Phe Cys Gly
1               5                   10                  15
```

<210> SEQ ID NO 656
<211> LENGTH: 15
<212> TYPE: PRT
<213> ORGANISM: Vespula vulgaris

<400> SEQUENCE: 656

```
Met Lys Lys Cys Val Lys Tyr His Phe Leu Ala Thr Pro Lys Gln
1               5                   10                  15
```

<210> SEQ ID NO 657
<211> LENGTH: 15
<212> TYPE: PRT
<213> ORGANISM: Vespula vulgaris

<400> SEQUENCE: 657

```
Val Lys Tyr His Phe Leu Ala Thr Pro Lys Gln Leu Cys Thr Phe
1               5                   10                  15
```

<210> SEQ ID NO 658
<211> LENGTH: 15
<212> TYPE: PRT
<213> ORGANISM: Vespula vulgaris

<400> SEQUENCE: 658

```
Lys Cys Val Lys Tyr His Phe Leu Ala Thr Pro Lys Gln Leu Cys
1               5                   10                  15
```

<210> SEQ ID NO 659
<211> LENGTH: 15
<212> TYPE: PRT
<213> ORGANISM: Vespula vulgaris -continued

```
<400> SEQUENCE: 659

Cys Val Lys Tyr His Phe Leu Ala Thr Pro Lys Gln Leu Cys Thr
1               5                   10                  15

<210> SEQ ID NO 660
<211> LENGTH: 15
<212> TYPE: PRT
<213> ORGANISM: Vespula vulgaris

<400> SEQUENCE: 660

Lys Lys Cys Val Lys Tyr His Phe Leu Ala Thr Pro Lys Gln Leu
1               5                   10                  15

<210> SEQ ID NO 661
<211> LENGTH: 15
<212> TYPE: PRT
<213> ORGANISM: Vespula vulgaris

<400> SEQUENCE: 661

Asp Val Asn Tyr Cys Val Tyr Asn Pro Asp Phe Pro Asn Tyr Tyr
1               5                   10                  15

<210> SEQ ID NO 662
<211> LENGTH: 15
<212> TYPE: PRT
<213> ORGANISM: Vespula vulgaris

<400> SEQUENCE: 662

Val Asn Tyr Cys Val Tyr Asn Pro Asp Phe Pro Asn Tyr Tyr Met
1               5                   10                  15

<210> SEQ ID NO 663
<211> LENGTH: 15
<212> TYPE: PRT
<213> ORGANISM: Vespula vulgaris

<400> SEQUENCE: 663

Asn Tyr Cys Val Tyr Asn Pro Asp Phe Pro Asn Tyr Tyr Met Gly
1               5                   10                  15

<210> SEQ ID NO 664
<211> LENGTH: 15
<212> TYPE: PRT
<213> ORGANISM: Vespula vulgaris

<400> SEQUENCE: 664

Tyr Cys Val Tyr Asn Pro Asp Phe Pro Asn Tyr Tyr Met Gly Glu
1               5                   10                  15

<210> SEQ ID NO 665
<211> LENGTH: 15
<212> TYPE: PRT
<213> ORGANISM: Vespula vulgaris

<400> SEQUENCE: 665

Cys Val Tyr Asn Pro Asp Phe Pro Asn Tyr Tyr Met Gly Glu His
1               5                   10                  15

<210> SEQ ID NO 666
<211> LENGTH: 15
<212> TYPE: PRT
<213> ORGANISM: Vespula vulgaris

<400> SEQUENCE: 666
```

Lys Tyr His Phe Leu Ala Thr Pro Lys Gln Leu Cys Thr Phe Asp
1               5                   10                  15

<210> SEQ ID NO 667
<211> LENGTH: 15
<212> TYPE: PRT
<213> ORGANISM: Vespula vulgaris

<400> SEQUENCE: 667

Tyr His Phe Leu Ala Thr Pro Lys Gln Leu Cys Thr Phe Asp Met
1               5                   10                  15

<210> SEQ ID NO 668
<211> LENGTH: 15
<212> TYPE: PRT
<213> ORGANISM: Vespula vulgaris

<400> SEQUENCE: 668

Leu Asn Cys Thr Val Phe Asp Val Pro Pro Ser Ser Asn Cys Ser
1               5                   10                  15

<210> SEQ ID NO 669
<211> LENGTH: 15
<212> TYPE: PRT
<213> ORGANISM: Vespula vulgaris

<400> SEQUENCE: 669

Val Thr Ser Tyr Leu Asp Phe Ile Thr Arg Ser Thr Pro Gly Glu
1               5                   10                  15

<210> SEQ ID NO 670
<211> LENGTH: 15
<212> TYPE: PRT
<213> ORGANISM: Vespula vulgaris

<400> SEQUENCE: 670

Thr Ser Tyr Leu Asp Phe Ile Thr Arg Ser Thr Pro Gly Glu Ile
1               5                   10                  15

<210> SEQ ID NO 671
<211> LENGTH: 15
<212> TYPE: PRT
<213> ORGANISM: Vespula vulgaris

<400> SEQUENCE: 671

Arg Val Thr Ser Tyr Leu Asp Phe Ile Thr Arg Ser Thr Pro Gly
1               5                   10                  15

<210> SEQ ID NO 672
<211> LENGTH: 15
<212> TYPE: PRT
<213> ORGANISM: Vespula vulgaris

<400> SEQUENCE: 672

Lys Cys Val Lys Tyr His Phe Leu Ala Thr Pro Lys Gln Leu Cys
1               5                   10                  15

<210> SEQ ID NO 673
<211> LENGTH: 15
<212> TYPE: PRT
<213> ORGANISM: Vespula vulgaris

<400> SEQUENCE: 673

Leu Arg Val Thr Ser Tyr Leu Asp Phe Ile Thr Arg Ser Thr Pro
1               5                   10                  15

<210> SEQ ID NO 674
<211> LENGTH: 15
<212> TYPE: PRT
<213> ORGANISM: Vespula vulgaris

<400> SEQUENCE: 674

Ser Lys Arg Ile Phe Leu Leu Gly Val Ile Asn Tyr Gly Arg Thr
1               5                   10                  15

<210> SEQ ID NO 675
<211> LENGTH: 15
<212> TYPE: PRT
<213> ORGANISM: Vespula vulgaris

<400> SEQUENCE: 675

Lys Arg Ile Phe Leu Leu Gly Val Ile Asn Tyr Gly Arg Thr Cys
1               5                   10                  15

<210> SEQ ID NO 676
<211> LENGTH: 15
<212> TYPE: PRT
<213> ORGANISM: Vespula vulgaris

<400> SEQUENCE: 676

Asn Leu Arg Val Thr Ser Tyr Leu Asp Phe Ile Thr Arg Ser Thr
1               5                   10                  15

<210> SEQ ID NO 677
<211> LENGTH: 15
<212> TYPE: PRT
<213> ORGANISM: Vespula vulgaris

<400> SEQUENCE: 677

Arg Ile Phe Leu Leu Gly Val Ile Asn Tyr Gly Arg Thr Cys Ala
1               5                   10                  15

<210> SEQ ID NO 678
<211> LENGTH: 15
<212> TYPE: PRT
<213> ORGANISM: Vespula vulgaris

<400> SEQUENCE: 678

Pro Asp Phe Pro Asn Tyr Tyr Met Gly Glu His Asn Cys Arg Trp
1               5                   10                  15

<210> SEQ ID NO 679
<211> LENGTH: 15
<212> TYPE: PRT
<213> ORGANISM: Vespula vulgaris

<400> SEQUENCE: 679

Phe Pro Asn Tyr Tyr Met Gly Glu His Asn Cys Arg Trp Ser Ala
1               5                   10                  15

<210> SEQ ID NO 680
<211> LENGTH: 15
<212> TYPE: PRT
<213> ORGANISM: Vespula vulgaris

<400> SEQUENCE: 680

Asp Phe Pro Asn Tyr Tyr Met Gly Glu His Asn Cys Arg Trp Ser
1               5                   10                  15

```
<210> SEQ ID NO 681
<211> LENGTH: 15
<212> TYPE: PRT
<213> ORGANISM: Vespula vulgaris

<400> SEQUENCE: 681

Ser Gly Gly Pro Ile Leu Trp Gln Asn Pro Lys Ser Lys Arg Ile
1               5                   10                  15

<210> SEQ ID NO 682
<211> LENGTH: 15
<212> TYPE: PRT
<213> ORGANISM: Vespula vulgaris

<400> SEQUENCE: 682

Leu Tyr Ile Leu Gly Val Val Gly Glu His Asn Thr Trp Ala
1               5                   10                  15

<210> SEQ ID NO 683
<211> LENGTH: 15
<212> TYPE: PRT
<213> ORGANISM: Vespula vulgaris

<400> SEQUENCE: 683

Pro Ala Cys Leu Pro Phe Tyr Tyr Met Gln Arg Asn Phe Val Asp
1               5                   10                  15

<210> SEQ ID NO 684
<211> LENGTH: 15
<212> TYPE: PRT
<213> ORGANISM: Vespula vulgaris

<400> SEQUENCE: 684

Ala Cys Leu Pro Phe Tyr Tyr Met Gln Arg Asn Phe Val Asp Thr
1               5                   10                  15

<210> SEQ ID NO 685
<211> LENGTH: 15
<212> TYPE: PRT
<213> ORGANISM: Vespula vulgaris

<400> SEQUENCE: 685

Pro Phe Tyr Tyr Met Gln Arg Asn Phe Val Asp Thr Val Val Thr
1               5                   10                  15

<210> SEQ ID NO 686
<211> LENGTH: 15
<212> TYPE: PRT
<213> ORGANISM: Vespula vulgaris

<400> SEQUENCE: 686

Cys Leu Pro Phe Tyr Tyr Met Gln Arg Asn Phe Val Asp Thr Val
1               5                   10                  15

<210> SEQ ID NO 687
<211> LENGTH: 15
<212> TYPE: PRT
<213> ORGANISM: Vespula vulgaris

<400> SEQUENCE: 687

Leu Pro Phe Tyr Tyr Met Gln Arg Asn Phe Val Asp Thr Val Val
1               5                   10                  15

<210> SEQ ID NO 688
<211> LENGTH: 15
```

```
<212> TYPE: PRT
<213> ORGANISM: Vespula vulgaris

<400> SEQUENCE: 688

Tyr Tyr Met Gln Arg Asn Phe Val Asp Thr Val Val Thr Ala Val
1               5                   10                  15

<210> SEQ ID NO 689
<211> LENGTH: 15
<212> TYPE: PRT
<213> ORGANISM: Vespula vulgaris

<400> SEQUENCE: 689

Phe Tyr Tyr Met Gln Arg Asn Phe Val Asp Thr Val Val Thr Ala
1               5                   10                  15

<210> SEQ ID NO 690
<211> LENGTH: 15
<212> TYPE: PRT
<213> ORGANISM: Vespula vulgaris

<400> SEQUENCE: 690

Glu Tyr Val Phe Cys Gly Leu Asn Ser Phe Ala Val Glu Ser Ile
1               5                   10                  15

<210> SEQ ID NO 691
<211> LENGTH: 15
<212> TYPE: PRT
<213> ORGANISM: Vespula vulgaris

<400> SEQUENCE: 691

Asp Asp Ile Glu Tyr Val Phe Cys Gly Leu Asn Ser Phe Ala Val
1               5                   10                  15

<210> SEQ ID NO 692
<211> LENGTH: 15
<212> TYPE: PRT
<213> ORGANISM: Vespula vulgaris

<400> SEQUENCE: 692

Asp Ile Glu Tyr Val Phe Cys Gly Leu Asn Ser Phe Ala Val Glu
1               5                   10                  15

<210> SEQ ID NO 693
<211> LENGTH: 15
<212> TYPE: PRT
<213> ORGANISM: Vespula vulgaris

<400> SEQUENCE: 693

Ile Glu Tyr Val Phe Cys Gly Leu Asn Ser Phe Ala Val Glu Ser
1               5                   10                  15

<210> SEQ ID NO 694
<211> LENGTH: 15
<212> TYPE: PRT
<213> ORGANISM: Vespula vulgaris

<400> SEQUENCE: 694

Tyr Val Phe Cys Gly Leu Asn Ser Phe Ala Val Glu Ser Ile Ala
1               5                   10                  15

<210> SEQ ID NO 695
<211> LENGTH: 15
<212> TYPE: PRT
<213> ORGANISM: Vespula vulgaris
```

-continued

<400> SEQUENCE: 695

Tyr Tyr Met Gln Arg Asn Phe Val Asp Thr Val Val Thr Ala Val
1               5                   10                  15

<210> SEQ ID NO 696
<211> LENGTH: 15
<212> TYPE: PRT
<213> ORGANISM: Vespula vulgaris

<400> SEQUENCE: 696

Ala Gly Ile Ile His Leu Ala Thr Arg Phe Leu Tyr Cys Gly Ala
1               5                   10                  15

<210> SEQ ID NO 697
<211> LENGTH: 15
<212> TYPE: PRT
<213> ORGANISM: Vespula vulgaris

<400> SEQUENCE: 697

Met Met Ala Gly Ile Ile His Leu Ala Thr Arg Phe Leu Tyr Cys
1               5                   10                  15

<210> SEQ ID NO 698
<211> LENGTH: 15
<212> TYPE: PRT
<213> ORGANISM: Vespula vulgaris

<400> SEQUENCE: 698

Met Gln Arg Asn Phe Val Asp Thr Val Val Thr Ala Val Gly Trp
1               5                   10                  15

<210> SEQ ID NO 699
<211> LENGTH: 15
<212> TYPE: PRT
<213> ORGANISM: Vespula vulgaris

<400> SEQUENCE: 699

Gln Arg Asn Phe Val Asp Thr Val Val Thr Ala Val Gly Trp Gly
1               5                   10                  15

<210> SEQ ID NO 700
<211> LENGTH: 15
<212> TYPE: PRT
<213> ORGANISM: Vespula vulgaris

<400> SEQUENCE: 700

Pro Met Met Ala Gly Ile Ile His Leu Ala Thr Arg Phe Leu Tyr
1               5                   10                  15

<210> SEQ ID NO 701
<211> LENGTH: 15
<212> TYPE: PRT
<213> ORGANISM: Vespula vulgaris

<400> SEQUENCE: 701

Tyr Met Gln Arg Asn Phe Val Asp Thr Val Val Thr Ala Val Gly
1               5                   10                  15

<210> SEQ ID NO 702
<211> LENGTH: 15
<212> TYPE: PRT
<213> ORGANISM: Vespula vulgaris

<400> SEQUENCE: 702

```
Trp Gly Leu Thr Asn Phe Tyr Gly Val Lys Ser Glu Val Leu Arg
1               5                   10                  15

<210> SEQ ID NO 703
<211> LENGTH: 15
<212> TYPE: PRT
<213> ORGANISM: Vespula vulgaris

<400> SEQUENCE: 703

Leu Thr Asn Phe Tyr Gly Val Lys Ser Glu Val Leu Arg Lys Val
1               5                   10                  15

<210> SEQ ID NO 704
<211> LENGTH: 15
<212> TYPE: PRT
<213> ORGANISM: Vespula vulgaris

<400> SEQUENCE: 704

Gly Trp Gly Leu Thr Asn Phe Tyr Gly Val Lys Ser Glu Val Leu
1               5                   10                  15

<210> SEQ ID NO 705
<211> LENGTH: 15
<212> TYPE: PRT
<213> ORGANISM: Vespula vulgaris

<400> SEQUENCE: 705

Thr Asn Phe Tyr Gly Val Lys Ser Glu Val Leu Arg Lys Val Asp
1               5                   10                  15

<210> SEQ ID NO 706
<211> LENGTH: 15
<212> TYPE: PRT
<213> ORGANISM: Vespula vulgaris

<400> SEQUENCE: 706

Val Phe Cys Gly Leu Asn Ser Phe Ala Val Glu Ser Ile Ala Ser
1               5                   10                  15

<210> SEQ ID NO 707
<211> LENGTH: 15
<212> TYPE: PRT
<213> ORGANISM: Vespula vulgaris

<400> SEQUENCE: 707

Phe Cys Gly Leu Asn Ser Phe Ala Val Glu Ser Ile Ala Ser Lys
1               5                   10                  15

<210> SEQ ID NO 708
<211> LENGTH: 9
<212> TYPE: PRT
<213> ORGANISM: Vespula vulgaris

<400> SEQUENCE: 708

Pro Gly Glu Ile Tyr Cys Gln Ala Tyr
1               5

<210> SEQ ID NO 709
<211> LENGTH: 15
<212> TYPE: PRT
<213> ORGANISM: Vespula vulgaris

<400> SEQUENCE: 709

Asn Cys Arg Trp Ser Ala Arg Ser Asn Thr Arg Ile Lys Leu Asn
```

<210> SEQ ID NO 710
<211> LENGTH: 15
<212> TYPE: PRT
<213> ORGANISM: Vespula vulgaris

<400> SEQUENCE: 710

Ala Pro Gly Val Asn Leu Arg Val Thr Ser Tyr Leu Asp Phe Ile
1               5                   10                  15

<210> SEQ ID NO 711
<211> LENGTH: 15
<212> TYPE: PRT
<213> ORGANISM: Vespula vulgaris

<400> SEQUENCE: 711

Gly Glu His Asn Cys Arg Trp Ser Ala Arg Ser Asn Thr Arg Ile
1               5                   10                  15

<210> SEQ ID NO 712
<211> LENGTH: 15
<212> TYPE: PRT
<213> ORGANISM: Vespula vulgaris

<400> SEQUENCE: 712

Glu Ala Pro Gly Val Asn Leu Arg Val Thr Ser Tyr Leu Asp Phe
1               5                   10                  15

<210> SEQ ID NO 713
<211> LENGTH: 15
<212> TYPE: PRT
<213> ORGANISM: Vespula vulgaris

<400> SEQUENCE: 713

His Asn Cys Arg Trp Ser Ala Arg Ser Asn Thr Arg Ile Lys Leu
1               5                   10                  15

<210> SEQ ID NO 714
<211> LENGTH: 15
<212> TYPE: PRT
<213> ORGANISM: Vespula vulgaris

<400> SEQUENCE: 714

Glu His Asn Cys Arg Trp Ser Ala Arg Ser Asn Thr Arg Ile Lys
1               5                   10                  15

<210> SEQ ID NO 715
<211> LENGTH: 15
<212> TYPE: PRT
<213> ORGANISM: Vespula vulgaris

<400> SEQUENCE: 715

Cys Arg Trp Ser Ala Arg Ser Asn Thr Arg Ile Lys Leu Asn Cys
1               5                   10                  15

<210> SEQ ID NO 716
<211> LENGTH: 15
<212> TYPE: PRT
<213> ORGANISM: Vespula vulgaris

<400> SEQUENCE: 716

His Val Leu Thr Ala Ala His Cys Val Ala Arg Tyr Lys Arg Ile
1               5                   10                  15

<210> SEQ ID NO 717
<211> LENGTH: 15
<212> TYPE: PRT
<213> ORGANISM: Vespula vulgaris

<400> SEQUENCE: 717

Thr Ala Ala His Cys Val Ala Arg Tyr Lys Arg Ile Leu Tyr Ile
1               5                   10                  15

<210> SEQ ID NO 718
<211> LENGTH: 15
<212> TYPE: PRT
<213> ORGANISM: Vespula vulgaris

<400> SEQUENCE: 718

Pro Ile Leu Trp Gln Asn Pro Lys Ser Lys Arg Ile Phe Leu Leu
1               5                   10                  15

<210> SEQ ID NO 719
<211> LENGTH: 15
<212> TYPE: PRT
<213> ORGANISM: Vespula vulgaris

<400> SEQUENCE: 719

Ala Ala His Cys Val Ala Arg Tyr Lys Arg Ile Leu Tyr Ile Leu
1               5                   10                  15

<210> SEQ ID NO 720
<211> LENGTH: 15
<212> TYPE: PRT
<213> ORGANISM: Vespula vulgaris

<400> SEQUENCE: 720

Gly Ile Ile His Leu Ala Thr Arg Phe Leu Tyr Cys Gly Ala Thr
1               5                   10                  15

<210> SEQ ID NO 721
<211> LENGTH: 15
<212> TYPE: PRT
<213> ORGANISM: Vespula vulgaris

<400> SEQUENCE: 721

Ile Leu Trp Gln Asn Pro Lys Ser Lys Arg Ile Phe Leu Leu Gly
1               5                   10                  15

<210> SEQ ID NO 722
<211> LENGTH: 15
<212> TYPE: PRT
<213> ORGANISM: Vespula vulgaris

<400> SEQUENCE: 722

Leu Pro Phe Tyr Tyr Met Gln Arg Asn Phe Val Asp Thr Val Val
1               5                   10                  15

<210> SEQ ID NO 723
<211> LENGTH: 15
<212> TYPE: PRT
<213> ORGANISM: Vespula vulgaris

<400> SEQUENCE: 723

Gly Pro Ile Leu Trp Gln Asn Pro Lys Ser Lys Arg Ile Phe Leu
1               5                   10                  15

<210> SEQ ID NO 724

```
<211> LENGTH: 15
<212> TYPE: PRT
<213> ORGANISM: Vespula vulgaris

<400> SEQUENCE: 724

Leu Ala Val Ile Lys Leu Gln Lys Arg Leu Lys Tyr Ser Met Arg
1               5                   10                  15

<210> SEQ ID NO 725
<211> LENGTH: 15
<212> TYPE: PRT
<213> ORGANISM: Vespula vulgaris

<400> SEQUENCE: 725

Asp Leu Ala Val Ile Lys Leu Gln Lys Arg Leu Lys Tyr Ser Met
1               5                   10                  15

<210> SEQ ID NO 726
<211> LENGTH: 15
<212> TYPE: PRT
<213> ORGANISM: Vespula vulgaris

<400> SEQUENCE: 726

Ala Val Ile Lys Leu Gln Lys Arg Leu Lys Tyr Ser Met Arg Ile
1               5                   10                  15

<210> SEQ ID NO 727
<211> LENGTH: 15
<212> TYPE: PRT
<213> ORGANISM: Vespula vulgaris

<400> SEQUENCE: 727

Leu Asn Asp Leu Ala Val Ile Lys Leu Gln Lys Arg Leu Lys Tyr
1               5                   10                  15

<210> SEQ ID NO 728
<211> LENGTH: 15
<212> TYPE: PRT
<213> ORGANISM: Vespula vulgaris

<400> SEQUENCE: 728

Asn Asp Leu Ala Val Ile Lys Leu Gln Lys Arg Leu Lys Tyr Ser
1               5                   10                  15

<210> SEQ ID NO 729
<211> LENGTH: 15
<212> TYPE: PRT
<213> ORGANISM: Vespula vulgaris

<400> SEQUENCE: 729

Val Ile Lys Leu Gln Lys Arg Leu Lys Tyr Ser Met Arg Ile Gly
1               5                   10                  15

<210> SEQ ID NO 730
<211> LENGTH: 15
<212> TYPE: PRT
<213> ORGANISM: Vespula vulgaris

<400> SEQUENCE: 730

Val Lys Tyr His Phe Leu Ala Thr Pro Lys Gln Leu Cys Thr Phe
1               5                   10                  15

<210> SEQ ID NO 731
<211> LENGTH: 15
<212> TYPE: PRT
```

```
<213> ORGANISM: Vespula vulgaris

<400> SEQUENCE: 731

Cys Val Lys Tyr His Phe Leu Ala Thr Pro Lys Gln Leu Cys Thr
1               5                   10                  15

<210> SEQ ID NO 732
<211> LENGTH: 15
<212> TYPE: PRT
<213> ORGANISM: Vespula vulgaris

<400> SEQUENCE: 732

Lys Cys Val Lys Tyr His Phe Leu Ala Thr Pro Lys Gln Leu Cys
1               5                   10                  15

<210> SEQ ID NO 733
<211> LENGTH: 15
<212> TYPE: PRT
<213> ORGANISM: Vespula vulgaris

<400> SEQUENCE: 733

Lys Lys Cys Val Lys Tyr His Phe Leu Ala Thr Pro Lys Gln Leu
1               5                   10                  15

<210> SEQ ID NO 734
<211> LENGTH: 15
<212> TYPE: PRT
<213> ORGANISM: Vespula vulgaris

<400> SEQUENCE: 734

Met Lys Lys Cys Val Lys Tyr His Phe Leu Ala Thr Pro Lys Gln
1               5                   10                  15

<210> SEQ ID NO 735
<211> LENGTH: 15
<212> TYPE: PRT
<213> ORGANISM: Vespula vulgaris

<400> SEQUENCE: 735

Thr Ser Tyr Leu Asp Phe Ile Thr Arg Ser Thr Pro Gly Glu Ile
1               5                   10                  15

<210> SEQ ID NO 736
<211> LENGTH: 15
<212> TYPE: PRT
<213> ORGANISM: Vespula vulgaris

<400> SEQUENCE: 736

Ser Tyr Leu Asp Phe Ile Thr Arg Ser Thr Pro Gly Glu Ile Tyr
1               5                   10                  15

<210> SEQ ID NO 737
<211> LENGTH: 15
<212> TYPE: PRT
<213> ORGANISM: Vespula vulgaris

<400> SEQUENCE: 737

Tyr Leu Asp Phe Ile Thr Arg Ser Thr Pro Gly Glu Ile Tyr Cys
1               5                   10                  15

<210> SEQ ID NO 738
<211> LENGTH: 15
<212> TYPE: PRT
<213> ORGANISM: Vespula vulgaris
```

-continued

<400> SEQUENCE: 738

Leu Asp Phe Ile Thr Arg Ser Thr Pro Gly Glu Ile Tyr Cys Gln
1               5                   10                  15

<210> SEQ ID NO 739
<211> LENGTH: 15
<212> TYPE: PRT
<213> ORGANISM: Vespula vulgaris

<400> SEQUENCE: 739

Asp Phe Ile Thr Arg Ser Thr Pro Gly Glu Ile Tyr Cys Gln Ala
1               5                   10                  15

<210> SEQ ID NO 740
<211> LENGTH: 15
<212> TYPE: PRT
<213> ORGANISM: Vespula vulgaris

<400> SEQUENCE: 740

Asn Glu Tyr Pro Met Met Ala Gly Ile Ile His Leu Ala Thr Arg
1               5                   10                  15

<210> SEQ ID NO 741
<211> LENGTH: 15
<212> TYPE: PRT
<213> ORGANISM: Vespula vulgaris

<400> SEQUENCE: 741

Val Asn Glu Tyr Pro Met Met Ala Gly Ile Ile His Leu Ala Thr
1               5                   10                  15

<210> SEQ ID NO 742
<211> LENGTH: 15
<212> TYPE: PRT
<213> ORGANISM: Vespula vulgaris

<400> SEQUENCE: 742

Thr Gly Val Asn Glu Tyr Pro Met Met Ala Gly Ile Ile His Leu
1               5                   10                  15

<210> SEQ ID NO 743
<211> LENGTH: 15
<212> TYPE: PRT
<213> ORGANISM: Vespula vulgaris

<400> SEQUENCE: 743

Glu Thr Gly Val Asn Glu Tyr Pro Met Met Ala Gly Ile Ile His
1               5                   10                  15

<210> SEQ ID NO 744
<211> LENGTH: 15
<212> TYPE: PRT
<213> ORGANISM: Vespula vulgaris

<400> SEQUENCE: 744

Gly Val Asn Glu Tyr Pro Met Met Ala Gly Ile Ile His Leu Ala
1               5                   10                  15

<210> SEQ ID NO 745
<211> LENGTH: 15
<212> TYPE: PRT
<213> ORGANISM: Vespula vulgaris

<400> SEQUENCE: 745

```
Glu Lys Cys Arg Cys Gly Trp Lys Asn Pro Ser Arg Ile Val Gly
1               5                   10                  15
```

<210> SEQ ID NO 746
<211> LENGTH: 15
<212> TYPE: PRT
<213> ORGANISM: Vespula vulgaris

<400> SEQUENCE: 746

```
Leu Ala Val Ile Lys Leu Gln Lys Arg Leu Lys Tyr Ser Met Arg
1               5                   10                  15
```

<210> SEQ ID NO 747
<211> LENGTH: 15
<212> TYPE: PRT
<213> ORGANISM: Vespula vulgaris

<400> SEQUENCE: 747

```
Tyr Pro Met Met Ala Gly Ile Ile His Leu Ala Thr Arg Phe Leu
1               5                   10                  15
```

<210> SEQ ID NO 748
<211> LENGTH: 15
<212> TYPE: PRT
<213> ORGANISM: Vespula vulgaris

<400> SEQUENCE: 748

```
Asp Leu Ala Val Ile Lys Leu Gln Lys Arg Leu Lys Tyr Ser Met
1               5                   10                  15
```

<210> SEQ ID NO 749
<211> LENGTH: 15
<212> TYPE: PRT
<213> ORGANISM: Vespula vulgaris

<400> SEQUENCE: 749

```
Lys Cys Arg Cys Gly Trp Lys Asn Pro Ser Arg Ile Val Gly Gly
1               5                   10                  15
```

<210> SEQ ID NO 750
<211> LENGTH: 15
<212> TYPE: PRT
<213> ORGANISM: Vespula vulgaris

<400> SEQUENCE: 750

```
Cys Arg Cys Gly Trp Lys Asn Pro Ser Arg Ile Val Gly Gly Val
1               5                   10                  15
```

<210> SEQ ID NO 751
<211> LENGTH: 15
<212> TYPE: PRT
<213> ORGANISM: Vespula vulgaris

<400> SEQUENCE: 751

```
Asn Asp Leu Ala Val Ile Lys Leu Gln Lys Arg Leu Lys Tyr Ser
1               5                   10                  15
```

<210> SEQ ID NO 752
<211> LENGTH: 15
<212> TYPE: PRT
<213> ORGANISM: Vespula vulgaris

<400> SEQUENCE: 752

```
Leu Asn Asp Leu Ala Val Ile Lys Leu Gln Lys Arg Leu Lys Tyr
1               5                   10                  15
```

<210> SEQ ID NO 753
<211> LENGTH: 15
<212> TYPE: PRT
<213> ORGANISM: Vespula vulgaris

<400> SEQUENCE: 753

Arg Cys Gly Trp Lys Asn Pro Ser Arg Ile Val Gly Gly Val Glu
1               5                   10                  15

<210> SEQ ID NO 754
<211> LENGTH: 15
<212> TYPE: PRT
<213> ORGANISM: Vespula vulgaris

<400> SEQUENCE: 754

Cys Gly Trp Lys Asn Pro Ser Arg Ile Val Gly Gly Val Glu Thr
1               5                   10                  15

<210> SEQ ID NO 755
<211> LENGTH: 15
<212> TYPE: PRT
<213> ORGANISM: Vespula vulgaris

<400> SEQUENCE: 755

Ala Val Ile Lys Leu Gln Lys Arg Leu Lys Tyr Ser Met Arg Ile
1               5                   10                  15

<210> SEQ ID NO 756
<211> LENGTH: 15
<212> TYPE: PRT
<213> ORGANISM: Vespula vulgaris

<400> SEQUENCE: 756

Pro Met Met Ala Gly Ile Ile His Leu Ala Thr Arg Phe Leu Tyr
1               5                   10                  15

<210> SEQ ID NO 757
<211> LENGTH: 15
<212> TYPE: PRT
<213> ORGANISM: Vespula vulgaris

<400> SEQUENCE: 757

Met Met Ala Gly Ile Ile His Leu Ala Thr Arg Phe Leu Tyr Cys
1               5                   10                  15

<210> SEQ ID NO 758
<211> LENGTH: 15
<212> TYPE: PRT
<213> ORGANISM: Vespula vulgaris

<400> SEQUENCE: 758

Glu Tyr Pro Met Met Ala Gly Ile Ile His Leu Ala Thr Arg Phe
1               5                   10                  15

<210> SEQ ID NO 759
<211> LENGTH: 15
<212> TYPE: PRT
<213> ORGANISM: Vespula vulgaris

<400> SEQUENCE: 759

Ala Gly Ile Ile His Leu Ala Thr Arg Phe Leu Tyr Cys Gly Ala
1               5                   10                  15

```
<210> SEQ ID NO 760
<211> LENGTH: 15
<212> TYPE: PRT
<213> ORGANISM: Vespula vulgaris

<400> SEQUENCE: 760

Met Ala Gly Ile Ile His Leu Ala Thr Arg Phe Leu Tyr Cys Gly
1               5                   10                  15

<210> SEQ ID NO 761
<211> LENGTH: 15
<212> TYPE: PRT
<213> ORGANISM: Vespula vulgaris

<400> SEQUENCE: 761

Arg Ile Phe Leu Leu Gly Val Ile Asn Tyr Gly Arg Thr Cys Ala
1               5                   10                  15

<210> SEQ ID NO 762
<211> LENGTH: 15
<212> TYPE: PRT
<213> ORGANISM: Vespula vulgaris

<400> SEQUENCE: 762

Ile Phe Leu Leu Gly Val Ile Asn Tyr Gly Arg Thr Cys Ala Asp
1               5                   10                  15

<210> SEQ ID NO 763
<211> LENGTH: 15
<212> TYPE: PRT
<213> ORGANISM: Vespula vulgaris

<400> SEQUENCE: 763

Leu Asn Asp Leu Ala Val Ile Lys Leu Gln Lys Arg Leu Lys Tyr
1               5                   10                  15

<210> SEQ ID NO 764
<211> LENGTH: 15
<212> TYPE: PRT
<213> ORGANISM: Vespula vulgaris

<400> SEQUENCE: 764

Leu Ala Val Ile Lys Leu Gln Lys Arg Leu Lys Tyr Ser Met Arg
1               5                   10                  15

<210> SEQ ID NO 765
<211> LENGTH: 15
<212> TYPE: PRT
<213> ORGANISM: Vespula vulgaris

<400> SEQUENCE: 765

Ala Arg Tyr Lys Arg Ile Leu Tyr Ile Leu Gly Val Val Val Gly
1               5                   10                  15

<210> SEQ ID NO 766
<211> LENGTH: 15
<212> TYPE: PRT
<213> ORGANISM: Vespula vulgaris

<400> SEQUENCE: 766

Asp Leu Ala Val Ile Lys Leu Gln Lys Arg Leu Lys Tyr Ser Met
1               5                   10                  15

<210> SEQ ID NO 767
<211> LENGTH: 15
```

-continued

<210> SEQ ID NO 767
<211> LENGTH: 15
<212> TYPE: PRT
<213> ORGANISM: Vespula vulgaris

<400> SEQUENCE: 767

Cys Gly Trp Lys Asn Pro Ser Arg Ile Val Gly Gly Val Glu Thr
1               5                   10                  15

<210> SEQ ID NO 768
<211> LENGTH: 15
<212> TYPE: PRT
<213> ORGANISM: Vespula vulgaris

<400> SEQUENCE: 768

Arg Tyr Lys Arg Ile Leu Tyr Ile Leu Gly Val Val Val Gly Glu
1               5                   10                  15

<210> SEQ ID NO 769
<211> LENGTH: 15
<212> TYPE: PRT
<213> ORGANISM: Vespula vulgaris

<400> SEQUENCE: 769

Asn Asp Leu Ala Val Ile Lys Leu Gln Lys Arg Leu Lys Tyr Ser
1               5                   10                  15

<210> SEQ ID NO 770
<211> LENGTH: 15
<212> TYPE: PRT
<213> ORGANISM: Vespula vulgaris

<400> SEQUENCE: 770

Cys Arg Cys Gly Trp Lys Asn Pro Ser Arg Ile Val Gly Gly Val
1               5                   10                  15

<210> SEQ ID NO 771
<211> LENGTH: 15
<212> TYPE: PRT
<213> ORGANISM: Vespula vulgaris

<400> SEQUENCE: 771

Lys Arg Ile Leu Tyr Ile Leu Gly Val Val Val Gly Glu His Asn
1               5                   10                  15

<210> SEQ ID NO 772
<211> LENGTH: 15
<212> TYPE: PRT
<213> ORGANISM: Vespula vulgaris

<400> SEQUENCE: 772

Glu Lys Cys Arg Cys Gly Trp Lys Asn Pro Ser Arg Ile Val Gly
1               5                   10                  15

<210> SEQ ID NO 773
<211> LENGTH: 15
<212> TYPE: PRT
<213> ORGANISM: Vespula vulgaris

<400> SEQUENCE: 773

Lys Cys Arg Cys Gly Trp Lys Asn Pro Ser Arg Ile Val Gly Gly
1               5                   10                  15

<210> SEQ ID NO 774
<211> LENGTH: 15
<212> TYPE: PRT
<213> ORGANISM: Vespula vulgaris -continued

<400> SEQUENCE: 774

Tyr Lys Arg Ile Leu Tyr Ile Leu Gly Val Val Val Gly Glu His
1               5                   10                  15

<210> SEQ ID NO 775
<211> LENGTH: 15
<212> TYPE: PRT
<213> ORGANISM: Vespula vulgaris

<400> SEQUENCE: 775

Ala Val Ile Lys Leu Gln Lys Arg Leu Lys Tyr Ser Met Arg Ile
1               5                   10                  15

<210> SEQ ID NO 776
<211> LENGTH: 15
<212> TYPE: PRT
<213> ORGANISM: Vespula vulgaris

<400> SEQUENCE: 776

Arg Ile Leu Tyr Ile Leu Gly Val Val Val Gly Glu His Asn Thr
1               5                   10                  15

<210> SEQ ID NO 777
<211> LENGTH: 15
<212> TYPE: PRT
<213> ORGANISM: Vespula vulgaris

<400> SEQUENCE: 777

Lys Arg Ile Phe Leu Leu Gly Val Ile Asn Tyr Gly Arg Thr Cys
1               5                   10                  15

<210> SEQ ID NO 778
<211> LENGTH: 15
<212> TYPE: PRT
<213> ORGANISM: Vespula vulgaris

<400> SEQUENCE: 778

Ser Lys Arg Ile Phe Leu Leu Gly Val Ile Asn Tyr Gly Arg Thr
1               5                   10                  15

<210> SEQ ID NO 779
<211> LENGTH: 15
<212> TYPE: PRT
<213> ORGANISM: Vespula vulgaris

<400> SEQUENCE: 779

Arg Cys Gly Trp Lys Asn Pro Ser Arg Ile Val Gly Gly Val Glu
1               5                   10                  15

<210> SEQ ID NO 780
<211> LENGTH: 15
<212> TYPE: PRT
<213> ORGANISM: Vespula vulgaris

<400> SEQUENCE: 780

Phe Leu Leu Gly Val Ile Asn Tyr Gly Arg Thr Cys Ala Asp Glu
1               5                   10                  15

<210> SEQ ID NO 781
<211> LENGTH: 15
<212> TYPE: PRT
<213> ORGANISM: Vespula vulgaris

<400> SEQUENCE: 781

Ile Lys Leu Gln Lys Arg Leu Lys Tyr Ser Met Arg Ile Gly Pro
1               5                   10                  15

<210> SEQ ID NO 782
<211> LENGTH: 15
<212> TYPE: PRT
<213> ORGANISM: Vespula vulgaris

<400> SEQUENCE: 782

Met Ala Gly Ile Ile His Leu Ala Thr Arg Phe Leu Tyr Cys Gly
1               5                   10                  15

<210> SEQ ID NO 783
<211> LENGTH: 15
<212> TYPE: PRT
<213> ORGANISM: Vespula vulgaris

<400> SEQUENCE: 783

Ile Ala Ser Lys Met Thr Ile Lys Phe His Ser Arg Tyr Asn Thr
1               5                   10                  15

<210> SEQ ID NO 784
<211> LENGTH: 15
<212> TYPE: PRT
<213> ORGANISM: Vespula vulgaris

<400> SEQUENCE: 784

Ala Asp Glu Ala Pro Gly Val Asn Leu Arg Val Thr Ser Tyr Leu
1               5                   10                  15

<210> SEQ ID NO 785
<211> LENGTH: 15
<212> TYPE: PRT
<213> ORGANISM: Vespula vulgaris

<400> SEQUENCE: 785

Asp Glu Ala Pro Gly Val Asn Leu Arg Val Thr Ser Tyr Leu Asp
1               5                   10                  15

<210> SEQ ID NO 786
<211> LENGTH: 15
<212> TYPE: PRT
<213> ORGANISM: Vespula vulgaris

<400> SEQUENCE: 786

Glu Ala Pro Gly Val Asn Leu Arg Val Thr Ser Tyr Leu Asp Phe
1               5                   10                  15

<210> SEQ ID NO 787
<211> LENGTH: 15
<212> TYPE: PRT
<213> ORGANISM: Vespula vulgaris

<400> SEQUENCE: 787

Ala Gly Ile Ile His Leu Ala Thr Arg Phe Leu Tyr Cys Gly Ala
1               5                   10                  15

<210> SEQ ID NO 788
<211> LENGTH: 15
<212> TYPE: PRT
<213> ORGANISM: Vespula vulgaris

<400> SEQUENCE: 788

Val Ile Lys Leu Gln Lys Arg Leu Lys Tyr Ser Met Arg Ile Gly

-continued

<210> SEQ ID NO 789
<211> LENGTH: 15
<212> TYPE: PRT
<213> ORGANISM: Vespula vulgaris

<400> SEQUENCE: 789

Thr Ala Val Gly Trp Gly Leu Thr Asn Phe Tyr Gly Val Lys Ser
1               5                   10                  15

<210> SEQ ID NO 790
<211> LENGTH: 15
<212> TYPE: PRT
<213> ORGANISM: Vespula vulgaris

<400> SEQUENCE: 790

Trp Lys Asn Pro Ser Arg Ile Val Gly Gly Val Glu Thr Gly Val
1               5                   10                  15

<210> SEQ ID NO 791
<211> LENGTH: 15
<212> TYPE: PRT
<213> ORGANISM: Vespula vulgaris

<400> SEQUENCE: 791

Trp Gly Leu Thr Asn Phe Tyr Gly Val Lys Ser Glu Val Leu Arg
1               5                   10                  15

<210> SEQ ID NO 792
<211> LENGTH: 15
<212> TYPE: PRT
<213> ORGANISM: Vespula vulgaris

<400> SEQUENCE: 792

Ala Pro Gly Val Asn Leu Arg Val Thr Ser Tyr Leu Asp Phe Ile
1               5                   10                  15

<210> SEQ ID NO 793
<211> LENGTH: 15
<212> TYPE: PRT
<213> ORGANISM: Vespula vulgaris

<400> SEQUENCE: 793

Met Met Ala Gly Ile Ile His Leu Ala Thr Arg Phe Leu Tyr Cys
1               5                   10                  15

<210> SEQ ID NO 794
<211> LENGTH: 15
<212> TYPE: PRT
<213> ORGANISM: Vespula vulgaris

<400> SEQUENCE: 794

Pro Met Met Ala Gly Ile Ile His Leu Ala Thr Arg Phe Leu Tyr
1               5                   10                  15

<210> SEQ ID NO 795
<211> LENGTH: 15
<212> TYPE: PRT
<213> ORGANISM: Vespula vulgaris

<400> SEQUENCE: 795

Gly Trp Lys Asn Pro Ser Arg Ile Val Gly Gly Val Glu Thr Gly
1               5                   10                  15

<210> SEQ ID NO 796
<211> LENGTH: 15
<212> TYPE: PRT
<213> ORGANISM: Vespula vulgaris

<400> SEQUENCE: 796

Leu Leu Gly Val Ile Asn Tyr Gly Arg Thr Cys Ala Asp Glu Ala
1               5                   10                  15

<210> SEQ ID NO 797
<211> LENGTH: 15
<212> TYPE: PRT
<213> ORGANISM: Vespula vulgaris

<400> SEQUENCE: 797

His Asn Thr Trp Ala Ile Asn Asp Thr Lys Ala Thr Gln Leu Tyr
1               5                   10                  15

<210> SEQ ID NO 798
<211> LENGTH: 15
<212> TYPE: PRT
<213> ORGANISM: Vespula vulgaris

<400> SEQUENCE: 798

Leu Thr Asn Phe Tyr Gly Val Lys Ser Glu Val Leu Arg Lys Val
1               5                   10                  15

<210> SEQ ID NO 799
<211> LENGTH: 15
<212> TYPE: PRT
<213> ORGANISM: Vespula vulgaris

<400> SEQUENCE: 799

Pro Gly Val Asn Leu Arg Val Thr Ser Tyr Leu Asp Phe Ile Thr
1               5                   10                  15

<210> SEQ ID NO 800
<211> LENGTH: 15
<212> TYPE: PRT
<213> ORGANISM: Vespula vulgaris

<400> SEQUENCE: 800

Leu Gly Val Ile Asn Tyr Gly Arg Thr Cys Ala Asp Glu Ala Pro
1               5                   10                  15

<210> SEQ ID NO 801
<211> LENGTH: 15
<212> TYPE: PRT
<213> ORGANISM: Vespula vulgaris

<400> SEQUENCE: 801

Asn Thr Trp Ala Ile Asn Asp Thr Lys Ala Thr Gln Leu Tyr Leu
1               5                   10                  15

<210> SEQ ID NO 802
<211> LENGTH: 15
<212> TYPE: PRT
<213> ORGANISM: Vespula vulgaris

<400> SEQUENCE: 802

Glu His Asn Thr Trp Ala Ile Asn Asp Thr Lys Ala Thr Gln Leu
1               5                   10                  15

<210> SEQ ID NO 803

```
<211> LENGTH: 15
<212> TYPE: PRT
<213> ORGANISM: Vespula vulgaris

<400> SEQUENCE: 803

Ile Leu Tyr Ile Leu Gly Val Val Gly Glu His Asn Thr Trp
1               5                   10                  15

<210> SEQ ID NO 804
<211> LENGTH: 15
<212> TYPE: PRT
<213> ORGANISM: Vespula vulgaris

<400> SEQUENCE: 804

Gly Ile Ile His Leu Ala Thr Arg Phe Leu Tyr Cys Gly Ala Thr
1               5                   10                  15

<210> SEQ ID NO 805
<211> LENGTH: 15
<212> TYPE: PRT
<213> ORGANISM: Vespula vulgaris

<400> SEQUENCE: 805

Val Gly Trp Gly Leu Thr Asn Phe Tyr Gly Val Lys Ser Glu Val
1               5                   10                  15

<210> SEQ ID NO 806
<211> LENGTH: 15
<212> TYPE: PRT
<213> ORGANISM: Vespula vulgaris

<400> SEQUENCE: 806

Ala Val Gly Trp Gly Leu Thr Asn Phe Tyr Gly Val Lys Ser Glu
1               5                   10                  15

<210> SEQ ID NO 807
<211> LENGTH: 15
<212> TYPE: PRT
<213> ORGANISM: Vespula vulgaris

<400> SEQUENCE: 807

Val Gly Glu His Asn Thr Trp Ala Ile Asn Asp Thr Lys Ala Thr
1               5                   10                  15

<210> SEQ ID NO 808
<211> LENGTH: 15
<212> TYPE: PRT
<213> ORGANISM: Vespula vulgaris

<400> SEQUENCE: 808

Lys Ser Lys Arg Ile Phe Leu Leu Gly Val Ile Asn Tyr Gly Arg
1               5                   10                  15

<210> SEQ ID NO 809
<211> LENGTH: 15
<212> TYPE: PRT
<213> ORGANISM: Vespula vulgaris

<400> SEQUENCE: 809

His Cys Val Ala Arg Tyr Lys Arg Ile Leu Tyr Ile Leu Gly Val
1               5                   10                  15

<210> SEQ ID NO 810
<211> LENGTH: 15
<212> TYPE: PRT
```

```
<213> ORGANISM: Vespula vulgaris

<400> SEQUENCE: 810

Ala Ser Lys Met Thr Ile Lys Phe His Ser Arg Tyr Asn Thr Tyr
1               5                   10                  15

<210> SEQ ID NO 811
<211> LENGTH: 15
<212> TYPE: PRT
<213> ORGANISM: Vespula vulgaris

<400> SEQUENCE: 811

Ala His Cys Val Ala Arg Tyr Lys Arg Ile Leu Tyr Ile Leu Gly
1               5                   10                  15

<210> SEQ ID NO 812
<211> LENGTH: 15
<212> TYPE: PRT
<213> ORGANISM: Vespula vulgaris

<400> SEQUENCE: 812

Pro Lys Ser Lys Arg Ile Phe Leu Leu Gly Val Ile Asn Tyr Gly
1               5                   10                  15

<210> SEQ ID NO 813
<211> LENGTH: 15
<212> TYPE: PRT
<213> ORGANISM: Vespula vulgaris

<400> SEQUENCE: 813

Ser Lys Met Thr Ile Lys Phe His Ser Arg Tyr Asn Thr Tyr Gly
1               5                   10                  15

<210> SEQ ID NO 814
<211> LENGTH: 15
<212> TYPE: PRT
<213> ORGANISM: Vespula vulgaris

<400> SEQUENCE: 814

Ala Arg Ser Asn Thr Arg Ile Lys Leu Asn Cys Thr Val Phe Asp
1               5                   10                  15

<210> SEQ ID NO 815
<211> LENGTH: 15
<212> TYPE: PRT
<213> ORGANISM: Vespula vulgaris

<400> SEQUENCE: 815

Gly Glu His Asn Thr Trp Ala Ile Asn Asp Thr Lys Ala Thr Gln
1               5                   10                  15

<210> SEQ ID NO 816
<211> LENGTH: 15
<212> TYPE: PRT
<213> ORGANISM: Vespula vulgaris

<400> SEQUENCE: 816

Arg Ser Asn Thr Arg Ile Lys Leu Asn Cys Thr Val Phe Asp Val
1               5                   10                  15

<210> SEQ ID NO 817
<211> LENGTH: 15
<212> TYPE: PRT
<213> ORGANISM: Vespula vulgaris
```

```
<400> SEQUENCE: 817

Val Ala Arg Tyr Lys Arg Ile Leu Tyr Ile Leu Gly Val Val Val
1               5                   10                  15

<210> SEQ ID NO 818
<211> LENGTH: 15
<212> TYPE: PRT
<213> ORGANISM: Vespula vulgaris

<400> SEQUENCE: 818

Leu Tyr Ile Leu Gly Val Val Gly Glu His Asn Thr Trp Ala
1               5                   10                  15

<210> SEQ ID NO 819
<211> LENGTH: 15
<212> TYPE: PRT
<213> ORGANISM: Vespula vulgaris

<400> SEQUENCE: 819

Lys Met Thr Ile Lys Phe His Ser Arg Tyr Asn Thr Tyr Gly Gly
1               5                   10                  15

<210> SEQ ID NO 820
<211> LENGTH: 15
<212> TYPE: PRT
<213> ORGANISM: Vespula vulgaris

<400> SEQUENCE: 820

Met Thr Ile Lys Phe His Ser Arg Tyr Asn Thr Tyr Gly Gly Lys
1               5                   10                  15

<210> SEQ ID NO 821
<211> LENGTH: 15
<212> TYPE: PRT
<213> ORGANISM: Vespula vulgaris

<400> SEQUENCE: 821

Val Val Thr Ala Val Gly Trp Gly Leu Thr Asn Phe Tyr Gly Val
1               5                   10                  15

<210> SEQ ID NO 822
<211> LENGTH: 15
<212> TYPE: PRT
<213> ORGANISM: Vespula vulgaris

<400> SEQUENCE: 822

Ser Asn Thr Arg Ile Lys Leu Asn Cys Thr Val Phe Asp Val Pro
1               5                   10                  15

<210> SEQ ID NO 823
<211> LENGTH: 15
<212> TYPE: PRT
<213> ORGANISM: Vespula vulgaris

<400> SEQUENCE: 823

Asn Thr Arg Ile Lys Leu Asn Cys Thr Val Phe Asp Val Pro Pro
1               5                   10                  15

<210> SEQ ID NO 824
<211> LENGTH: 15
<212> TYPE: PRT
<213> ORGANISM: Vespula vulgaris

<400> SEQUENCE: 824
```

-continued

Thr Asn Phe Tyr Gly Val Lys Ser Glu Val Leu Arg Lys Val Asp
1               5                   10                  15

<210> SEQ ID NO 825
<211> LENGTH: 15
<212> TYPE: PRT
<213> ORGANISM: Vespula vulgaris

<400> SEQUENCE: 825

Val Thr Ala Val Gly Trp Gly Leu Thr Asn Phe Tyr Gly Val Lys
1               5                   10                  15

<210> SEQ ID NO 826
<211> LENGTH: 15
<212> TYPE: PRT
<213> ORGANISM: Vespula vulgaris

<400> SEQUENCE: 826

Asn Phe Tyr Gly Val Lys Ser Glu Val Leu Arg Lys Val Asp Leu
1               5                   10                  15

<210> SEQ ID NO 827
<211> LENGTH: 15
<212> TYPE: PRT
<213> ORGANISM: Vespula vulgaris

<400> SEQUENCE: 827

Lys Leu Asn Asp Leu Ala Val Ile Lys Leu Gln Lys Arg Leu Lys
1               5                   10                  15

<210> SEQ ID NO 828
<211> LENGTH: 15
<212> TYPE: PRT
<213> ORGANISM: Vespula vulgaris

<400> SEQUENCE: 828

Thr Arg Ile Lys Leu Asn Cys Thr Val Phe Asp Val Pro Pro Ser
1               5                   10                  15

<210> SEQ ID NO 829
<211> LENGTH: 15
<212> TYPE: PRT
<213> ORGANISM: Vespula vulgaris

<400> SEQUENCE: 829

Asp Thr Val Val Thr Ala Val Gly Trp Gly Leu Thr Asn Phe Tyr
1               5                   10                  15

<210> SEQ ID NO 830
<211> LENGTH: 15
<212> TYPE: PRT
<213> ORGANISM: Vespula vulgaris

<400> SEQUENCE: 830

Gly Leu Thr Asn Phe Tyr Gly Val Lys Ser Glu Val Leu Arg Lys
1               5                   10                  15

<210> SEQ ID NO 831
<211> LENGTH: 15
<212> TYPE: PRT
<213> ORGANISM: Vespula vulgaris

<400> SEQUENCE: 831

Cys Val Ala Arg Tyr Lys Arg Ile Leu Tyr Ile Leu Gly Val Val
1               5                   10                  15

<210> SEQ ID NO 832
<211> LENGTH: 15
<212> TYPE: PRT
<213> ORGANISM: Vespula vulgaris

<400> SEQUENCE: 832

Tyr Pro Met Met Ala Gly Ile Ile His Leu Ala Thr Arg Phe Leu
1               5                   10                  15

<210> SEQ ID NO 833
<211> LENGTH: 15
<212> TYPE: PRT
<213> ORGANISM: Vespula vulgaris

<400> SEQUENCE: 833

Pro Lys Leu Asn Asp Leu Ala Val Ile Lys Leu Gln Lys Arg Leu
1               5                   10                  15

<210> SEQ ID NO 834
<211> LENGTH: 15
<212> TYPE: PRT
<213> ORGANISM: Vespula vulgaris

<400> SEQUENCE: 834

Arg Pro Lys Leu Asn Asp Leu Ala Val Ile Lys Leu Gln Lys Arg
1               5                   10                  15

<210> SEQ ID NO 835
<211> LENGTH: 15
<212> TYPE: PRT
<213> ORGANISM: Vespula vulgaris

<400> SEQUENCE: 835

Asn Pro Lys Ser Lys Arg Ile Phe Leu Leu Gly Val Ile Asn Tyr
1               5                   10                  15

<210> SEQ ID NO 836
<211> LENGTH: 15
<212> TYPE: PRT
<213> ORGANISM: Vespula vulgaris

<400> SEQUENCE: 836

Ile Lys Phe His Ser Arg Tyr Asn Thr Tyr Gly Gly Lys Phe Arg
1               5                   10                  15

<210> SEQ ID NO 837
<211> LENGTH: 15
<212> TYPE: PRT
<213> ORGANISM: Vespula vulgaris

<400> SEQUENCE: 837

Gly Trp Gly Leu Thr Asn Phe Tyr Gly Val Lys Ser Glu Val Leu
1               5                   10                  15

<210> SEQ ID NO 838
<211> LENGTH: 15
<212> TYPE: PRT
<213> ORGANISM: Vespula vulgaris

<400> SEQUENCE: 838

Thr Val Val Thr Ala Val Gly Trp Gly Leu Thr Asn Phe Tyr Gly
1               5                   10                  15

```
<210> SEQ ID NO 839
<211> LENGTH: 15
<212> TYPE: PRT
<213> ORGANISM: Vespula vulgaris

<400> SEQUENCE: 839

Leu Gln Lys Arg Leu Lys Tyr Ser Met Arg Ile Gly Pro Ala Cys
1               5                   10                  15

<210> SEQ ID NO 840
<211> LENGTH: 15
<212> TYPE: PRT
<213> ORGANISM: Vespula vulgaris

<400> SEQUENCE: 840

Thr Trp Ala Ile Asn Asp Thr Lys Ala Thr Gln Leu Tyr Leu Ile
1               5                   10                  15

<210> SEQ ID NO 841
<211> LENGTH: 15
<212> TYPE: PRT
<213> ORGANISM: Vespula vulgaris

<400> SEQUENCE: 841

Asp Leu His Val Val Ser Met Lys Lys Cys Val Lys Tyr His Phe
1               5                   10                  15

<210> SEQ ID NO 842
<211> LENGTH: 15
<212> TYPE: PRT
<213> ORGANISM: Vespula vulgaris

<400> SEQUENCE: 842

Trp Ala Ile Asn Asp Thr Lys Ala Thr Gln Leu Tyr Leu Ile Asp
1               5                   10                  15

<210> SEQ ID NO 843
<211> LENGTH: 15
<212> TYPE: PRT
<213> ORGANISM: Vespula vulgaris

<400> SEQUENCE: 843

Leu His Val Val Ser Met Lys Lys Cys Val Lys Tyr His Phe Leu
1               5                   10                  15

<210> SEQ ID NO 844
<211> LENGTH: 15
<212> TYPE: PRT
<213> ORGANISM: Vespula vulgaris

<400> SEQUENCE: 844

Ile Ile His Leu Ala Thr Arg Phe Leu Tyr Cys Gly Ala Thr Ile
1               5                   10                  15

<210> SEQ ID NO 845
<211> LENGTH: 15
<212> TYPE: PRT
<213> ORGANISM: Vespula vulgaris

<400> SEQUENCE: 845

Ser Phe Ala Val Glu Ser Ile Ala Ser Lys Met Thr Ile Lys Phe
1               5                   10                  15

<210> SEQ ID NO 846
<211> LENGTH: 15
```

```
<212> TYPE: PRT
<213> ORGANISM: Vespula vulgaris

<400> SEQUENCE: 846

Ala Val Glu Ser Ile Ala Ser Lys Met Thr Ile Lys Phe His Ser
1               5                   10                  15

<210> SEQ ID NO 847
<211> LENGTH: 15
<212> TYPE: PRT
<213> ORGANISM: Vespula vulgaris

<400> SEQUENCE: 847

Lys Leu Gln Lys Arg Leu Lys Tyr Ser Met Arg Ile Gly Pro Ala
1               5                   10                  15

<210> SEQ ID NO 848
<211> LENGTH: 15
<212> TYPE: PRT
<213> ORGANISM: Vespula vulgaris

<400> SEQUENCE: 848

Phe Ala Val Glu Ser Ile Ala Ser Lys Met Thr Ile Lys Phe His
1               5                   10                  15

<210> SEQ ID NO 849
<211> LENGTH: 15
<212> TYPE: PRT
<213> ORGANISM: Vespula vulgaris

<400> SEQUENCE: 849

Ser Lys Arg Ile Phe Leu Leu Gly Val Ile Asn Tyr Gly Arg Thr
1               5                   10                  15

<210> SEQ ID NO 850
<211> LENGTH: 15
<212> TYPE: PRT
<213> ORGANISM: Vespula vulgaris

<400> SEQUENCE: 850

Lys Ser Lys Arg Ile Phe Leu Leu Gly Val Ile Asn Tyr Gly Arg
1               5                   10                  15

<210> SEQ ID NO 851
<211> LENGTH: 15
<212> TYPE: PRT
<213> ORGANISM: Vespula vulgaris

<400> SEQUENCE: 851

Lys Arg Ile Phe Leu Leu Gly Val Ile Asn Tyr Gly Arg Thr Cys
1               5                   10                  15

<210> SEQ ID NO 852
<211> LENGTH: 15
<212> TYPE: PRT
<213> ORGANISM: Vespula vulgaris

<400> SEQUENCE: 852

Arg Ile Phe Leu Leu Gly Val Ile Asn Tyr Gly Arg Thr Cys Ala
1               5                   10                  15

<210> SEQ ID NO 853
<211> LENGTH: 15
<212> TYPE: PRT
<213> ORGANISM: Vespula vulgaris
```

```
<400> SEQUENCE: 853

Ile Phe Leu Leu Gly Val Ile Asn Tyr Gly Arg Thr Cys Ala Asp
1               5                   10                  15

<210> SEQ ID NO 854
<211> LENGTH: 15
<212> TYPE: PRT
<213> ORGANISM: Vespula vulgaris

<400> SEQUENCE: 854

Val Lys Ser Glu Val Leu Arg Lys Val Asp Leu His Val Val Ser
1               5                   10                  15

<210> SEQ ID NO 855
<211> LENGTH: 15
<212> TYPE: PRT
<213> ORGANISM: Vespula vulgaris

<400> SEQUENCE: 855

Gly Val Lys Ser Glu Val Leu Arg Lys Val Asp Leu His Val Val
1               5                   10                  15

<210> SEQ ID NO 856
<211> LENGTH: 15
<212> TYPE: PRT
<213> ORGANISM: Vespula vulgaris

<400> SEQUENCE: 856

Ser Glu Val Leu Arg Lys Val Asp Leu His Val Val Ser Met Lys
1               5                   10                  15

<210> SEQ ID NO 857
<211> LENGTH: 15
<212> TYPE: PRT
<213> ORGANISM: Vespula vulgaris

<400> SEQUENCE: 857

Lys Ser Glu Val Leu Arg Lys Val Asp Leu His Val Val Ser Met
1               5                   10                  15

<210> SEQ ID NO 858
<211> LENGTH: 15
<212> TYPE: PRT
<213> ORGANISM: Vespula vulgaris

<400> SEQUENCE: 858

Phe Leu Leu Gly Val Ile Asn Tyr Gly Arg Thr Cys Ala Asp Glu
1               5                   10                  15

<210> SEQ ID NO 859
<211> LENGTH: 15
<212> TYPE: PRT
<213> ORGANISM: Vespula vulgaris

<400> SEQUENCE: 859

Tyr Asn Pro Asp Phe Pro Asn Tyr Tyr Met Gly Glu His Asn Cys
1               5                   10                  15

<210> SEQ ID NO 860
<211> LENGTH: 15
<212> TYPE: PRT
<213> ORGANISM: Vespula vulgaris

<400> SEQUENCE: 860
```

```
Glu Val Leu Arg Lys Val Asp Leu His Val Val Ser Met Lys Lys
1               5                   10                  15
```

<210> SEQ ID NO 861
<211> LENGTH: 15
<212> TYPE: PRT
<213> ORGANISM: Vespula vulgaris

<400> SEQUENCE: 861

```
Asn Asp Leu Ala Val Ile Lys Leu Gln Lys Arg Leu Lys Tyr Ser
1               5                   10                  15
```

<210> SEQ ID NO 862
<211> LENGTH: 15
<212> TYPE: PRT
<213> ORGANISM: Vespula vulgaris

<400> SEQUENCE: 862

```
Leu Leu Gly Val Ile Asn Tyr Gly Arg Thr Cys Ala Asp Glu Ala
1               5                   10                  15
```

<210> SEQ ID NO 863
<211> LENGTH: 15
<212> TYPE: PRT
<213> ORGANISM: Vespula vulgaris

<400> SEQUENCE: 863

```
Leu Asn Asp Leu Ala Val Ile Lys Leu Gln Lys Arg Leu Lys Tyr
1               5                   10                  15
```

<210> SEQ ID NO 864
<211> LENGTH: 15
<212> TYPE: PRT
<213> ORGANISM: Vespula vulgaris

<400> SEQUENCE: 864

```
Lys Leu Asn Asp Leu Ala Val Ile Lys Leu Gln Lys Arg Leu Lys
1               5                   10                  15
```

<210> SEQ ID NO 865
<211> LENGTH: 15
<212> TYPE: PRT
<213> ORGANISM: Vespula vulgaris

<400> SEQUENCE: 865

```
Ala Arg Tyr Lys Arg Ile Leu Tyr Ile Leu Gly Val Val Val Gly
1               5                   10                  15
```

<210> SEQ ID NO 866
<211> LENGTH: 15
<212> TYPE: PRT
<213> ORGANISM: Vespula vulgaris

<400> SEQUENCE: 866

```
Tyr Lys Arg Ile Leu Tyr Ile Leu Gly Val Val Val Gly Glu His
1               5                   10                  15
```

<210> SEQ ID NO 867
<211> LENGTH: 15
<212> TYPE: PRT
<213> ORGANISM: Vespula vulgaris

<400> SEQUENCE: 867

```
Val Leu Arg Lys Val Asp Leu His Val Val Ser Met Lys Lys Cys
```

<210> SEQ ID NO 868
<211> LENGTH: 15
<212> TYPE: PRT
<213> ORGANISM: Vespula vulgaris

<400> SEQUENCE: 868

Lys Arg Ile Leu Tyr Ile Leu Gly Val Val Gly Glu His Asn
1               5                   10                  15

<210> SEQ ID NO 869
<211> LENGTH: 15
<212> TYPE: PRT
<213> ORGANISM: Vespula vulgaris

<400> SEQUENCE: 869

Pro Lys Leu Asn Asp Leu Ala Val Ile Lys Leu Gln Lys Arg Leu
1               5                   10                  15

<210> SEQ ID NO 870
<211> LENGTH: 15
<212> TYPE: PRT
<213> ORGANISM: Vespula vulgaris

<400> SEQUENCE: 870

Asp Leu Ala Val Ile Lys Leu Gln Lys Arg Leu Lys Tyr Ser Met
1               5                   10                  15

<210> SEQ ID NO 871
<211> LENGTH: 15
<212> TYPE: PRT
<213> ORGANISM: Vespula vulgaris

<400> SEQUENCE: 871

Arg Tyr Lys Arg Ile Leu Tyr Ile Leu Gly Val Val Val Gly Glu
1               5                   10                  15

<210> SEQ ID NO 872
<211> LENGTH: 15
<212> TYPE: PRT
<213> ORGANISM: Vespula vulgaris

<400> SEQUENCE: 872

Trp Gly Leu Thr Asn Phe Tyr Gly Val Lys Ser Glu Val Leu Arg
1               5                   10                  15

<210> SEQ ID NO 873
<211> LENGTH: 15
<212> TYPE: PRT
<213> ORGANISM: Vespula vulgaris

<400> SEQUENCE: 873

Leu Thr Asn Phe Tyr Gly Val Lys Ser Glu Val Leu Arg Lys Val
1               5                   10                  15

<210> SEQ ID NO 874
<211> LENGTH: 15
<212> TYPE: PRT
<213> ORGANISM: Vespula vulgaris

<400> SEQUENCE: 874

Arg Pro Lys Leu Asn Asp Leu Ala Val Ile Lys Leu Gln Lys Arg
1               5                   10                  15

<210> SEQ ID NO 875
<211> LENGTH: 15
<212> TYPE: PRT
<213> ORGANISM: Vespula vulgaris

<400> SEQUENCE: 875

Val Ala Arg Tyr Lys Arg Ile Leu Tyr Ile Leu Gly Val Val Val
1               5                   10                  15

<210> SEQ ID NO 876
<211> LENGTH: 15
<212> TYPE: PRT
<213> ORGANISM: Vespula vulgaris

<400> SEQUENCE: 876

Arg Lys Val Asp Leu His Val Val Ser Met Lys Lys Cys Val Lys
1               5                   10                  15

<210> SEQ ID NO 877
<211> LENGTH: 15
<212> TYPE: PRT
<213> ORGANISM: Vespula vulgaris

<400> SEQUENCE: 877

Val Asp Leu His Val Val Ser Met Lys Lys Cys Val Lys Tyr His
1               5                   10                  15

<210> SEQ ID NO 878
<211> LENGTH: 15
<212> TYPE: PRT
<213> ORGANISM: Vespula vulgaris

<400> SEQUENCE: 878

Lys Val Asp Leu His Val Val Ser Met Lys Lys Cys Val Lys Tyr
1               5                   10                  15

<210> SEQ ID NO 879
<211> LENGTH: 15
<212> TYPE: PRT
<213> ORGANISM: Vespula vulgaris

<400> SEQUENCE: 879

Ala Val Ile Lys Leu Gln Lys Arg Leu Lys Tyr Ser Met Arg Ile
1               5                   10                  15

<210> SEQ ID NO 880
<211> LENGTH: 15
<212> TYPE: PRT
<213> ORGANISM: Vespula vulgaris

<400> SEQUENCE: 880

Tyr Gly Val Lys Ser Glu Val Leu Arg Lys Val Asp Leu His Val
1               5                   10                  15

<210> SEQ ID NO 881
<211> LENGTH: 15
<212> TYPE: PRT
<213> ORGANISM: Vespula vulgaris

<400> SEQUENCE: 881

Arg Ile Leu Tyr Ile Leu Gly Val Val Val Gly Glu His Asn Thr
1               5                   10                  15

<210> SEQ ID NO 882

```
<211> LENGTH: 15
<212> TYPE: PRT
<213> ORGANISM: Vespula vulgaris

<400> SEQUENCE: 882

Glu Lys Cys Arg Cys Gly Trp Lys Asn Pro Ser Arg Ile Val Gly
1               5                   10                  15

<210> SEQ ID NO 883
<211> LENGTH: 15
<212> TYPE: PRT
<213> ORGANISM: Vespula vulgaris

<400> SEQUENCE: 883

Gly Trp Gly Leu Thr Asn Phe Tyr Gly Val Lys Ser Glu Val Leu
1               5                   10                  15

<210> SEQ ID NO 884
<211> LENGTH: 15
<212> TYPE: PRT
<213> ORGANISM: Vespula vulgaris

<400> SEQUENCE: 884

His Cys Val Ala Arg Tyr Lys Arg Ile Leu Tyr Ile Leu Gly Val
1               5                   10                  15

<210> SEQ ID NO 885
<211> LENGTH: 15
<212> TYPE: PRT
<213> ORGANISM: Vespula vulgaris

<400> SEQUENCE: 885

Val Ile Lys Leu Gln Lys Arg Leu Lys Tyr Ser Met Arg Ile Gly
1               5                   10                  15

<210> SEQ ID NO 886
<211> LENGTH: 15
<212> TYPE: PRT
<213> ORGANISM: Vespula vulgaris

<400> SEQUENCE: 886

Cys Val Ala Arg Tyr Lys Arg Ile Leu Tyr Ile Leu Gly Val Val
1               5                   10                  15

<210> SEQ ID NO 887
<211> LENGTH: 15
<212> TYPE: PRT
<213> ORGANISM: Vespula vulgaris

<400> SEQUENCE: 887

Asp Leu His Val Val Ser Met Lys Lys Cys Val Lys Tyr His Phe
1               5                   10                  15

<210> SEQ ID NO 888
<211> LENGTH: 15
<212> TYPE: PRT
<213> ORGANISM: Vespula vulgaris

<400> SEQUENCE: 888

Leu His Val Val Ser Met Lys Lys Cys Val Lys Tyr His Phe Leu
1               5                   10                  15

<210> SEQ ID NO 889
<211> LENGTH: 15
<212> TYPE: PRT
```

<213> ORGANISM: Vespula vulgaris

<400> SEQUENCE: 889

Thr Asn Phe Tyr Gly Val Lys Ser Glu Val Leu Arg Lys Val Asp
1               5                   10                  15

<210> SEQ ID NO 890
<211> LENGTH: 15
<212> TYPE: PRT
<213> ORGANISM: Vespula vulgaris

<400> SEQUENCE: 890

Lys Cys Arg Cys Gly Trp Lys Asn Pro Ser Arg Ile Val Gly Gly
1               5                   10                  15

<210> SEQ ID NO 891
<211> LENGTH: 15
<212> TYPE: PRT
<213> ORGANISM: Vespula vulgaris

<400> SEQUENCE: 891

Gly Leu Thr Asn Phe Tyr Gly Val Lys Ser Glu Val Leu Arg Lys
1               5                   10                  15

<210> SEQ ID NO 892
<211> LENGTH: 15
<212> TYPE: PRT
<213> ORGANISM: Vespula vulgaris

<400> SEQUENCE: 892

Asp Ser Gly Gly Pro Ile Leu Trp Gln Asn Pro Lys Ser Lys Arg
1               5                   10                  15

<210> SEQ ID NO 893
<211> LENGTH: 15
<212> TYPE: PRT
<213> ORGANISM: Vespula vulgaris

<400> SEQUENCE: 893

Ser Gly Gly Pro Ile Leu Trp Gln Asn Pro Lys Ser Lys Arg Ile
1               5                   10                  15

<210> SEQ ID NO 894
<211> LENGTH: 15
<212> TYPE: PRT
<213> ORGANISM: Vespula vulgaris

<400> SEQUENCE: 894

Gly Gly Pro Ile Leu Trp Gln Asn Pro Lys Ser Lys Arg Ile Phe
1               5                   10                  15

<210> SEQ ID NO 895
<211> LENGTH: 15
<212> TYPE: PRT
<213> ORGANISM: Vespula vulgaris

<400> SEQUENCE: 895

Gly Pro Ile Leu Trp Gln Asn Pro Lys Ser Lys Arg Ile Phe Leu
1               5                   10                  15

<210> SEQ ID NO 896
<211> LENGTH: 15
<212> TYPE: PRT
<213> ORGANISM: Vespula vulgaris -continued

<400> SEQUENCE: 896

Phe Asp Ser Gly Gly Pro Ile Leu Trp Gln Asn Pro Lys Ser Lys
1               5                   10                  15

<210> SEQ ID NO 897
<211> LENGTH: 15
<212> TYPE: PRT
<213> ORGANISM: Vespula vulgaris

<400> SEQUENCE: 897

Pro Ile Leu Trp Gln Asn Pro Lys Ser Lys Arg Ile Phe Leu Leu
1               5                   10                  15

<210> SEQ ID NO 898
<211> LENGTH: 15
<212> TYPE: PRT
<213> ORGANISM: Vespula vulgaris

<400> SEQUENCE: 898

Leu Ala Val Ile Lys Leu Gln Lys Arg Leu Lys Tyr Ser Met Arg
1               5                   10                  15

<210> SEQ ID NO 899
<211> LENGTH: 15
<212> TYPE: PRT
<213> ORGANISM: Vespula vulgaris

<400> SEQUENCE: 899

Asp Leu Ala Val Ile Lys Leu Gln Lys Arg Leu Lys Tyr Ser Met
1               5                   10                  15

<210> SEQ ID NO 900
<211> LENGTH: 15
<212> TYPE: PRT
<213> ORGANISM: Vespula vulgaris

<400> SEQUENCE: 900

Leu Asn Asp Leu Ala Val Ile Lys Leu Gln Lys Arg Leu Lys Tyr
1               5                   10                  15

<210> SEQ ID NO 901
<211> LENGTH: 15
<212> TYPE: PRT
<213> ORGANISM: Vespula vulgaris

<400> SEQUENCE: 901

Asn Asp Leu Ala Val Ile Lys Leu Gln Lys Arg Leu Lys Tyr Ser
1               5                   10                  15

<210> SEQ ID NO 902
<211> LENGTH: 15
<212> TYPE: PRT
<213> ORGANISM: Vespula vulgaris

<400> SEQUENCE: 902

Ile Leu Trp Gln Asn Pro Lys Ser Lys Arg Ile Phe Leu Leu Gly
1               5                   10                  15

<210> SEQ ID NO 903
<211> LENGTH: 15
<212> TYPE: PRT
<213> ORGANISM: Vespula vulgaris

<400> SEQUENCE: 903

```
Asp Phe Pro Asn Tyr Tyr Met Gly Glu His Asn Cys Arg Trp Ser
1               5                   10                  15

<210> SEQ ID NO 904
<211> LENGTH: 15
<212> TYPE: PRT
<213> ORGANISM: Vespula vulgaris

<400> SEQUENCE: 904

Phe Pro Asn Tyr Tyr Met Gly Glu His Asn Cys Arg Trp Ser Ala
1               5                   10                  15

<210> SEQ ID NO 905
<211> LENGTH: 15
<212> TYPE: PRT
<213> ORGANISM: Vespula vulgaris

<400> SEQUENCE: 905

Asn Pro Asp Phe Pro Asn Tyr Tyr Met Gly Glu His Asn Cys Arg
1               5                   10                  15

<210> SEQ ID NO 906
<211> LENGTH: 15
<212> TYPE: PRT
<213> ORGANISM: Vespula vulgaris

<400> SEQUENCE: 906

Gly Gly Pro Ile Leu Trp Gln Asn Pro Lys Ser Lys Arg Ile Phe
1               5                   10                  15

<210> SEQ ID NO 907
<211> LENGTH: 15
<212> TYPE: PRT
<213> ORGANISM: Vespula vulgaris

<400> SEQUENCE: 907

Ser Gly Gly Pro Ile Leu Trp Gln Asn Pro Lys Ser Lys Arg Ile
1               5                   10                  15

<210> SEQ ID NO 908
<211> LENGTH: 15
<212> TYPE: PRT
<213> ORGANISM: Vespula vulgaris

<400> SEQUENCE: 908

Gly Pro Ile Leu Trp Gln Asn Pro Lys Ser Lys Arg Ile Phe Leu
1               5                   10                  15

<210> SEQ ID NO 909
<211> LENGTH: 15
<212> TYPE: PRT
<213> ORGANISM: Vespula vulgaris

<400> SEQUENCE: 909

Ile Ile Val His Pro Asn Tyr Arg Pro Lys Leu Asn Asp Leu Ala
1               5                   10                  15

<210> SEQ ID NO 910
<211> LENGTH: 15
<212> TYPE: PRT
<213> ORGANISM: Vespula vulgaris

<400> SEQUENCE: 910

Pro Ile Leu Trp Gln Asn Pro Lys Ser Lys Arg Ile Phe Leu Leu
1               5                   10                  15
```

<210> SEQ ID NO 911
<211> LENGTH: 15
<212> TYPE: PRT
<213> ORGANISM: Vespula vulgaris

<400> SEQUENCE: 911

Ile Leu Trp Gln Asn Pro Lys Ser Lys Arg Ile Phe Leu Leu Gly
1               5                   10                  15

<210> SEQ ID NO 912
<211> LENGTH: 15
<212> TYPE: PRT
<213> ORGANISM: Vespula vulgaris

<400> SEQUENCE: 912

Ile Val His Pro Asn Tyr Arg Pro Lys Leu Asn Asp Leu Ala Val
1               5                   10                  15

<210> SEQ ID NO 913
<211> LENGTH: 15
<212> TYPE: PRT
<213> ORGANISM: Vespula vulgaris

<400> SEQUENCE: 913

Asp Asp Ile Ile Val His Pro Asn Tyr Arg Pro Lys Leu Asn Asp
1               5                   10                  15

<210> SEQ ID NO 914
<211> LENGTH: 15
<212> TYPE: PRT
<213> ORGANISM: Vespula vulgaris

<400> SEQUENCE: 914

Ile Asp Asp Ile Ile Val His Pro Asn Tyr Arg Pro Lys Leu Asn
1               5                   10                  15

<210> SEQ ID NO 915
<211> LENGTH: 15
<212> TYPE: PRT
<213> ORGANISM: Vespula vulgaris

<400> SEQUENCE: 915

Leu Ile Asp Asp Ile Ile Val His Pro Asn Tyr Arg Pro Lys Leu
1               5                   10                  15

<210> SEQ ID NO 916
<211> LENGTH: 15
<212> TYPE: PRT
<213> ORGANISM: Vespula vulgaris

<400> SEQUENCE: 916

Asp Ser Gly Gly Pro Ile Leu Trp Gln Asn Pro Lys Ser Lys Arg
1               5                   10                  15

<210> SEQ ID NO 917
<211> LENGTH: 15
<212> TYPE: PRT
<213> ORGANISM: Vespula vulgaris

<400> SEQUENCE: 917

Val His Pro Asn Tyr Arg Pro Lys Leu Asn Asp Leu Ala Val Ile
1               5                   10                  15

<210> SEQ ID NO 918
<211> LENGTH: 15
<212> TYPE: PRT
<213> ORGANISM: Vespula vulgaris

<400> SEQUENCE: 918

Asp Ile Ile Val His Pro Asn Tyr Arg Pro Lys Leu Asn Asp Leu
1               5                   10                  15

<210> SEQ ID NO 919
<211> LENGTH: 45
<212> TYPE: DNA
<213> ORGANISM: Vespula vulgaris

<400> SEQUENCE: 919
gagtacgttt tctgtggatt aaattctttt gcagtggaat caata          45

<210> SEQ ID NO 920
<211> LENGTH: 45
<212> TYPE: DNA
<213> ORGANISM: Vespula vulgaris

<400> SEQUENCE: 920
cttacgaatt tttatggtgt caagtctgaa gttttgagaa aagtc          45

<210> SEQ ID NO 921
<211> LENGTH: 45
<212> TYPE: DNA
<213> ORGANISM: Vespula vulgaris

<400> SEQUENCE: 921
atggctggta taatacatct tgcaacgcgt tttctctatt gcggt          45

<210> SEQ ID NO 922
<211> LENGTH: 45
<212> TYPE: DNA
<213> ORGANISM: Vespula vulgaris

<400> SEQUENCE: 922
tataaaagga ttttatatat tctaggagtt gttgttggag aacat          45

<210> SEQ ID NO 923
<211> LENGTH: 45
<212> TYPE: DNA
<213> ORGANISM: Vespula vulgaris

<400> SEQUENCE: 923
gcgaggtata aaaggatttt atatattcta ggagttgttg ttgga          45

<210> SEQ ID NO 924
<211> LENGTH: 45
<212> TYPE: DNA
<213> ORGANISM: Vespula vulgaris

<400> SEQUENCE: 924
gcaacgcgtt ttctctattg cggtgcaact ataataactc cgcaa          45

<210> SEQ ID NO 925
<211> LENGTH: 45
<212> TYPE: DNA
<213> ORGANISM: Vespula vulgaris

<400> SEQUENCE: 925
tcttttgcag tggaatcaat agcatcgaaa atgactataa aattc          45

<210> SEQ ID NO 926
<211> LENGTH: 45
<212> TYPE: DNA
<213> ORGANISM: Vespula vulgaris

<400> SEQUENCE: 926
tgtcttccgt tctattacat gcagcgaaac tttgtagaca ctgtt         45

<210> SEQ ID NO 927
<211> LENGTH: 45
<212> TYPE: DNA
<213> ORGANISM: Vespula vulgaris

<400> SEQUENCE: 927
ccaattttat ggcaaaatcc aaaaagcaaa cgtattttcc ttctt         45

<210> SEQ ID NO 928
<211> LENGTH: 45
<212> TYPE: DNA
<213> ORGANISM: Vespula vulgaris

<400> SEQUENCE: 928
tgcgtcaagt atcactttct ggctacacct aagcaacttt gtaca         45

<210> SEQ ID NO 929
<211> LENGTH: 45
<212> TYPE: DNA
<213> ORGANISM: Vespula vulgaris

<400> SEQUENCE: 929
gtgaatgaat atcctatgat ggctggtata atacatcttg caacg         45

<210> SEQ ID NO 930
<211> LENGTH: 45
<212> TYPE: DNA
<213> ORGANISM: Vespula vulgaris

<400> SEQUENCE: 930
acatgggcaa ttaacgatac aaaggcaact caactttatc ttatt         45

<210> SEQ ID NO 931
<211> LENGTH: 45
<212> TYPE: DNA
<213> ORGANISM: Vespula vulgaris

<400> SEQUENCE: 931
catccgaatt ataggccaaa attaaacgat ttagctgtta taaaa         45

<210> SEQ ID NO 932
<211> LENGTH: 45
<212> TYPE: DNA
<213> ORGANISM: Vespula vulgaris

<400> SEQUENCE: 932
aattgtcggt ggagtgctag gagcaatact cgaattaaat tgaat         45

<210> SEQ ID NO 933
<211> LENGTH: 45
<212> TYPE: DNA
<213> ORGANISM: Vespula vulgaris

<400> SEQUENCE: 933
ggtgcaacta taataactcc gcaacatgta ttaacggctg ctcat    45

<210> SEQ ID NO 934
<211> LENGTH: 45
<212> TYPE: DNA
<213> ORGANISM: Vespula vulgaris

<400> SEQUENCE: 934
aggccaaaat taaacgattt agctgttata aaattgcaga agagg    45

<210> SEQ ID NO 935
<211> LENGTH: 45
<212> TYPE: DNA
<213> ORGANISM: Vespula vulgaris

<400> SEQUENCE: 935
gtaggatggg gtcttacgaa tttttatggt gtcaagtctg aagtt    45

<210> SEQ ID NO 936
<211> LENGTH: 45
<212> TYPE: DNA
<213> ORGANISM: Vespula vulgaris

<400> SEQUENCE: 936
tttgtagaca ctgttgttac agctgtagga tggggtctta cgaat    45

<210> SEQ ID NO 937
<211> LENGTH: 45
<212> TYPE: DNA
<213> ORGANISM: Vespula vulgaris

<400> SEQUENCE: 937
cagcgaaact ttgtagacac tgttgttaca gctgtaggat ggggt    45

<210> SEQ ID NO 938
<211> LENGTH: 45
<212> TYPE: DNA
<213> ORGANISM: Vespula vulgaris

<400> SEQUENCE: 938
tgtggattaa attcttttgc agtggaatca atagcatcga aaatg    45

<210> SEQ ID NO 939
<211> LENGTH: 45
<212> TYPE: DNA
<213> ORGANISM: Vespula vulgaris

<400> SEQUENCE: 939
ttaaaatatt ctatgagaat tggtccagct tgtcttccgt tctat    45

<210> SEQ ID NO 940
<211> LENGTH: 45
<212> TYPE: DNA
<213> ORGANISM: Vespula vulgaris

<400> SEQUENCE: 940
gagtacgttt tctgtggatt aaattctttt gcagtggaat caata    45

<210> SEQ ID NO 941
<211> LENGTH: 45
<212> TYPE: DNA
<213> ORGANISM: Vespula vulgaris

<400> SEQUENCE: 941
tataaaagga ttttatatat tctaggagtt gttgttggag aacat      45

<210> SEQ ID NO 942
<211> LENGTH: 45
<212> TYPE: DNA
<213> ORGANISM: Vespula vulgaris

<400> SEQUENCE: 942
atggctggta taatacatct tgcaacgcgt tttctctatt gcggt      45

<210> SEQ ID NO 943
<211> LENGTH: 45
<212> TYPE: DNA
<213> ORGANISM: Vespula vulgaris

<400> SEQUENCE: 943
cttacgaatt tttatggtgt caagtctgaa gttttgagaa aagtc      45

<210> SEQ ID NO 944
<211> LENGTH: 45
<212> TYPE: DNA
<213> ORGANISM: Vespula vulgaris

<400> SEQUENCE: 944
tgtcttccgt tctattacat gcagcgaaac tttgtagaca ctgtt      45

<210> SEQ ID NO 945
<211> LENGTH: 45
<212> TYPE: DNA
<213> ORGANISM: Vespula vulgaris

<400> SEQUENCE: 945 cgtatttcc ttcttggagt catcaattat ggaagaacat gtgcc       45

<210> SEQ ID NO 946
<211> LENGTH: 45
<212> TYPE: DNA
<213> ORGANISM: Vespula vulgaris

<400> SEQUENCE: 946
tcttttgcag tggaatcaat agcatcgaaa atgactataa aattc      45

<210> SEQ ID NO 947
<211> LENGTH: 45
<212> TYPE: DNA
<213> ORGANISM: Vespula vulgaris

<400> SEQUENCE: 947
gcaacgcgtt ttctctattg cggtgcaact ataataactc cgcaa      45

<210> SEQ ID NO 948
<211> LENGTH: 45
<212> TYPE: DNA
<213> ORGANISM: Vespula vulgaris

<400> SEQUENCE: 948
tgcgttgcga ggtataaaag gattttatat attctaggag ttgtt      45

<210> SEQ ID NO 949
<211> LENGTH: 45
<212> TYPE: DNA
<213> ORGANISM: Vespula vulgaris

<400> SEQUENCE: 949
gtagacactg ttgttacagc tgtaggatgg ggtcttacga atttt    45

<210> SEQ ID NO 950
<211> LENGTH: 45
<212> TYPE: DNA
<213> ORGANISM: Vespula vulgaris

<400> SEQUENCE: 950
gtgaatgaat atcctatgat ggctggtata atacatcttg caacg    45

<210> SEQ ID NO 951
<211> LENGTH: 45
<212> TYPE: DNA
<213> ORGANISM: Vespula vulgaris

<400> SEQUENCE: 951
gaatatccta tgatggctgg tataatacat cttgcaacgc gtttt    45

<210> SEQ ID NO 952
<211> LENGTH: 45
<212> TYPE: DNA
<213> ORGANISM: Vespula vulgaris

<400> SEQUENCE: 952
tgcgtcaagt atcactttct ggctacacct aagcaacttt gtaca    45

<210> SEQ ID NO 953
<211> LENGTH: 45
<212> TYPE: DNA
<213> ORGANISM: Vespula vulgaris

<400> SEQUENCE: 953
ttaaaatatt ctatgagaat tggtccagct tgtcttccgt tctat    45

<210> SEQ ID NO 954
<211> LENGTH: 45
<212> TYPE: DNA
<213> ORGANISM: Vespula vulgaris

<400> SEQUENCE: 954
acatgggcaa ttaacgatac aaaggcaact caactttatc ttatt    45

<210> SEQ ID NO 955
<211> LENGTH: 45
<212> TYPE: DNA
<213> ORGANISM: Vespula vulgaris

<400> SEQUENCE: 955
gtaggatggg gtcttacgaa tttttatggt gtcaagtctg aagtt    45

<210> SEQ ID NO 956
<211> LENGTH: 45
<212> TYPE: DNA
<213> ORGANISM: Vespula vulgaris

<400> SEQUENCE: 956
atggctggta taatacatct tgcaacgcgt tttctctatt gcggt    45

<210> SEQ ID NO 957
<211> LENGTH: 45
<212> TYPE: DNA
<213> ORGANISM: Vespula vulgaris
<210> SEQ ID NO 958
<211> LENGTH: 45
<212> TYPE: DNA
<213> ORGANISM: Vespula vulgaris

<400> SEQUENCE: 958
cttacgaatt tttatggtgt caagtctgaa gttttgagaa aagtc    45

<210> SEQ ID NO 959
<211> LENGTH: 45
<212> TYPE: DNA
<213> ORGANISM: Vespula vulgaris

<400> SEQUENCE: 959
gagtacgttt tctgtggatt aaattctttt gcagtggaat caata    45

<210> SEQ ID NO 960
<211> LENGTH: 45
<212> TYPE: DNA
<213> ORGANISM: Vespula vulgaris

<400> SEQUENCE: 960
ccaattttat ggcaaaatcc aaaaagcaaa cgtattttcc ttctt    45

<210> SEQ ID NO 961
<211> LENGTH: 45
<212> TYPE: DNA
<213> ORGANISM: Vespula vulgaris

<400> SEQUENCE: 961
gcaacgcgtt ttctctattg cggtgcaact ataataactc cgcaa    45

<210> SEQ ID NO 962
<211> LENGTH: 45
<212> TYPE: DNA
<213> ORGANISM: Vespula vulgaris

<400> SEQUENCE: 962
aattgtcggt ggagtgctag gagcaatact cgaattaaat tgaat    45

<210> SEQ ID NO 963
<211> LENGTH: 45
<212> TYPE: DNA
<213> ORGANISM: Vespula vulgaris

<400> SEQUENCE: 963
tcttttgcag tggaatcaat agcatcgaaa atgactataa aattc    45

<210> SEQ ID NO 964
<211> LENGTH: 45
<212> TYPE: DNA
<213> ORGANISM: Vespula vulgaris

<400> SEQUENCE: 964
aggccaaaat taaacgattt agctgttata aaattgcaga agagg    45

<210> SEQ ID NO 965
<211> LENGTH: 45
<212> TYPE: DNA (Note: SEQ ID NO 957 shown at top of continued section)

<400> SEQUENCE: 957
tataaaagga ttttatatat tctaggagtt gttgttggag aacat    45

<213> ORGANISM: Vespula vulgaris

<400> SEQUENCE: 965
tataaaagga ttttatatat tctaggagtt gttgttggag aacat    45

<210> SEQ ID NO 966
<211> LENGTH: 45
<212> TYPE: DNA
<213> ORGANISM: Vespula vulgaris

<400> SEQUENCE: 966
gagtacgttt tctgtggatt aaattctttt gcagtggaat caata    45

<210> SEQ ID NO 967
<211> LENGTH: 45
<212> TYPE: DNA
<213> ORGANISM: Vespula vulgaris

<400> SEQUENCE: 967
cttacgaatt tttatggtgt caagtctgaa gttttgagaa aagtc    45

<210> SEQ ID NO 968
<211> LENGTH: 45
<212> TYPE: DNA
<213> ORGANISM: Vespula vulgaris

<400> SEQUENCE: 968
atggctggta taatacatct tgcaacgcgt tttctctatt gcggt    45

<210> SEQ ID NO 969
<211> LENGTH: 45
<212> TYPE: DNA
<213> ORGANISM: Vespula vulgaris

<400> SEQUENCE: 969
cgtattttcc ttcttggagt catcaattat ggaagaacat gtgcc    45

<210> SEQ ID NO 970
<211> LENGTH: 45
<212> TYPE: DNA
<213> ORGANISM: Vespula vulgaris

<400> SEQUENCE: 970
tcttttgcag tggaatcaat agcatcgaaa atgactataa aattc    45

<210> SEQ ID NO 971
<211> LENGTH: 45
<212> TYPE: DNA
<213> ORGANISM: Vespula vulgaris

<400> SEQUENCE: 971
tgtcttccgt tctattacat gcagcgaaac tttgtagaca ctgtt    45

<210> SEQ ID NO 972
<211> LENGTH: 45
<212> TYPE: DNA
<213> ORGANISM: Vespula vulgaris

<400> SEQUENCE: 972
gcaacgcgtt ttctctattg cggtgcaact ataataactc cgcaa    45

<210> SEQ ID NO 973
<211> LENGTH: 45

```
<212> TYPE: DNA
<213> ORGANISM: Vespula vulgaris

<400> SEQUENCE: 973
tttgtagaca ctgttgttac agctgtagga tggggtctta cgaat          45

<210> SEQ ID NO 974
<211> LENGTH: 45
<212> TYPE: DNA
<213> ORGANISM: Vespula vulgaris

<400> SEQUENCE: 974
gagtacgttt tctgtggatt aaattctttt gcagtggaat caata          45

<210> SEQ ID NO 975
<211> LENGTH: 45
<212> TYPE: DNA
<213> ORGANISM: Vespula vulgaris

<400> SEQUENCE: 975
cttacgaatt tttatggtgt caagtctgaa gttttgagaa aagtc          45

<210> SEQ ID NO 976
<211> LENGTH: 45
<212> TYPE: DNA
<213> ORGANISM: Vespula vulgaris

<400> SEQUENCE: 976
atggctggta taatacatct tgcaacgcgt tttctctatt gcggt          45

<210> SEQ ID NO 977
<211> LENGTH: 45
<212> TYPE: DNA
<213> ORGANISM: Vespula vulgaris

<400> SEQUENCE: 977
tataaaagga ttttatatat tctaggagtt gttgttggag aacat          45

<210> SEQ ID NO 978
<211> LENGTH: 45
<212> TYPE: DNA
<213> ORGANISM: Vespula vulgaris

<400> SEQUENCE: 978
gcgaggtata aaaggatttt atatattcta ggagttgttg ttgga          45

<210> SEQ ID NO 979
<211> LENGTH: 45
<212> TYPE: DNA
<213> ORGANISM: Vespula vulgaris

<400> SEQUENCE: 979
gcaacgcgtt ttctctattg cggtgcaact ataataactc cgcaa          45

<210> SEQ ID NO 980
<211> LENGTH: 45
<212> TYPE: DNA
<213> ORGANISM: Vespula vulgaris

<400> SEQUENCE: 980
tcttttgcag tggaatcaat agcatcgaaa atgactataa aattc          45

<210> SEQ ID NO 981
```

```
<211> LENGTH: 45
<212> TYPE: DNA
<213> ORGANISM: Vespula vulgaris

<400> SEQUENCE: 981
tgtcttccgt tctattacat gcagcgaaac tttgtagaca ctgtt              45

<210> SEQ ID NO 982
<211> LENGTH: 45
<212> TYPE: DNA
<213> ORGANISM: Vespula vulgaris

<400> SEQUENCE: 982
ccaattttat ggcaaaatcc aaaaagcaaa cgtattttcc ttctt              45

<210> SEQ ID NO 983
<211> LENGTH: 45
<212> TYPE: DNA
<213> ORGANISM: Vespula vulgaris

<400> SEQUENCE: 983
tgcgtcaagt atcactttct ggctacacct aagcaacttt gtaca              45

<210> SEQ ID NO 984
<211> LENGTH: 45
<212> TYPE: DNA
<213> ORGANISM: Vespula vulgaris

<400> SEQUENCE: 984
gtgaatgaat atcctatgat ggctggtata atacatcttg caacg              45

<210> SEQ ID NO 985
<211> LENGTH: 45
<212> TYPE: DNA
<213> ORGANISM: Vespula vulgaris

<400> SEQUENCE: 985
acatgggcaa ttaacgatac aaaggcaact caactttatc ttatt              45

<210> SEQ ID NO 986
<211> LENGTH: 45
<212> TYPE: DNA
<213> ORGANISM: Vespula vulgaris

<400> SEQUENCE: 986
catccgaatt ataggccaaa attaaacgat ttagctgtta taaaa              45

<210> SEQ ID NO 987
<211> LENGTH: 45
<212> TYPE: DNA
<213> ORGANISM: Vespula vulgaris

<400> SEQUENCE: 987
aattgtcggt ggagtgctag gagcaatact cgaattaaat tgaat              45

<210> SEQ ID NO 988
<211> LENGTH: 45
<212> TYPE: DNA
<213> ORGANISM: Vespula vulgaris

<400> SEQUENCE: 988
ggtgcaacta taataactcc gcaacatgta ttaacggctg ctcat              45
```

<210> SEQ ID NO 989
<211> LENGTH: 45
<212> TYPE: DNA
<213> ORGANISM: Vespula vulgaris

<400> SEQUENCE: 989
aggccaaaat taaacgattt agctgttata aaattgcaga agagg    45

<210> SEQ ID NO 990
<211> LENGTH: 45
<212> TYPE: DNA
<213> ORGANISM: Vespula vulgaris

<400> SEQUENCE: 990
gtaggatggg gtcttacgaa tttttatggt gtcaagtctg aagtt    45

<210> SEQ ID NO 991
<211> LENGTH: 45
<212> TYPE: DNA
<213> ORGANISM: Vespula vulgaris

<400> SEQUENCE: 991
tttgtagaca ctgttgttac agctgtagga tggggtctta cgaat    45

<210> SEQ ID NO 992
<211> LENGTH: 45
<212> TYPE: DNA
<213> ORGANISM: Vespula vulgaris

<400> SEQUENCE: 992
cagcgaaact ttgtagacac tgttgttaca gctgtaggat ggggt    45

<210> SEQ ID NO 993
<211> LENGTH: 45
<212> TYPE: DNA
<213> ORGANISM: Vespula vulgaris

<400> SEQUENCE: 993
tgtggattaa attcttttgc agtggaatca atagcatcga aaatg    45

<210> SEQ ID NO 994
<211> LENGTH: 45
<212> TYPE: DNA
<213> ORGANISM: Vespula vulgaris

<400> SEQUENCE: 994
ttaaaatatt ctatgagaat tggtccagct tgtcttccgt tctat    45

<210> SEQ ID NO 995
<211> LENGTH: 45
<212> TYPE: DNA
<213> ORGANISM: Vespula vulgaris

<400> SEQUENCE: 995
tataaaagga ttttatatat tctaggagtt gttgttggag aacat    45

<210> SEQ ID NO 996
<211> LENGTH: 45
<212> TYPE: DNA
<213> ORGANISM: Vespula vulgaris

<400> SEQUENCE: 996
cttacgaatt tttatggtgt caagtctgaa gttttgagaa aagtc    45

<210> SEQ ID NO 997
<211> LENGTH: 45
<212> TYPE: DNA
<213> ORGANISM: Vespula vulgaris

<400> SEQUENCE: 997
gagtacgttt tctgtggatt aaattctttt gcagtggaat caata           45

<210> SEQ ID NO 998
<211> LENGTH: 45
<212> TYPE: DNA
<213> ORGANISM: Vespula vulgaris

<400> SEQUENCE: 998
atggctggta taatacatct tgcaacgcgt tttctctatt gcggt           45

<210> SEQ ID NO 999
<211> LENGTH: 45
<212> TYPE: DNA
<213> ORGANISM: Vespula vulgaris

<400> SEQUENCE: 999
tcttttgcag tggaatcaat agcatcgaaa atgactataa aattc           45

<210> SEQ ID NO 1000
<211> LENGTH: 45
<212> TYPE: DNA
<213> ORGANISM: Vespula vulgaris

<400> SEQUENCE: 1000
tgtcttccgt tctattacat gcagcgaaac tttgtagaca ctgtt           45

<210> SEQ ID NO 1001
<211> LENGTH: 45
<212> TYPE: DNA
<213> ORGANISM: Vespula vulgaris

<400> SEQUENCE: 1001
cgtattttcc ttcttggagt catcaattat ggaagaacat gtgcc           45

<210> SEQ ID NO 1002
<211> LENGTH: 45
<212> TYPE: DNA
<213> ORGANISM: Vespula vulgaris

<400> SEQUENCE: 1002
gtgaatgaat atcctatgat ggctggtata atacatcttg caacg           45

<210> SEQ ID NO 1003
<211> LENGTH: 45
<212> TYPE: DNA
<213> ORGANISM: Vespula vulgaris

<400> SEQUENCE: 1003
gcaacgcgtt ttctctattg cggtgcaact ataataactc cgcaa           45

<210> SEQ ID NO 1004
<211> LENGTH: 45
<212> TYPE: DNA
<213> ORGANISM: Vespula vulgaris

<400> SEQUENCE: 1004
tgcgttgcga ggtataaaag gattttatat attctaggag ttgtt           45

<210> SEQ ID NO 1005
<211> LENGTH: 45
<212> TYPE: DNA
<213> ORGANISM: Vespula vulgaris

<400> SEQUENCE: 1005
gtagacactg ttgttacagc tgtaggatgg ggtcttacga atttt    45

<210> SEQ ID NO 1006
<211> LENGTH: 45
<212> TYPE: DNA
<213> ORGANISM: Vespula vulgaris

<400> SEQUENCE: 1006
gtaggatggg gtcttacgaa tttttatggt gtcaagtctg aagtt    45

<210> SEQ ID NO 1007
<211> LENGTH: 45
<212> TYPE: DNA
<213> ORGANISM: Vespula vulgaris

<400> SEQUENCE: 1007
gagtacgttt tctgtggatt aaattctttt gcagtggaat caata    45

<210> SEQ ID NO 1008
<211> LENGTH: 45
<212> TYPE: DNA
<213> ORGANISM: Vespula vulgaris

<400> SEQUENCE: 1008
cttacgaatt tttatggtgt caagtctgaa gttttgagaa aagtc    45

<210> SEQ ID NO 1009
<211> LENGTH: 45
<212> TYPE: DNA
<213> ORGANISM: Vespula vulgaris

<400> SEQUENCE: 1009
atggctggta taatacatct tgcaacgcgt tttctctatt gcggt    45

<210> SEQ ID NO 1010
<211> LENGTH: 45
<212> TYPE: DNA
<213> ORGANISM: Vespula vulgaris

<400> SEQUENCE: 1010
tataaaagga ttttatatat tctaggagtt gttgttggag aacat    45

<210> SEQ ID NO 1011
<211> LENGTH: 45
<212> TYPE: DNA
<213> ORGANISM: Vespula vulgaris

<400> SEQUENCE: 1011
gcgaggtata aaaggatttt atatattcta ggagttgttg ttgga    45

<210> SEQ ID NO 1012
<211> LENGTH: 45
<212> TYPE: DNA
<213> ORGANISM: Vespula vulgaris

<400> SEQUENCE: 1012
gcaacgcgtt ttctctattg cggtgcaact ataataactc cgcaa         45

<210> SEQ ID NO 1013
<211> LENGTH: 45
<212> TYPE: DNA
<213> ORGANISM: Vespula vulgaris

<400> SEQUENCE: 1013
tcttttgcag tggaatcaat agcatcgaaa atgactataa aattc         45

<210> SEQ ID NO 1014
<211> LENGTH: 45
<212> TYPE: DNA
<213> ORGANISM: Vespula vulgaris

<400> SEQUENCE: 1014
tgtcttccgt tctattacat gcagcgaaac tttgtagaca ctgtt         45

<210> SEQ ID NO 1015
<211> LENGTH: 45
<212> TYPE: DNA
<213> ORGANISM: Vespula vulgaris

<400> SEQUENCE: 1015
ccaattttat ggcaaaatcc aaaaagcaaa cgtattttcc ttctt         45

<210> SEQ ID NO 1016
<211> LENGTH: 45
<212> TYPE: DNA
<213> ORGANISM: Vespula vulgaris

<400> SEQUENCE: 1016
tgcgtcaagt atcactttct ggctacacct aagcaacttt gtaca         45

<210> SEQ ID NO 1017
<211> LENGTH: 45
<212> TYPE: DNA
<213> ORGANISM: Vespula vulgaris

<400> SEQUENCE: 1017
gtgaatgaat atcctatgat ggctggtata atacatcttg caacg         45

<210> SEQ ID NO 1018
<211> LENGTH: 45
<212> TYPE: DNA
<213> ORGANISM: Vespula vulgaris

<400> SEQUENCE: 1018
acatgggcaa ttaacgatac aaaggcaact caactttatc ttatt         45

<210> SEQ ID NO 1019
<211> LENGTH: 45
<212> TYPE: DNA
<213> ORGANISM: Vespula vulgaris

<400> SEQUENCE: 1019
catccgaatt ataggccaaa attaaacgat ttagctgtta taaaa         45

<210> SEQ ID NO 1020
<211> LENGTH: 45
<212> TYPE: DNA
<213> ORGANISM: Vespula vulgaris

<400> SEQUENCE: 1020
aattgtcggt ggagtgctag gagcaatact cgaattaaat tgaat                     45

<210> SEQ ID NO 1021
<211> LENGTH: 45
<212> TYPE: DNA
<213> ORGANISM: Vespula vulgaris

<400> SEQUENCE: 1021
ggtgcaacta taataactcc gcaacatgta ttaacggctg ctcat                     45

<210> SEQ ID NO 1022
<211> LENGTH: 45
<212> TYPE: DNA
<213> ORGANISM: Vespula vulgaris

<400> SEQUENCE: 1022
aggccaaaat taaacgattt agctgttata aaattgcaga agagg                     45

<210> SEQ ID NO 1023
<211> LENGTH: 45
<212> TYPE: DNA
<213> ORGANISM: Vespula vulgaris

<400> SEQUENCE: 1023
gtaggatggg gtcttacgaa tttttatggt gtcaagtctg aagtt                     45

<210> SEQ ID NO 1024
<211> LENGTH: 45
<212> TYPE: DNA
<213> ORGANISM: Vespula vulgaris

<400> SEQUENCE: 1024
tttgtagaca ctgttgttac agctgtagga tggggtctta cgaat                     45

<210> SEQ ID NO 1025
<211> LENGTH: 45
<212> TYPE: DNA
<213> ORGANISM: Vespula vulgaris

<400> SEQUENCE: 1025
cagcgaaact ttgtagacac tgttgttaca gctgtaggat ggggt                     45

<210> SEQ ID NO 1026
<211> LENGTH: 45
<212> TYPE: DNA
<213> ORGANISM: Vespula vulgaris

<400> SEQUENCE: 1026
tgtggattaa attcttttgc agtggaatca atagcatcga aaatg                     45

<210> SEQ ID NO 1027
<211> LENGTH: 45
<212> TYPE: DNA
<213> ORGANISM: Vespula vulgaris

<400> SEQUENCE: 1027
ttaaaatatt ctatgagaat tggtccagct tgtcttccgt tctat                     45

<210> SEQ ID NO 1028
<211> LENGTH: 45
<212> TYPE: DNA
<213> ORGANISM: Vespula vulgaris

```
<400> SEQUENCE: 1028
gagtacgttt tctgtggatt aaattctttt gcagtggaat caata              45

<210> SEQ ID NO 1029
<211> LENGTH: 45
<212> TYPE: DNA
<213> ORGANISM: Vespula vulgaris

<400> SEQUENCE: 1029
cttacgaatt tttatggtgt caagtctgaa gttttgagaa aagtc              45

<210> SEQ ID NO 1030
<211> LENGTH: 45
<212> TYPE: DNA
<213> ORGANISM: Vespula vulgaris

<400> SEQUENCE: 1030
atggctggta taatacatct tgcaacgcgt tttctctatt gcggt              45

<210> SEQ ID NO 1031
<211> LENGTH: 45
<212> TYPE: DNA
<213> ORGANISM: Vespula vulgaris

<400> SEQUENCE: 1031
tataaaagga ttttatatat tctaggagtt gttgttggag aacat              45

<210> SEQ ID NO 1032
<211> LENGTH: 45
<212> TYPE: DNA
<213> ORGANISM: Vespula vulgaris

<400> SEQUENCE: 1032
gcgaggtata aaaggatttt atatattcta ggagttgttg ttgga              45

<210> SEQ ID NO 1033
<211> LENGTH: 45
<212> TYPE: DNA
<213> ORGANISM: Vespula vulgaris

<400> SEQUENCE: 1033
gcaacgcgtt ttctctattg cggtgcaact ataataactc cgcaa              45

<210> SEQ ID NO 1034
<211> LENGTH: 45
<212> TYPE: DNA
<213> ORGANISM: Vespula vulgaris

<400> SEQUENCE: 1034
tcttttgcag tggaatcaat agcatcgaaa atgactataa aattc              45

<210> SEQ ID NO 1035
<211> LENGTH: 45
<212> TYPE: DNA
<213> ORGANISM: Vespula vulgaris

<400> SEQUENCE: 1035
tgtcttccgt tctattacat gcagcgaaac tttgtagaca ctgtt              45

<210> SEQ ID NO 1036
<211> LENGTH: 45
<212> TYPE: DNA
<213> ORGANISM: Vespula vulgaris
```

```
<400> SEQUENCE: 1036
ccaattttat ggcaaaatcc aaaaagcaaa cgtattttcc ttctt                  45

<210> SEQ ID NO 1037
<211> LENGTH: 45
<212> TYPE: DNA
<213> ORGANISM: Vespula vulgaris

<400> SEQUENCE: 1037
tgcgtcaagt atcactttct ggctacacct aagcaacttt gtaca                  45

<210> SEQ ID NO 1038
<211> LENGTH: 45
<212> TYPE: DNA
<213> ORGANISM: Vespula vulgaris

<400> SEQUENCE: 1038
gtgaatgaat atcctatgat ggctggtata atacatcttg caacg                  45

<210> SEQ ID NO 1039
<211> LENGTH: 45
<212> TYPE: DNA
<213> ORGANISM: Vespula vulgaris

<400> SEQUENCE: 1039
acatgggcaa ttaacgatac aaaggcaact caactttatc ttatt                  45

<210> SEQ ID NO 1040
<211> LENGTH: 45
<212> TYPE: DNA
<213> ORGANISM: Vespula vulgaris

<400> SEQUENCE: 1040
catccgaatt ataggccaaa attaaacgat ttagctgtta taaaa                  45

<210> SEQ ID NO 1041
<211> LENGTH: 45
<212> TYPE: DNA
<213> ORGANISM: Vespula vulgaris

<400> SEQUENCE: 1041
aattgtcggt ggagtgctag gagcaatact cgaattaaat tgaat                  45

<210> SEQ ID NO 1042
<211> LENGTH: 45
<212> TYPE: DNA
<213> ORGANISM: Vespula vulgaris

<400> SEQUENCE: 1042
ggtgcaacta taataactcc gcaacatgta ttaacggctg ctcat                  45

<210> SEQ ID NO 1043
<211> LENGTH: 45
<212> TYPE: DNA
<213> ORGANISM: Vespula vulgaris

<400> SEQUENCE: 1043
aggccaaaat taaacgattt agctgttata aaattgcaga agagg                  45

<210> SEQ ID NO 1044
<211> LENGTH: 45
<212> TYPE: DNA
```

```
<213> ORGANISM: Vespula vulgaris

<400> SEQUENCE: 1044
gtaggatggg gtcttacgaa tttttatggt gtcaagtctg aagtt            45

<210> SEQ ID NO 1045
<211> LENGTH: 45
<212> TYPE: DNA
<213> ORGANISM: Vespula vulgaris

<400> SEQUENCE: 1045
tttgtagaca ctgttgttac agctgtagga tggggtctta cgaat            45

<210> SEQ ID NO 1046
<211> LENGTH: 45
<212> TYPE: DNA
<213> ORGANISM: Vespula vulgaris

<400> SEQUENCE: 1046
cagcgaaact tgtagacac tgttgttaca gctgtaggat ggggt             45

<210> SEQ ID NO 1047
<211> LENGTH: 45
<212> TYPE: DNA
<213> ORGANISM: Vespula vulgaris

<400> SEQUENCE: 1047
tgtggattaa attcttttgc agtggaatca atagcatcga aaatg            45

<210> SEQ ID NO 1048
<211> LENGTH: 45
<212> TYPE: DNA
<213> ORGANISM: Vespula vulgaris

<400> SEQUENCE: 1048
ttaaaatatt ctatgagaat tggtccagct tgtcttccgt tctat            45

<210> SEQ ID NO 1049
<211> LENGTH: 45
<212> TYPE: DNA
<213> ORGANISM: Vespula vulgaris

<400> SEQUENCE: 1049
gagtacgttt tctgtggatt aaattctttt gcagtggaat caata            45

<210> SEQ ID NO 1050
<211> LENGTH: 45
<212> TYPE: DNA
<213> ORGANISM: Vespula vulgaris

<400> SEQUENCE: 1050
cttacgaatt tttatggtgt caagtctgaa gttttgagaa aagtc            45

<210> SEQ ID NO 1051
<211> LENGTH: 45
<212> TYPE: DNA
<213> ORGANISM: Vespula vulgaris

<400> SEQUENCE: 1051
tataaaagga ttttatatat tctaggagtt gttgttggag aacat            45

<210> SEQ ID NO 1052
<211> LENGTH: 45
```

<212> TYPE: DNA
<213> ORGANISM: Vespula vulgaris

<400> SEQUENCE: 1052
atggctggta taatacatct tgcaacgcgt tttctctatt gcggt                45

<210> SEQ ID NO 1053
<211> LENGTH: 45
<212> TYPE: DNA
<213> ORGANISM: Vespula vulgaris

<400> SEQUENCE: 1053
ccaattttat ggcaaaatcc aaaaagcaaa cgtattttcc ttctt                45

<210> SEQ ID NO 1054
<211> LENGTH: 45
<212> TYPE: DNA
<213> ORGANISM: Vespula vulgaris

<400> SEQUENCE: 1054
tcttttgcag tggaatcaat agcatcgaaa atgactataa aattc                45

<210> SEQ ID NO 1055
<211> LENGTH: 45
<212> TYPE: DNA
<213> ORGANISM: Vespula vulgaris

<400> SEQUENCE: 1055
gcaacgcgtt ttctctattg cggtgcaact ataataactc cgcaa                45

<210> SEQ ID NO 1056
<211> LENGTH: 45
<212> TYPE: DNA
<213> ORGANISM: Vespula vulgaris

<400> SEQUENCE: 1056
tgtcttccgt tctattacat gcagcgaaac tttgtagaca ctgtt                45

<210> SEQ ID NO 1057
<211> LENGTH: 45
<212> TYPE: DNA
<213> ORGANISM: Vespula vulgaris

<400> SEQUENCE: 1057
gttgcgaggt ataaaaggat tttatatatt ctaggagttg ttgtt                45

<210> SEQ ID NO 1058
<211> LENGTH: 45
<212> TYPE: DNA
<213> ORGANISM: Vespula vulgaris

<400> SEQUENCE: 1058
gtgaatgaat atcctatgat ggctggtata atacatcttg caacg                45

<210> SEQ ID NO 1059
<211> LENGTH: 45
<212> TYPE: DNA
<213> ORGANISM: Vespula vulgaris

<400> SEQUENCE: 1059
aattgtcggt ggagtgctag gagcaatact cgaattaaat tgaat                45

<210> SEQ ID NO 1060

```
<211> LENGTH: 45
<212> TYPE: DNA
<213> ORGANISM: Vespula vulgaris

<400> SEQUENCE: 1060
tgcgtcaagt atcactttct ggctacacct aagcaacttt gtaca              45

<210> SEQ ID NO 1061
<211> LENGTH: 45
<212> TYPE: DNA
<213> ORGANISM: Vespula vulgaris

<400> SEQUENCE: 1061
catccgaatt ataggccaaa attaaacgat ttagctgtta taaaa              45

<210> SEQ ID NO 1062
<211> LENGTH: 45
<212> TYPE: DNA
<213> ORGANISM: Vespula vulgaris

<400> SEQUENCE: 1062
aggccaaaat taaacgattt agctgttata aaattgcaga agagg              45

<210> SEQ ID NO 1063
<211> LENGTH: 45
<212> TYPE: DNA
<213> ORGANISM: Vespula vulgaris

<400> SEQUENCE: 1063
gtaggatggg gtcttacgaa tttttatggt gtcaagtctg aagtt              45

<210> SEQ ID NO 1064
<211> LENGTH: 45
<212> TYPE: DNA
<213> ORGANISM: Vespula vulgaris

<400> SEQUENCE: 1064
acatgggcaa ttaacgatac aaaggcaact caactttatc ttatt              45

<210> SEQ ID NO 1065
<211> LENGTH: 45
<212> TYPE: DNA
<213> ORGANISM: Vespula vulgaris

<400> SEQUENCE: 1065
gagtacgttt tctgtggatt aaattctttt gcagtggaat caata              45

<210> SEQ ID NO 1066
<211> LENGTH: 45
<212> TYPE: DNA
<213> ORGANISM: Vespula vulgaris

<400> SEQUENCE: 1066
cttacgaatt tttatggtgt caagtctgaa gttttgagaa aagtc              45

<210> SEQ ID NO 1067
<211> LENGTH: 45
<212> TYPE: DNA
<213> ORGANISM: Vespula vulgaris

<400> SEQUENCE: 1067
tataaaagga ttttatatat tctaggagtt gttgttggag aacat              45
```

```
<210> SEQ ID NO 1068
<211> LENGTH: 45
<212> TYPE: DNA
<213> ORGANISM: Vespula vulgaris

<400> SEQUENCE: 1068
atggctggta taatacatct tgcaacgcgt tttctctatt gcggt          45

<210> SEQ ID NO 1069
<211> LENGTH: 45
<212> TYPE: DNA
<213> ORGANISM: Vespula vulgaris

<400> SEQUENCE: 1069
ccaattttat ggcaaaatcc aaaaagcaaa cgtattttcc ttctt          45

<210> SEQ ID NO 1070
<211> LENGTH: 45
<212> TYPE: DNA
<213> ORGANISM: Vespula vulgaris

<400> SEQUENCE: 1070
gcgaggtata aaggatttt atatattcta ggagttgttg ttgga           45

<210> SEQ ID NO 1071
<211> LENGTH: 45
<212> TYPE: DNA
<213> ORGANISM: Vespula vulgaris

<400> SEQUENCE: 1071
gcaacgcgtt ttctctattg cggtgcaact ataataactc cgcaa          45

<210> SEQ ID NO 1072
<211> LENGTH: 45
<212> TYPE: DNA
<213> ORGANISM: Vespula vulgaris

<400> SEQUENCE: 1072
tcttttgcag tggaatcaat agcatcgaaa atgactataa aattc          45

<210> SEQ ID NO 1073
<211> LENGTH: 45
<212> TYPE: DNA
<213> ORGANISM: Vespula vulgaris

<400> SEQUENCE: 1073
tgtcttccgt tctattacat gcagcgaaac tttgtagaca ctgtt          45

<210> SEQ ID NO 1074
<211> LENGTH: 45
<212> TYPE: DNA
<213> ORGANISM: Vespula vulgaris

<400> SEQUENCE: 1074
tgcgtcaagt atcactttct ggctacacct aagcaacttt gtaca          45

<210> SEQ ID NO 1075
<211> LENGTH: 45
<212> TYPE: DNA
<213> ORGANISM: Vespula vulgaris

<400> SEQUENCE: 1075
aattgtcggt ggagtgctag gagcaatact cgaattaaat tgaat          45
```

<210> SEQ ID NO 1076
<211> LENGTH: 45
<212> TYPE: DNA
<213> ORGANISM: Vespula vulgaris

<400> SEQUENCE: 1076
catccgaatt ataggccaaa attaaacgat ttagctgtta taaaa            45

<210> SEQ ID NO 1077
<211> LENGTH: 45
<212> TYPE: DNA
<213> ORGANISM: Vespula vulgaris

<400> SEQUENCE: 1077
gtgaatgaat atcctatgat ggctggtata atacatcttg caacg            45

<210> SEQ ID NO 1078
<211> LENGTH: 45
<212> TYPE: DNA
<213> ORGANISM: Vespula vulgaris

<400> SEQUENCE: 1078
cagcgaaact ttgtagacac tgttgttaca gctgtaggat ggggt            45

<210> SEQ ID NO 1079
<211> LENGTH: 45
<212> TYPE: DNA
<213> ORGANISM: Vespula vulgaris

<400> SEQUENCE: 1079
acatgggcaa ttaacgatac aaaggcaact caactttatc ttatt            45

<210> SEQ ID NO 1080
<211> LENGTH: 45
<212> TYPE: DNA
<213> ORGANISM: Vespula vulgaris

<400> SEQUENCE: 1080
aggccaaaat taaacgattt agctgttata aaattgcaga agagg            45

<210> SEQ ID NO 1081
<211> LENGTH: 45
<212> TYPE: DNA
<213> ORGANISM: Vespula vulgaris

<400> SEQUENCE: 1081
gtaggatggg gtcttacgaa tttttatggt gtcaagtctg aagtt            45

<210> SEQ ID NO 1082
<211> LENGTH: 45
<212> TYPE: DNA
<213> ORGANISM: Vespula vulgaris

<400> SEQUENCE: 1082
gagtacgttt tctgtggatt aaattctttt gcagtggaat caata            45

<210> SEQ ID NO 1083
<211> LENGTH: 45
<212> TYPE: DNA
<213> ORGANISM: Vespula vulgaris

<400> SEQUENCE: 1083
cttacgaatt tttatggtgt caagtctgaa gttttgagaa aagtc            45

<210> SEQ ID NO 1084
<211> LENGTH: 45
<212> TYPE: DNA
<213> ORGANISM: Vespula vulgaris

<400> SEQUENCE: 1084
atggctggta taatacatct tgcaacgcgt tttctctatt gcggt                45

<210> SEQ ID NO 1085
<211> LENGTH: 45
<212> TYPE: DNA
<213> ORGANISM: Vespula vulgaris

<400> SEQUENCE: 1085
tataaaagga ttttatatat tctaggagtt gttgttggag aacat                45

<210> SEQ ID NO 1086
<211> LENGTH: 45
<212> TYPE: DNA
<213> ORGANISM: Vespula vulgaris

<400> SEQUENCE: 1086
ccaattttat ggcaaaatcc aaaaagcaaa cgtatttttcc ttctt                45

<210> SEQ ID NO 1087
<211> LENGTH: 45
<212> TYPE: DNA
<213> ORGANISM: Vespula vulgaris

<400> SEQUENCE: 1087
gcaacgcgtt ttctctattg cggtgcaact ataataactc cgcaa                45

<210> SEQ ID NO 1088
<211> LENGTH: 45
<212> TYPE: DNA
<213> ORGANISM: Vespula vulgaris

<400> SEQUENCE: 1088
tcttttgcag tggaatcaat agcatcgaaa atgactataa aattc                45

<210> SEQ ID NO 1089
<211> LENGTH: 45
<212> TYPE: DNA
<213> ORGANISM: Vespula vulgaris

<400> SEQUENCE: 1089
tgtcttccgt tctattacat gcagcgaaac tttgtagaca ctgtt                45

<210> SEQ ID NO 1090
<211> LENGTH: 45
<212> TYPE: DNA
<213> ORGANISM: Vespula vulgaris

<400> SEQUENCE: 1090
gcgaggtata aaaggatttt atatattcta ggagttgttg ttgga                45

<210> SEQ ID NO 1091
<211> LENGTH: 45
<212> TYPE: DNA
<213> ORGANISM: Vespula vulgaris

<400> SEQUENCE: 1091

```
tgcgtcaagt atcactttct ggctacacct aagcaacttt gtaca          45

<210> SEQ ID NO 1092
<211> LENGTH: 45
<212> TYPE: DNA
<213> ORGANISM: Vespula vulgaris

<400> SEQUENCE: 1092
gtcaagtatc actttctggc tacacctaag caactttgta cattc          45

<210> SEQ ID NO 1093
<211> LENGTH: 45
<212> TYPE: DNA
<213> ORGANISM: Vespula vulgaris

<400> SEQUENCE: 1093
acatgggcaa ttaacgatac aaaggcaact caactttatc ttatt          45

<210> SEQ ID NO 1094
<211> LENGTH: 45
<212> TYPE: DNA
<213> ORGANISM: Vespula vulgaris

<400> SEQUENCE: 1094
cagcgaaact ttgtagacac tgttgttaca gctgtaggat ggggt          45

<210> SEQ ID NO 1095
<211> LENGTH: 45
<212> TYPE: DNA
<213> ORGANISM: Vespula vulgaris

<400> SEQUENCE: 1095
aattgtcggt ggagtgctag gagcaatact cgaattaaat tgaat          45

<210> SEQ ID NO 1096
<211> LENGTH: 45
<212> TYPE: DNA
<213> ORGANISM: Vespula vulgaris

<400> SEQUENCE: 1096
catccgaatt ataggccaaa attaaacgat ttagctgtta taaaa          45

<210> SEQ ID NO 1097
<211> LENGTH: 45
<212> TYPE: DNA
<213> ORGANISM: Vespula vulgaris

<400> SEQUENCE: 1097
gtgaatgaat atcctatgat ggctggtata atacatcttg caacg          45

<210> SEQ ID NO 1098
<211> LENGTH: 45
<212> TYPE: DNA
<213> ORGANISM: Vespula vulgaris

<400> SEQUENCE: 1098
ggtgcaacta taataactcc gcaacatgta ttaacggctg ctcat          45

<210> SEQ ID NO 1099
<211> LENGTH: 45
<212> TYPE: DNA
<213> ORGANISM: Vespula vulgaris

<400> SEQUENCE: 1099
```
gagtacgttt tctgtggatt aaattctttt gcagtggaat caata    45

<210> SEQ ID NO 1100
<211> LENGTH: 45
<212> TYPE: DNA
<213> ORGANISM: Vespula vulgaris

<400> SEQUENCE: 1100
cttacgaatt tttatggtgt caagtctgaa gttttgagaa aagtc    45

<210> SEQ ID NO 1101
<211> LENGTH: 45
<212> TYPE: DNA
<213> ORGANISM: Vespula vulgaris

<400> SEQUENCE: 1101
atggctggta taatacatct tgcaacgcgt tttctctatt gcggt    45

<210> SEQ ID NO 1102
<211> LENGTH: 45
<212> TYPE: DNA
<213> ORGANISM: Vespula vulgaris

<400> SEQUENCE: 1102
tataaaagga ttttatatat tctaggagtt gttgttggag aacat    45

<210> SEQ ID NO 1103
<211> LENGTH: 45
<212> TYPE: DNA
<213> ORGANISM: Vespula vulgaris

<400> SEQUENCE: 1103
gcgaggtata aaaggatttt atatattcta ggagttgttg ttgga    45

<210> SEQ ID NO 1104
<211> LENGTH: 45
<212> TYPE: DNA
<213> ORGANISM: Vespula vulgaris

<400> SEQUENCE: 1104
gcaacgcgtt ttctctattg cggtgcaact ataataactc cgcaa    45

<210> SEQ ID NO 1105
<211> LENGTH: 45
<212> TYPE: DNA
<213> ORGANISM: Vespula vulgaris

<400> SEQUENCE: 1105
tcttttgcag tggaatcaat agcatcgaaa atgactataa aattc    45

<210> SEQ ID NO 1106
<211> LENGTH: 45
<212> TYPE: DNA
<213> ORGANISM: Vespula vulgaris

<400> SEQUENCE: 1106
tgtcttccgt tctattacat gcagcgaaac tttgtagaca ctgtt    45

<210> SEQ ID NO 1107
<211> LENGTH: 45
<212> TYPE: DNA
<213> ORGANISM: Vespula vulgaris -continued

<400> SEQUENCE: 1107
ccaattttat ggcaaaatcc aaaaagcaaa cgtattttcc ttctt    45

<210> SEQ ID NO 1108
<211> LENGTH: 45
<212> TYPE: DNA
<213> ORGANISM: Vespula vulgaris

<400> SEQUENCE: 1108
tgcgtcaagt atcactttct ggctacacct aagcaacttt gtaca    45

<210> SEQ ID NO 1109
<211> LENGTH: 45
<212> TYPE: DNA
<213> ORGANISM: Vespula vulgaris

<400> SEQUENCE: 1109
gtgaatgaat atcctatgat ggctggtata atacatcttg caacg    45

<210> SEQ ID NO 1110
<211> LENGTH: 45
<212> TYPE: DNA
<213> ORGANISM: Vespula vulgaris

<400> SEQUENCE: 1110
acatgggcaa ttaacgatac aaaggcaact caactttatc ttatt    45

<210> SEQ ID NO 1111
<211> LENGTH: 45
<212> TYPE: DNA
<213> ORGANISM: Vespula vulgaris

<400> SEQUENCE: 1111
catccgaatt ataggccaaa attaaacgat ttagctgtta taaaa    45

<210> SEQ ID NO 1112
<211> LENGTH: 45
<212> TYPE: DNA
<213> ORGANISM: Vespula vulgaris

<400> SEQUENCE: 1112
aattgtcggt ggagtgctag gagcaatact cgaattaaat tgaat    45

<210> SEQ ID NO 1113
<211> LENGTH: 45
<212> TYPE: DNA
<213> ORGANISM: Vespula vulgaris

<400> SEQUENCE: 1113
ggtgcaacta taataactcc gcaacatgta ttaacggctg ctcat    45

<210> SEQ ID NO 1114
<211> LENGTH: 45
<212> TYPE: DNA
<213> ORGANISM: Vespula vulgaris

<400> SEQUENCE: 1114
aggccaaaat taaacgattt agctgttata aaattgcaga agagg    45

<210> SEQ ID NO 1115
<211> LENGTH: 45
<212> TYPE: DNA
<213> ORGANISM: Vespula vulgaris

<400> SEQUENCE: 1115
gtaggatggg gtcttacgaa tttttatggt gtcaagtctg aagtt    45

<210> SEQ ID NO 1116
<211> LENGTH: 45
<212> TYPE: DNA
<213> ORGANISM: Vespula vulgaris

<400> SEQUENCE: 1116
tttgtagaca ctgttgttac agctgtagga tggggtctta cgaat    45

<210> SEQ ID NO 1117
<211> LENGTH: 45
<212> TYPE: DNA
<213> ORGANISM: Vespula vulgaris

<400> SEQUENCE: 1117
cagcgaaact ttgtagacac tgttgttaca gctgtaggat ggggt    45

<210> SEQ ID NO 1118
<211> LENGTH: 45
<212> TYPE: DNA
<213> ORGANISM: Vespula vulgaris

<400> SEQUENCE: 1118
tgtggattaa attcttttgc agtggaatca atagcatcga aaatg    45

<210> SEQ ID NO 1119
<211> LENGTH: 45
<212> TYPE: DNA
<213> ORGANISM: Vespula vulgaris

<400> SEQUENCE: 1119 ttaaatatt ctatgagaat tggtccagct tgtcttccgt tctat    45

<210> SEQ ID NO 1120
<211> LENGTH: 45
<212> TYPE: DNA
<213> ORGANISM: Vespula vulgaris

<400> SEQUENCE: 1120
gagtacgttt tctgtggatt aaattctttt gcagtggaat caata    45

<210> SEQ ID NO 1121
<211> LENGTH: 45
<212> TYPE: DNA
<213> ORGANISM: Vespula vulgaris

<400> SEQUENCE: 1121
cttacgaatt tttatggtgt caagtctgaa gttttgagaa aagtc    45

<210> SEQ ID NO 1122
<211> LENGTH: 45
<212> TYPE: DNA
<213> ORGANISM: Vespula vulgaris

<400> SEQUENCE: 1122
tataaaagga ttttatatat tctaggagtt gttgttggag aacat    45

<210> SEQ ID NO 1123
<211> LENGTH: 45
<212> TYPE: DNA

<213> ORGANISM: Vespula vulgaris

<400> SEQUENCE: 1123
atggctggta atacatctct tgcaacgcgt tttctctatt gcggt    45

<210> SEQ ID NO 1124
<211> LENGTH: 45
<212> TYPE: DNA
<213> ORGANISM: Vespula vulgaris

<400> SEQUENCE: 1124
ccaattttat ggcaaaatcc aaaaagcaaa cgtattttcc ttctt    45

<210> SEQ ID NO 1125
<211> LENGTH: 45
<212> TYPE: DNA
<213> ORGANISM: Vespula vulgaris

<400> SEQUENCE: 1125
tcttttgcag tggaatcaat agcatcgaaa atgactataa aattc    45

<210> SEQ ID NO 1126
<211> LENGTH: 45
<212> TYPE: DNA
<213> ORGANISM: Vespula vulgaris

<400> SEQUENCE: 1126
tgcgtcaagt atcactttct ggctacacct aagcaacttt gtaca    45

<210> SEQ ID NO 1127
<211> LENGTH: 45
<212> TYPE: DNA
<213> ORGANISM: Vespula vulgaris

<400> SEQUENCE: 1127
tgtcttccgt tctattacat gcagcgaaac tttgtagaca ctgtt    45

<210> SEQ ID NO 1128
<211> LENGTH: 45
<212> TYPE: DNA
<213> ORGANISM: Vespula vulgaris

<400> SEQUENCE: 1128
cgtattttcc ttcttggagt catcaattat ggaagaacat gtgcc    45

<210> SEQ ID NO 1129
<211> LENGTH: 45
<212> TYPE: DNA
<213> ORGANISM: Vespula vulgaris

<400> SEQUENCE: 1129
cttccgttct attacatgca gcgaaacttt gtagacactg ttgtt    45

<210> SEQ ID NO 1130
<211> LENGTH: 45
<212> TYPE: DNA
<213> ORGANISM: Vespula vulgaris

<400> SEQUENCE: 1130
gttgcgaggt ataaaaggat tttatatatt ctaggagttg ttgtt    45

<210> SEQ ID NO 1131
<211> LENGTH: 45

<212> TYPE: DNA
<213> ORGANISM: Vespula vulgaris

<400> SEQUENCE: 1131
gcaacgcgtt ttctctattg cggtgcaact ataataactc cgcaa    45

<210> SEQ ID NO 1132
<211> LENGTH: 45
<212> TYPE: DNA
<213> ORGANISM: Vespula vulgaris

<400> SEQUENCE: 1132
gtgaatgaat atcctatgat ggctggtata atacatcttg caacg    45

<210> SEQ ID NO 1133
<211> LENGTH: 45
<212> TYPE: DNA
<213> ORGANISM: Vespula vulgaris

<400> SEQUENCE: 1133
cagcgaaact ttgtagacac tgttgttaca gctgtaggat ggggt    45

<210> SEQ ID NO 1134
<211> LENGTH: 45
<212> TYPE: DNA
<213> ORGANISM: Vespula vulgaris

<400> SEQUENCE: 1134
aattgtcggt ggagtgctag gagcaatact cgaattaaat tgaat    45

<210> SEQ ID NO 1135
<211> LENGTH: 45
<212> TYPE: DNA
<213> ORGANISM: Vespula vulgaris

<400> SEQUENCE: 1135
gtaggatggg gtcttacgaa ttttatggt gtcaagtctg aagtt    45

<210> SEQ ID NO 1136
<211> LENGTH: 45
<212> TYPE: DNA
<213> ORGANISM: Vespula vulgaris

<400> SEQUENCE: 1136
catccgaatt ataggccaaa attaaacgat ttagctgtta taaaa    45

<210> SEQ ID NO 1137
<211> LENGTH: 45
<212> TYPE: DNA
<213> ORGANISM: Vespula vulgaris

<400> SEQUENCE: 1137
acatgggcaa ttaacgatac aaaggcaact caactttatc ttatt    45

<210> SEQ ID NO 1138
<211> LENGTH: 45
<212> TYPE: DNA
<213> ORGANISM: Vespula vulgaris

<400> SEQUENCE: 1138
actataaaat tccattcaag atacaatact tatggaggca aattt    45

<210> SEQ ID NO 1139

<211> LENGTH: 45
<212> TYPE: DNA
<213> ORGANISM: Vespula vulgaris

<400> SEQUENCE: 1139
tttgtagaca ctgttgttac agctgtagga tggggtctta cgaat          45

<210> SEQ ID NO 1140
<211> LENGTH: 45
<212> TYPE: DNA
<213> ORGANISM: Vespula vulgaris

<400> SEQUENCE: 1140
tacacccaaa aattaaaatc agatgttaat tattgcgtgt ataat          45

<210> SEQ ID NO 1141
<211> LENGTH: 45
<212> TYPE: DNA
<213> ORGANISM: Vespula vulgaris

<400> SEQUENCE: 1141
ggtgcaacta taataactcc gcaacatgta ttaacggctg ctcat          45

<210> SEQ ID NO 1142
<211> LENGTH: 45
<212> TYPE: DNA
<213> ORGANISM: Vespula vulgaris

<400> SEQUENCE: 1142
aggttaaaat attctatgag aattggtcca gcttgtcttc cgttc          45

<210> SEQ ID NO 1143
<211> LENGTH: 45
<212> TYPE: DNA
<213> ORGANISM: Vespula vulgaris

<400> SEQUENCE: 1143
tataatcctg attttccgaa ttattacatg ggagaacata attgt          45

<210> SEQ ID NO 1144
<211> LENGTH: 45
<212> TYPE: DNA
<213> ORGANISM: Vespula vulgaris

<400> SEQUENCE: 1144
gagtacgttt tctgtggatt aaattctttt gcagtggaat caata          45

<210> SEQ ID NO 1145
<211> LENGTH: 45
<212> TYPE: DNA
<213> ORGANISM: Vespula vulgaris

<400> SEQUENCE: 1145
atggctggta taatacatct tgcaacgcgt tttctctatt gcggt          45

<210> SEQ ID NO 1146
<211> LENGTH: 45
<212> TYPE: DNA
<213> ORGANISM: Vespula vulgaris

<400> SEQUENCE: 1146
cttacgaatt tttatggtgt caagtctgaa gttttgagaa aagtc          45

```
<210> SEQ ID NO 1147
<211> LENGTH: 45
<212> TYPE: DNA
<213> ORGANISM: Vespula vulgaris

<400> SEQUENCE: 1147
tataaaagga ttttatatat tctaggagtt gttgttggag aacat          45

<210> SEQ ID NO 1148
<211> LENGTH: 45
<212> TYPE: DNA
<213> ORGANISM: Vespula vulgaris

<400> SEQUENCE: 1148
gcaacgcgtt ttctctattg cggtgcaact ataataactc cgcaa          45

<210> SEQ ID NO 1149
<211> LENGTH: 45
<212> TYPE: DNA
<213> ORGANISM: Vespula vulgaris

<400> SEQUENCE: 1149
tcttttgcag tggaatcaat agcatcgaaa atgactataa aattc          45

<210> SEQ ID NO 1150
<211> LENGTH: 45
<212> TYPE: DNA
<213> ORGANISM: Vespula vulgaris

<400> SEQUENCE: 1150
acatgggcaa ttaacgatac aaaggcaact caactttatc ttatt          45

<210> SEQ ID NO 1151
<211> LENGTH: 45
<212> TYPE: DNA
<213> ORGANISM: Vespula vulgaris

<400> SEQUENCE: 1151
tgtcttccgt tctattacat gcagcgaaac tttgtagaca ctgtt          45

<210> SEQ ID NO 1152
<211> LENGTH: 45
<212> TYPE: DNA
<213> ORGANISM: Vespula vulgaris

<400> SEQUENCE: 1152 ccaatttat ggcaaaatcc aaaaagcaaa cgtattttcc ttctt           45

<210> SEQ ID NO 1153
<211> LENGTH: 45
<212> TYPE: DNA
<213> ORGANISM: Vespula vulgaris

<400> SEQUENCE: 1153
tgcgtcaagt atcactttct ggctacacct aagcaacttt gtaca          45

<210> SEQ ID NO 1154
<211> LENGTH: 45
<212> TYPE: DNA
<213> ORGANISM: Vespula vulgaris

<400> SEQUENCE: 1154
tgtggattaa attcttttgc agtggaatca atagcatcga aaatg          45
```

<210> SEQ ID NO 1155
<211> LENGTH: 45
<212> TYPE: DNA
<213> ORGANISM: Vespula vulgaris

<400> SEQUENCE: 1155
cagcgaaact tgtagacac tgttgttaca gctgtaggat ggggt        45

<210> SEQ ID NO 1156
<211> LENGTH: 45
<212> TYPE: DNA
<213> ORGANISM: Vespula vulgaris

<400> SEQUENCE: 1156
tttgtagaca ctgttgttac agctgtagga tggggtctta cgaat        45

<210> SEQ ID NO 1157
<211> LENGTH: 45
<212> TYPE: DNA
<213> ORGANISM: Vespula vulgaris

<400> SEQUENCE: 1157
aggccaaaat taaacgattt agctgttata aaattgcaga agagg        45

<210> SEQ ID NO 1158
<211> LENGTH: 45
<212> TYPE: DNA
<213> ORGANISM: Vespula vulgaris

<400> SEQUENCE: 1158
tgcgttgcga ggtataaaag gattttatat attctaggag ttgtt        45

<210> SEQ ID NO 1159
<211> LENGTH: 45
<212> TYPE: DNA
<213> ORGANISM: Vespula vulgaris

<400> SEQUENCE: 1159
aattgtcggt ggagtgctag gagcaatact cgaattaaat tgaat        45

<210> SEQ ID NO 1160
<211> LENGTH: 45
<212> TYPE: DNA
<213> ORGANISM: Vespula vulgaris

<400> SEQUENCE: 1160
gtgaatgaat atcctatgat ggctggtata atacatcttg caacg        45

<210> SEQ ID NO 1161
<211> LENGTH: 45
<212> TYPE: DNA
<213> ORGANISM: Vespula vulgaris

<400> SEQUENCE: 1161
actccgcaac atgtattaac ggctgctcat tgcgttgcga ggtat        45

<210> SEQ ID NO 1162
<211> LENGTH: 45
<212> TYPE: DNA
<213> ORGANISM: Vespula vulgaris

<400> SEQUENCE: 1162
ttaaaatatt ctatgagaat tggtccagct tgtcttccgt tctat        45

<210> SEQ ID NO 1163
<211> LENGTH: 45
<212> TYPE: DNA
<213> ORGANISM: Vespula vulgaris

<400> SEQUENCE: 1163
cttacgaatt tttatggtgt caagtctgaa gttttgagaa aagtc                45

<210> SEQ ID NO 1164
<211> LENGTH: 45
<212> TYPE: DNA
<213> ORGANISM: Vespula vulgaris

<400> SEQUENCE: 1164
gagtacgttt tctgtggatt aaattctttt gcagtggaat caata                45

<210> SEQ ID NO 1165
<211> LENGTH: 45
<212> TYPE: DNA
<213> ORGANISM: Vespula vulgaris

<400> SEQUENCE: 1165
tataaaagga ttttatatat tctaggagtt gttgttggag aacat                45

<210> SEQ ID NO 1166
<211> LENGTH: 45
<212> TYPE: DNA
<213> ORGANISM: Vespula vulgaris

<400> SEQUENCE: 1166
atggctggta taatacatct tgcaacgcgt tttctctatt gcggt                45

<210> SEQ ID NO 1167
<211> LENGTH: 45
<212> TYPE: DNA
<213> ORGANISM: Vespula vulgaris

<400> SEQUENCE: 1167
ccaattttat ggcaaaatcc aaaaagcaaa cgtattttcc ttctt                45

<210> SEQ ID NO 1168
<211> LENGTH: 45
<212> TYPE: DNA
<213> ORGANISM: Vespula vulgaris

<400> SEQUENCE: 1168
tcttttgcag tggaatcaat agcatcgaaa atgactataa aattc                45

<210> SEQ ID NO 1169
<211> LENGTH: 45
<212> TYPE: DNA
<213> ORGANISM: Vespula vulgaris

<400> SEQUENCE: 1169
gcaacgcgtt ttctctattg cggtgcaact ataataactc cgcaa                45

<210> SEQ ID NO 1170
<211> LENGTH: 45
<212> TYPE: DNA
<213> ORGANISM: Vespula vulgaris

<400> SEQUENCE: 1170
aattgtcggt ggagtgctag gagcaatact cgaattaaat tgaat            45

<210> SEQ ID NO 1171
<211> LENGTH: 45
<212> TYPE: DNA
<213> ORGANISM: Vespula vulgaris

<400> SEQUENCE: 1171
tgtcttccgt tctattacat gcagcgaaac tttgtagaca ctgtt            45

<210> SEQ ID NO 1172
<211> LENGTH: 45
<212> TYPE: DNA
<213> ORGANISM: Vespula vulgaris

<400> SEQUENCE: 1172
tgcgttgcga ggtataaaag gattttatat attctaggag ttgtt            45

<210> SEQ ID NO 1173
<211> LENGTH: 45
<212> TYPE: DNA
<213> ORGANISM: Vespula vulgaris

<400> SEQUENCE: 1173
gtgaatgaat atcctatgat ggctggtata atacatcttg caacg            45

<210> SEQ ID NO 1174
<211> LENGTH: 45
<212> TYPE: DNA
<213> ORGANISM: Vespula vulgaris

<400> SEQUENCE: 1174
aggccaaaat taaacgattt agctgttata aaattgcaga agagg            45

<210> SEQ ID NO 1175
<211> LENGTH: 45
<212> TYPE: DNA
<213> ORGANISM: Vespula vulgaris

<400> SEQUENCE: 1175
catccgaatt ataggccaaa attaaacgat ttagctgtta taaaa            45

<210> SEQ ID NO 1176
<211> LENGTH: 45
<212> TYPE: DNA
<213> ORGANISM: Vespula vulgaris

<400> SEQUENCE: 1176
acatgggcaa ttaacgatac aaaggcaact caactttatc ttatt            45

<210> SEQ ID NO 1177
<211> LENGTH: 45
<212> TYPE: DNA
<213> ORGANISM: Vespula vulgaris

<400> SEQUENCE: 1177
gtaggatggg gtcttacgaa tttttatggt gtcaagtctg aagtt            45

<210> SEQ ID NO 1178
<211> LENGTH: 45
<212> TYPE: DNA
<213> ORGANISM: Vespula vulgaris

<400> SEQUENCE: 1178

```
ccaattttat ggcaaaatcc aaaaagcaaa cgtattttcc ttctt              45

<210> SEQ ID NO 1179
<211> LENGTH: 45
<212> TYPE: DNA
<213> ORGANISM: Vespula vulgaris

<400> SEQUENCE: 1179
cttacgaatt tttatggtgt caagtctgaa gttttgagaa aagtc              45

<210> SEQ ID NO 1180
<211> LENGTH: 45
<212> TYPE: DNA
<213> ORGANISM: Vespula vulgaris

<400> SEQUENCE: 1180
gagtacgttt tctgtggatt aaattctttt gcagtggaat caata              45

<210> SEQ ID NO 1181
<211> LENGTH: 45
<212> TYPE: DNA
<213> ORGANISM: Vespula vulgaris

<400> SEQUENCE: 1181
tacacccaaa aattaaaatc agatgttaat tattgcgtgt ataat              45

<210> SEQ ID NO 1182
<211> LENGTH: 45
<212> TYPE: DNA
<213> ORGANISM: Vespula vulgaris

<400> SEQUENCE: 1182
aattgtcggt ggagtgctag gagcaatact cgaattaaat tgaat              45

<210> SEQ ID NO 1183
<211> LENGTH: 45
<212> TYPE: DNA
<213> ORGANISM: Vespula vulgaris

<400> SEQUENCE: 1183
gagtacgttt tctgtggatt aaattctttt gcagtggaat caata              45

<210> SEQ ID NO 1184
<211> LENGTH: 45
<212> TYPE: DNA
<213> ORGANISM: Vespula vulgaris

<400> SEQUENCE: 1184
cttacgaatt tttatggtgt caagtctgaa gttttgagaa aagtc              45

<210> SEQ ID NO 1185
<211> LENGTH: 45
<212> TYPE: DNA
<213> ORGANISM: Vespula vulgaris

<400> SEQUENCE: 1185
atggctggta taatacatct tgcaacgcgt tttctctatt gcggt              45

<210> SEQ ID NO 1186
<211> LENGTH: 45
<212> TYPE: DNA
<213> ORGANISM: Vespula vulgaris
```

<400> SEQUENCE: 1186
tataaaagga ttttatatat tctaggagtt gttgttggag aacat        45

<210> SEQ ID NO 1187
<211> LENGTH: 45
<212> TYPE: DNA
<213> ORGANISM: Vespula vulgaris

<400> SEQUENCE: 1187
ccaattttat ggcaaaatcc aaaaagcaaa cgtattttcc ttctt        45

<210> SEQ ID NO 1188
<211> LENGTH: 45
<212> TYPE: DNA
<213> ORGANISM: Vespula vulgaris

<400> SEQUENCE: 1188
gcgaggtata aaaggatttt atatattcta ggagttgttg ttgga        45

<210> SEQ ID NO 1189
<211> LENGTH: 45
<212> TYPE: DNA
<213> ORGANISM: Vespula vulgaris

<400> SEQUENCE: 1189
tcttttgcag tggaatcaat agcatcgaaa atgactataa aattc        45

<210> SEQ ID NO 1190
<211> LENGTH: 45
<212> TYPE: DNA
<213> ORGANISM: Vespula vulgaris

<400> SEQUENCE: 1190
tgtcttccgt tctattacat gcagcgaaac tttgtagaca ctgtt        45

<210> SEQ ID NO 1191
<211> LENGTH: 45
<212> TYPE: DNA
<213> ORGANISM: Vespula vulgaris

<400> SEQUENCE: 1191
gcaacgcgtt ttctctattg cggtgcaact ataataactc cgcaa        45

<210> SEQ ID NO 1192
<211> LENGTH: 45
<212> TYPE: DNA
<213> ORGANISM: Vespula vulgaris

<400> SEQUENCE: 1192
acatgggcaa ttaacgatac aaaggcaact caactttatc ttatt        45

<210> SEQ ID NO 1193
<211> LENGTH: 45
<212> TYPE: DNA
<213> ORGANISM: Vespula vulgaris

<400> SEQUENCE: 1193
aattgtcggt ggagtgctag gagcaatact cgaattaaat tgaat        45

<210> SEQ ID NO 1194
<211> LENGTH: 45
<212> TYPE: DNA
<213> ORGANISM: Vespula vulgaris

<400> SEQUENCE: 1194
tgcgtcaagt atcactttct ggctacacct aagcaacttt gtaca          45

<210> SEQ ID NO 1195
<211> LENGTH: 45
<212> TYPE: DNA
<213> ORGANISM: Vespula vulgaris

<400> SEQUENCE: 1195
catccgaatt ataggccaaa attaaacgat ttagctgtta taaaa          45

<210> SEQ ID NO 1196
<211> LENGTH: 45
<212> TYPE: DNA
<213> ORGANISM: Vespula vulgaris

<400> SEQUENCE: 1196
gtgaatgaat atcctatgat ggctggtata atacatcttg caacg          45

<210> SEQ ID NO 1197
<211> LENGTH: 45
<212> TYPE: DNA
<213> ORGANISM: Vespula vulgaris

<400> SEQUENCE: 1197
aggccaaaat taaacgattt agctgttata aaattgcaga agagg          45

<210> SEQ ID NO 1198
<211> LENGTH: 45
<212> TYPE: DNA
<213> ORGANISM: Vespula vulgaris

<400> SEQUENCE: 1198
cagcgaaact ttgtagacac tgttgttaca gctgtaggat ggggt          45

<210> SEQ ID NO 1199
<211> LENGTH: 45
<212> TYPE: DNA
<213> ORGANISM: Vespula vulgaris

<400> SEQUENCE: 1199
tgtggattaa attcttttgc agtggaatca atagcatcga aaatg          45

<210> SEQ ID NO 1200
<211> LENGTH: 45
<212> TYPE: DNA
<213> ORGANISM: Vespula vulgaris

<400> SEQUENCE: 1200
ggtgcaacta taataactcc gcaacatgta ttaacggctg ctcat          45

<210> SEQ ID NO 1201
<211> LENGTH: 45
<212> TYPE: DNA
<213> ORGANISM: Vespula vulgaris

<400> SEQUENCE: 1201
gtaggatggg gtcttacgaa tttttatggt gtcaagtctg aagtt          45

<210> SEQ ID NO 1202
<211> LENGTH: 45
<212> TYPE: DNA

```
<213> ORGANISM: Vespula vulgaris

<400> SEQUENCE: 1202
tttgtagaca ctgttgttac agctgtagga tggggtctta cgaat           45

<210> SEQ ID NO 1203
<211> LENGTH: 45
<212> TYPE: DNA
<213> ORGANISM: Vespula vulgaris

<400> SEQUENCE: 1203
ttaaaatatt ctatgagaat tggtccagct tgtcttccgt tctat           45

<210> SEQ ID NO 1204
<211> LENGTH: 45
<212> TYPE: DNA
<213> ORGANISM: Vespula vulgaris

<400> SEQUENCE: 1204
actccgcaac atgtattaac ggctgctcat tgcgttgcga ggtat           45

<210> SEQ ID NO 1205
<211> LENGTH: 45
<212> TYPE: DNA
<213> ORGANISM: Vespula vulgaris

<400> SEQUENCE: 1205
aggttaaaat attctatgag aattggtcca gcttgtcttc cgttc           45

<210> SEQ ID NO 1206
<211> LENGTH: 45
<212> TYPE: DNA
<213> ORGANISM: Vespula vulgaris

<400> SEQUENCE: 1206
gagtacgttt tctgtggatt aaattctttt gcagtggaat caata           45

<210> SEQ ID NO 1207
<211> LENGTH: 45
<212> TYPE: DNA
<213> ORGANISM: Vespula vulgaris

<400> SEQUENCE: 1207
cttacgaatt tttatggtgt caagtctgaa gttttgagaa aagtc           45

<210> SEQ ID NO 1208
<211> LENGTH: 45
<212> TYPE: DNA
<213> ORGANISM: Vespula vulgaris

<400> SEQUENCE: 1208
atggctggta taatacatct tgcaacgcgt tttctctatt gcggt           45

<210> SEQ ID NO 1209
<211> LENGTH: 45
<212> TYPE: DNA
<213> ORGANISM: Vespula vulgaris

<400> SEQUENCE: 1209
tataaaagga ttttatatat tctaggagtt gttgttggag aacat           45

<210> SEQ ID NO 1210
<211> LENGTH: 45
```

<212> TYPE: DNA
<213> ORGANISM: Vespula vulgaris

<400> SEQUENCE: 1210
tgtcttccgt tctattacat gcagcgaaac tttgtagaca ctgtt    45

<210> SEQ ID NO 1211
<211> LENGTH: 45
<212> TYPE: DNA
<213> ORGANISM: Vespula vulgaris

<400> SEQUENCE: 1211
gcaacgcgtt ttctctattg cggtgcaact ataataactc cgcaa    45

<210> SEQ ID NO 1212
<211> LENGTH: 45
<212> TYPE: DNA
<213> ORGANISM: Vespula vulgaris

<400> SEQUENCE: 1212
gttgcgaggt ataaaaggat tttatatatt ctaggagttg ttgtt    45

<210> SEQ ID NO 1213
<211> LENGTH: 45
<212> TYPE: DNA
<213> ORGANISM: Vespula vulgaris

<400> SEQUENCE: 1213
tgcgtcaagt atcactttct ggctacacct aagcaacttt gtaca    45

<210> SEQ ID NO 1214
<211> LENGTH: 45
<212> TYPE: DNA
<213> ORGANISM: Vespula vulgaris

<400> SEQUENCE: 1214
tcttttgcag tggaatcaat agcatcgaaa atgactataa aattc    45

<210> SEQ ID NO 1215
<211> LENGTH: 45
<212> TYPE: DNA
<213> ORGANISM: Vespula vulgaris

<400> SEQUENCE: 1215
gtgaatgaat atcctatgat ggctggtata atacatcttg caacg    45

<210> SEQ ID NO 1216
<211> LENGTH: 45
<212> TYPE: DNA
<213> ORGANISM: Vespula vulgaris

<400> SEQUENCE: 1216
ccaattttat ggcaaaatcc aaaaagcaaa cgtattttcc ttctt    45

<210> SEQ ID NO 1217
<211> LENGTH: 45
<212> TYPE: DNA
<213> ORGANISM: Vespula vulgaris

<400> SEQUENCE: 1217
gtaggatggg gtcttacgaa tttttatggt gtcaagtctg aagtt    45

<210> SEQ ID NO 1218

```
<211> LENGTH: 45
<212> TYPE: DNA
<213> ORGANISM: Vespula vulgaris

<400> SEQUENCE: 1218
aggccaaaat taaacgattt agctgttata aaattgcaga agagg          45

<210> SEQ ID NO 1219
<211> LENGTH: 45
<212> TYPE: DNA
<213> ORGANISM: Vespula vulgaris

<400> SEQUENCE: 1219
acatgggcaa ttaacgatac aaaggcaact caactttatc ttatt          45

<210> SEQ ID NO 1220
<211> LENGTH: 45
<212> TYPE: DNA
<213> ORGANISM: Vespula vulgaris

<400> SEQUENCE: 1220
ggtgcaacta taataactcc gcaacatgta ttaacggctg ctcat          45

<210> SEQ ID NO 1221
<211> LENGTH: 45
<212> TYPE: DNA
<213> ORGANISM: Vespula vulgaris

<400> SEQUENCE: 1221
gagtacgttt tctgtggatt aaattctttt gcagtggaat caata          45

<210> SEQ ID NO 1222
<211> LENGTH: 45
<212> TYPE: DNA
<213> ORGANISM: Vespula vulgaris

<400> SEQUENCE: 1222
cttacgaatt tttatggtgt caagtctgaa gttttgagaa aagtc          45

<210> SEQ ID NO 1223
<211> LENGTH: 45
<212> TYPE: DNA
<213> ORGANISM: Vespula vulgaris

<400> SEQUENCE: 1223
atggctggta taatacatct tgcaacgcgt tttctctatt gcggt          45

<210> SEQ ID NO 1224
<211> LENGTH: 45
<212> TYPE: DNA
<213> ORGANISM: Vespula vulgaris

<400> SEQUENCE: 1224
tataaaagga tttttatatat tctaggagtt gttgttggag aacat          45

<210> SEQ ID NO 1225
<211> LENGTH: 45
<212> TYPE: DNA
<213> ORGANISM: Vespula vulgaris

<400> SEQUENCE: 1225
gcgaggtata aaaggatttt atatattcta ggagttgttg ttgga          45
```

```
<210> SEQ ID NO 1226
<211> LENGTH: 45
<212> TYPE: DNA
<213> ORGANISM: Vespula vulgaris

<400> SEQUENCE: 1226
gcaacgcgtt ttctctattg cggtgcaact ataataactc cgcaa            45

<210> SEQ ID NO 1227
<211> LENGTH: 45
<212> TYPE: DNA
<213> ORGANISM: Vespula vulgaris

<400> SEQUENCE: 1227
tcttttgcag tggaatcaat agcatcgaaa atgactataa aattc            45

<210> SEQ ID NO 1228
<211> LENGTH: 45
<212> TYPE: DNA
<213> ORGANISM: Vespula vulgaris

<400> SEQUENCE: 1228
tgtcttccgt tctattacat gcagcgaaac tttgtagaca ctgtt            45

<210> SEQ ID NO 1229
<211> LENGTH: 45
<212> TYPE: DNA
<213> ORGANISM: Vespula vulgaris

<400> SEQUENCE: 1229
ccaattttat ggcaaaatcc aaaaagcaaa cgtattttcc ttctt            45

<210> SEQ ID NO 1230
<211> LENGTH: 45
<212> TYPE: DNA
<213> ORGANISM: Vespula vulgaris

<400> SEQUENCE: 1230
tgcgtcaagt atcactttct ggctacacct aagcaacttt gtaca            45

<210> SEQ ID NO 1231
<211> LENGTH: 45
<212> TYPE: DNA
<213> ORGANISM: Vespula vulgaris

<400> SEQUENCE: 1231
gtgaatgaat atcctatgat ggctggtata atacatcttg caacg            45

<210> SEQ ID NO 1232
<211> LENGTH: 45
<212> TYPE: DNA
<213> ORGANISM: Vespula vulgaris

<400> SEQUENCE: 1232
acatgggcaa ttaacgatac aaaggcaact caactttatc ttatt            45

<210> SEQ ID NO 1233
<211> LENGTH: 45
<212> TYPE: DNA
<213> ORGANISM: Vespula vulgaris

<400> SEQUENCE: 1233
catccgaatt ataggccaaa attaaacgat ttagctgtta taaaa            45
```

<210> SEQ ID NO 1234
<211> LENGTH: 45
<212> TYPE: DNA
<213> ORGANISM: Vespula vulgaris

<400> SEQUENCE: 1234
aattgtcggt ggagtgctag gagcaatact cgaattaaat tgaat            45

<210> SEQ ID NO 1235
<211> LENGTH: 45
<212> TYPE: DNA
<213> ORGANISM: Vespula vulgaris

<400> SEQUENCE: 1235
ggtgcaacta taataactcc gcaacatgta ttaacggctg ctcat            45

<210> SEQ ID NO 1236
<211> LENGTH: 45
<212> TYPE: DNA
<213> ORGANISM: Vespula vulgaris

<400> SEQUENCE: 1236
aggccaaaat taaacgattt agctgttata aaattgcaga agagg            45

<210> SEQ ID NO 1237
<211> LENGTH: 45
<212> TYPE: DNA
<213> ORGANISM: Vespula vulgaris

<400> SEQUENCE: 1237
gtaggatggg gtcttacgaa tttttatggt gtcaagtctg aagtt            45

<210> SEQ ID NO 1238
<211> LENGTH: 45
<212> TYPE: DNA
<213> ORGANISM: Vespula vulgaris

<400> SEQUENCE: 1238
tttgtagaca ctgttgttac agctgtagga tggggtctta cgaat            45

<210> SEQ ID NO 1239
<211> LENGTH: 45
<212> TYPE: DNA
<213> ORGANISM: Vespula vulgaris

<400> SEQUENCE: 1239
cagcgaaact ttgtagacac tgttgttaca gctgtaggat ggggt            45

<210> SEQ ID NO 1240
<211> LENGTH: 45
<212> TYPE: DNA
<213> ORGANISM: Vespula vulgaris

<400> SEQUENCE: 1240
tgtggattaa attcttttgc agtggaatca atagcatcga aaatg            45

<210> SEQ ID NO 1241
<211> LENGTH: 45
<212> TYPE: DNA
<213> ORGANISM: Vespula vulgaris

<400> SEQUENCE: 1241
ttaaaatatt ctatgagaat tggtccagct tgtcttccgt tctat            45

<210> SEQ ID NO 1242
<211> LENGTH: 15
<212> TYPE: PRT
<213> ORGANISM: Vespula vulgaris

<400> SEQUENCE: 1242

Glu Tyr Val Phe Cys Gly Leu Asn Ser Phe Ala Val Glu Ser Ile
1               5                   10                  15

<210> SEQ ID NO 1243
<211> LENGTH: 15
<212> TYPE: PRT
<213> ORGANISM: Vespula vulgaris

<400> SEQUENCE: 1243

Leu Thr Asn Phe Tyr Gly Val Lys Ser Glu Val Leu Arg Lys Val
1               5                   10                  15

<210> SEQ ID NO 1244
<211> LENGTH: 15
<212> TYPE: PRT
<213> ORGANISM: Vespula vulgaris

<400> SEQUENCE: 1244

Met Ala Gly Ile Ile His Leu Ala Thr Arg Phe Leu Tyr Cys Gly
1               5                   10                  15

<210> SEQ ID NO 1245
<211> LENGTH: 15
<212> TYPE: PRT
<213> ORGANISM: Vespula vulgaris

<400> SEQUENCE: 1245

Tyr Lys Arg Ile Leu Tyr Ile Leu Gly Val Val Gly Glu His
1               5                   10                  15

<210> SEQ ID NO 1246
<211> LENGTH: 15
<212> TYPE: PRT
<213> ORGANISM: Vespula vulgaris

<400> SEQUENCE: 1246

Ala Arg Tyr Lys Arg Ile Leu Tyr Ile Leu Gly Val Val Val Gly
1               5                   10                  15

<210> SEQ ID NO 1247
<211> LENGTH: 15
<212> TYPE: PRT
<213> ORGANISM: Vespula vulgaris

<400> SEQUENCE: 1247

Ala Thr Arg Phe Leu Tyr Cys Gly Ala Thr Ile Ile Thr Pro Gln
1               5                   10                  15

<210> SEQ ID NO 1248
<211> LENGTH: 15
<212> TYPE: PRT
<213> ORGANISM: Vespula vulgaris

<400> SEQUENCE: 1248

Ser Phe Ala Val Glu Ser Ile Ala Ser Lys Met Thr Ile Lys Phe
1               5                   10                  15

<210> SEQ ID NO 1249
<211> LENGTH: 15
<212> TYPE: PRT
<213> ORGANISM: Vespula vulgaris

<400> SEQUENCE: 1249

Cys Leu Pro Phe Tyr Tyr Met Gln Arg Asn Phe Val Asp Thr Val
1               5                   10                  15

<210> SEQ ID NO 1250
<211> LENGTH: 15
<212> TYPE: PRT
<213> ORGANISM: Vespula vulgaris

<400> SEQUENCE: 1250

Pro Ile Leu Trp Gln Asn Pro Lys Ser Lys Arg Ile Phe Leu Leu
1               5                   10                  15

<210> SEQ ID NO 1251
<211> LENGTH: 15
<212> TYPE: PRT
<213> ORGANISM: Vespula vulgaris

<400> SEQUENCE: 1251

Cys Val Lys Tyr His Phe Leu Ala Thr Pro Lys Gln Leu Cys Thr
1               5                   10                  15

<210> SEQ ID NO 1252
<211> LENGTH: 15
<212> TYPE: PRT
<213> ORGANISM: Vespula vulgaris

<400> SEQUENCE: 1252

Val Asn Glu Tyr Pro Met Met Ala Gly Ile Ile His Leu Ala Thr
1               5                   10                  15

<210> SEQ ID NO 1253
<211> LENGTH: 15
<212> TYPE: PRT
<213> ORGANISM: Vespula vulgaris

<400> SEQUENCE: 1253

Thr Trp Ala Ile Asn Asp Thr Lys Ala Thr Gln Leu Tyr Leu Ile
1               5                   10                  15

<210> SEQ ID NO 1254
<211> LENGTH: 15
<212> TYPE: PRT
<213> ORGANISM: Vespula vulgaris

<400> SEQUENCE: 1254

His Pro Asn Tyr Arg Pro Lys Leu Asn Asp Leu Ala Val Ile Lys
1               5                   10                  15

<210> SEQ ID NO 1255
<211> LENGTH: 15
<212> TYPE: PRT
<213> ORGANISM: Vespula vulgaris

<400> SEQUENCE: 1255

Asn Cys Arg Trp Ser Ala Arg Ser Asn Thr Arg Ile Lys Leu Asn
1               5                   10                  15

<210> SEQ ID NO 1256
<211> LENGTH: 15

```
<212> TYPE: PRT
<213> ORGANISM: Vespula vulgaris

<400> SEQUENCE: 1256

Gly Ala Thr Ile Ile Thr Pro Gln His Val Leu Thr Ala Ala His
1               5                   10                  15

<210> SEQ ID NO 1257
<211> LENGTH: 15
<212> TYPE: PRT
<213> ORGANISM: Vespula vulgaris

<400> SEQUENCE: 1257

Arg Pro Lys Leu Asn Asp Leu Ala Val Ile Lys Leu Gln Lys Arg
1               5                   10                  15

<210> SEQ ID NO 1258
<211> LENGTH: 15
<212> TYPE: PRT
<213> ORGANISM: Vespula vulgaris

<400> SEQUENCE: 1258

Val Gly Trp Gly Leu Thr Asn Phe Tyr Gly Val Lys Ser Glu Val
1               5                   10                  15

<210> SEQ ID NO 1259
<211> LENGTH: 15
<212> TYPE: PRT
<213> ORGANISM: Vespula vulgaris

<400> SEQUENCE: 1259

Phe Val Asp Thr Val Val Thr Ala Val Gly Trp Gly Leu Thr Asn
1               5                   10                  15

<210> SEQ ID NO 1260
<211> LENGTH: 15
<212> TYPE: PRT
<213> ORGANISM: Vespula vulgaris

<400> SEQUENCE: 1260

Gln Arg Asn Phe Val Asp Thr Val Val Thr Ala Val Gly Trp Gly
1               5                   10                  15

<210> SEQ ID NO 1261
<211> LENGTH: 15
<212> TYPE: PRT
<213> ORGANISM: Vespula vulgaris

<400> SEQUENCE: 1261

Cys Gly Leu Asn Ser Phe Ala Val Glu Ser Ile Ala Ser Lys Met
1               5                   10                  15

<210> SEQ ID NO 1262
<211> LENGTH: 15
<212> TYPE: PRT
<213> ORGANISM: Vespula vulgaris

<400> SEQUENCE: 1262

Leu Lys Tyr Ser Met Arg Ile Gly Pro Ala Cys Leu Pro Phe Tyr
1               5                   10                  15

<210> SEQ ID NO 1263
<211> LENGTH: 15
<212> TYPE: PRT
<213> ORGANISM: Vespula vulgaris
```

<400> SEQUENCE: 1263

Glu Tyr Val Phe Cys Gly Leu Asn Ser Phe Ala Val Glu Ser Ile
1               5                   10                  15

<210> SEQ ID NO 1264
<211> LENGTH: 15
<212> TYPE: PRT
<213> ORGANISM: Vespula vulgaris

<400> SEQUENCE: 1264

Tyr Lys Arg Ile Leu Tyr Ile Leu Gly Val Val Val Gly Glu His
1               5                   10                  15

<210> SEQ ID NO 1265
<211> LENGTH: 15
<212> TYPE: PRT
<213> ORGANISM: Vespula vulgaris

<400> SEQUENCE: 1265

Met Ala Gly Ile Ile His Leu Ala Thr Arg Phe Leu Tyr Cys Gly
1               5                   10                  15

<210> SEQ ID NO 1266
<211> LENGTH: 15
<212> TYPE: PRT
<213> ORGANISM: Vespula vulgaris

<400> SEQUENCE: 1266

Leu Thr Asn Phe Tyr Gly Val Lys Ser Glu Val Leu Arg Lys Val
1               5                   10                  15

<210> SEQ ID NO 1267
<211> LENGTH: 15
<212> TYPE: PRT
<213> ORGANISM: Vespula vulgaris

<400> SEQUENCE: 1267

Cys Leu Pro Phe Tyr Tyr Met Gln Arg Asn Phe Val Asp Thr Val
1               5                   10                  15

<210> SEQ ID NO 1268
<211> LENGTH: 15
<212> TYPE: PRT
<213> ORGANISM: Vespula vulgaris

<400> SEQUENCE: 1268

Arg Ile Phe Leu Leu Gly Val Ile Asn Tyr Gly Arg Thr Cys Ala
1               5                   10                  15

<210> SEQ ID NO 1269
<211> LENGTH: 15
<212> TYPE: PRT
<213> ORGANISM: Vespula vulgaris

<400> SEQUENCE: 1269

Ser Phe Ala Val Glu Ser Ile Ala Ser Lys Met Thr Ile Lys Phe
1               5                   10                  15

<210> SEQ ID NO 1270
<211> LENGTH: 15
<212> TYPE: PRT
<213> ORGANISM: Vespula vulgaris

<400> SEQUENCE: 1270

Ala Thr Arg Phe Leu Tyr Cys Gly Ala Thr Ile Ile Thr Pro Gln
1               5                   10                  15

<210> SEQ ID NO 1271
<211> LENGTH: 15
<212> TYPE: PRT
<213> ORGANISM: Vespula vulgaris

<400> SEQUENCE: 1271

Cys Val Ala Arg Tyr Lys Arg Ile Leu Tyr Ile Leu Gly Val Val
1               5                   10                  15

<210> SEQ ID NO 1272
<211> LENGTH: 15
<212> TYPE: PRT
<213> ORGANISM: Vespula vulgaris

<400> SEQUENCE: 1272

Val Asp Thr Val Val Thr Ala Val Gly Trp Gly Leu Thr Asn Phe
1               5                   10                  15

<210> SEQ ID NO 1273
<211> LENGTH: 15
<212> TYPE: PRT
<213> ORGANISM: Vespula vulgaris

<400> SEQUENCE: 1273

Val Asn Glu Tyr Pro Met Met Ala Gly Ile Ile His Leu Ala Thr
1               5                   10                  15

<210> SEQ ID NO 1274
<211> LENGTH: 15
<212> TYPE: PRT
<213> ORGANISM: Vespula vulgaris

<400> SEQUENCE: 1274

Glu Tyr Pro Met Met Ala Gly Ile Ile His Leu Ala Thr Arg Phe
1               5                   10                  15

<210> SEQ ID NO 1275
<211> LENGTH: 15
<212> TYPE: PRT
<213> ORGANISM: Vespula vulgaris

<400> SEQUENCE: 1275

Cys Val Lys Tyr His Phe Leu Ala Thr Pro Lys Gln Leu Cys Thr
1               5                   10                  15

<210> SEQ ID NO 1276
<211> LENGTH: 15
<212> TYPE: PRT
<213> ORGANISM: Vespula vulgaris

<400> SEQUENCE: 1276

Leu Lys Tyr Ser Met Arg Ile Gly Pro Ala Cys Leu Pro Phe Tyr
1               5                   10                  15

<210> SEQ ID NO 1277
<211> LENGTH: 15
<212> TYPE: PRT
<213> ORGANISM: Vespula vulgaris

<400> SEQUENCE: 1277

Thr Trp Ala Ile Asn Asp Thr Lys Ala Thr Gln Leu Tyr Leu Ile

```
<210> SEQ ID NO 1278
<211> LENGTH: 15
<212> TYPE: PRT
<213> ORGANISM: Vespula vulgaris

<400> SEQUENCE: 1278

Val Gly Trp Gly Leu Thr Asn Phe Tyr Gly Val Lys Ser Glu Val
1               5                   10                  15

<210> SEQ ID NO 1279
<211> LENGTH: 15
<212> TYPE: PRT
<213> ORGANISM: Vespula vulgaris

<400> SEQUENCE: 1279

Met Ala Gly Ile Ile His Leu Ala Thr Arg Phe Leu Tyr Cys Gly
1               5                   10                  15

<210> SEQ ID NO 1280
<211> LENGTH: 15
<212> TYPE: PRT
<213> ORGANISM: Vespula vulgaris

<400> SEQUENCE: 1280

Tyr Lys Arg Ile Leu Tyr Ile Leu Gly Val Val Val Gly Glu His
1               5                   10                  15

<210> SEQ ID NO 1281
<211> LENGTH: 15
<212> TYPE: PRT
<213> ORGANISM: Vespula vulgaris

<400> SEQUENCE: 1281

Leu Thr Asn Phe Tyr Gly Val Lys Ser Glu Val Leu Arg Lys Val
1               5                   10                  15

<210> SEQ ID NO 1282
<211> LENGTH: 15
<212> TYPE: PRT
<213> ORGANISM: Vespula vulgaris

<400> SEQUENCE: 1282

Glu Tyr Val Phe Cys Gly Leu Asn Ser Phe Ala Val Glu Ser Ile
1               5                   10                  15

<210> SEQ ID NO 1283
<211> LENGTH: 15
<212> TYPE: PRT
<213> ORGANISM: Vespula vulgaris

<400> SEQUENCE: 1283

Pro Ile Leu Trp Gln Asn Pro Lys Ser Lys Arg Ile Phe Leu Leu
1               5                   10                  15

<210> SEQ ID NO 1284
<211> LENGTH: 15
<212> TYPE: PRT
<213> ORGANISM: Vespula vulgaris

<400> SEQUENCE: 1284

Ala Thr Arg Phe Leu Tyr Cys Gly Ala Thr Ile Ile Thr Pro Gln
1               5                   10                  15
```

<210> SEQ ID NO 1285
<211> LENGTH: 15
<212> TYPE: PRT
<213> ORGANISM: Vespula vulgaris

<400> SEQUENCE: 1285

Asn Cys Arg Trp Ser Ala Arg Ser Asn Thr Arg Ile Lys Leu Asn
1               5                   10                  15

<210> SEQ ID NO 1286
<211> LENGTH: 15
<212> TYPE: PRT
<213> ORGANISM: Vespula vulgaris

<400> SEQUENCE: 1286

Ser Phe Ala Val Glu Ser Ile Ala Ser Lys Met Thr Ile Lys Phe
1               5                   10                  15

<210> SEQ ID NO 1287
<211> LENGTH: 15
<212> TYPE: PRT
<213> ORGANISM: Vespula vulgaris

<400> SEQUENCE: 1287

Arg Pro Lys Leu Asn Asp Leu Ala Val Ile Lys Leu Gln Lys Arg
1               5                   10                  15

<210> SEQ ID NO 1288
<211> LENGTH: 15
<212> TYPE: PRT
<213> ORGANISM: Vespula vulgaris

<400> SEQUENCE: 1288

Tyr Lys Arg Ile Leu Tyr Ile Leu Gly Val Val Val Gly Glu His
1               5                   10                  15

<210> SEQ ID NO 1289
<211> LENGTH: 15
<212> TYPE: PRT
<213> ORGANISM: Vespula vulgaris

<400> SEQUENCE: 1289

Glu Tyr Val Phe Cys Gly Leu Asn Ser Phe Ala Val Glu Ser Ile
1               5                   10                  15

<210> SEQ ID NO 1290
<211> LENGTH: 15
<212> TYPE: PRT
<213> ORGANISM: Vespula vulgaris

<400> SEQUENCE: 1290

Leu Thr Asn Phe Tyr Gly Val Lys Ser Glu Val Leu Arg Lys Val
1               5                   10                  15

<210> SEQ ID NO 1291
<211> LENGTH: 15
<212> TYPE: PRT
<213> ORGANISM: Vespula vulgaris

<400> SEQUENCE: 1291

Met Ala Gly Ile Ile His Leu Ala Thr Arg Phe Leu Tyr Cys Gly
1               5                   10                  15

<210> SEQ ID NO 1292

```
<211> LENGTH: 15
<212> TYPE: PRT
<213> ORGANISM: Vespula vulgaris

<400> SEQUENCE: 1292

Arg Ile Phe Leu Leu Gly Val Ile Asn Tyr Gly Arg Thr Cys Ala
1               5                   10                  15

<210> SEQ ID NO 1293
<211> LENGTH: 15
<212> TYPE: PRT
<213> ORGANISM: Vespula vulgaris

<400> SEQUENCE: 1293

Ser Phe Ala Val Glu Ser Ile Ala Ser Lys Met Thr Ile Lys Phe
1               5                   10                  15

<210> SEQ ID NO 1294
<211> LENGTH: 15
<212> TYPE: PRT
<213> ORGANISM: Vespula vulgaris

<400> SEQUENCE: 1294

Cys Leu Pro Phe Tyr Tyr Met Gln Arg Asn Phe Val Asp Thr Val
1               5                   10                  15

<210> SEQ ID NO 1295
<211> LENGTH: 15
<212> TYPE: PRT
<213> ORGANISM: Vespula vulgaris

<400> SEQUENCE: 1295

Ala Thr Arg Phe Leu Tyr Cys Gly Ala Thr Ile Ile Thr Pro Gln
1               5                   10                  15

<210> SEQ ID NO 1296
<211> LENGTH: 15
<212> TYPE: PRT
<213> ORGANISM: Vespula vulgaris

<400> SEQUENCE: 1296

Phe Val Asp Thr Val Val Thr Ala Val Gly Trp Gly Leu Thr Asn
1               5                   10                  15

<210> SEQ ID NO 1297
<211> LENGTH: 15
<212> TYPE: PRT
<213> ORGANISM: Vespula vulgaris

<400> SEQUENCE: 1297

Glu Tyr Val Phe Cys Gly Leu Asn Ser Phe Ala Val Glu Ser Ile
1               5                   10                  15

<210> SEQ ID NO 1298
<211> LENGTH: 15
<212> TYPE: PRT
<213> ORGANISM: Vespula vulgaris

<400> SEQUENCE: 1298

Leu Thr Asn Phe Tyr Gly Val Lys Ser Glu Val Leu Arg Lys Val
1               5                   10                  15

<210> SEQ ID NO 1299
<211> LENGTH: 15
<212> TYPE: PRT
```

```
<213> ORGANISM: Vespula vulgaris

<400> SEQUENCE: 1299

Met Ala Gly Ile Ile His Leu Ala Thr Arg Phe Leu Tyr Cys Gly
1               5                   10                  15

<210> SEQ ID NO 1300
<211> LENGTH: 15
<212> TYPE: PRT
<213> ORGANISM: Vespula vulgaris

<400> SEQUENCE: 1300

Tyr Lys Arg Ile Leu Tyr Ile Leu Gly Val Val Gly Glu His
1               5                   10                  15

<210> SEQ ID NO 1301
<211> LENGTH: 15
<212> TYPE: PRT
<213> ORGANISM: Vespula vulgaris

<400> SEQUENCE: 1301

Ala Arg Tyr Lys Arg Ile Leu Tyr Ile Leu Gly Val Val Gly
1               5                   10                  15

<210> SEQ ID NO 1302
<211> LENGTH: 15
<212> TYPE: PRT
<213> ORGANISM: Vespula vulgaris

<400> SEQUENCE: 1302

Ala Thr Arg Phe Leu Tyr Cys Gly Ala Thr Ile Ile Thr Pro Gln
1               5                   10                  15

<210> SEQ ID NO 1303
<211> LENGTH: 15
<212> TYPE: PRT
<213> ORGANISM: Vespula vulgaris

<400> SEQUENCE: 1303

Ser Phe Ala Val Glu Ser Ile Ala Ser Lys Met Thr Ile Lys Phe
1               5                   10                  15

<210> SEQ ID NO 1304
<211> LENGTH: 15
<212> TYPE: PRT
<213> ORGANISM: Vespula vulgaris

<400> SEQUENCE: 1304

Cys Leu Pro Phe Tyr Tyr Met Gln Arg Asn Phe Val Asp Thr Val
1               5                   10                  15

<210> SEQ ID NO 1305
<211> LENGTH: 15
<212> TYPE: PRT
<213> ORGANISM: Vespula vulgaris

<400> SEQUENCE: 1305

Pro Ile Leu Trp Gln Asn Pro Lys Ser Lys Arg Ile Phe Leu Leu
1               5                   10                  15

<210> SEQ ID NO 1306
<211> LENGTH: 15
<212> TYPE: PRT
<213> ORGANISM: Vespula vulgaris
```

```
<400> SEQUENCE: 1306

Cys Val Lys Tyr His Phe Leu Ala Thr Pro Lys Gln Leu Cys Thr
1               5                   10                  15

<210> SEQ ID NO 1307
<211> LENGTH: 15
<212> TYPE: PRT
<213> ORGANISM: Vespula vulgaris

<400> SEQUENCE: 1307

Val Asn Glu Tyr Pro Met Met Ala Gly Ile Ile His Leu Ala Thr
1               5                   10                  15

<210> SEQ ID NO 1308
<211> LENGTH: 15
<212> TYPE: PRT
<213> ORGANISM: Vespula vulgaris

<400> SEQUENCE: 1308

Thr Trp Ala Ile Asn Asp Thr Lys Ala Thr Gln Leu Tyr Leu Ile
1               5                   10                  15

<210> SEQ ID NO 1309
<211> LENGTH: 15
<212> TYPE: PRT
<213> ORGANISM: Vespula vulgaris

<400> SEQUENCE: 1309

His Pro Asn Tyr Arg Pro Lys Leu Asn Asp Leu Ala Val Ile Lys
1               5                   10                  15

<210> SEQ ID NO 1310
<211> LENGTH: 15
<212> TYPE: PRT
<213> ORGANISM: Vespula vulgaris

<400> SEQUENCE: 1310

Asn Cys Arg Trp Ser Ala Arg Ser Asn Thr Arg Ile Lys Leu Asn
1               5                   10                  15

<210> SEQ ID NO 1311
<211> LENGTH: 15
<212> TYPE: PRT
<213> ORGANISM: Vespula vulgaris

<400> SEQUENCE: 1311

Gly Ala Thr Ile Ile Thr Pro Gln His Val Leu Thr Ala Ala His
1               5                   10                  15

<210> SEQ ID NO 1312
<211> LENGTH: 15
<212> TYPE: PRT
<213> ORGANISM: Vespula vulgaris

<400> SEQUENCE: 1312

Arg Pro Lys Leu Asn Asp Leu Ala Val Ile Lys Leu Gln Lys Arg
1               5                   10                  15

<210> SEQ ID NO 1313
<211> LENGTH: 15
<212> TYPE: PRT
<213> ORGANISM: Vespula vulgaris

<400> SEQUENCE: 1313
```

Val Gly Trp Gly Leu Thr Asn Phe Tyr Gly Val Lys Ser Glu Val
1               5                   10                  15

<210> SEQ ID NO 1314
<211> LENGTH: 15
<212> TYPE: PRT
<213> ORGANISM: Vespula vulgaris

<400> SEQUENCE: 1314

Phe Val Asp Thr Val Val Thr Ala Val Gly Trp Gly Leu Thr Asn
1               5                   10                  15

<210> SEQ ID NO 1315
<211> LENGTH: 15
<212> TYPE: PRT
<213> ORGANISM: Vespula vulgaris

<400> SEQUENCE: 1315

Gln Arg Asn Phe Val Asp Thr Val Val Thr Ala Val Gly Trp Gly
1               5                   10                  15

<210> SEQ ID NO 1316
<211> LENGTH: 15
<212> TYPE: PRT
<213> ORGANISM: Vespula vulgaris

<400> SEQUENCE: 1316

Cys Gly Leu Asn Ser Phe Ala Val Glu Ser Ile Ala Ser Lys Met
1               5                   10                  15

<210> SEQ ID NO 1317
<211> LENGTH: 15
<212> TYPE: PRT
<213> ORGANISM: Vespula vulgaris

<400> SEQUENCE: 1317

Leu Lys Tyr Ser Met Arg Ile Gly Pro Ala Cys Leu Pro Phe Tyr
1               5                   10                  15

<210> SEQ ID NO 1318
<211> LENGTH: 15
<212> TYPE: PRT
<213> ORGANISM: Vespula vulgaris

<400> SEQUENCE: 1318

Tyr Lys Arg Ile Leu Tyr Ile Leu Gly Val Val Val Gly Glu His
1               5                   10                  15

<210> SEQ ID NO 1319
<211> LENGTH: 15
<212> TYPE: PRT
<213> ORGANISM: Vespula vulgaris

<400> SEQUENCE: 1319

Leu Thr Asn Phe Tyr Gly Val Lys Ser Glu Val Leu Arg Lys Val
1               5                   10                  15

<210> SEQ ID NO 1320
<211> LENGTH: 15
<212> TYPE: PRT
<213> ORGANISM: Vespula vulgaris

<400> SEQUENCE: 1320

Glu Tyr Val Phe Cys Gly Leu Asn Ser Phe Ala Val Glu Ser Ile
1               5                   10                  15

```
<210> SEQ ID NO 1321
<211> LENGTH: 15
<212> TYPE: PRT
<213> ORGANISM: Vespula vulgaris

<400> SEQUENCE: 1321

Met Ala Gly Ile Ile His Leu Ala Thr Arg Phe Leu Tyr Cys Gly
1               5                   10                  15

<210> SEQ ID NO 1322
<211> LENGTH: 15
<212> TYPE: PRT
<213> ORGANISM: Vespula vulgaris

<400> SEQUENCE: 1322

Ser Phe Ala Val Glu Ser Ile Ala Ser Lys Met Thr Ile Lys Phe
1               5                   10                  15

<210> SEQ ID NO 1323
<211> LENGTH: 15
<212> TYPE: PRT
<213> ORGANISM: Vespula vulgaris

<400> SEQUENCE: 1323

Cys Leu Pro Phe Tyr Tyr Met Gln Arg Asn Phe Val Asp Thr Val
1               5                   10                  15

<210> SEQ ID NO 1324
<211> LENGTH: 15
<212> TYPE: PRT
<213> ORGANISM: Vespula vulgaris

<400> SEQUENCE: 1324

Arg Ile Phe Leu Leu Gly Val Ile Asn Tyr Gly Arg Thr Cys Ala
1               5                   10                  15

<210> SEQ ID NO 1325
<211> LENGTH: 15
<212> TYPE: PRT
<213> ORGANISM: Vespula vulgaris

<400> SEQUENCE: 1325

Val Asn Glu Tyr Pro Met Met Ala Gly Ile Ile His Leu Ala Thr
1               5                   10                  15

<210> SEQ ID NO 1326
<211> LENGTH: 15
<212> TYPE: PRT
<213> ORGANISM: Vespula vulgaris

<400> SEQUENCE: 1326

Ala Thr Arg Phe Leu Tyr Cys Gly Ala Thr Ile Ile Thr Pro Gln
1               5                   10                  15

<210> SEQ ID NO 1327
<211> LENGTH: 15
<212> TYPE: PRT
<213> ORGANISM: Vespula vulgaris

<400> SEQUENCE: 1327

Cys Val Ala Arg Tyr Lys Arg Ile Leu Tyr Ile Leu Gly Val Val
1               5                   10                  15
```

```
<210> SEQ ID NO 1328
<211> LENGTH: 15
<212> TYPE: PRT
<213> ORGANISM: Vespula vulgaris

<400> SEQUENCE: 1328

Val Asp Thr Val Val Thr Ala Val Gly Trp Gly Leu Thr Asn Phe
1               5                   10                  15

<210> SEQ ID NO 1329
<211> LENGTH: 15
<212> TYPE: PRT
<213> ORGANISM: Vespula vulgaris

<400> SEQUENCE: 1329

Val Gly Trp Gly Leu Thr Asn Phe Tyr Gly Val Lys Ser Glu Val
1               5                   10                  15

<210> SEQ ID NO 1330
<211> LENGTH: 15
<212> TYPE: PRT
<213> ORGANISM: Vespula vulgaris

<400> SEQUENCE: 1330

Glu Tyr Val Phe Cys Gly Leu Asn Ser Phe Ala Val Glu Ser Ile
1               5                   10                  15

<210> SEQ ID NO 1331
<211> LENGTH: 15
<212> TYPE: PRT
<213> ORGANISM: Vespula vulgaris

<400> SEQUENCE: 1331

Leu Thr Asn Phe Tyr Gly Val Lys Ser Glu Val Leu Arg Lys Val
1               5                   10                  15

<210> SEQ ID NO 1332
<211> LENGTH: 15
<212> TYPE: PRT
<213> ORGANISM: Vespula vulgaris

<400> SEQUENCE: 1332

Met Ala Gly Ile Ile His Leu Ala Thr Arg Phe Leu Tyr Cys Gly
1               5                   10                  15

<210> SEQ ID NO 1333
<211> LENGTH: 15
<212> TYPE: PRT
<213> ORGANISM: Vespula vulgaris

<400> SEQUENCE: 1333

Tyr Lys Arg Ile Leu Tyr Ile Leu Gly Val Val Gly Glu His
1               5                   10                  15

<210> SEQ ID NO 1334
<211> LENGTH: 15
<212> TYPE: PRT
<213> ORGANISM: Vespula vulgaris

<400> SEQUENCE: 1334

Ala Arg Tyr Lys Arg Ile Leu Tyr Ile Leu Gly Val Val Gly
1               5                   10                  15

<210> SEQ ID NO 1335
<211> LENGTH: 15
```

```
<212> TYPE: PRT
<213> ORGANISM: Vespula vulgaris

<400> SEQUENCE: 1335

Ala Thr Arg Phe Leu Tyr Cys Gly Ala Thr Ile Ile Thr Pro Gln
1               5                   10                  15

<210> SEQ ID NO 1336
<211> LENGTH: 15
<212> TYPE: PRT
<213> ORGANISM: Vespula vulgaris

<400> SEQUENCE: 1336

Ser Phe Ala Val Glu Ser Ile Ala Ser Lys Met Thr Ile Lys Phe
1               5                   10                  15

<210> SEQ ID NO 1337
<211> LENGTH: 15
<212> TYPE: PRT
<213> ORGANISM: Vespula vulgaris

<400> SEQUENCE: 1337

Cys Leu Pro Phe Tyr Tyr Met Gln Arg Asn Phe Val Asp Thr Val
1               5                   10                  15

<210> SEQ ID NO 1338
<211> LENGTH: 15
<212> TYPE: PRT
<213> ORGANISM: Vespula vulgaris

<400> SEQUENCE: 1338

Pro Ile Leu Trp Gln Asn Pro Lys Ser Lys Arg Ile Phe Leu Leu
1               5                   10                  15

<210> SEQ ID NO 1339
<211> LENGTH: 15
<212> TYPE: PRT
<213> ORGANISM: Vespula vulgaris

<400> SEQUENCE: 1339

Cys Val Lys Tyr His Phe Leu Ala Thr Pro Lys Gln Leu Cys Thr
1               5                   10                  15

<210> SEQ ID NO 1340
<211> LENGTH: 15
<212> TYPE: PRT
<213> ORGANISM: Vespula vulgaris

<400> SEQUENCE: 1340

Val Asn Glu Tyr Pro Met Met Ala Gly Ile Ile His Leu Ala Thr
1               5                   10                  15

<210> SEQ ID NO 1341
<211> LENGTH: 15
<212> TYPE: PRT
<213> ORGANISM: Vespula vulgaris

<400> SEQUENCE: 1341

Thr Trp Ala Ile Asn Asp Thr Lys Ala Thr Gln Leu Tyr Leu Ile
1               5                   10                  15

<210> SEQ ID NO 1342
<211> LENGTH: 15
<212> TYPE: PRT
<213> ORGANISM: Vespula vulgaris
```

<400> SEQUENCE: 1342

His Pro Asn Tyr Arg Pro Lys Leu Asn Asp Leu Ala Val Ile Lys
1               5                   10                  15

<210> SEQ ID NO 1343
<211> LENGTH: 15
<212> TYPE: PRT
<213> ORGANISM: Vespula vulgaris

<400> SEQUENCE: 1343

Asn Cys Arg Trp Ser Ala Arg Ser Asn Thr Arg Ile Lys Leu Asn
1               5                   10                  15

<210> SEQ ID NO 1344
<211> LENGTH: 15
<212> TYPE: PRT
<213> ORGANISM: Vespula vulgaris

<400> SEQUENCE: 1344

Gly Ala Thr Ile Ile Thr Pro Gln His Val Leu Thr Ala Ala His
1               5                   10                  15

<210> SEQ ID NO 1345
<211> LENGTH: 15
<212> TYPE: PRT
<213> ORGANISM: Vespula vulgaris

<400> SEQUENCE: 1345

Arg Pro Lys Leu Asn Asp Leu Ala Val Ile Lys Leu Gln Lys Arg
1               5                   10                  15

<210> SEQ ID NO 1346
<211> LENGTH: 15
<212> TYPE: PRT
<213> ORGANISM: Vespula vulgaris

<400> SEQUENCE: 1346

Val Gly Trp Gly Leu Thr Asn Phe Tyr Gly Val Lys Ser Glu Val
1               5                   10                  15

<210> SEQ ID NO 1347
<211> LENGTH: 15
<212> TYPE: PRT
<213> ORGANISM: Vespula vulgaris

<400> SEQUENCE: 1347

Phe Val Asp Thr Val Val Thr Ala Val Gly Trp Gly Leu Thr Asn
1               5                   10                  15

<210> SEQ ID NO 1348
<211> LENGTH: 15
<212> TYPE: PRT
<213> ORGANISM: Vespula vulgaris

<400> SEQUENCE: 1348

Gln Arg Asn Phe Val Asp Thr Val Val Thr Ala Val Gly Trp Gly
1               5                   10                  15

<210> SEQ ID NO 1349
<211> LENGTH: 15
<212> TYPE: PRT
<213> ORGANISM: Vespula vulgaris

<400> SEQUENCE: 1349

```
Cys Gly Leu Asn Ser Phe Ala Val Glu Ser Ile Ala Ser Lys Met
1               5                   10                  15

<210> SEQ ID NO 1350
<211> LENGTH: 15
<212> TYPE: PRT
<213> ORGANISM: Vespula vulgaris

<400> SEQUENCE: 1350

Leu Lys Tyr Ser Met Arg Ile Gly Pro Ala Cys Leu Pro Phe Tyr
1               5                   10                  15

<210> SEQ ID NO 1351
<211> LENGTH: 15
<212> TYPE: PRT
<213> ORGANISM: Vespula vulgaris

<400> SEQUENCE: 1351

Glu Tyr Val Phe Cys Gly Leu Asn Ser Phe Ala Val Glu Ser Ile
1               5                   10                  15

<210> SEQ ID NO 1352
<211> LENGTH: 15
<212> TYPE: PRT
<213> ORGANISM: Vespula vulgaris

<400> SEQUENCE: 1352

Leu Thr Asn Phe Tyr Gly Val Lys Ser Glu Val Leu Arg Lys Val
1               5                   10                  15

<210> SEQ ID NO 1353
<211> LENGTH: 15
<212> TYPE: PRT
<213> ORGANISM: Vespula vulgaris

<400> SEQUENCE: 1353

Met Ala Gly Ile Ile His Leu Ala Thr Arg Phe Leu Tyr Cys Gly
1               5                   10                  15

<210> SEQ ID NO 1354
<211> LENGTH: 15
<212> TYPE: PRT
<213> ORGANISM: Vespula vulgaris

<400> SEQUENCE: 1354

Tyr Lys Arg Ile Leu Tyr Ile Leu Gly Val Val Gly Glu His
1               5                   10                  15

<210> SEQ ID NO 1355
<211> LENGTH: 15
<212> TYPE: PRT
<213> ORGANISM: Vespula vulgaris

<400> SEQUENCE: 1355

Ala Arg Tyr Lys Arg Ile Leu Tyr Ile Leu Gly Val Val Val Gly
1               5                   10                  15

<210> SEQ ID NO 1356
<211> LENGTH: 15
<212> TYPE: PRT
<213> ORGANISM: Vespula vulgaris

<400> SEQUENCE: 1356

Ala Thr Arg Phe Leu Tyr Cys Gly Ala Thr Ile Ile Thr Pro Gln
```

```
1               5                  10                  15
```

<210> SEQ ID NO 1357
<211> LENGTH: 15
<212> TYPE: PRT
<213> ORGANISM: Vespula vulgaris

<400> SEQUENCE: 1357

```
Ser Phe Ala Val Glu Ser Ile Ala Ser Lys Met Thr Ile Lys Phe
1               5                  10                  15
```

<210> SEQ ID NO 1358
<211> LENGTH: 15
<212> TYPE: PRT
<213> ORGANISM: Vespula vulgaris

<400> SEQUENCE: 1358

```
Cys Leu Pro Phe Tyr Tyr Met Gln Arg Asn Phe Val Asp Thr Val
1               5                  10                  15
```

<210> SEQ ID NO 1359
<211> LENGTH: 15
<212> TYPE: PRT
<213> ORGANISM: Vespula vulgaris

<400> SEQUENCE: 1359

```
Pro Ile Leu Trp Gln Asn Pro Lys Ser Lys Arg Ile Phe Leu Leu
1               5                  10                  15
```

<210> SEQ ID NO 1360
<211> LENGTH: 15
<212> TYPE: PRT
<213> ORGANISM: Vespula vulgaris

<400> SEQUENCE: 1360

```
Cys Val Lys Tyr His Phe Leu Ala Thr Pro Lys Gln Leu Cys Thr
1               5                  10                  15
```

<210> SEQ ID NO 1361
<211> LENGTH: 15
<212> TYPE: PRT
<213> ORGANISM: Vespula vulgaris

<400> SEQUENCE: 1361

```
Val Asn Glu Tyr Pro Met Met Ala Gly Ile Ile His Leu Ala Thr
1               5                  10                  15
```

<210> SEQ ID NO 1362
<211> LENGTH: 15
<212> TYPE: PRT
<213> ORGANISM: Vespula vulgaris

<400> SEQUENCE: 1362

```
Thr Trp Ala Ile Asn Asp Thr Lys Ala Thr Gln Leu Tyr Leu Ile
1               5                  10                  15
```

<210> SEQ ID NO 1363
<211> LENGTH: 15
<212> TYPE: PRT
<213> ORGANISM: Vespula vulgaris

<400> SEQUENCE: 1363

```
His Pro Asn Tyr Arg Pro Lys Leu Asn Asp Leu Ala Val Ile Lys
1               5                  10                  15
```

<210> SEQ ID NO 1364
<211> LENGTH: 15
<212> TYPE: PRT
<213> ORGANISM: Vespula vulgaris

<400> SEQUENCE: 1364

Asn Cys Arg Trp Ser Ala Arg Ser Asn Thr Arg Ile Lys Leu Asn
1               5                   10                  15

<210> SEQ ID NO 1365
<211> LENGTH: 15
<212> TYPE: PRT
<213> ORGANISM: Vespula vulgaris

<400> SEQUENCE: 1365

Gly Ala Thr Ile Ile Thr Pro Gln His Val Leu Thr Ala Ala His
1               5                   10                  15

<210> SEQ ID NO 1366
<211> LENGTH: 15
<212> TYPE: PRT
<213> ORGANISM: Vespula vulgaris

<400> SEQUENCE: 1366

Arg Pro Lys Leu Asn Asp Leu Ala Val Ile Lys Leu Gln Lys Arg
1               5                   10                  15

<210> SEQ ID NO 1367
<211> LENGTH: 15
<212> TYPE: PRT
<213> ORGANISM: Vespula vulgaris

<400> SEQUENCE: 1367

Val Gly Trp Gly Leu Thr Asn Phe Tyr Gly Val Lys Ser Glu Val
1               5                   10                  15

<210> SEQ ID NO 1368
<211> LENGTH: 15
<212> TYPE: PRT
<213> ORGANISM: Vespula vulgaris

<400> SEQUENCE: 1368

Phe Val Asp Thr Val Val Thr Ala Val Gly Trp Gly Leu Thr Asn
1               5                   10                  15

<210> SEQ ID NO 1369
<211> LENGTH: 15
<212> TYPE: PRT
<213> ORGANISM: Vespula vulgaris

<400> SEQUENCE: 1369

Gln Arg Asn Phe Val Asp Thr Val Val Thr Ala Val Gly Trp Gly
1               5                   10                  15

<210> SEQ ID NO 1370
<211> LENGTH: 15
<212> TYPE: PRT
<213> ORGANISM: Vespula vulgaris

<400> SEQUENCE: 1370

Cys Gly Leu Asn Ser Phe Ala Val Glu Ser Ile Ala Ser Lys Met
1               5                   10                  15

<210> SEQ ID NO 1371

```
<211> LENGTH: 15
<212> TYPE: PRT
<213> ORGANISM: Vespula vulgaris

<400> SEQUENCE: 1371

Leu Lys Tyr Ser Met Arg Ile Gly Pro Ala Cys Leu Pro Phe Tyr
1               5                   10                  15

<210> SEQ ID NO 1372
<211> LENGTH: 15
<212> TYPE: PRT
<213> ORGANISM: Vespula vulgaris

<400> SEQUENCE: 1372

Glu Tyr Val Phe Cys Gly Leu Asn Ser Phe Ala Val Glu Ser Ile
1               5                   10                  15

<210> SEQ ID NO 1373
<211> LENGTH: 15
<212> TYPE: PRT
<213> ORGANISM: Vespula vulgaris

<400> SEQUENCE: 1373

Leu Thr Asn Phe Tyr Gly Val Lys Ser Glu Val Leu Arg Lys Val
1               5                   10                  15

<210> SEQ ID NO 1374
<211> LENGTH: 15
<212> TYPE: PRT
<213> ORGANISM: Vespula vulgaris

<400> SEQUENCE: 1374

Tyr Lys Arg Ile Leu Tyr Ile Leu Gly Val Val Val Gly Glu His
1               5                   10                  15

<210> SEQ ID NO 1375
<211> LENGTH: 15
<212> TYPE: PRT
<213> ORGANISM: Vespula vulgaris

<400> SEQUENCE: 1375

Met Ala Gly Ile Ile His Leu Ala Thr Arg Phe Leu Tyr Cys Gly
1               5                   10                  15

<210> SEQ ID NO 1376
<211> LENGTH: 15
<212> TYPE: PRT
<213> ORGANISM: Vespula vulgaris

<400> SEQUENCE: 1376

Pro Ile Leu Trp Gln Asn Pro Lys Ser Lys Arg Ile Phe Leu Leu
1               5                   10                  15

<210> SEQ ID NO 1377
<211> LENGTH: 15
<212> TYPE: PRT
<213> ORGANISM: Vespula vulgaris

<400> SEQUENCE: 1377

Ser Phe Ala Val Glu Ser Ile Ala Ser Lys Met Thr Ile Lys Phe
1               5                   10                  15

<210> SEQ ID NO 1378
<211> LENGTH: 15
<212> TYPE: PRT
```

<213> ORGANISM: Vespula vulgaris

<400> SEQUENCE: 1378

Ala Thr Arg Phe Leu Tyr Cys Gly Ala Thr Ile Ile Thr Pro Gln
1 5 10 15

<210> SEQ ID NO 1379
<211> LENGTH: 15
<212> TYPE: PRT
<213> ORGANISM: Vespula vulgaris

<400> SEQUENCE: 1379

Cys Leu Pro Phe Tyr Tyr Met Gln Arg Asn Phe Val Asp Thr Val
1 5 10 15

<210> SEQ ID NO 1380
<211> LENGTH: 15
<212> TYPE: PRT
<213> ORGANISM: Vespula vulgaris

<400> SEQUENCE: 1380

Val Ala Arg Tyr Lys Arg Ile Leu Tyr Ile Leu Gly Val Val Val
1 5 10 15

<210> SEQ ID NO 1381
<211> LENGTH: 15
<212> TYPE: PRT
<213> ORGANISM: Vespula vulgaris

<400> SEQUENCE: 1381

Val Asn Glu Tyr Pro Met Met Ala Gly Ile Ile His Leu Ala Thr
1 5 10 15

<210> SEQ ID NO 1382
<211> LENGTH: 15
<212> TYPE: PRT
<213> ORGANISM: Vespula vulgaris

<400> SEQUENCE: 1382

Asn Cys Arg Trp Ser Ala Arg Ser Asn Thr Arg Ile Lys Leu Asn
1 5 10 15

<210> SEQ ID NO 1383
<211> LENGTH: 15
<212> TYPE: PRT
<213> ORGANISM: Vespula vulgaris

<400> SEQUENCE: 1383

Cys Val Lys Tyr His Phe Leu Ala Thr Pro Lys Gln Leu Cys Thr
1 5 10 15

<210> SEQ ID NO 1384
<211> LENGTH: 15
<212> TYPE: PRT
<213> ORGANISM: Vespula vulgaris

<400> SEQUENCE: 1384

His Pro Asn Tyr Arg Pro Lys Leu Asn Asp Leu Ala Val Ile Lys
1 5 10 15

<210> SEQ ID NO 1385
<211> LENGTH: 15
<212> TYPE: PRT
<213> ORGANISM: Vespula vulgaris -continued

```
<400> SEQUENCE: 1385

Arg Pro Lys Leu Asn Asp Leu Ala Val Ile Lys Leu Gln Lys Arg
1               5                   10                  15

<210> SEQ ID NO 1386
<211> LENGTH: 15
<212> TYPE: PRT
<213> ORGANISM: Vespula vulgaris

<400> SEQUENCE: 1386

Val Gly Trp Gly Leu Thr Asn Phe Tyr Gly Val Lys Ser Glu Val
1               5                   10                  15

<210> SEQ ID NO 1387
<211> LENGTH: 15
<212> TYPE: PRT
<213> ORGANISM: Vespula vulgaris

<400> SEQUENCE: 1387

Thr Trp Ala Ile Asn Asp Thr Lys Ala Thr Gln Leu Tyr Leu Ile
1               5                   10                  15

<210> SEQ ID NO 1388
<211> LENGTH: 15
<212> TYPE: PRT
<213> ORGANISM: Vespula vulgaris

<400> SEQUENCE: 1388

Glu Tyr Val Phe Cys Gly Leu Asn Ser Phe Ala Val Glu Ser Ile
1               5                   10                  15

<210> SEQ ID NO 1389
<211> LENGTH: 15
<212> TYPE: PRT
<213> ORGANISM: Vespula vulgaris

<400> SEQUENCE: 1389

Leu Thr Asn Phe Tyr Gly Val Lys Ser Glu Val Leu Arg Lys Val
1               5                   10                  15

<210> SEQ ID NO 1390
<211> LENGTH: 15
<212> TYPE: PRT
<213> ORGANISM: Vespula vulgaris

<400> SEQUENCE: 1390

Tyr Lys Arg Ile Leu Tyr Ile Leu Gly Val Val Val Gly Glu His
1               5                   10                  15

<210> SEQ ID NO 1391
<211> LENGTH: 15
<212> TYPE: PRT
<213> ORGANISM: Vespula vulgaris

<400> SEQUENCE: 1391

Met Ala Gly Ile Ile His Leu Ala Thr Arg Phe Leu Tyr Cys Gly
1               5                   10                  15

<210> SEQ ID NO 1392
<211> LENGTH: 15
<212> TYPE: PRT
<213> ORGANISM: Vespula vulgaris

<400> SEQUENCE: 1392
```

```
Pro Ile Leu Trp Gln Asn Pro Lys Ser Lys Arg Ile Phe Leu Leu
1               5                   10                  15
```

<210> SEQ ID NO 1393
<211> LENGTH: 15
<212> TYPE: PRT
<213> ORGANISM: Vespula vulgaris

<400> SEQUENCE: 1393

```
Ala Arg Tyr Lys Arg Ile Leu Tyr Ile Leu Gly Val Val Val Gly
1               5                   10                  15
```

<210> SEQ ID NO 1394
<211> LENGTH: 15
<212> TYPE: PRT
<213> ORGANISM: Vespula vulgaris

<400> SEQUENCE: 1394

```
Ala Thr Arg Phe Leu Tyr Cys Gly Ala Thr Ile Ile Thr Pro Gln
1               5                   10                  15
```

<210> SEQ ID NO 1395
<211> LENGTH: 15
<212> TYPE: PRT
<213> ORGANISM: Vespula vulgaris

<400> SEQUENCE: 1395

```
Ser Phe Ala Val Glu Ser Ile Ala Ser Lys Met Thr Ile Lys Phe
1               5                   10                  15
```

<210> SEQ ID NO 1396
<211> LENGTH: 15
<212> TYPE: PRT
<213> ORGANISM: Vespula vulgaris

<400> SEQUENCE: 1396

```
Cys Leu Pro Phe Tyr Tyr Met Gln Arg Asn Phe Val Asp Thr Val
1               5                   10                  15
```

<210> SEQ ID NO 1397
<211> LENGTH: 15
<212> TYPE: PRT
<213> ORGANISM: Vespula vulgaris

<400> SEQUENCE: 1397

```
Cys Val Lys Tyr His Phe Leu Ala Thr Pro Lys Gln Leu Cys Thr
1               5                   10                  15
```

<210> SEQ ID NO 1398
<211> LENGTH: 15
<212> TYPE: PRT
<213> ORGANISM: Vespula vulgaris

<400> SEQUENCE: 1398

```
Asn Cys Arg Trp Ser Ala Arg Ser Asn Thr Arg Ile Lys Leu Asn
1               5                   10                  15
```

<210> SEQ ID NO 1399
<211> LENGTH: 15
<212> TYPE: PRT
<213> ORGANISM: Vespula vulgaris

<400> SEQUENCE: 1399

```
His Pro Asn Tyr Arg Pro Lys Leu Asn Asp Leu Ala Val Ile Lys
1               5                   10                  15
```

```
<210> SEQ ID NO 1400
<211> LENGTH: 15
<212> TYPE: PRT
<213> ORGANISM: Vespula vulgaris

<400> SEQUENCE: 1400

Val Asn Glu Tyr Pro Met Met Ala Gly Ile Ile His Leu Ala Thr
1               5                   10                  15

<210> SEQ ID NO 1401
<211> LENGTH: 15
<212> TYPE: PRT
<213> ORGANISM: Vespula vulgaris

<400> SEQUENCE: 1401

Gln Arg Asn Phe Val Asp Thr Val Val Thr Ala Val Gly Trp Gly
1               5                   10                  15

<210> SEQ ID NO 1402
<211> LENGTH: 15
<212> TYPE: PRT
<213> ORGANISM: Vespula vulgaris

<400> SEQUENCE: 1402

Thr Trp Ala Ile Asn Asp Thr Lys Ala Thr Gln Leu Tyr Leu Ile
1               5                   10                  15

<210> SEQ ID NO 1403
<211> LENGTH: 15
<212> TYPE: PRT
<213> ORGANISM: Vespula vulgaris

<400> SEQUENCE: 1403

Arg Pro Lys Leu Asn Asp Leu Ala Val Ile Lys Leu Gln Lys Arg
1               5                   10                  15

<210> SEQ ID NO 1404
<211> LENGTH: 15
<212> TYPE: PRT
<213> ORGANISM: Vespula vulgaris

<400> SEQUENCE: 1404

Val Gly Trp Gly Leu Thr Asn Phe Tyr Gly Val Lys Ser Glu Val
1               5                   10                  15

<210> SEQ ID NO 1405
<211> LENGTH: 15
<212> TYPE: PRT
<213> ORGANISM: Vespula vulgaris

<400> SEQUENCE: 1405

Glu Tyr Val Phe Cys Gly Leu Asn Ser Phe Ala Val Glu Ser Ile
1               5                   10                  15

<210> SEQ ID NO 1406
<211> LENGTH: 15
<212> TYPE: PRT
<213> ORGANISM: Vespula vulgaris

<400> SEQUENCE: 1406

Leu Thr Asn Phe Tyr Gly Val Lys Ser Glu Val Leu Arg Lys Val
1               5                   10                  15
```

```
<210> SEQ ID NO 1407
<211> LENGTH: 15
<212> TYPE: PRT
<213> ORGANISM: Vespula vulgaris

<400> SEQUENCE: 1407

Met Ala Gly Ile Ile His Leu Ala Thr Arg Phe Leu Tyr Cys Gly
1               5                   10                  15

<210> SEQ ID NO 1408
<211> LENGTH: 15
<212> TYPE: PRT
<213> ORGANISM: Vespula vulgaris

<400> SEQUENCE: 1408

Tyr Lys Arg Ile Leu Tyr Ile Leu Gly Val Val Val Gly Glu His
1               5                   10                  15

<210> SEQ ID NO 1409
<211> LENGTH: 15
<212> TYPE: PRT
<213> ORGANISM: Vespula vulgaris

<400> SEQUENCE: 1409

Pro Ile Leu Trp Gln Asn Pro Lys Ser Lys Arg Ile Phe Leu Leu
1               5                   10                  15

<210> SEQ ID NO 1410
<211> LENGTH: 15
<212> TYPE: PRT
<213> ORGANISM: Vespula vulgaris

<400> SEQUENCE: 1410

Ala Thr Arg Phe Leu Tyr Cys Gly Ala Thr Ile Ile Thr Pro Gln
1               5                   10                  15

<210> SEQ ID NO 1411
<211> LENGTH: 15
<212> TYPE: PRT
<213> ORGANISM: Vespula vulgaris

<400> SEQUENCE: 1411

Ser Phe Ala Val Glu Ser Ile Ala Ser Lys Met Thr Ile Lys Phe
1               5                   10                  15

<210> SEQ ID NO 1412
<211> LENGTH: 15
<212> TYPE: PRT
<213> ORGANISM: Vespula vulgaris

<400> SEQUENCE: 1412

Cys Leu Pro Phe Tyr Tyr Met Gln Arg Asn Phe Val Asp Thr Val
1               5                   10                  15

<210> SEQ ID NO 1413
<211> LENGTH: 15
<212> TYPE: PRT
<213> ORGANISM: Vespula vulgaris

<400> SEQUENCE: 1413

Ala Arg Tyr Lys Arg Ile Leu Tyr Ile Leu Gly Val Val Val Gly
1               5                   10                  15

<210> SEQ ID NO 1414
<211> LENGTH: 15
```

-continued

<212> TYPE: PRT
<213> ORGANISM: Vespula vulgaris

<400> SEQUENCE: 1414

Cys Val Lys Tyr His Phe Leu Ala Thr Pro Lys Gln Leu Cys Thr
1               5                   10                  15

<210> SEQ ID NO 1415
<211> LENGTH: 15
<212> TYPE: PRT
<213> ORGANISM: Vespula vulgaris

<400> SEQUENCE: 1415

Val Lys Tyr His Phe Leu Ala Thr Pro Lys Gln Leu Cys Thr Phe
1               5                   10                  15

<210> SEQ ID NO 1416
<211> LENGTH: 15
<212> TYPE: PRT
<213> ORGANISM: Vespula vulgaris

<400> SEQUENCE: 1416

Thr Trp Ala Ile Asn Asp Thr Lys Ala Thr Gln Leu Tyr Leu Ile
1               5                   10                  15

<210> SEQ ID NO 1417
<211> LENGTH: 15
<212> TYPE: PRT
<213> ORGANISM: Vespula vulgaris

<400> SEQUENCE: 1417

Gln Arg Asn Phe Val Asp Thr Val Val Thr Ala Val Gly Trp Gly
1               5                   10                  15

<210> SEQ ID NO 1418
<211> LENGTH: 15
<212> TYPE: PRT
<213> ORGANISM: Vespula vulgaris

<400> SEQUENCE: 1418

Asn Cys Arg Trp Ser Ala Arg Ser Asn Thr Arg Ile Lys Leu Asn
1               5                   10                  15

<210> SEQ ID NO 1419
<211> LENGTH: 15
<212> TYPE: PRT
<213> ORGANISM: Vespula vulgaris

<400> SEQUENCE: 1419

His Pro Asn Tyr Arg Pro Lys Leu Asn Asp Leu Ala Val Ile Lys
1               5                   10                  15

<210> SEQ ID NO 1420
<211> LENGTH: 15
<212> TYPE: PRT
<213> ORGANISM: Vespula vulgaris

<400> SEQUENCE: 1420

Val Asn Glu Tyr Pro Met Met Ala Gly Ile Ile His Leu Ala Thr
1               5                   10                  15

<210> SEQ ID NO 1421
<211> LENGTH: 15
<212> TYPE: PRT
<213> ORGANISM: Vespula vulgaris

<400> SEQUENCE: 1421

Gly Ala Thr Ile Ile Thr Pro Gln His Val Leu Thr Ala Ala His
1               5                   10                  15

<210> SEQ ID NO 1422
<211> LENGTH: 15
<212> TYPE: PRT
<213> ORGANISM: Vespula vulgaris

<400> SEQUENCE: 1422

Glu Tyr Val Phe Cys Gly Leu Asn Ser Phe Ala Val Glu Ser Ile
1               5                   10                  15

<210> SEQ ID NO 1423
<211> LENGTH: 15
<212> TYPE: PRT
<213> ORGANISM: Vespula vulgaris

<400> SEQUENCE: 1423

Leu Thr Asn Phe Tyr Gly Val Lys Ser Glu Val Leu Arg Lys Val
1               5                   10                  15

<210> SEQ ID NO 1424
<211> LENGTH: 15
<212> TYPE: PRT
<213> ORGANISM: Vespula vulgaris

<400> SEQUENCE: 1424

Met Ala Gly Ile Ile His Leu Ala Thr Arg Phe Leu Tyr Cys Gly
1               5                   10                  15

<210> SEQ ID NO 1425
<211> LENGTH: 15
<212> TYPE: PRT
<213> ORGANISM: Vespula vulgaris

<400> SEQUENCE: 1425

Tyr Lys Arg Ile Leu Tyr Ile Leu Gly Val Val Val Gly Glu His
1               5                   10                  15

<210> SEQ ID NO 1426
<211> LENGTH: 15
<212> TYPE: PRT
<213> ORGANISM: Vespula vulgaris

<400> SEQUENCE: 1426

Ala Arg Tyr Lys Arg Ile Leu Tyr Ile Leu Gly Val Val Val Gly
1               5                   10                  15

<210> SEQ ID NO 1427
<211> LENGTH: 15
<212> TYPE: PRT
<213> ORGANISM: Vespula vulgaris

<400> SEQUENCE: 1427

Ala Thr Arg Phe Leu Tyr Cys Gly Ala Thr Ile Ile Thr Pro Gln
1               5                   10                  15

<210> SEQ ID NO 1428
<211> LENGTH: 15
<212> TYPE: PRT
<213> ORGANISM: Vespula vulgaris

<400> SEQUENCE: 1428

Ser Phe Ala Val Glu Ser Ile Ala Ser Lys Met Thr Ile Lys Phe
1               5                   10                  15

<210> SEQ ID NO 1429
<211> LENGTH: 15
<212> TYPE: PRT
<213> ORGANISM: Vespula vulgaris

<400> SEQUENCE: 1429

Cys Leu Pro Phe Tyr Tyr Met Gln Arg Asn Phe Val Asp Thr Val
1               5                   10                  15

<210> SEQ ID NO 1430
<211> LENGTH: 15
<212> TYPE: PRT
<213> ORGANISM: Vespula vulgaris

<400> SEQUENCE: 1430

Pro Ile Leu Trp Gln Asn Pro Lys Ser Lys Arg Ile Phe Leu Leu
1               5                   10                  15

<210> SEQ ID NO 1431
<211> LENGTH: 15
<212> TYPE: PRT
<213> ORGANISM: Vespula vulgaris

<400> SEQUENCE: 1431

Cys Val Lys Tyr His Phe Leu Ala Thr Pro Lys Gln Leu Cys Thr
1               5                   10                  15

<210> SEQ ID NO 1432
<211> LENGTH: 15
<212> TYPE: PRT
<213> ORGANISM: Vespula vulgaris

<400> SEQUENCE: 1432

Val Asn Glu Tyr Pro Met Met Ala Gly Ile Ile His Leu Ala Thr
1               5                   10                  15

<210> SEQ ID NO 1433
<211> LENGTH: 15
<212> TYPE: PRT
<213> ORGANISM: Vespula vulgaris

<400> SEQUENCE: 1433

Thr Trp Ala Ile Asn Asp Thr Lys Ala Thr Gln Leu Tyr Leu Ile
1               5                   10                  15

<210> SEQ ID NO 1434
<211> LENGTH: 15
<212> TYPE: PRT
<213> ORGANISM: Vespula vulgaris

<400> SEQUENCE: 1434

His Pro Asn Tyr Arg Pro Lys Leu Asn Asp Leu Ala Val Ile Lys
1               5                   10                  15

<210> SEQ ID NO 1435
<211> LENGTH: 15
<212> TYPE: PRT
<213> ORGANISM: Vespula vulgaris

<400> SEQUENCE: 1435

Asn Cys Arg Trp Ser Ala Arg Ser Asn Thr Arg Ile Lys Leu Asn

-continued

```
1               5                   10                  15

<210> SEQ ID NO 1436
<211> LENGTH: 15
<212> TYPE: PRT
<213> ORGANISM: Vespula vulgaris

<400> SEQUENCE: 1436

Gly Ala Thr Ile Ile Thr Pro Gln His Val Leu Thr Ala Ala His
1               5                   10                  15

<210> SEQ ID NO 1437
<211> LENGTH: 15
<212> TYPE: PRT
<213> ORGANISM: Vespula vulgaris

<400> SEQUENCE: 1437

Arg Pro Lys Leu Asn Asp Leu Ala Val Ile Lys Leu Gln Lys Arg
1               5                   10                  15

<210> SEQ ID NO 1438
<211> LENGTH: 15
<212> TYPE: PRT
<213> ORGANISM: Vespula vulgaris

<400> SEQUENCE: 1438

Val Gly Trp Gly Leu Thr Asn Phe Tyr Gly Val Lys Ser Glu Val
1               5                   10                  15

<210> SEQ ID NO 1439
<211> LENGTH: 15
<212> TYPE: PRT
<213> ORGANISM: Vespula vulgaris

<400> SEQUENCE: 1439

Phe Val Asp Thr Val Val Thr Ala Val Gly Trp Gly Leu Thr Asn
1               5                   10                  15

<210> SEQ ID NO 1440
<211> LENGTH: 15
<212> TYPE: PRT
<213> ORGANISM: Vespula vulgaris

<400> SEQUENCE: 1440

Gln Arg Asn Phe Val Asp Thr Val Val Thr Ala Val Gly Trp Gly
1               5                   10                  15

<210> SEQ ID NO 1441
<211> LENGTH: 15
<212> TYPE: PRT
<213> ORGANISM: Vespula vulgaris

<400> SEQUENCE: 1441

Cys Gly Leu Asn Ser Phe Ala Val Glu Ser Ile Ala Ser Lys Met
1               5                   10                  15

<210> SEQ ID NO 1442
<211> LENGTH: 15
<212> TYPE: PRT
<213> ORGANISM: Vespula vulgaris

<400> SEQUENCE: 1442

Leu Lys Tyr Ser Met Arg Ile Gly Pro Ala Cys Leu Pro Phe Tyr
1               5                   10                  15
```

<210> SEQ ID NO 1443
<211> LENGTH: 15
<212> TYPE: PRT
<213> ORGANISM: Vespula vulgaris

<400> SEQUENCE: 1443

Glu Tyr Val Phe Cys Gly Leu Asn Ser Phe Ala Val Glu Ser Ile
1               5                   10                  15

<210> SEQ ID NO 1444
<211> LENGTH: 15
<212> TYPE: PRT
<213> ORGANISM: Vespula vulgaris

<400> SEQUENCE: 1444

Leu Thr Asn Phe Tyr Gly Val Lys Ser Glu Val Leu Arg Lys Val
1               5                   10                  15

<210> SEQ ID NO 1445
<211> LENGTH: 15
<212> TYPE: PRT
<213> ORGANISM: Vespula vulgaris

<400> SEQUENCE: 1445

Tyr Lys Arg Ile Leu Tyr Ile Leu Gly Val Val Gly Glu His
1               5                   10                  15

<210> SEQ ID NO 1446
<211> LENGTH: 15
<212> TYPE: PRT
<213> ORGANISM: Vespula vulgaris

<400> SEQUENCE: 1446

Met Ala Gly Ile Ile His Leu Ala Thr Arg Phe Leu Tyr Cys Gly
1               5                   10                  15

<210> SEQ ID NO 1447
<211> LENGTH: 15
<212> TYPE: PRT
<213> ORGANISM: Vespula vulgaris

<400> SEQUENCE: 1447

Pro Ile Leu Trp Gln Asn Pro Lys Ser Lys Arg Ile Phe Leu Leu
1               5                   10                  15

<210> SEQ ID NO 1448
<211> LENGTH: 15
<212> TYPE: PRT
<213> ORGANISM: Vespula vulgaris

<400> SEQUENCE: 1448

Ser Phe Ala Val Glu Ser Ile Ala Ser Lys Met Thr Ile Lys Phe
1               5                   10                  15

<210> SEQ ID NO 1449
<211> LENGTH: 15
<212> TYPE: PRT
<213> ORGANISM: Vespula vulgaris

<400> SEQUENCE: 1449

Cys Val Lys Tyr His Phe Leu Ala Thr Pro Lys Gln Leu Cys Thr
1               5                   10                  15

<210> SEQ ID NO 1450

```
<211> LENGTH: 15
<212> TYPE: PRT
<213> ORGANISM: Vespula vulgaris

<400> SEQUENCE: 1450

Cys Leu Pro Phe Tyr Tyr Met Gln Arg Asn Phe Val Asp Thr Val
1               5                   10                  15

<210> SEQ ID NO 1451
<211> LENGTH: 15
<212> TYPE: PRT
<213> ORGANISM: Vespula vulgaris

<400> SEQUENCE: 1451

Arg Ile Phe Leu Leu Gly Val Ile Asn Tyr Gly Arg Thr Cys Ala
1               5                   10                  15

<210> SEQ ID NO 1452
<211> LENGTH: 15
<212> TYPE: PRT
<213> ORGANISM: Vespula vulgaris

<400> SEQUENCE: 1452

Leu Pro Phe Tyr Tyr Met Gln Arg Asn Phe Val Asp Thr Val Val
1               5                   10                  15

<210> SEQ ID NO 1453
<211> LENGTH: 15
<212> TYPE: PRT
<213> ORGANISM: Vespula vulgaris

<400> SEQUENCE: 1453

Val Ala Arg Tyr Lys Arg Ile Leu Tyr Ile Leu Gly Val Val Val
1               5                   10                  15

<210> SEQ ID NO 1454
<211> LENGTH: 15
<212> TYPE: PRT
<213> ORGANISM: Vespula vulgaris

<400> SEQUENCE: 1454

Ala Thr Arg Phe Leu Tyr Cys Gly Ala Thr Ile Ile Thr Pro Gln
1               5                   10                  15

<210> SEQ ID NO 1455
<211> LENGTH: 15
<212> TYPE: PRT
<213> ORGANISM: Vespula vulgaris

<400> SEQUENCE: 1455

Val Asn Glu Tyr Pro Met Met Ala Gly Ile Ile His Leu Ala Thr
1               5                   10                  15

<210> SEQ ID NO 1456
<211> LENGTH: 15
<212> TYPE: PRT
<213> ORGANISM: Vespula vulgaris

<400> SEQUENCE: 1456

Gln Arg Asn Phe Val Asp Thr Val Val Thr Ala Val Gly Trp Gly
1               5                   10                  15

<210> SEQ ID NO 1457
<211> LENGTH: 15
<212> TYPE: PRT
```

-continued

<213> ORGANISM: Vespula vulgaris

<400> SEQUENCE: 1457

Asn Cys Arg Trp Ser Ala Arg Ser Asn Thr Arg Ile Lys Leu Asn
1               5                   10                  15

<210> SEQ ID NO 1458
<211> LENGTH: 15
<212> TYPE: PRT
<213> ORGANISM: Vespula vulgaris

<400> SEQUENCE: 1458

Val Gly Trp Gly Leu Thr Asn Phe Tyr Gly Val Lys Ser Glu Val
1               5                   10                  15

<210> SEQ ID NO 1459
<211> LENGTH: 15
<212> TYPE: PRT
<213> ORGANISM: Vespula vulgaris

<400> SEQUENCE: 1459

His Pro Asn Tyr Arg Pro Lys Leu Asn Asp Leu Ala Val Ile Lys
1               5                   10                  15

<210> SEQ ID NO 1460
<211> LENGTH: 15
<212> TYPE: PRT
<213> ORGANISM: Vespula vulgaris

<400> SEQUENCE: 1460

Thr Trp Ala Ile Asn Asp Thr Lys Ala Thr Gln Leu Tyr Leu Ile
1               5                   10                  15

<210> SEQ ID NO 1461
<211> LENGTH: 15
<212> TYPE: PRT
<213> ORGANISM: Vespula vulgaris

<400> SEQUENCE: 1461

Thr Ile Lys Phe His Ser Arg Tyr Asn Thr Tyr Gly Gly Lys Phe
1               5                   10                  15

<210> SEQ ID NO 1462
<211> LENGTH: 15
<212> TYPE: PRT
<213> ORGANISM: Vespula vulgaris

<400> SEQUENCE: 1462

Phe Val Asp Thr Val Val Thr Ala Val Gly Trp Gly Leu Thr Asn
1               5                   10                  15

<210> SEQ ID NO 1463
<211> LENGTH: 15
<212> TYPE: PRT
<213> ORGANISM: Vespula vulgaris

<400> SEQUENCE: 1463

Tyr Thr Gln Lys Leu Lys Ser Asp Val Asn Tyr Cys Val Tyr Asn
1               5                   10                  15

<210> SEQ ID NO 1464
<211> LENGTH: 15
<212> TYPE: PRT
<213> ORGANISM: Vespula vulgaris

<400> SEQUENCE: 1464

Gly Ala Thr Ile Ile Thr Pro Gln His Val Leu Thr Ala Ala His
1               5                   10                  15

<210> SEQ ID NO 1465
<211> LENGTH: 15
<212> TYPE: PRT
<213> ORGANISM: Vespula vulgaris

<400> SEQUENCE: 1465

Arg Leu Lys Tyr Ser Met Arg Ile Gly Pro Ala Cys Leu Pro Phe
1               5                   10                  15

<210> SEQ ID NO 1466
<211> LENGTH: 15
<212> TYPE: PRT
<213> ORGANISM: Vespula vulgaris

<400> SEQUENCE: 1466

Tyr Asn Pro Asp Phe Pro Asn Tyr Tyr Met Gly Glu His Asn Cys
1               5                   10                  15

<210> SEQ ID NO 1467
<211> LENGTH: 15
<212> TYPE: PRT
<213> ORGANISM: Vespula vulgaris

<400> SEQUENCE: 1467

Glu Tyr Val Phe Cys Gly Leu Asn Ser Phe Ala Val Glu Ser Ile
1               5                   10                  15

<210> SEQ ID NO 1468
<211> LENGTH: 15
<212> TYPE: PRT
<213> ORGANISM: Vespula vulgaris

<400> SEQUENCE: 1468

Met Ala Gly Ile Ile His Leu Ala Thr Arg Phe Leu Tyr Cys Gly
1               5                   10                  15

<210> SEQ ID NO 1469
<211> LENGTH: 15
<212> TYPE: PRT
<213> ORGANISM: Vespula vulgaris

<400> SEQUENCE: 1469

Leu Thr Asn Phe Tyr Gly Val Lys Ser Glu Val Leu Arg Lys Val
1               5                   10                  15

<210> SEQ ID NO 1470
<211> LENGTH: 15
<212> TYPE: PRT
<213> ORGANISM: Vespula vulgaris

<400> SEQUENCE: 1470

Tyr Lys Arg Ile Leu Tyr Ile Leu Gly Val Val Val Gly Glu His
1               5                   10                  15

<210> SEQ ID NO 1471
<211> LENGTH: 15
<212> TYPE: PRT
<213> ORGANISM: Vespula vulgaris

<400> SEQUENCE: 1471

```
Ala Thr Arg Phe Leu Tyr Cys Gly Ala Thr Ile Ile Thr Pro Gln
1               5                   10                  15

<210> SEQ ID NO 1472
<211> LENGTH: 15
<212> TYPE: PRT
<213> ORGANISM: Vespula vulgaris

<400> SEQUENCE: 1472

Ser Phe Ala Val Glu Ser Ile Ala Ser Lys Met Thr Ile Lys Phe
1               5                   10                  15

<210> SEQ ID NO 1473
<211> LENGTH: 15
<212> TYPE: PRT
<213> ORGANISM: Vespula vulgaris

<400> SEQUENCE: 1473

Thr Trp Ala Ile Asn Asp Thr Lys Ala Thr Gln Leu Tyr Leu Ile
1               5                   10                  15

<210> SEQ ID NO 1474
<211> LENGTH: 15
<212> TYPE: PRT
<213> ORGANISM: Vespula vulgaris

<400> SEQUENCE: 1474

Cys Leu Pro Phe Tyr Tyr Met Gln Arg Asn Phe Val Asp Thr Val
1               5                   10                  15

<210> SEQ ID NO 1475
<211> LENGTH: 15
<212> TYPE: PRT
<213> ORGANISM: Vespula vulgaris

<400> SEQUENCE: 1475

Pro Ile Leu Trp Gln Asn Pro Lys Ser Lys Arg Ile Phe Leu Leu
1               5                   10                  15

<210> SEQ ID NO 1476
<211> LENGTH: 15
<212> TYPE: PRT
<213> ORGANISM: Vespula vulgaris

<400> SEQUENCE: 1476

Cys Val Lys Tyr His Phe Leu Ala Thr Pro Lys Gln Leu Cys Thr
1               5                   10                  15

<210> SEQ ID NO 1477
<211> LENGTH: 15
<212> TYPE: PRT
<213> ORGANISM: Vespula vulgaris

<400> SEQUENCE: 1477

Cys Gly Leu Asn Ser Phe Ala Val Glu Ser Ile Ala Ser Lys Met
1               5                   10                  15

<210> SEQ ID NO 1478
<211> LENGTH: 15
<212> TYPE: PRT
<213> ORGANISM: Vespula vulgaris

<400> SEQUENCE: 1478

Gln Arg Asn Phe Val Asp Thr Val Val Thr Ala Val Gly Trp Gly
1               5                   10                  15
```

```
<210> SEQ ID NO 1479
<211> LENGTH: 15
<212> TYPE: PRT
<213> ORGANISM: Vespula vulgaris

<400> SEQUENCE: 1479

Phe Val Asp Thr Val Val Thr Ala Val Gly Trp Gly Leu Thr Asn
1               5                   10                  15

<210> SEQ ID NO 1480
<211> LENGTH: 15
<212> TYPE: PRT
<213> ORGANISM: Vespula vulgaris

<400> SEQUENCE: 1480

Arg Pro Lys Leu Asn Asp Leu Ala Val Ile Lys Leu Gln Lys Arg
1               5                   10                  15

<210> SEQ ID NO 1481
<211> LENGTH: 15
<212> TYPE: PRT
<213> ORGANISM: Vespula vulgaris

<400> SEQUENCE: 1481

Cys Val Ala Arg Tyr Lys Arg Ile Leu Tyr Ile Leu Gly Val Val
1               5                   10                  15

<210> SEQ ID NO 1482
<211> LENGTH: 15
<212> TYPE: PRT
<213> ORGANISM: Vespula vulgaris

<400> SEQUENCE: 1482

Asn Cys Arg Trp Ser Ala Arg Ser Asn Thr Arg Ile Lys Leu Asn
1               5                   10                  15

<210> SEQ ID NO 1483
<211> LENGTH: 15
<212> TYPE: PRT
<213> ORGANISM: Vespula vulgaris

<400> SEQUENCE: 1483

Val Asn Glu Tyr Pro Met Met Ala Gly Ile Ile His Leu Ala Thr
1               5                   10                  15

<210> SEQ ID NO 1484
<211> LENGTH: 15
<212> TYPE: PRT
<213> ORGANISM: Vespula vulgaris

<400> SEQUENCE: 1484

Thr Pro Gln His Val Leu Thr Ala Ala His Cys Val Ala Arg Tyr
1               5                   10                  15

<210> SEQ ID NO 1485
<211> LENGTH: 15
<212> TYPE: PRT
<213> ORGANISM: Vespula vulgaris

<400> SEQUENCE: 1485

Leu Lys Tyr Ser Met Arg Ile Gly Pro Ala Cys Leu Pro Phe Tyr
1               5                   10                  15
```

```
<210> SEQ ID NO 1486
<211> LENGTH: 15
<212> TYPE: PRT
<213> ORGANISM: Vespula vulgaris

<400> SEQUENCE: 1486

Leu Thr Asn Phe Tyr Gly Val Lys Ser Glu Val Leu Arg Lys Val
1               5                   10                  15

<210> SEQ ID NO 1487
<211> LENGTH: 15
<212> TYPE: PRT
<213> ORGANISM: Vespula vulgaris

<400> SEQUENCE: 1487

Glu Tyr Val Phe Cys Gly Leu Asn Ser Phe Ala Val Glu Ser Ile
1               5                   10                  15

<210> SEQ ID NO 1488
<211> LENGTH: 15
<212> TYPE: PRT
<213> ORGANISM: Vespula vulgaris

<400> SEQUENCE: 1488

Tyr Lys Arg Ile Leu Tyr Ile Leu Gly Val Val Val Gly Glu His
1               5                   10                  15

<210> SEQ ID NO 1489
<211> LENGTH: 15
<212> TYPE: PRT
<213> ORGANISM: Vespula vulgaris

<400> SEQUENCE: 1489

Met Ala Gly Ile Ile His Leu Ala Thr Arg Phe Leu Tyr Cys Gly
1               5                   10                  15

<210> SEQ ID NO 1490
<211> LENGTH: 15
<212> TYPE: PRT
<213> ORGANISM: Vespula vulgaris

<400> SEQUENCE: 1490

Pro Ile Leu Trp Gln Asn Pro Lys Ser Lys Arg Ile Phe Leu Leu
1               5                   10                  15

<210> SEQ ID NO 1491
<211> LENGTH: 15
<212> TYPE: PRT
<213> ORGANISM: Vespula vulgaris

<400> SEQUENCE: 1491

Ser Phe Ala Val Glu Ser Ile Ala Ser Lys Met Thr Ile Lys Phe
1               5                   10                  15

<210> SEQ ID NO 1492
<211> LENGTH: 15
<212> TYPE: PRT
<213> ORGANISM: Vespula vulgaris

<400> SEQUENCE: 1492

Ala Thr Arg Phe Leu Tyr Cys Gly Ala Thr Ile Ile Thr Pro Gln
1               5                   10                  15

<210> SEQ ID NO 1493
<211> LENGTH: 15
```

```
<212> TYPE: PRT
<213> ORGANISM: Vespula vulgaris

<400> SEQUENCE: 1493

Asn Cys Arg Trp Ser Ala Arg Ser Asn Thr Arg Ile Lys Leu Asn
1               5                   10                  15

<210> SEQ ID NO 1494
<211> LENGTH: 15
<212> TYPE: PRT
<213> ORGANISM: Vespula vulgaris

<400> SEQUENCE: 1494

Cys Leu Pro Phe Tyr Tyr Met Gln Arg Asn Phe Val Asp Thr Val
1               5                   10                  15

<210> SEQ ID NO 1495
<211> LENGTH: 15
<212> TYPE: PRT
<213> ORGANISM: Vespula vulgaris

<400> SEQUENCE: 1495

Cys Val Ala Arg Tyr Lys Arg Ile Leu Tyr Ile Leu Gly Val Val
1               5                   10                  15

<210> SEQ ID NO 1496
<211> LENGTH: 15
<212> TYPE: PRT
<213> ORGANISM: Vespula vulgaris

<400> SEQUENCE: 1496

Val Asn Glu Tyr Pro Met Met Ala Gly Ile Ile His Leu Ala Thr
1               5                   10                  15

<210> SEQ ID NO 1497
<211> LENGTH: 15
<212> TYPE: PRT
<213> ORGANISM: Vespula vulgaris

<400> SEQUENCE: 1497

Arg Pro Lys Leu Asn Asp Leu Ala Val Ile Lys Leu Gln Lys Arg
1               5                   10                  15

<210> SEQ ID NO 1498
<211> LENGTH: 15
<212> TYPE: PRT
<213> ORGANISM: Vespula vulgaris

<400> SEQUENCE: 1498

His Pro Asn Tyr Arg Pro Lys Leu Asn Asp Leu Ala Val Ile Lys
1               5                   10                  15

<210> SEQ ID NO 1499
<211> LENGTH: 15
<212> TYPE: PRT
<213> ORGANISM: Vespula vulgaris

<400> SEQUENCE: 1499

Thr Trp Ala Ile Asn Asp Thr Lys Ala Thr Gln Leu Tyr Leu Ile
1               5                   10                  15

<210> SEQ ID NO 1500
<211> LENGTH: 15
<212> TYPE: PRT
<213> ORGANISM: Vespula vulgaris
```

<400> SEQUENCE: 1500

Val Gly Trp Gly Leu Thr Asn Phe Tyr Gly Val Lys Ser Glu Val
1               5                   10                  15

<210> SEQ ID NO 1501
<211> LENGTH: 15
<212> TYPE: PRT
<213> ORGANISM: Vespula vulgaris

<400> SEQUENCE: 1501

Pro Ile Leu Trp Gln Asn Pro Lys Ser Lys Arg Ile Phe Leu Leu
1               5                   10                  15

<210> SEQ ID NO 1502
<211> LENGTH: 15
<212> TYPE: PRT
<213> ORGANISM: Vespula vulgaris

<400> SEQUENCE: 1502

Leu Thr Asn Phe Tyr Gly Val Lys Ser Glu Val Leu Arg Lys Val
1               5                   10                  15

<210> SEQ ID NO 1503
<211> LENGTH: 15
<212> TYPE: PRT
<213> ORGANISM: Vespula vulgaris

<400> SEQUENCE: 1503

Glu Tyr Val Phe Cys Gly Leu Asn Ser Phe Ala Val Glu Ser Ile
1               5                   10                  15

<210> SEQ ID NO 1504
<211> LENGTH: 15
<212> TYPE: PRT
<213> ORGANISM: Vespula vulgaris

<400> SEQUENCE: 1504

Tyr Thr Gln Lys Leu Lys Ser Asp Val Asn Tyr Cys Val Tyr Asn
1               5                   10                  15

<210> SEQ ID NO 1505
<211> LENGTH: 15
<212> TYPE: PRT
<213> ORGANISM: Vespula vulgaris

<400> SEQUENCE: 1505

Asn Cys Arg Trp Ser Ala Arg Ser Asn Thr Arg Ile Lys Leu Asn
1               5                   10                  15

<210> SEQ ID NO 1506
<211> LENGTH: 15
<212> TYPE: PRT
<213> ORGANISM: Vespula vulgaris

<400> SEQUENCE: 1506

Glu Tyr Val Phe Cys Gly Leu Asn Ser Phe Ala Val Glu Ser Ile
1               5                   10                  15

<210> SEQ ID NO 1507
<211> LENGTH: 15
<212> TYPE: PRT
<213> ORGANISM: Vespula vulgaris

<400> SEQUENCE: 1507

```
Leu Thr Asn Phe Tyr Gly Val Lys Ser Glu Val Leu Arg Lys Val
1               5                   10                  15

<210> SEQ ID NO 1508
<211> LENGTH: 15
<212> TYPE: PRT
<213> ORGANISM: Vespula vulgaris

<400> SEQUENCE: 1508

Met Ala Gly Ile Ile His Leu Ala Thr Arg Phe Leu Tyr Cys Gly
1               5                   10                  15

<210> SEQ ID NO 1509
<211> LENGTH: 15
<212> TYPE: PRT
<213> ORGANISM: Vespula vulgaris

<400> SEQUENCE: 1509

Tyr Lys Arg Ile Leu Tyr Ile Leu Gly Val Val Val Gly Glu His
1               5                   10                  15

<210> SEQ ID NO 1510
<211> LENGTH: 15
<212> TYPE: PRT
<213> ORGANISM: Vespula vulgaris

<400> SEQUENCE: 1510

Pro Ile Leu Trp Gln Asn Pro Lys Ser Lys Arg Ile Phe Leu Leu
1               5                   10                  15

<210> SEQ ID NO 1511
<211> LENGTH: 15
<212> TYPE: PRT
<213> ORGANISM: Vespula vulgaris

<400> SEQUENCE: 1511

Ala Arg Tyr Lys Arg Ile Leu Tyr Ile Leu Gly Val Val Val Gly
1               5                   10                  15

<210> SEQ ID NO 1512
<211> LENGTH: 15
<212> TYPE: PRT
<213> ORGANISM: Vespula vulgaris

<400> SEQUENCE: 1512

Ser Phe Ala Val Glu Ser Ile Ala Ser Lys Met Thr Ile Lys Phe
1               5                   10                  15

<210> SEQ ID NO 1513
<211> LENGTH: 15
<212> TYPE: PRT
<213> ORGANISM: Vespula vulgaris

<400> SEQUENCE: 1513

Cys Leu Pro Phe Tyr Tyr Met Gln Arg Asn Phe Val Asp Thr Val
1               5                   10                  15

<210> SEQ ID NO 1514
<211> LENGTH: 15
<212> TYPE: PRT
<213> ORGANISM: Vespula vulgaris

<400> SEQUENCE: 1514

Ala Thr Arg Phe Leu Tyr Cys Gly Ala Thr Ile Ile Thr Pro Gln
```

-continued

```
1               5                   10                  15

<210> SEQ ID NO 1515
<211> LENGTH: 15
<212> TYPE: PRT
<213> ORGANISM: Vespula vulgaris

<400> SEQUENCE: 1515

Thr Trp Ala Ile Asn Asp Thr Lys Ala Thr Gln Leu Tyr Leu Ile
1               5                   10                  15

<210> SEQ ID NO 1516
<211> LENGTH: 15
<212> TYPE: PRT
<213> ORGANISM: Vespula vulgaris

<400> SEQUENCE: 1516

Asn Cys Arg Trp Ser Ala Arg Ser Asn Thr Arg Ile Lys Leu Asn
1               5                   10                  15

<210> SEQ ID NO 1517
<211> LENGTH: 15
<212> TYPE: PRT
<213> ORGANISM: Vespula vulgaris

<400> SEQUENCE: 1517

Cys Val Lys Tyr His Phe Leu Ala Thr Pro Lys Gln Leu Cys Thr
1               5                   10                  15

<210> SEQ ID NO 1518
<211> LENGTH: 15
<212> TYPE: PRT
<213> ORGANISM: Vespula vulgaris

<400> SEQUENCE: 1518

His Pro Asn Tyr Arg Pro Lys Leu Asn Asp Leu Ala Val Ile Lys
1               5                   10                  15

<210> SEQ ID NO 1519
<211> LENGTH: 15
<212> TYPE: PRT
<213> ORGANISM: Vespula vulgaris

<400> SEQUENCE: 1519

Val Asn Glu Tyr Pro Met Met Ala Gly Ile Ile His Leu Ala Thr
1               5                   10                  15

<210> SEQ ID NO 1520
<211> LENGTH: 15
<212> TYPE: PRT
<213> ORGANISM: Vespula vulgaris

<400> SEQUENCE: 1520

Arg Pro Lys Leu Asn Asp Leu Ala Val Ile Lys Leu Gln Lys Arg
1               5                   10                  15

<210> SEQ ID NO 1521
<211> LENGTH: 15
<212> TYPE: PRT
<213> ORGANISM: Vespula vulgaris

<400> SEQUENCE: 1521

Gln Arg Asn Phe Val Asp Thr Val Val Thr Ala Val Gly Trp Gly
1               5                   10                  15
```

<210> SEQ ID NO 1522
<211> LENGTH: 15
<212> TYPE: PRT
<213> ORGANISM: Vespula vulgaris

<400> SEQUENCE: 1522

Cys Gly Leu Asn Ser Phe Ala Val Glu Ser Ile Ala Ser Lys Met
1               5                   10                  15

<210> SEQ ID NO 1523
<211> LENGTH: 15
<212> TYPE: PRT
<213> ORGANISM: Vespula vulgaris

<400> SEQUENCE: 1523

Gly Ala Thr Ile Ile Thr Pro Gln His Val Leu Thr Ala Ala His
1               5                   10                  15

<210> SEQ ID NO 1524
<211> LENGTH: 15
<212> TYPE: PRT
<213> ORGANISM: Vespula vulgaris

<400> SEQUENCE: 1524

Val Gly Trp Gly Leu Thr Asn Phe Tyr Gly Val Lys Ser Glu Val
1               5                   10                  15

<210> SEQ ID NO 1525
<211> LENGTH: 15
<212> TYPE: PRT
<213> ORGANISM: Vespula vulgaris

<400> SEQUENCE: 1525

Phe Val Asp Thr Val Val Thr Ala Val Gly Trp Gly Leu Thr Asn
1               5                   10                  15

<210> SEQ ID NO 1526
<211> LENGTH: 15
<212> TYPE: PRT
<213> ORGANISM: Vespula vulgaris

<400> SEQUENCE: 1526

Leu Lys Tyr Ser Met Arg Ile Gly Pro Ala Cys Leu Pro Phe Tyr
1               5                   10                  15

<210> SEQ ID NO 1527
<211> LENGTH: 15
<212> TYPE: PRT
<213> ORGANISM: Vespula vulgaris

<400> SEQUENCE: 1527

Thr Pro Gln His Val Leu Thr Ala Ala His Cys Val Ala Arg Tyr
1               5                   10                  15

<210> SEQ ID NO 1528
<211> LENGTH: 15
<212> TYPE: PRT
<213> ORGANISM: Vespula vulgaris

<400> SEQUENCE: 1528

Arg Leu Lys Tyr Ser Met Arg Ile Gly Pro Ala Cys Leu Pro Phe
1               5                   10                  15

<210> SEQ ID NO 1529

-continued

```
<211> LENGTH: 15
<212> TYPE: PRT
<213> ORGANISM: Vespula vulgaris

<400> SEQUENCE: 1529

Glu Tyr Val Phe Cys Gly Leu Asn Ser Phe Ala Val Glu Ser Ile
1               5                   10                  15

<210> SEQ ID NO 1530
<211> LENGTH: 15
<212> TYPE: PRT
<213> ORGANISM: Vespula vulgaris

<400> SEQUENCE: 1530

Leu Thr Asn Phe Tyr Gly Val Lys Ser Glu Val Leu Arg Lys Val
1               5                   10                  15

<210> SEQ ID NO 1531
<211> LENGTH: 15
<212> TYPE: PRT
<213> ORGANISM: Vespula vulgaris

<400> SEQUENCE: 1531

Met Ala Gly Ile Ile His Leu Ala Thr Arg Phe Leu Tyr Cys Gly
1               5                   10                  15

<210> SEQ ID NO 1532
<211> LENGTH: 15
<212> TYPE: PRT
<213> ORGANISM: Vespula vulgaris

<400> SEQUENCE: 1532

Tyr Lys Arg Ile Leu Tyr Ile Leu Gly Val Val Val Gly Glu His
1               5                   10                  15

<210> SEQ ID NO 1533
<211> LENGTH: 15
<212> TYPE: PRT
<213> ORGANISM: Vespula vulgaris

<400> SEQUENCE: 1533

Cys Leu Pro Phe Tyr Tyr Met Gln Arg Asn Phe Val Asp Thr Val
1               5                   10                  15

<210> SEQ ID NO 1534
<211> LENGTH: 15
<212> TYPE: PRT
<213> ORGANISM: Vespula vulgaris

<400> SEQUENCE: 1534

Ala Thr Arg Phe Leu Tyr Cys Gly Ala Thr Ile Ile Thr Pro Gln
1               5                   10                  15

<210> SEQ ID NO 1535
<211> LENGTH: 15
<212> TYPE: PRT
<213> ORGANISM: Vespula vulgaris

<400> SEQUENCE: 1535

Val Ala Arg Tyr Lys Arg Ile Leu Tyr Ile Leu Gly Val Val Val
1               5                   10                  15

<210> SEQ ID NO 1536
<211> LENGTH: 15
<212> TYPE: PRT
```

```
<213> ORGANISM: Vespula vulgaris

<400> SEQUENCE: 1536

Cys Val Lys Tyr His Phe Leu Ala Thr Pro Lys Gln Leu Cys Thr
1               5                   10                  15

<210> SEQ ID NO 1537
<211> LENGTH: 15
<212> TYPE: PRT
<213> ORGANISM: Vespula vulgaris

<400> SEQUENCE: 1537

Ser Phe Ala Val Glu Ser Ile Ala Ser Lys Met Thr Ile Lys Phe
1               5                   10                  15

<210> SEQ ID NO 1538
<211> LENGTH: 15
<212> TYPE: PRT
<213> ORGANISM: Vespula vulgaris

<400> SEQUENCE: 1538

Val Asn Glu Tyr Pro Met Met Ala Gly Ile Ile His Leu Ala Thr
1               5                   10                  15

<210> SEQ ID NO 1539
<211> LENGTH: 15
<212> TYPE: PRT
<213> ORGANISM: Vespula vulgaris

<400> SEQUENCE: 1539

Pro Ile Leu Trp Gln Asn Pro Lys Ser Lys Arg Ile Phe Leu Leu
1               5                   10                  15

<210> SEQ ID NO 1540
<211> LENGTH: 15
<212> TYPE: PRT
<213> ORGANISM: Vespula vulgaris

<400> SEQUENCE: 1540

Val Gly Trp Gly Leu Thr Asn Phe Tyr Gly Val Lys Ser Glu Val
1               5                   10                  15

<210> SEQ ID NO 1541
<211> LENGTH: 15
<212> TYPE: PRT
<213> ORGANISM: Vespula vulgaris

<400> SEQUENCE: 1541

Arg Pro Lys Leu Asn Asp Leu Ala Val Ile Lys Leu Gln Lys Arg
1               5                   10                  15

<210> SEQ ID NO 1542
<211> LENGTH: 15
<212> TYPE: PRT
<213> ORGANISM: Vespula vulgaris

<400> SEQUENCE: 1542

Thr Trp Ala Ile Asn Asp Thr Lys Ala Thr Gln Leu Tyr Leu Ile
1               5                   10                  15

<210> SEQ ID NO 1543
<211> LENGTH: 15
<212> TYPE: PRT
<213> ORGANISM: Vespula vulgaris
```

```
<400> SEQUENCE: 1543

Gly Ala Thr Ile Ile Thr Pro Gln His Val Leu Thr Ala Ala His
1               5                   10                  15

<210> SEQ ID NO 1544
<211> LENGTH: 15
<212> TYPE: PRT
<213> ORGANISM: Vespula vulgaris

<400> SEQUENCE: 1544

Glu Tyr Val Phe Cys Gly Leu Asn Ser Phe Ala Val Glu Ser Ile
1               5                   10                  15

<210> SEQ ID NO 1545
<211> LENGTH: 15
<212> TYPE: PRT
<213> ORGANISM: Vespula vulgaris

<400> SEQUENCE: 1545

Leu Thr Asn Phe Tyr Gly Val Lys Ser Glu Val Leu Arg Lys Val
1               5                   10                  15

<210> SEQ ID NO 1546
<211> LENGTH: 15
<212> TYPE: PRT
<213> ORGANISM: Vespula vulgaris

<400> SEQUENCE: 1546

Met Ala Gly Ile Ile His Leu Ala Thr Arg Phe Leu Tyr Cys Gly
1               5                   10                  15

<210> SEQ ID NO 1547
<211> LENGTH: 15
<212> TYPE: PRT
<213> ORGANISM: Vespula vulgaris

<400> SEQUENCE: 1547

Tyr Lys Arg Ile Leu Tyr Ile Leu Gly Val Val Gly Glu His
1               5                   10                  15

<210> SEQ ID NO 1548
<211> LENGTH: 15
<212> TYPE: PRT
<213> ORGANISM: Vespula vulgaris

<400> SEQUENCE: 1548

Ala Arg Tyr Lys Arg Ile Leu Tyr Ile Leu Gly Val Val Val Gly
1               5                   10                  15

<210> SEQ ID NO 1549
<211> LENGTH: 15
<212> TYPE: PRT
<213> ORGANISM: Vespula vulgaris

<400> SEQUENCE: 1549

Ala Thr Arg Phe Leu Tyr Cys Gly Ala Thr Ile Ile Thr Pro Gln
1               5                   10                  15

<210> SEQ ID NO 1550
<211> LENGTH: 15
<212> TYPE: PRT
<213> ORGANISM: Vespula vulgaris

<400> SEQUENCE: 1550
```

Ser Phe Ala Val Glu Ser Ile Ala Ser Lys Met Thr Ile Lys Phe
1               5                   10                  15

<210> SEQ ID NO 1551
<211> LENGTH: 15
<212> TYPE: PRT
<213> ORGANISM: Vespula vulgaris

<400> SEQUENCE: 1551

Cys Leu Pro Phe Tyr Tyr Met Gln Arg Asn Phe Val Asp Thr Val
1               5                   10                  15

<210> SEQ ID NO 1552
<211> LENGTH: 15
<212> TYPE: PRT
<213> ORGANISM: Vespula vulgaris

<400> SEQUENCE: 1552

Pro Ile Leu Trp Gln Asn Pro Lys Ser Lys Arg Ile Phe Leu Leu
1               5                   10                  15

<210> SEQ ID NO 1553
<211> LENGTH: 15
<212> TYPE: PRT
<213> ORGANISM: Vespula vulgaris

<400> SEQUENCE: 1553

Cys Val Lys Tyr His Phe Leu Ala Thr Pro Lys Gln Leu Cys Thr
1               5                   10                  15

<210> SEQ ID NO 1554
<211> LENGTH: 15
<212> TYPE: PRT
<213> ORGANISM: Vespula vulgaris

<400> SEQUENCE: 1554

Val Asn Glu Tyr Pro Met Met Ala Gly Ile Ile His Leu Ala Thr
1               5                   10                  15

<210> SEQ ID NO 1555
<211> LENGTH: 15
<212> TYPE: PRT
<213> ORGANISM: Vespula vulgaris

<400> SEQUENCE: 1555

Thr Trp Ala Ile Asn Asp Thr Lys Ala Thr Gln Leu Tyr Leu Ile
1               5                   10                  15

<210> SEQ ID NO 1556
<211> LENGTH: 15
<212> TYPE: PRT
<213> ORGANISM: Vespula vulgaris

<400> SEQUENCE: 1556

His Pro Asn Tyr Arg Pro Lys Leu Asn Asp Leu Ala Val Ile Lys
1               5                   10                  15

<210> SEQ ID NO 1557
<211> LENGTH: 15
<212> TYPE: PRT
<213> ORGANISM: Vespula vulgaris

<400> SEQUENCE: 1557

Asn Cys Arg Trp Ser Ala Arg Ser Asn Thr Arg Ile Lys Leu Asn
1               5                   10                  15

<210> SEQ ID NO 1558
<211> LENGTH: 15
<212> TYPE: PRT
<213> ORGANISM: Vespula vulgaris

<400> SEQUENCE: 1558

Gly Ala Thr Ile Ile Thr Pro Gln His Val Leu Thr Ala Ala His
1               5                   10                  15

<210> SEQ ID NO 1559
<211> LENGTH: 15
<212> TYPE: PRT
<213> ORGANISM: Vespula vulgaris

<400> SEQUENCE: 1559

Arg Pro Lys Leu Asn Asp Leu Ala Val Ile Lys Leu Gln Lys Arg
1               5                   10                  15

<210> SEQ ID NO 1560
<211> LENGTH: 15
<212> TYPE: PRT
<213> ORGANISM: Vespula vulgaris

<400> SEQUENCE: 1560

Val Gly Trp Gly Leu Thr Asn Phe Tyr Gly Val Lys Ser Glu Val
1               5                   10                  15

<210> SEQ ID NO 1561
<211> LENGTH: 15
<212> TYPE: PRT
<213> ORGANISM: Vespula vulgaris

<400> SEQUENCE: 1561

Phe Val Asp Thr Val Val Thr Ala Val Gly Trp Gly Leu Thr Asn
1               5                   10                  15

<210> SEQ ID NO 1562
<211> LENGTH: 15
<212> TYPE: PRT
<213> ORGANISM: Vespula vulgaris

<400> SEQUENCE: 1562

Gln Arg Asn Phe Val Asp Thr Val Val Thr Ala Val Gly Trp Gly
1               5                   10                  15

<210> SEQ ID NO 1563
<211> LENGTH: 15
<212> TYPE: PRT
<213> ORGANISM: Vespula vulgaris

<400> SEQUENCE: 1563

Cys Gly Leu Asn Ser Phe Ala Val Glu Ser Ile Ala Ser Lys Met
1               5                   10                  15

<210> SEQ ID NO 1564
<211> LENGTH: 15
<212> TYPE: PRT
<213> ORGANISM: Vespula vulgaris

<400> SEQUENCE: 1564

Leu Lys Tyr Ser Met Arg Ile Gly Pro Ala Cys Leu Pro Phe Tyr
1               5                   10                  15

```
<210> SEQ ID NO 1565
<211> LENGTH: 1
<212> TYPE: PRT
<213> ORGANISM: Vespula vulgaris

<400> SEQUENCE: 1565

Thr
1

<210> SEQ ID NO 1566
<211> LENGTH: 3
<212> TYPE: PRT
<213> ORGANISM: Vespula vulgaris

<400> SEQUENCE: 1566

Lys Leu Lys
1

<210> SEQ ID NO 1567
<211> LENGTH: 8
<212> TYPE: PRT
<213> ORGANISM: Vespula vulgaris

<400> SEQUENCE: 1567

Pro Asp Phe Pro Asn Tyr Tyr Met
1               5

<210> SEQ ID NO 1568
<211> LENGTH: 5
<212> TYPE: PRT
<213> ORGANISM: Vespula vulgaris

<400> SEQUENCE: 1568

Ser Ala Arg Ser Asn
1               5

<210> SEQ ID NO 1569
<211> LENGTH: 8
<212> TYPE: PRT
<213> ORGANISM: Vespula vulgaris

<400> SEQUENCE: 1569

Asp Val Pro Pro Ser Ser Asn Cys
1               5

<210> SEQ ID NO 1570
<211> LENGTH: 1
<212> TYPE: PRT
<213> ORGANISM: Vespula vulgaris

<400> SEQUENCE: 1570

Asp
1

<210> SEQ ID NO 1571
<211> LENGTH: 3
<212> TYPE: PRT
<213> ORGANISM: Vespula vulgaris

<400> SEQUENCE: 1571

Asn Thr Tyr
1

<210> SEQ ID NO 1572
<211> LENGTH: 10
```

```
<212> TYPE: PRT
<213> ORGANISM: Vespula vulgaris

<400> SEQUENCE: 1572

Trp Lys Asn Pro Ser Arg Ile Val Gly Gly
1               5                   10

<210> SEQ ID NO 1573
<211> LENGTH: 9
<212> TYPE: PRT
<213> ORGANISM: Vespula vulgaris

<400> SEQUENCE: 1573

Thr Trp Ala Ile Asn Asp Thr Lys Ala
1               5

<210> SEQ ID NO 1574
<211> LENGTH: 5
<212> TYPE: PRT
<213> ORGANISM: Vespula vulgaris

<400> SEQUENCE: 1574

Asn Tyr Arg Pro Lys
1               5

<210> SEQ ID NO 1575
<211> LENGTH: 10
<212> TYPE: PRT
<213> ORGANISM: Vespula vulgaris

<400> SEQUENCE: 1575

Ala Cys Gln Phe Asp Ser Gly Gly Pro Ile
1               5                   10

<210> SEQ ID NO 1576
<211> LENGTH: 9
<212> TYPE: PRT
<213> ORGANISM: Vespula vulgaris

<400> SEQUENCE: 1576

Thr Cys Ala Asp Glu Ala Pro Gly Val
1               5

<210> SEQ ID NO 1577
<211> LENGTH: 7
<212> TYPE: PRT
<213> ORGANISM: Vespula vulgaris

<400> SEQUENCE: 1577

Arg Ser Thr Pro Gly Glu Ile
1               5
```

The invention claimed is:

1. A cDNA molecule having a nucleic acid sequence selected from the group consisting of:
   i) the nucleotide sequence as shown in SEQ ID NO:1; and
   ii) a nucleic acid sequence that is at least 90% identical to the nucleic acid sequence as shown in SEQ ID NO:1 and encodes a proteolytically active polypeptide.

2. The nucleic acid molecule of claim 1, wherein the nucleotide sequence of said nucleic acid molecule encodes the *Vespula* venom protease Ves v 4 polypeptide or a proteolytically active fragment thereof.

3. The nucleic acid molecule of claim 1 encoding a protease comprising
   one or more B cell epitopes of the *Vespula* venom protease Ves v 4,
   one or more T cell epitopes of the *Vespula* venom protease Ves v 4, or
   one or more B cell epitopes and one or more T cell epitopes of the *Vespula* venom protease Ves v 4.

4. The nucleic acid molecule of claim 1, wherein the protease-encoding nucleic acid molecule has been modified by site-directed mutagenesis to replace at least nucleotide at one or more of the native N-glycosylation site-encoding positions 205-213, 238-246, 433-441, and 646-654 of SEQ ID NO:1 with a different nucleotide wherein the modification affects one or more of the native N-glycosylation sites of the encoded polypeptide.

5. The nucleic acid molecule of claim 4, wherein the protease-encoding nucleic acid molecule encodes a Ves v 4 fusion protein comprising an N-terminal or C-terminal fusion partner.

6. A vector comprising the protease-encoding nucleic acid molecule of claim 1 operationally associated with a promoter.

7. A host cell transformed with the vector of claim 6.

8. A nucleic acid molecule comprising a nucleic acid sequence selected from the group consisting of:
   i) the cDNA nucleotide sequence as shown in SEQ ID NO:1; and
   ii) a nucleic acid sequence that is at least 90% identical to the cDNA nucleotide sequence as shown in SEQ ID NO:1 and that encodes a proteolytically active polypeptide,
   wherein said nucleic acid sequence is operationally associated with transcription and/or translation elements suitable for expression in a host cell, or in a cell-free translation system.

* * * * *